United States Patent
Blery et al.

(10) Patent No.: US 10,577,416 B2
(45) Date of Patent: Mar. 3, 2020

(54) MICA BINDING AGENTS

(71) Applicant: INNATE PHARMA, S.A., Marseilles (FR)

(72) Inventors: Mathieu Blery, Marseilles (FR); Laurent Gauthier, Marseilles (FR); Ivan Perrot, Cassis (FR); Cecile Bonnafous, Marseilles (FR)

(73) Assignee: Innate Pharma, S.A., Marseilles (FR)

( * ) Notice: Subject to any disclaimer, the term of this patent is extended or adjusted under 35 U.S.C. 154(b) by 693 days.

(21) Appl. No.: 14/377,274

(22) PCT Filed: Feb. 7, 2013

(86) PCT No.: PCT/EP2013/052439
§ 371 (c)(1),
(2) Date: Aug. 7, 2014

(87) PCT Pub. No.: WO2013/117647
PCT Pub. Date: Aug. 15, 2013

(65) Prior Publication Data
US 2015/0191542 A1 Jul. 9, 2015

Related U.S. Application Data

(60) Provisional application No. 61/595,902, filed on Feb. 7, 2012, provisional application No. 61/625,841, filed on Apr. 18, 2012.

(51) Int. Cl.
C07K 16/28 (2006.01)
A61K 39/00 (2006.01)
G01N 33/569 (2006.01)

(52) U.S. Cl.
CPC .......... *C07K 16/28* (2013.01); *C07K 16/2833* (2013.01); *G01N 33/56977* (2013.01); *A61K 2039/505* (2013.01); *C07K 2317/24* (2013.01); *C07K 2317/33* (2013.01); *C07K 2317/34* (2013.01); *C07K 2317/732* (2013.01); *C07K 2317/734* (2013.01); *C07K 2317/76* (2013.01); *C07K 2317/92* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 5,229,275 A | 7/1993 | Goroff | |
| 5,567,610 A | 10/1996 | Borrebaeck et al. | |
| 6,737,056 B1 | 5/2004 | Presta | |
| 6,821,505 B2 | 11/2004 | Ward | |
| 7,122,637 B2 | 10/2006 | Presta | |
| 7,183,387 B1 | 2/2007 | Presta | |
| 7,317,091 B2 | 1/2008 | Lazar et al. | |
| 7,332,581 B2 | 2/2008 | Presta | |
| 7,335,742 B2 | 2/2008 | Presta | |
| 7,355,008 B2 | 4/2008 | Stavenhagen et al. | |
| 7,371,826 B2 | 5/2008 | Presta | |
| 7,416,727 B2 | 8/2008 | Presta | |
| 7,425,619 B2 | 9/2008 | Koenig et al. | |
| 7,521,542 B2 | 4/2009 | Johnson et al. | |
| 7,632,497 B2 | 12/2009 | Stavenhagen | |
| 7,786,270 B2 | 8/2010 | Johnson et al. | |
| 7,884,264 B2 | 2/2011 | Dickey et al. | |
| 7,960,512 B2 | 6/2011 | Stavenhagen et al. | |
| 8,217,147 B2 | 7/2012 | Stavenhagen et al. | |
| 8,778,339 B2 | 7/2014 | Tuaillon et al. | |
| 8,802,091 B2 | 8/2014 | Johnson et al. | |
| 8,871,204 B2 | 10/2014 | Brezski et al. | |
| 9,051,577 B2 | 6/2015 | Schuster et al. | |
| 2003/0157108 A1 | 8/2003 | Presta | |
| 2005/0054832 A1 | 3/2005 | Lazar et al. | |
| 2007/0148164 A1 | 6/2007 | Farrington et al. | |
| 2009/0029393 A1 | 1/2009 | Teillaud et al. | |
| 2009/0098124 A1 | 4/2009 | Stavenhagen | |
| 2009/0208500 A1 | 8/2009 | Joly et al. | |
| 2010/0226912 A1 | 9/2010 | Mehtali | |
| 2017/0267764 A1 | 9/2017 | Blery et al. | |

FOREIGN PATENT DOCUMENTS

| | | |
|---|---|---|
| EP | 1176195 | 1/2002 |
| WO | WO 98/19167 | 5/1998 |
| WO | WO 1999/54342 | 10/1999 |
| WO | WO 1999/58572 | 11/1999 |
| WO | WO 2003/089616 | 10/2003 |
| WO | WO 2007/055926 | 5/2007 |
| WO | WO 2008/036981 | 3/2008 |
| WO | WO2008/131406 A2 * | 10/2008 |
| WO | WO 2013/049517 | 4/2013 |
| WO | WO 2013/117647 | 8/2013 |
| WO | WO 2017/157895 | 9/2017 |

OTHER PUBLICATIONS

Waldhauer and Steinle (Oncogene 2008, 27, 5932-5943).*
Bauer et al (Science, 1999, 285: 727-729).*
Torres and Casadevall (Trends in Immunology, 2007, 29(2): 91-97).*
Tarek et al (JCI, 2012, 122(9): 3260-3270).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*

(Continued)

*Primary Examiner* — G. R. Ewoldt
*Assistant Examiner* — Marianne DiBrino
(74) *Attorney, Agent, or Firm* — Knobbe, Martens, Olson & Bear, LLP

(57) ABSTRACT

The present invention relates to methods for the treatment of disorders mediated by MICA-expressing cells using antibodies, antibody fragments, and derivatives thereof that specifically bind MICA. The invention also relates to antibodies; cells producing such antibodies; methods of making such antibodies; fragments, variants, and derivatives of the antibodies; and pharmaceutical compositions comprising the same.

3 Claims, 18 Drawing Sheets
Specification includes a Sequence Listing.

(56) References Cited

OTHER PUBLICATIONS

Poosarla et al (Biotechn. Bioeng., 2017, 114(6): 1331-1342) (Year: 2017).*

Torres and Casadevall (Trend. Immunol., 2008, 29(2): 91-97) (Year: 2008).*

Goeij and Lambert (Curr. Opin. Immunol. 2016, 40: 14-23) (Year: 2016).*

Spreu, J. et al. "Human Cytomegalovirus-Encoded UL16 Discriminates MIC Molecules by Their α2 Domains" *The Journal of Immunology*, Aug. 18, 2006, pp. 3143-3149, vol. 177, No. 5.

Bamomab [Online] "Anti-Human MICA/B Monoclonal Antibody BAMO1" Jan. 1, 2004, p. 1, retrieved from the internet, URL: amomab.com, XP055248333.

Wongsena, W. et al. "Production and characterization of monoclonal antibodies against major histocompatibility complex class I chain-related gene A" *Tissue Antigens*, Nov. 1, 2008, pp. 431-440, vol. 72, No. 5.

Zou, Y. et al. "MICA is a Target for Complement-Dependent Cytotoxicity With Mouse Monoclonal Antibodies and Human Alloantibodies" *Human Immunology*, Jan. 1, 2002, pp. 30-39, vol. 63, No. 1.

Tang, B. et al. "Evaluation of human major histocompatibility complex class I chain-related A as a potential target for tumor imaging" *Cancer Letters*, Jan. 30, 2008, pp. 99-106, vol. 263, No. 1.

Duquesnoy, R. J. et al. "Structurally based epitope analysis of major histocompatibility complex class I-related chain A (MICA) antibody specificity patterns" *Human Immunology*, Dec. 1, 2008, pp. 826-832, vol. 69, No. 12.

Suarez-Alvarez, B. et al. "Identification of Epitopes and Immunodominant Regions on the MICA Protein Defined by Alloantibodies From Kidney Transplant Patients" *Transplantation*, Aug. 15, 2009, pp. S68-S77, vol. 88, No. 3S.

Zou, Y. et al. "Polymorphisms of MICA recognized by human alloantibodies" *Immunogenetics*, 2009, pp. 91-100, vol. 61, No. 2.

Abhinandan et al., "Analysis and improvements to Kabat and structurally correct numbering of antibody variable domains", Mol Immunol. (2008) 45(14): 3832-3839.

Altschul et al., "Basic Local Alignment Search Tool", J Mol Biol. (1990) 215: 403-410.

Andersson et al "Blockade of NKG2D Ameliorates Disease in Mide With Collagen-Induced Arthritis", Arthritis Rheum. (2011) 63(9): 2617-2629.

Arreygue-Garcia et al., "Augmented serum level of major histocompatibility complex class I-related chain A (MICA) protein and reduced NKG2D expression on NK and T cells in patients with cervical cancer and precursor lesions", BMC Cancer (2008) 8:16; 10 pages.

Ashiru et al., "Natural Killer Cell Cytotoxicity is Suppressed by Exposure to the Human NKG2D Ligand MICA*008 that is shed by Tumor Cells in Exosomes", Cancer Res. (2010) 70(2): 481-489.

Bahram et al., "A second lineage of mammalian major histocompatibility complex class I genes", PNAS (1994) 91: 6259-6263.

Bahram et al., "Nucleotide sequence of the human MHC class I MICA gene", Immunogenetics (1996) 44(1): 80-81.

Carrillo et al., "The Multiple Sequence Alignment Problem in Biology", SIAM J Appl Math. (1988) 48(5): 1073-1082.

Chothia et al., "Canonical Structures for the Hypervariable Regions of Immunoglobulins", J Mol Biol. (1987) 196: 901-917.

Chu et al., "Industrial choices for protein production by large-scale cell culture", Curr Opin Biotechnol. (2001) 12(2): 180-187.

Clackson et al., "A Hot Spot of Binding Energy in a Hormone-Receptor Interface", Science (1995) 267: 383-386.

Correale et al., "Dendritic Cell-mediated Cross-presentation of Antigens Derived from Colon Carcinoma Cells Exposed to a Highly Cytotoxic Multidrug Regimen with Gemcitabine, Oxaliplatin, 5-Fluorouracil, and Leucovorin, Elicits a Powerful Human Antigen-specific CTL Response with Antitumor Activity in Vitro", J Immunol. (2005) 175: 820-828.

Cosman et al., "ULBPs, Novel MHC Class I-related Molecules, bind to CMV Glycoprotein UL16 and stimulate NK cytotoxicity through the NKG2D receptor", Immunity (2001) 14: 123-133.

Devereux et al., "A comprehesive set of sequence analysis programs for the VAX", Nucl Acids Res. (1984) 12(1): 387-395.

Downard K.M., "Contributions of mass spectrometry to structural immunology", J Mass Spectrom. (2000) 35: 493-503.

Ehring H., "Hydrogen Exchange/Electrospray Ionization Mass Spectrometry Studies of Structural Features of Proteins and Protein/Protein Interactions", Anal Biochem. (1999) 267: 252-259.

Engen et al., "Investigating protein structure and dynamics by hydrogen exchange MS", Anal Chem. (2001) 73(9): 256A-265A.

Fägerstam et al., "Detection of Antigen-Antibody Interactions by Surface Plasmon Resonance", J Mol Recog. (1990) 3(5/6): 208-214.

Frigoul et al., "MICA: Standardized IMGT allele nomenclature, polymorphisms and diseases", Recent Res Devel Human Genet., (2005) 3: 95-145.

Gasser et al., "The DNA damage pathway regulates innate immune system ligands for the NKG2D receptor", Nature (2005) 436(7054): 1186-1190.

GenBank (NCBI) Accession Nos. AAB41060, AAB41063, AAB41066 and AAB41067 MHC class I chain-related protein A, partial [*Homo sapiens*], (Jan. 21, 1997) Retrieved Jan. 3, 2018; 8 pages.

GenBank (NCBI) Accession No. M83237, "cDNA Expression Vector RSV.5(neo)", (Apr. 6, 2001) Retrieved Jan. 3, 2018; 3 pages.

GenBank (NCBI) Accession No. CAI18747; MHC class I polypeptide-related sequence B [*Homo sapiens*], (Jan. 13, 2009) Retrieved Jan. 3, 2018; 2 pages.

GenBank (NCBI) Accession No. AAD27008; MHC class I chain-related protein A, partial [*Homo sapiens*], (Jul. 26, 2016) Retrieved Jan. 3, 2018; 2 pages.

GenBank (NCBI) Accession No. AAD50293; Transmembrane adapter protein KAP10 [*Homo sapiens*], (Dec. 30, 2016) Retrieved Jan. 3, 2018; 1 pages.

GenBank (NCBI) Accession No. NM_007360; "*Homo sapiens* killer cell lectin like receptor K1 (KLRK1), mRNA", (Nov. 12, 2017) Retrieved Jan. 3, 2018; 5 pages.

GenBank (NCBI) Accession No. AAG29425; "Membrane protein DAP10 [*Homo sapiens*]", (Aug. 9, 2001) Retrieved Jan. 5, 2018; 1 page.

GenBank (NCBI) Accession No. J00228; "*Homo sapiens* immunoglobulin gamma-1 heavy chain constant region (IGHG1) gene, partial cds", (Dec. 2, 1998) Retrieved Jan. 5, 2018; 3 pages.

Green et al., "Antigen-specific human monoclonal antibodies from mice engineered with human Ig heavy and light chain YACs", Nat Genet. (1994) 7(1): 13-21.

Gribskov et al., [Eds.], "Sequence Analysis Primer", Stockton Press (1991), Table of Contents, 7 pages.

Griffin et al., [Eds.] "Computer Analysis of Sequence Data—Part I", Humana Press, NJ, (1994) Table of Contents; 8 pages.

Groh et al., "Tumour-derived soluble MIC ligands impair expression of NKG2D and T-cell activation", Nature (2002) 419(6908) 734-738.

Groh et al., "Stimulation of T cell autoreactivity by anomalous expression of NKG2D and its MIC ligands in rheumatoid arthritis", PNAS (2003) 100(16) 9452-9457.

Harlow et al., [Eds.] "Antibodies: A Laboratory Manual", Cold Spring Harbor Laboratory Press, Cold Spring Harbor, N.Y., 1988; Table of Contents, 9 pages.

Hassan et al. "Frontline: Optimal T cell activation requires the engagement of CD6 and CD166", Eur J Immunol. (2004) 34: 1-11.

Huang et al., "NMR Identification of Epitopes of Lyme Disease Antigen OspA to Monoclonal Antibodies", J Mol Biol. (1998) 281: 61-67.

Jinushi et al., "Impairment of natural killer cell and dendritic cell functions by the soluble form of MHC class I-related chain A in advanced human hepatocellular carcinomas", J Hepatol. (2005) 43(6): 1013-1020.

Kaas et al., "IMGT/3Dstructure-DB and IMGT/StructuralQuery, a database and a tool for immunoglobulin, T cell receptor and MHC structural data", Nucl Acids Res. (2004) 32: D208-D210.

Kaiser et al., "Disulphide-isomerase-enabled shedding of tumour-associated NKG2D ligands", Nature (2007) 447(7143): 482-486.

(56) References Cited

OTHER PUBLICATIONS

Kiselar et al., "Direct Identification of Protein Epitopes by Mass Spectrometry without immobilization of antibody and isolation of natibody-peptide complexes", Anal Chem. (1999) 71: 1792-1801.
Kröger et al., "Epitope-mapping of transglutaminase with parallel label-free optical detection", Biosen Bioelec. (2002) 17: 937-944.
Lefranc et al., "IMGT—Choreography for Immunogenetics and Immunoinformatics", In Silico Biology (2005) 5: 45-60.
Leipert et al., "Investigation of the Molecular Recognition of Amino Acids by Cyclopeptides with Reflectometric Interference Spectroscopy", Angew Chem Int Ed. (1998) 37(23): 3308-3311.
Lesk A.M. [Ed.], "Computational Molecular Biology", Oxford University Press (1988), Table of Contents, 4 pages.
Li et al., "Complex structure of the activating immunoreceptor NKG2D and its MHC class I-like ligand MICA", Nat Immunol. (2001) 2: 443-451.
Lonberg et al., "Antigen-specific human antibodies from mice comprising four distinct genetic modifications", Nature (1994) 368: 856-859.
McCafferty et al., "Phage antibodies: Filamentous phage displaying antibody variable domains", Nature (1990) 348: 552-553.
Meyer et al., "Saturation Transfer Difference NMR Spectroscopy for Identifying Ligand Epitopes and Binding Specificities", E. Schering Res Found Workshop (2004) 44: 149-167.
Müller, "Determination of Affinity and Specificity of Anti-Hapten Antibodies by Competititve Radioimmunoassay", Meth Enzymol. (1983) 92: 589-601.
Nice et al., "Mapping of the antibody- and receptor-binding domains of granulocyte colony-stimulating factor using an optical biosensor", J Chromatography (1993) 646: 159-168.
Ogasawara et al., "NKG2D Blockade prevents autoimmune diabetes in NOD Mice", Immunity (2004) 20: 757-767.
Petersdorf et al., "Population study of allelic diversity in the human MHC class I-related MIC-A gene", Immunogenetics (1999) 49(7-8): 605-612.
Plückthun A., "Mono- and Bivalent Antibody Fragments Produced in *Escherichia coli*: Engineering, Folding and Antigen Binding", Immunol. Rev. (1992) 130: 151-188.
Presta et al., "Engineering therapeutic antibodies for improved function", Biochem Soc Trans (2002) 30(4): 487-490.
Raulet et al., "Regulation of ligands for the NKG2D activation receptor", Annu Rev Immunol. (2013) 31: 413-441.
Remington: The Science and Practic of Pharmacy; Gennaro A.R. [Ed.], 19th Edition, Mack Publishing Co., (1995); Table of content, 5 pages.
Salih et al, "Cutting Edge: Down-regulation of MICA on human tumors by proteolytic shedding", J Immunol. (2002) 169: 4098-4102.
Salih et al., "Functional expression and release of ligands for the activating immunoreceptor NKG2D in leukemia", Blood (2003) 102(4): 1389-1396.
Saunal et al., "Mapping of viral conformational epitopes using biosensor measurements", J Immunol Meth. (1995) 183: 33-41.
Shields et al., "High Resolution Mapping of the Binding Site on Human IgG1 for FcgammaRI, FcgammaRII, FcgammaRIII, and FcRn and Design of IgG1 Variants with Improved Binding to the FcgammaR", J Biol Chem. (2001) 276(9): 6591-6604.
Shields et al., "Lack of Fucose on Human IgG1 N-Linked Oligosaccharide Improves Binding to Human FcgammaRIII and antibody-dependent Cellular Toxicity", J Biol Chem. (2002) 277(30): 26733-26740.
Skerra A., "Bacterial expression of immunoglobulin fragments", Curr Opin Immunol. (1993) 5: 256-262.
Smith D.W. [Ed.], "Biocomputing—Informatics and Genome Projects", Academic Press, Inc. (1994), Table of Contents, 7 pages.
Steigerwald et al., "Human IgG1 antibodies antagonizing activating receptor NKG2D on natural killer cells", mAbs (2009) 1(2):115-127.
Steinle et al., "Interactions of Human NKG2D with its ligands MICA, MICB, and homologs of the mouse RAE-1 protein family", Immunogen. (2001) 53: 279-287.
Tarentino et al., "The Isolation and structure of the core oligosaccharide sequences of IgM", Biochemistry (1975) 14(25): 5516-5523.
Taylor et al., "Human immunoglobulin transgenes undergo rearrangement, somatic mutation and class switching in mice that lack endogenous IgM", Int Immunol. (1994) 6(4): 579-591.
Tsuboi et al., "A novel strategy for evasion of NK cell immunity by tumours expressing core2 O-glycans", EMBO J (2011) 30(15): 3173-3185.
Umana et al., "Engineered glycoforms of an antineuroblastoma IgG1 with optimized antibody-dependent cellular cytotoxic activity", Nat Biotech. (1999) 17: 176-180.
Von Heijne G. "Sequence Analysis in Molecular Biology—Treasure Trove or Trivial Pursuit", Academic Press, Inc. (1987); Table of Content, 5 pages.
Von Lilienfeld-Toal et al., "Reduced immune effector cell NKG2D expression and increased levels of soluble NKG2D ligands in multiple myeloma may not be causally linked", Cancer Immunol Immunother. (2010) 59(6): 829-839.
Waldhauer et al., "Tumor-Associated MICA is shed by ADAM Proteases", Cancer Research (2008) 68(15): 6368-76.
Wang et al., "Identification of a Fab interaction footprint site on an icosahedral virus by cryoelectron microscopy and X-ray crystallography", Nature (1992) 355: 275-278.
Wells J.A., "Binding in the growth hormone receptor complex", PNAS (1996) 93: 1-6.
Wright et al., "Effect of glycosylation on antibody function: Implications for genetic engineering", Trends Biotechnol. (1997) 15(1): 26-32.
Yamane-Ohnuki et al., "Establishment of FUT8 Knockout Chinese Hamster Ovary Cells: An ideal host cell line for producing completely defucosylated antibodies with enhanced antibody-dependent cellular cytotoxicity", Biotech Bioeng. (2004) 87: 614-622.
Zhou et al., "Development of a simple and rapid method for producing non-fucosylated oligomannose containing antibodies with increased effector function", Biotechnol Bioeng. (2008) 99(3): 652-665.
International Search Report and Written Opinion dated Jul. 25, 2013 for Application No. PCT/EP2013/052439.
International Preliminary Report on Patentability dated Aug. 12, 2014 for Application No. PCT/EP2013/052439.
European Search Report dated Feb. 24, 2016 for Application No. 13704064.8.
International Search Report and Written Opinion dated May 17, 2017 for Application No. PCT/EP2017/055920, filed Mar. 14, 2017.
Sela-Culang et al., "The structual basis of antibody-antigen recognition", Front Immunol. 2013, 4:Article 302, 13 pages.
U.S. Office Action dated Nov. 19, 2018 for U.S. Appl. No. 15/458,123, filed Mar. 14, 2017.
U.S. Response dated Feb. 19, 2019 for U.S. Appl. No. 15/458,123, filed Mar. 14, 2017.
U.S. Office Action dated Mar. 15, 2019 for U.S. Appl. No. 15/458,123, filed Mar. 14, 2017.

* cited by examiner

A.

B.

MICA BINDING AGENTS

CROSS-REFERENCE TO RELATED APPLICATIONS

This application is the U.S. national stage application of International Patent Application No. PCT/EP2013/052439, filed Feb. 7, 2013, which claims the benefit of U.S. Provisional Application Nos. 61/595,902, filed 7 Feb. 2012 and 61/625,841, filed 18 Apr. 2012; all of which are incorporated herein by reference in their entirety; including any drawings.

REFERENCE TO SEQUENCE LISTING

The present application is being filed along with a Sequence Listing in electronic format. The Sequence Listing for this application is labeled "Seq-List-replace.txt" which was created on Feb. 23, 2015 and is 104 KB. The information in the electronic format of the Sequence Listing is incorporated herein by reference in its entirety.

FIELD OF THE INVENTION

The present invention provides antigen-binding proteins capable of binding to MICA polypeptides. The antigen-binding proteins have increased activity in the treatment of disorders characterized by MICA-expressing cells, particularly tumor cells.

BACKGROUND

The immunoreceptor NKG2D is normally expressed on human T cells (e.g. CD8+ T cells, γδ T cells) and NK cells. On pre-activated CD8+ cells, NKG2D functions as a synergistic co-stimulator of CD28 and TCR signalling via DAP10 association, whereas in NK cells it functions as a direct activator. Upon ligand engagement, NKG2D therefore conveys directly activating or costimulatory signals via the paired DAP10 adaptor protein, thereby promoting cancer and infectious disease immunity.

Various ligands for human NKG2D (hNKG2D) have been identified and characterized, including the major histocompatibility complex class I-related chain A and B polypeptides (MICA and MICB), the UL16-binding protein (ULBP) family, and the retinoic acid early transcript-1 (RAET1) family. MICA is frequently associated with epithelial tumors, induced by microbial infections, and aberrantly expressed in certain autoimmune disease lesions. The structure of MICA is similar to the protein fold of MHC class I, with an α 1α2 platform domain and a membrane-proximal Ig-like α3 domain (Li et al 2001 Nat. Immunol. 2:443). MICA and its close relative MICB, which also serves as a ligand for NKG2D, are both polymorphic and the polymorphism has been shown to affect the affinity for NKG2D (Steinle et al. 2001 Immunogenetics 53:279).

In the mouse, which lacks MHC class I chain (MIC) genes, a family of proteins structurally related to ULBP, the retinoic acid early (RAE-1) molecules function as ligands for NKG2D. RAE-1 expression has been shown to be induced by carcinogens and to stimulate antitumor activities of T cells. Murine NKG2D, however, recognizes human MICA polypeptides (Wiemann (2005) J. Immunol. 175:820-829).

The role MICA in cancer biology has been complicated by the fact that MICA is released as a soluble form from the cell surface of tumor cells (e.g., *019 allele) and on the surface of exosomes (*08 allele) (Ashiru et al (2010) Cancer Res. 70(2):481-489)). Soluble MICA (sMICA) can be detected for example at high levels in sera of patients with gastrointestinal malignancies (Salih et al, 2002 J. Immunol. 169: 4098). The MMPs ADAM10 and ADAM17, as well as the disulfide isomerase Erp5, have been reported to have a role in cleavage and shedding of MICA (Waldhauer (2008) Cancer Research 68 (15) 6368-76; Kaiser et al (2007) Nature; and Salih (2002) J. Immunol 169: 4098-4102). Membrane bound MICA has been reported to downmodulate the expression of NKG2D on NK and/or T cells (Von Lilienfeld-Toal et al. (2010) Cancer Immunol. Immunother.). Notably, Wiemann (2005), supra, examined MICA Tg mice and concluded that down-regulation of surface NKG2D on nontransgenic splenocytes was most pronounced after cocultivation with splenocytes from MICA transgenic mice in vitro, and only marginally following treatment with sera from H2Kb-MICA mice, whereas incubation with control cells and sera from nontgLM, respectively, had no effect and that overall data suggest that reduced surface NKG2D on H2-K-MICA NK cells results in NKG2D dysfunction and that NKG2D downregulation is primarily caused by a persistent exposure to cellbound MICA in vivo.

Reports have also emerged that NKG2D on NK cells is downregulated by sMICA (Groh et al. (2002) Nature; Arreygue-Garcia (2008) BMC; Jinushi et al. (2005) J. Hepatol.), leading to less reactive NK cells. This rationale may have emerged because similar systems have been observed among other protein families such as the Ig-like and the TNF superfamily have been shown to be released as a soluble form and that release of the molecules affects cell-cell interactions by reduction of ligand densities and modulates NK cells bearing the respective receptor (Salih 2002). Consequently, attempts to generate anti-MICA antibodies have focused on development of antibodies that inhibit MICA shedding.

It has also been reported that expression of NKG2D ligands MICA and MICB on healthy cells can break the balance between immune activation and tolerance, and trigger autoimmunity. Genetic linkage studies have shown that some MICA alleles are positively associated with type 1 diabetes, and development of disease in prediabetic NOD mice expressing Rae1 on their islet cells can be completely prevented by treatment with NKG2D-blocking mAbs, which reduce expansion and function of autoreactive CD8+ T cells. MICA and MICB molecules are also dramatically upregulated in RA synoviocytes and activate the T cells in an NKG2D-dependent manner. Moreover, rheumatoid arthritis patients have been reported to have high levels of IL-15 and TNF-α in the sera and inflamed joints which induce expression of NKG2D on CD4+CD28− subset of T cells. In Celiac disease, massive infiltration of intraepithelial NKG2D+ CD8+ cd T lymphocytes in the gut has been reported, and MIC proteins become strongly expressed on the surface of epithelial cells in patients with active disease. In inflammatory bowel disorders, increased levels of MIC expression were found on intestinal epithelial cells and it the number of intestinal epithelial CD4+ T cells expressing NKG2D was found to correlate with intestinal inflammation.

Approaches to date to treat inflammation based on the NKG2D system have focused on blockade of NKG2D itself rather than its ligands (Ogasawara et al. (2004) Immunity 20(6):757-767; Andersson et al (2011) Arthritis. Rheum. 63(9):2617-2629; Steigerwald et al (2009) MAbs 1(2):115-127. One possibility is that this focus on NKG2D rather than its ligand is due to the perceived difficulty of targeting the NKG2D ligand system which includes a variety of ligands and in some cases a large number of alleles.

For MICA and MICB, there are over 50 MICA alleles and at least 13 MICB alleles recognized. There is only 43% amino acid identity across the MIC polypeptides in the α1α2 domain (the domain involved in the NKG2D interface), and 80% of the amino acid substitutions are non-conservative (Steinle et al. (2001) Immunogenetics 53: 279-287; Steinle et al. (1998) Proc. Natl. Acad. Sci. U.S.A. 95:12510-12515), suggesting that it will be unlikely to obtain antibodies that are effective for a majority of individuals in a population. Additionally, the methionine/valine bimorphism at position 129 in MICA determines differences in NKG2D binding, and although the side chain of residue 129 is partially buried and forms hydrophobic interactions with glutamine 136, alanine 139 and methionine 140 in the first α2 helical stretch, it may be associated with a difference in conformation in this domain in comparison with valine 129 forms of MICA (Steinle et al (2001) Immunogenetics 53: 279-287).

In conclusion, there is a need for new approaches to target MICA with therapeutic agents.

SUMMARY OF THE INVENTION

In one aspect, the invention results, inter alia, from the discovery of antibodies with high affinity across human MICA alleles (as well as on non-human primate MICA).

The antibodies notably bind one or more MICA alleles from each of two major MICA groups that are determined to represent the main families of MICA: Group 1 alleles that bind NKG2D strongly (including MICA*001, *002, *007, *012, *017 and *018) and Group 2 that bind NKG2D weakly (MICA*004, *006, *008, *009 and *019). By binding to an epitope present on the subset MICA*001, *004, *007 and *008 or *001, *004, *007, *008 and *019, the antibodies cover the alleles of both groups that are present in almost all individuals. Optionally, the antibodies have an EC50 of no more than 5 µg/ml, optionally no more than 3 µg/ml, no more than 2 µg/ml, no more than 1 µg/ml or no more than 0.5 µg/ml for binding to cells made to express at their surface *001, to cells made to express at their surface *004, to cells made to express at their surface *007 and to cells made to express at their surface *008.

High affinity binding is advantageous, inter alia, for an antibody to effectively mediate CDC and ADCC. The invention provides epitopes on MICA within the α1 and/or α2 domains that are optimal antibody binding regions for inducing high ADCC and/or CDC activity yet still are found across principal MICA alleles. The epitopes are generally on the lateral side of the α1 and/or α2 domains and are either entirely outside the NKG2D binding surface or partly overlapping with the NKG2D binding surface. Additionally, α3 epitopes are identified that exhibit enhanced ADCC/CDC and multiple-allele binding characteristics.

Subgroups of antibodies were also identified that block the interaction of MICA with NKG2D. In addition to induction of ADCC and CDC activity when comprising Fc domains that are bound by Fcγ receptors or blockade of pro-inflammatory activity when comprising Fc domains that are not substantially bound by Fcγ receptors, these antibodies were useful for their ability to be able to block sMICA-induced downmodulation of NKG2D.

Other subgroups of antibodies were also identified that did not block the ability of MICA on the surface of cells (e.g. tumor cells, transfectands) to induce NKG2D activity in a NKG2D-expressing immune cell that is brought into contact with said MICA-expressing cell in the presence of anti-MICA antibody. In addition to induction of ADCC and CDC activity, these antibodies were useful for their ability to avoid inhibition of NKG2D such that NKG2D-expression immune effector cells remain able to lyse target cells via NKG2D (e.g. in addition to any Fcγ receptor-mediated mechanism).

Recombinant and cell surface bound MICA appear to be capable of different conformations and binding cell-bound MICA may have distant effects on the MICA protein. Particularly surprisingly, blockade of the ability of MICA on the surface of cells (e.g. tumor cells, transfectants) to induce signaling by NKG2D did not always correlate with ability to block MICA-NKG2D interactions when recombinant proteins were used (BIACORE™ surface plasmon resonance (SPR) analytical system study). Also, particularly surprisingly, while pan-allele antibodies were not found completely within the NKG2D binding zone on the plateau of the α1α2 domain, MICA blockade of the ability of MICA on the surface of cells (e.g. tumor cells, transfectants) to induce signaling by NKG2D did not correlate with the location of the binding epitope. Some antibodies located far from the NKG2D interaction area were able to block induction of NKG2D activity while some antibodies near the NKG2D binding area or with partial overlap did not block induction of NKG2D activity. Antibodies furthermore differed in the ability to mediate CDC as a function of their epitopes.

Group 1 alleles of MICA generally have M at residue 129 while Group 2 alleles have V at residue 129. In one embodiment, MICA groups are characterized by the presence of a methionine (M) or valine (V) residue at position 129 of the MICA polypeptide, wherein M is associated with a MICA form that binds strongly to NKG2D and V is associated with lower binding to NKG2D.

In one embodiment, the invention provides antibodies that cross-react with a MICA allele having a methionine at position 129 and a MICA allele having a valine at position 129. In one aspect the invention provides a monoclonal antibody that specifically binds to a human MICA polypeptide having a methionine at position 129 and a human MICA polypeptide having a valine at position 129. Optionally, the antibodies have an EC50 of no more than 5 µg/ml, optionally no more than 3 µg/ml, no more than 2 µg/ml, no more than 1 µg/ml or no more than 0.5 µg/ml for binding to cells made to express at their surface a human MICA polypeptide having a methionine at position 129 and to cells made to express at their surface a human MICA polypeptide having a valine at position 129.

In one embodiment the antibody further binds to a MICB polypeptide having a valine at position 152 (e.g., to a MICB polypeptide of SEQ ID NO: 6).

The binding regions discovered remain present on glycosylated MICA, notably MICA with glycosylation expressed preferentially by human tumor cells.

In one embodiment, the present invention results, inter alia, from the discovery of antibodies that are effective in vitro and in vivo in inducing effector cell lysis (e.g. NK cells and/or T cells) of MICA-expressing tumor cells while blocking the interaction of MICA with NKG2D. Antibodies that block NKG2D-MICA interactions be advantageous in that such antibodies may prevent the sMICA-induced downregulation of NKG2D as shown herein. Such blocking antibodies may be particular useful for the treatment of patients having high levels of soluble MICA, e.g. in circulation. In another embodiment, the present invention provides antibodies that are effective in vitro and in vivo in inducing effector cell lysis (e.g. NK cells and/or T cells) of MICA-expressing tumor cells and that inhibit sMICA-induced downmodulation of NKG2D expression on the surface of an immune effector cell without substantially blocking shedding of MICA from MICA-expressing cells (e.g. tumor cells). Such antibodies can inhibit sMICA-induced downmodulation of NKG2D expression by inhibiting the interaction of MICA with NKG2D. Optionally the antibody comprises the light and heavy chain CDRs, optionally with one or more amino acid modifications in a CDR, of 9C10, 19E9, 12A10, 18E8, 14B4 or 10F3.

In another embodiment, the present invention provides antibodies that are effective in vitro and in vivo in inducing effector cell lysis (e.g. NK cells and/or T cells) of MICA-expressing tumor cells without substantially blocking shedding of MICA from MICA-expressing cells (e.g. tumor cells) and without substantially blocking the interaction of MICA with NKG2D. Optionally the antibody comprises the light and heavy chain CDRs, optionally with one or more amino acid modifications in a CDR, of 6E4, 20C6, 16A8, 15F9 10A7 or 14B4.

In one embodiment, antibodies that bind to the α1α2 domain (the domain involved in the NKG2D interface) are provided that cross-react with multiple MICA alleles (e.g. a MICA allele having a methionine at position 129 and a MICA allele having a valine at position 129; a MICA*001, *004, *007 and *008 allele) and bind with high affinity to such MICA alleles (e.g. an EC50 of no more than 5 µg/ml, optionally no more than 3 µg/ml, no more than 2 µg/ml, no more than 1 µg/ml or no more than 0.5 µg/ml for binding to cells made to express at their surface said allele of a human MICA polypeptide). Optionally, the antibodies bind to regions on the α1α2 domain that are located outside or partially outside the the NKG2D interface, but not completely within the NKG2D interface.

Binding to MICA alleles and related EC50 values can be assessed using, e.g., flow cytometry, according to the methods of Example 3 herein.

In another embodiment, the present invention results from the discovery of antibodies that bind the α1 and/or α2 domain of MICA without substantially blocking the interaction of MICA with NKG2D (e.g. wherein MICA and NKG2D are each expressed at the surface of cells). Such antibodies can optionally be characterized as not competing with hNKG2D in binding to MICA. Optionally the antibodies do not inhibit the ability of MICA to induce NKG2D activity in a NKG2D-expressing cell. Such antibodies can optionally be characterized as not decreasing or blocking the ability of a NKG2D-expressing effector cell (e.g. a CD16-negative effector cell) to lyse a MICA-expressing target cell. The antibodies will optionally not substantially block shedding of MICA from tumor cells.

In one embodiment, a non-blocking α1α2 domain antibody binds an epitope on a MICA polypeptide of SEQ ID NO:1 comprising one or two residues selected from the group consisting of K81 and D82, one or two residues selected from the group consisting of Q83 and K84, one, two or three residues selected from the group consisting of H109, Y111 and L116, optionally residue D113, one, two or three residues selected from the group consisting of Q131, S132 and Q136, one, two or three residues selected from the group consisting of S133, R134 and T137, and/or 1, 2, 3 or 4 residues selected from the group consisting of M140, N141, R143 and N144 (e.g. antibody 20C6 and 10A7).

In one embodiment, a non-blocking α1α2 domain antibody bind an epitope comprising one or two residues selected from the group consisting of R6 and N8, one or two residues selected from the group consisting of E97 and H99, one, two or three residues selected from the group consisting of E100, D101 and N102, one, two or three residues selected from the group consisting of S103, T104 and R105, optionally residue E115, and/or one, two or three residues selected from the group consisting of L178, R179 and R180 (e.g. antibody 15F9).

In one embodiment, a non-blocking α1α2 domain antibody binds an epitope comprising one or two residues selected from the group consisting of Q48 and W49 of the MICA polypeptide of SEQ ID NO: 1, and/or 1, 2, 3 or 4 residues selected from the group consisting of E51, D52, V53 and L54 of the MICA polypeptide of SEQ ID NO: 1 (e.g. antibody 6E4).

In another embodiment, the present invention results, inter alia, from the discovery of antibodies that bind the α3 domain of MICA, wherein the antibodies do not inhibit the interaction of MICA with NKG2D (e.g. wherein MICA and NKG2D are each expressed at the surface of cells). Optionally the antibodies do not substantially blocking shedding of MICA from tumor cells. Optionally, such an antibody can optionally be characterized as not competing with hNKG2D in binding to MICA.

In one embodiment, a non-blocking α3 domain antibody binds an epitope comprising one, two or three residues selected from the group consisting of S224, H225 and D226, one, two or three residues selected from the group consisting of T227, Q228 and Q229, and/or one or two residues selected from the group consisting of W230 and D232 (e.g. antibody 16A8).

In another embodiment, the present invention results from the discovery of antibodies that bind the α1 and/or α2 domain of MICA and inhibit the interaction of MICA with NKG2D (e.g. wherein MICA and NKG2D are each expressed at the surface of cells). Such an antibody can optionally be characterized as competing with hNKG2D in binding to MICA. The antibodies will optionally inhibit sMICA-induced downmodulation of NKG2D expression on the surface of an immune effector cell without substantially blocking shedding of MICA from tumor cells.

In one embodiment, a blocking α1α2 domain antibody binds an epitope comprising one, two or three residues selected from the group consisting of E100, D101 and N102, one, two or three residues selected from the group consisting of S103, T104 and R105, one or two residues selected from the group consisting of N121 and E123, and/or one or two residues selected from the group consisting of T124 and E126 (e.g. antibody 19E9, 18E8 and 10F3).

In one embodiment, a blocking α1α2 antibody binds an epitope comprising 1, 2 or 3 residues selected from the group consisting of N56, K57 and T58 of the MICA polypeptide of SEQ ID NO: 1, and/or one or two residues selected from the group consisting of R61 and R64 of the MICA polypeptide of SEQ ID NO: 1 (e.g. antibody 9C10 and 12A10).

In another embodiment, the present invention results, inter alia, from the discovery of antibodies that bind the α3 domain of MICA, wherein the antibodies inhibit the interaction of MICA with NKG2D (e.g. wherein MICA and NKG2D are each expressed at the surface of cells). Optionally the antibodies do not substantially blocking shedding of MICA from tumor cells. Optionally, such an antibody can optionally be characterized as competing with hNKG2D in binding to MICA. The antibodies will optionally inhibit sMICA-induced downmodulation of NKG2D expression on the surface of an immune effector cell. The antibodies may substantially block shedding of MICA from tumor cells or may optionally not substantially block shedding of MICA from tumor cells.

In one embodiment, a blocking α3 domain antibody binds an epitope comprising one, two or three residues selected from the group consisting of T227, Q228 and Q229 (antibody 14B4).

Without wishing to be bound by theory, it is believed that despite the scientific literature which assumes a causal relationship between MICA (e.g., sMICA or membrane-bound MICA) and NKG2D downregulation and impairment of effector cells, MICA does not itself in tumor settings always cause substantial impairment of effector cells. In particular, while sMICA can cause downregulation of NKG2D, the concentrations of sMICA that occur in vivo may in many cases be too low to itself cause significant NKG2D downregulation (see Example 9). Furthermore, in tumor settings (e.g. established or advanced disease), the patient is generally in an immunosuppressed state via a number of non-MICA components (e.g. TGF-beta) that have the potential, among other effects, to cause the downmodulation of NKG2D. Consequently, agents that block or do not block NKG2D-MICA interactions and do not inhibit MICA shedding are efficacious in treatment of cancers so long as they are capable of inducing CDC and/or ADCC. Antibodies that do not block NKG2D-MICA interactions be advantageous because MICA-expressing tumor cells have the potential to remain recognizable by NKG2D on immunocompetent effector cells that are present (e.g. as immunocompetence re-establishes in a patient during or subsequent to a treatment, for treatments having a long duration, repeated administration or administered at high doses). Antibodies that block NKG2D-MICA interactions be advantageous in that such antibodies may prevent the MICA-induced downregulation of NKG2D (see Example 9). Such blocking antibodies may be particularly useful for the treatment of patients having high levels of soluble MICA, e.g. in circulation.

In one embodiment, the present invention provides a MICA binding compound, preferably an antibody that specifically binds to a MICA polypeptide (an anti-MICA antibody), without detectably reducing binding between MICA and NKG2D (e.g., the interaction of surface MICA on tumor cells with surface NKG2D on effector cells), e.g., without substantially blocking the interaction of MICA and NKG2D. In one embodiment, the present invention provides a MICA binding compound (e.g. a MICA-binding polypeptide) that binds to a MICA polypeptide without substantially blocking shedding of MICA from tumor cells. In one embodiment, the present invention provides an MICA binding compound that binds to a MICA polypeptide without substantially blocking the interaction of MICA with NKG2D and without substantially blocking shedding of MICA from tumor cells.

In another embodiment, the present invention provides antibodies that bind human MICA (particularly in the α1 and/or α2 domains) that recognize major MICA alleles MICA*001, MICA*004, MICA*008 and optionally further MICA*007 and/or MICA*019. In one embodiment, the antibodies optionally further recognize MICA of a non-human primate specie (e.g. cynomolgus monkey). In one embodiment, the antibodies optionally further recognize a MICB polypeptide comprising the amino acid sequence of SEQ ID NO 6. Optionally, in another embodiment, these antibodies further do not recognize MICB. Optionally the antibodies do not substantially block shedding of MICA from tumor cells. Optionally the antibodies do not substantially block the interaction of MICA with NKG2D.

In one embodiment, the present invention provides an antibody that specifically binds to a glycosylated MICA polypeptide expressed by a human tumor cell.

In one embodiment, the present invention provides an antibody that specifically binds to a MICA polypeptide expressed by a non-human primate cell.

In one embodiment, the present invention provides an antibody that specifically binds to a MICA polypeptide (an anti-MICA antibody), wherein the antibody binds a polypeptide of SEQ ID NO 2 (MICA*004) and/or a polypeptide of SEQ ID NO 4 (MICA*008). In one embodiment, the antibody further binds a polypeptide of SEQ ID NO 1 (MICA*001). In one embodiment, the present invention provides an antibody that specifically binds to a MICA polypeptide, wherein the antibody binds a polypeptide of SEQ ID NO 5 (MICA*019). In one embodiment, the antibody further binds a polypeptide of SEQ ID NO 3 (MICA*007). In one embodiment, the present invention provides an antibody that specifically binds to a MICA polypeptide, wherein the antibody binds a polypeptide of SEQ ID NO 2 (MICA*004), a polypeptide of SEQ ID NO 4 (MICA*008) and a polypeptide of SEQ ID NO 5 (MICA*019). In one embodiment, the present invention provides an antibody that specifically binds to a MICA polypeptide, wherein the antibody binds a polypeptide of SEQ ID NO 1 (MICA*001), a polypeptide of SEQ ID NO 2 (MICA*004), a polypeptide of SEQ ID NO 4 (MICA*008), and a polypeptide of SEQ ID NO 5 (MICA*019), optionally further wherein the antibody binds a polypeptide of SEQ ID NO 3 (MICA*007). By binding to alleles MICA*001, -*004, and *008, (and advantageously further *007 and *019) across both Group 1 and Group 2 of MICA alleles, virtually the entire human population will be suitable for treatment with such an anti-MICA agent of the invention. In any embodiment, a polypeptide of SEQ ID NOS 1-5 may comprise an O-glycan (N-acetyllactosamine linked to serine or threonine). In any embodiment, a polypeptide of SEQ ID NOS 1-5 may comprise a core2 O-glycan (an O-glycan comprising an N-acetylglucosamine branch connected to N-acetylgalactosamine) and/or an N-linked glycan. In one embodiment, the antibody binds to a MICA polypeptide without substantially blocking the interaction of MICA with NKG2D and/or without substantially blocking shedding of MICA from tumor cells. In one embodiment, the antibody binds the α1 and/or α2 domain of MICA. In one embodiment, the antibody binds the α3 domain of MICA.

Preferably the compound is an antibody, optionally a tetrameric antibody comprising two Ig heavy chains and two Ig light chains. Preferably the antibody has binding affinity ($K_D$), optionally wherein binding affinity is bivalent, for a human MICA polypeptide at of less than $10^{-9}$ M, preferably less than $10^{-10}$ M, or preferably less than $10^{-11}$ M. Preferably the antibody is a depleting antibody, optionally wherein the antibody induces ADCC and/or CDC toward a MICA-expressing tumor cell.

In a specific embodiment, the present invention provides an antibody that mediates depletion of MICA-expressing tumor cells by an NK or T cell (e.g., in vivo or in vitro) without substantially inhibiting NKG2D-mediated cytotoxicity of a hNKG2D-expressing NK or T cell.

In a specific embodiment, an antibody of the invention does not compete with hNKG2D in binding to MICA.

In a specific embodiment, when an antibody of the invention is bound to MICA on a MICA-expressing cell, the MICA-expressing cell does not substantially reduce the amount of cell-surface hNKG2D upon binding via, e.g., stimulating down-modulation and/or internalization of hNKG2D, has a high affinity and slow off-rate, cross-reacts with cynomolgus and/or rhesus MICA, and is of a depleting isotype such as, e.g., human IgG1.

In one aspect, the invention provides an antibody that specifically binds MICA, wherein the antibody has one or more (including any combination thereof, or all of) of the following properties:

(a) has a Kd of less than $10^{-8}$ M, preferably less than $10^{-9}$ M, or preferably less than $10^{-10}$M for binding to a MICA polypeptide;

(b) binds to at least one residue in the segment corresponding to residues of a domain selected from the group consisting of 1-88, 89-181 and 182-274 of the MICA polypeptide of SEQ ID NO: 1 and/or binds to an epitope (one or more amino acid residues on MICA) as described herein;

(c) binds to two, three, four or five of the MICA*001, *004, *007, *008, and *019 polypeptides, respectively comprising a sequence of SEQ ID NOS: 1-5;

(d) does not substantially block shedding of MICA from tumor cells;

(e) does not substantially block the interaction of MICA with NKG2D (e.g., the interaction of surface MICA on tumor cells with surface NKG2D on effector cells);

(f) does not cause a substantial decrease in lysis of MICA-expressing cells by effector cells (e.g., NKG2D+ CD16− NK cells);

(g) induces complement dependent cytoxicity (CDC) and/or antibody dependent cellular cytoxicity (ADCC) toward a cell that expresses MICA on its surface; and (h) competes for binding to a MICA polypeptide with antibody 6E4, 20C6, 16A8, 15F9 and 10A7.

In any of the embodiments herein, an antibody of the invention may be characterized by any one or more features of (a)-(h), above.

In one embodiment, provided is a method of testing an anti-MICA antibody, said method comprising: (i) assessing whether the antibody blocks shedding of MICA from MICA-expressing cells and/or (ii) assessing whether the antibody blocks the interaction of MICA with NKG2D. Step (i) may optionally comprise bringing the antibody that binds a MICA polypeptide into contact with a cell expressing a MICA polypeptide. Step (ii) may optionally comprise bringing the antibody that binds a MICA polypeptide into contact with a MICA polypeptide (e.g. an isolated polypeptide or a polypeptide expressed on the surface of a cell), in the presence of an NKG2D polypeptide (e.g. an isolated polypeptide or a polypeptide expressed on the surface of a cell).

In another embodiment, provided is a method of producing an antibody that binds a MICA polypeptide in a mammalian subject, optionally for the treatment of a cancer, said method comprising the steps of: a) providing a plurality of antibodies, optionally immunizing a non-human mammal with an immunogen comprising a MICA polypeptide; and b) performing a selection step to select an antibody from the plurality, the step comprises:

(i) testing whether an antibody binds to a human MICA polypeptide, optionally one, two, three, four or all of the polypeptides of SEQ ID NOS 1-5, and selecting the antibody if it binds to a human MICA polypeptide(s); and/or (ii) testing whether an antibody blocks shedding of MICA from MICA-expressing cells, and selecting the antibody if it does not block shedding; and/or (iii) testing whether an antibody blocks the interaction of MICA (e.g. surface MICA) with NKG2D, preferably testing wherein the antibody causes a substantial decrease in lysis of MICA-expressing cells by effector cells (e.g., NKG2D+ CD16− NK cells, and selecting the antibody if it does not block the interaction of MICA (e.g. surface MICA) with NKG2D, preferably wherein the antibody does not cause a substantial decrease in lysis of MICA-expressing cells.

In one aspect, the invention results, inter alia, from the discovery of blocking anti-MICA antibodies having high affinity across the major human MICA alleles from the two main groups of MICA alleles (as well as on non-human primate MICA and MICB). In one embodiment, MICA groups are characterized by the presence of a methionine (M) or valine (V) residue at position 129 of the MICA polypeptide, wherein M is associated with a MICA form that binds strongly to NKG2D and V is associated with lower binding to NKG2D. In one embodiment, the invention provides blocking antibodies that cross-react with a MICA allele having a methionine at position 129 and a MICA allele having a valine at position 129. In one aspect the invention provides a monoclonal antibody that specifically binds to a human MICA polypeptide having a methionine at position 129 and a human MICA polypeptide having a valine at position 129, wherein said antibody inhibits MICA-mediated hNKG2D activity. In one embodiment the antibody further binds antibody binds to a MICB polypeptide having a valine at position 152 (e.g., to a MICB polypeptide of SEQ ID NO: 1). Preferably, said antibody inhibits MICB-mediated hNKG2D activity. MICB polypeptides having a valine at position 152 are reported to show strong binding to soluble NKG2D. Antibodies that bind MICB polypeptides having valine at position 152 and MICA polypeptides having methionine at position 129 may be advantageous in individuals who have greater susceptibility or severe disease arising from alleles with strong binding to NKG2D.

The blocking anti-MICA antibodies of the invention also cross-react (bind) one or more high prevalence alleles from each of two major MICA groups that are determined to represent the main families of MICA: group 1 alleles that bind NKG2D strongly (including MICA*001, *002, *007, *012, *017 and *018) and group 2 that bind NKG2D weakly (MICA*004, *006, *008, *009 and *019). By binding to an epitope present on the subset MICA*001, *004, *007, *008 and *019, the antibodies cover the alleles of both groups that are present in almost all individuals. Group 1 alleles of MICA generally have M at residue 129 while Group 2 alleles have V at residue 129.

In another aspect, the present invention results, inter alia, from the discovery of antibodies against MICA (as well as on non-human primate MICA and MICB) against certain epitopes are significantly more efficient in NKG2D blockade that either other anti-MICA antibodies or anti-NKG2D antibodies, and are also more effective in blocking NKG2D-mediated cytotoxicity than what would be expected from their ability to bind MICA. In particular, anti-MICA antibodies with affinities in the picomolar range were 4-log better in inhibition than anti-MICA antibodies having a 2-log lesser affinity ($K_D$).

Blocking MICA antibodies of the invention may be characterized by the ability to prevent any competition with, displacement by, or residual binding of, NKG2D. Other high affinity NKG2D or MICA antibodies may leave open some displacement by their ligand (e.g., MICA/ULPBs/RAET1 or NKG2D, respectively). Also, as observed from crystal structures of the NKG2D-MICA interaction, NKG2D acts as a homo-dimer and has two symmetrical surfaces (one on each NKG2D chain) that interact with the top of the MICA α1α2 platform domain. The two NKG2D chains both contribute to the interaction by binding to distinctly differences surfaces of the asymmetric MICA platform domain (see e.g., Li et al. (2001) Nature Immunol. 2(5):443-450). The antibodies of the invention may thus optionally block the MICA-NKG2D interaction fully, e.g., by blocking (e.g. interfering, competing with) the binding of both NKG2D monomers in an NKG2D homodimer to a MICA polypeptide. Other MICA antibodies (or NKG2D antibodies) may block completely only one of the two NKG2D binding sites.

Treatment with the blocking anti-MICA antibodies of the invention, in addition to their use to deplete MICA-expressing cells when used as depleting antibody (e.g. IgG1 or IgG3 isotype), provides a means to target MICA (and MICB) in inflammatory conditions believed to be driven by MICA and/or B-mediated activation of NKG2D, without reducing causing unwanted broader immune system inhibition by reducing the number of NKG2D receptors available for binding to other ligands (e.g. ULBPs) and subsequent activation. The possibility of such fully blocking anti-MICA antibodies also open the possibility of local delivery of anti-MICA antibodies to sites of inflammation (e.g. into joints or other sites of inflammation in arthritis patients) without causing a generalized immunosuppressive effect caused by administration of NKG2D antibodies.

In one embodiment, the present invention antibodies that are effective in vitro and in vivo in inhibiting effector cell lysis (e.g. NK cells and/or T cells) of MICA-expressing cells and substantially block the interaction of MICA with NKG2D.

In one embodiment, particularly when used in the treatment of inflammatory or autoimmune disorders, the antibody of the invention is a non-depleting antibody that substantially reduces or inhibits NKG2D activation, NKG2D-signalling, activation of NKG2D-expressing NK or T cells, or lysis of MICA-expressing cells by effector cells (e.g., NKG2D+ CD16− NK cells).

In one embodiment, the present invention provides a MICA binding compound, preferably an antibody that specifically binds to a MICA polypeptide (an anti-MICA antibody) and reduces (e.g. substantially eliminates) binding between MICA and hNKG2D (e.g., the interaction of surface MICA on cells with surface NKG2D on effector cells).

In one embodiment, an anti-MICA antibody or binding compound further specifically binds to a MICB polypeptide and reduces (e.g. substantially eliminates) binding between MICB and hNKG2D.

In one embodiment, the invention provides an antibody that competes with hNKG2D in binding to MICA (and optionally MICB) and prevents hNKG2D from binding to MICA (and optionally MICB).

In one embodiment, the invention provides an antibody that inhibits or blocks the interaction of a MICA (and optionally MICB) polypeptide with both hNKG2D chains of an hNKG2D homodimer. Optionally, the antibody blocks the interaction of both an α1 domain of a MICA polypeptide (and optionally MICB polypeptide) and an α1 domain of a MICA polypeptide (and optionally MICB polypeptide), with an hNKG2D homodimer (e.g, the antibody inhibits the interaction of a MICA α1α2 platform with both hNKG2D chains of an hNKG2D homodimer).

In one embodiment, an antibody of the invention does not substantially bind to a HCMV, UL18, ULBP1, ULBP 2, ULBP 3, ULBP 4, ULBP 5 or ULBP 6 polypeptide (see Champsaur et al (2010) Immunol. Rev. 235: 267-285).

In one embodiment, the present invention provides an antibody that specifically binds to a common determinant on a human MICA polypeptide (e.g. a naturally occurring MICA allele) having a methionine at position 129 and a human MICA polypeptide (e.g. a naturally occurring MICA allele) having a valine at position 129, optionally further specifically binds to a common determinant on a human MICB polypeptide (e.g. a naturally occurring MICB allele) having a valine at position 152 wherein the antibody reduces (e.g. substantially eliminates) binding between MICA and NKG2D (and optionally between MICB and NKG2D).

In a further embodiment, the present invention results, inter alia, from the discovery of antibodies that bind human MICA, preferably in the α1α2 platform domain (i.e. the α1 and/or α2 domain), and that recognize major MICA alleles MICA*001, MICA*004, MICA*008 and optionally further MICA*007 and/or MICA*019, and optionally further recognize MICA of a non-human primate specie (e.g. cynomolgus monkey), and optionally further recognize MICB. In one embodiment, the antibodies further recognize a MICB polypeptide comprising an amino acid sequence of SEQ ID NO: 6. Optionally the antibodies furthermore do not substantially inhibit shedding of MICA from tumor cells.

In one embodiment, the present invention provides an antibody that specifically binds to a MICA polypeptide (an anti-MICA antibody), wherein the antibody reduces (e.g. substantially eliminates) binding between MICA and NKG2D and wherein the antibody binds a polypeptide of SEQ ID NO: 2 (MICA*004) and/or a polypeptide of SEQ ID NO: 4 (MICA*008). In one embodiment, the antibody further binds a polypeptide of SEQ ID NO: 1 (MICA*001). In one embodiment, the present invention provides an antibody that specifically binds to a MICA polypeptide, wherein the antibody binds a polypeptide of SEQ ID NO: 5 (MICA*019). In one embodiment, the antibody further binds a polypeptide of SEQ ID NO: 3 (MICA*007). In one embodiment, the present invention provides an antibody that specifically binds to a MICA polypeptide, wherein the antibody binds a polypeptide of SEQ ID NO: 2 (MICA*004), a polypeptide of SEQ ID NO: 4 (MICA*008) and a polypeptide of SEQ ID NO: 5 (MICA*019). In one embodiment, the present invention provides an antibody that specifically binds to a MICA polypeptide, wherein the antibody binds a polypeptide of SEQ ID NO: 1 (MICA*001), a polypeptide of SEQ ID NO: 2 (MICA*004), a polypeptide of SEQ ID NO: 4 (MICA*008), and a polypeptide of SEQ ID NO: 5 (MICA*019), optionally further wherein the antibody binds a polypeptide of SEQ ID NO: 3 (MICA*007). By binding to alleles MICA*001, -*004, and *008, (and advantageously further *007 and *019) across both Group 1 and Group 2 of MICA alleles, virtually the entire human population will be suitable for treatment with such an anti-MICA agent of the invention. In one embodiment, the antibody binds the α1 and/or α2 domain of MICA.

Preferably the compound is an antibody, optionally a tetrameric antibody comprising two Ig heavy chains and two Ig light chains.

Preferably the antibody has binding affinity ($K_D$), optionally wherein binding affinity is monovalent or bivalent, for a human MICA and/or MICB polypeptide (e.g. any one or more or all MICA and/or MICB alleles referred to herein) of less than $10^{-9}$ M, preferably less than $10^{-10}$ M, preferably less than $10^{-11}$ M, preferably less than $10^{-12}$ M, or preferably less than $10^{-13}$ M. Preferably the antibody is a tetrameric antibody comprising two Ig heavy chains and two Ig light chains and the $K_D$ is bivalent. Optionally, the antibody has an EC50 for binding to cells made to express a particular MICA and/or MICB polypeptide, for example any one or more or all MICA and/or MICB alleles referred to herein) of no more than 10, 5, or 1 μg/ml. Examples of suitable cells are C1R-MICA cells.

In one embodiment, particularly when the antibody is for use in treating or preventing inflammatory or autoimmune disease, the compound is a non-depleting antibody (an antibody that does not deplete cells to which it binds). Preferably the antibody is a chimeric, humanized or human antibody. Preferably the antibody does not comprise a constant region capable of being bound by an Fcγ3A receptor (CD16), e.g. an antibody of the human IgG4 subtype or an antibody fragment lacking an Fc domain. Preferably the antibody comprises a heavy chain constant region of human IgG4 isotype.

In one embodiment, the antibody specifically binds to a MICA polypeptide expressed by a non-human primate cell. In a specific embodiment, an antibody of the invention has a high affinity and slow off-rate for binding to human MICA, and cross-reacts with cynomolgus (*Macaca fascicularis*) and/or rhesus (*Macaca mulatta*) MICA.

In one aspect, the invention provides an antibody that specifically binds MICA, wherein the antibody has one or more (including any combination thereof, or all of) of the following properties:

(a) has a $K_D$ of less than $10^{-9}$ M, preferably less than $10^{-10}$ M, preferably less than $10^{-11}$ M, preferably less than $10^{-12}$ M, or preferably less than $10^{-13}$M for binding to a MICA polypeptide, preferably wherein the antibody has an affinity of said $K_D$ for each MICA polypeptide alleles MICA*001, *004, and *008, optionally further *007 and/or *019;

(b) binds to at least one residue in the segment corresponding to residues of a domain selected from the group consisting of 1-88 or 89-181 of the MICA polypeptide of SEQ ID NO: 1, and/or binds to an epitope (residues on MICA) as described herein;

(c) binds to a human MICA polypeptide (e.g. a naturally occurring MICA allele) having a methionine at position 129 and a human MICA polypeptide (e.g. a naturally occurring MICA allele) having a valine at position 129. wherein the antibody reduces (e.g. substantially eliminates) binding between MICA and NKG2D; and/or binds to a human MICB polypeptide (e.g. a naturally occurring MICA allele) having a valine at position 152;

(d) binds to two, three, four or five of the MICA*001, *004, *007, *008, and *019 polypeptides, respectively comprising a sequence of SEQ ID NOS: 1-5;

(e) does not substantially block shedding of MICA from tumor cells;

(f) inhibit and/or substantially block the interaction of MICA with NKG2D (e.g., the interaction of surface MICA on tumor cells with surface NKG2D on effector cells), optionally wherein the antibodies block the interaction of MICA with both NKG2D chains within a NKG2D homodimer.

(g) are capable of reducing or inhibiting MICA-mediated NKG2D activation, NKG2D-signalling, activation of NKG2D-expressing NK or T cells, or lysis of MICA-expressing cells by effector cells (e.g., NKG2D+ CD16− NK cells);

(h) does or does not (e.g. depending on whether the mAb is found by CD16, depending on the nature of the Fc region of the antibody) substantially induces complement dependent cytotoxicity (CDC) and/or antibody dependent cellular cytotoxicity (ADCC) toward a cell that expresses MICA on its surface;

(i) are capable of reducing or inhibiting sMICA-mediated downmodulation of NKG2D expression on the surface of NKG2D-expression cells (e.g. T cells or NK cells); and (j) competes for binding to a MICA polypeptide with antibody 9C10, 19E9, 12A10, 18E8 or 10F3.

In any of the embodiments herein, an antibody of the invention may be characterized by any one or more features of (a)-(j), above.

In one embodiment, provided is a method of testing an anti-MICA antibody, said method comprising: (i) assessing whether the antibody binds with high affinity to both a MICA polypeptide having a methionine at residue 129 and a MICA polypeptide having a valine at residue 129 (and optionally further a MICB polypeptide having a methionine at residue 152), and (ii) assessing whether the antibody blocks the interaction of MICA (and optionally MICB) with NKG2D. In one embodiment, provided is a method of testing an anti-MICA antibody, said method comprising: (i) assessing whether the antibody binds with high affinity to two, three, four or five of the MICA*001, *004, *007, *008, and *019 polypeptides, respectively comprising a sequence of SEQ ID NOS: 1-5 and (ii) assessing whether the antibody blocks the interaction of MICA with NKG2D. Step (i) may optionally comprise bringing the antibody that binds a MICA polypeptide into contact with a cell expressing a MICA polypeptide. Step (ii) may optionally comprise bringing the antibody that binds a MICA polypeptide into contact with a MICA polypeptide (e.g. an isolated polypeptide or a polypeptide expressed on the surface of a cell), in the presence of an NKG2D polypeptide (e.g. an isolated polypeptide or a polypeptide expressed on the surface of a cell). An antibody that binds said MICA polypeptides in step (i) and blocks the interaction of MICA with NKG2D in step (ii) can be identified and/or selected as a candidate treatment for an inflammatory or autoimmune disorder.

In another embodiment, provided is a method of producing an antibody that binds a MICA polypeptide in a mammalian subject, optionally for the treatment of a cancer, said method comprising the steps of: a) providing a plurality of antibodies, optionally immunizing a non-human mammal with an immunogen comprising a MICA polypeptide or producing a phage display library of antibodies; and b) performing a selection step to select an antibody from said plurality, the step comprising:

(i) testing whether an antibody binds with high affinity to a human MICA polypeptide, optionally one, two, three or all of the MICA*001, *004, *007, *008, and *019 alleles, e.g., polypeptides respectively comprising a sequence of SEQ ID NOS: 1-5, and selecting an antibody if it binds with high affinity to said MICA polypeptide; and/or (ii) testing whether an antibody blocks the interaction of MICA (e.g. surface MICA, any one, two, three or all of the MICA*001, *004, *007, *008, and *019 alleles) with hNKG2D, and/or reduces or inhibits NKG2D activation, NKG2D-signalling, activation of NKG2D-expressing NK or T cells, or lysis of MICA-expressing cells by effector cells (e.g., NKG2D+ T cells, NKG2D+ CD16+ NK cells, NKG2D+ CD16− NK cells), and selecting an antibody if it blocks the interaction of MICA with hNKG2D; and/or.

(iii) testing whether an antibody reduces or inhibits NKG2D downmodulation (decrease of cell surface expression) in a NKG2D-expressing cell when said NKG2D-expressing cell is brought into contact with soluble MICA polypeptide in the presence of the antibody, and selecting an antibody if it antibody reduces or inhibits NKG2D downmodulation.

The method may optionally comprise a selection step (iv) comprising testing whether an antibody blocks shedding of MICA from MICA-expressing cells, and selecting the antibody if it does not block shedding.

In one embodiment, an antibody of the invention binds an epitope comprising 1, 2, 3, 4, 5, 6, 7 or more residues of a human MICA polypeptide selected from the group consisting of R6, N8, Q48, W49, E51, D52, V53, L54, N56, K57, T58, R61, R64, K81, D82, Q83, K84, E97, H99, E100, D101, N102, S103, T104, R105, H109, Y111, D113, E115, L116, N121, E123, T124, E126, Q131, S132, S133, R134, Q136, T137, M140, N141, R143, N144, L178, R179, R180, S224, H225, D226, T227, Q228, Q229, W230 and D232 (with reference to a MICA of any of SEQ ID NOS 1-5).

In one embodiment, the present invention provides a MICA binding compound, preferably an anti-MICA antibody, which binds at least partly, or optionally completely, within the α1 and/or α2 domain of MICA polypeptides. The α1 and α2 domains are located within amino acid residues 1 to 88 (optionally 1-85) and 89 to 181 (optionally 86-181), respectively, with reference to the MICA polypeptide of SEQ ID NO 1. Optionally, in any of the embodiments herein, the antibody binds to an amino acid residue within the α1 domain of a MICA polypeptide (residues amino acid residues 1 to 88 (optionally 1-85) of SEQ ID NO 1). Optionally, in any of the embodiments herein, the antibody binds to an amino acid residue within the α2 domain of a MICA polypeptide (residues amino acid residues 89 to 181 (optionally 86-181) of SEQ ID NO 1). Optionally, in any of the embodiments herein, the antibody binds to amino acid residues within the α1 and α2 domain of a MICA polypeptide.

In one embodiment, an antibody binds an epitope comprising one or two residues selected from the group consisting of Q48 and W49, and/or 1, 2, 3 or 4 residues selected from the group consisting of E51, D52, V53 and L54 (antibody 6E4).

In one embodiment, an antibody binds an epitope comprising 1, 2 or 3 residues selected from the group consisting of N56, K57 and T58, and/or one or two residues selected from the group consisting of R61 and R64 (antibody 9C10 and 12A10).

In one embodiment, an antibody binds an epitope comprising one or two residues selected from the group consisting of K81 and D82, one or two residues selected from the group consisting of Q83 and K84, one, two or three residues selected from the group consisting of H109, Y111 and L116, optionally residue D113, one, two or three residues selected from the group consisting of S133, R134 and T137, and/or 1, 2, 3 or 4 residues selected from the group consisting of M140, N141, R143 and N144 (antibody 20C6).

In one embodiment, an antibody binds an epitope comprising one or two residues selected from the group consisting of K81 and D82, one or two residues selected from the group consisting of Q83 and K84, one, two or three residues selected from the group consisting of H109, Y111 and L116, optionally residue D113, one, two or three residues selected from the group consisting of Q131, S132 and Q136, and/or 1, 2, 3 or 4 residues selected from the group consisting of M140, N141, R143 and N144 (antibody 10A7).

In one embodiment, an antibody binds an epitope comprising one, two or three residues selected from the group consisting of E100, D101 and N102, one, two or three residues selected from the group consisting of S103, T104 and R105, one or two residues selected from the group consisting of N121 and E123, and/or one or two residues selected from the group consisting of T124 and E126 (antibody 19E9 and 18E8).

In one embodiment, the antibodies bind an epitope comprising one or two residues selected from the group consisting of R6 and N8, one or two residues selected from the group consisting of E97 and H99, one, two or three residues selected from the group consisting of E100, D101 and N102, one, two or three residues selected from the group consisting of S103, T104 and R105, optionally residue E115, and/or one, two or three residues selected from the group consisting of L178, R179 and R180 (antibody 15F9).

In one embodiment, the present invention provides a MICA binding compound, preferably an anti-MICA antibody, that binds at least partly within the α3 domain of MICA polypeptides. The α3 domain is located within amino acid residues 182 to 274, respectively, with reference to the MICA polypeptide of SEQ ID NO 1. In one embodiment, an antibody binds an epitope comprising one, two or three residues selected from the group consisting of T227, Q228 and Q229 (antibody 14B4 and 16A8). In one embodiment, an antibody binds an epitope comprising one, two or three residues selected from the group consisting of S224, H225 and D226, one, two or three residues selected from the group consisting of T227, Q228 and Q229, and/or one or two residues selected from the group consisting of W230 and D232 (antibody 16A8).

Optionally, binding of the antibody to a MICA polypeptide having a mutation at any of the foregoing residues within the α1 and/or α2 domain is substantially reduced, in comparison to binding to a wild-type MICA polypeptide of SEQ ID NO: 1.

The present invention provides that the use of anti-MICA antibodies can be useful for the treatment of cancers, inflammatory and autoimmune disorders, e.g. in human subjects.

In one aspect, an antibody an antibody that does not inhibit the interaction between NKG2D and MICA, or an antibody that inhibits the interaction between NKG2D and MICA, will be a depleting antibody. Such antibodies are particularly useful in the treatment of cancers but may also be used in inflammation and autoimmune disorders. Antibodies can be used with or without coupling to a toxic or other agent, depending on the desired effect or use made of the antibodies. In one embodiment, the anti-MICA antibody is a "naked antibody" and is not coupled to a toxic agent, optionally the naked antibody comprises an Fc region modified to increase binding to an Fcγ receptor, e.g., CD16. In one embodiment, a naked or coupled antibody comprises a heavy chain comprising a human Fc region (e.g. IgG1) that binds Fcγ receptors (e.g. CD16). Optionally such antibody induces complement dependent cytoxicity (CDC) and/or antibody dependent cellular cytoxicity (ADCC) toward a cell that expresses MICA on its surface.

Optionally, in any embodiment, the antibody (e.g. IgG1, antibody fragment, etc.) further comprises a toxic agent (e.g. a chemotherapeutic agent) that is toxic to a cell.

In one aspect, an antibody an antibody that inhibits MICA-induced NKG2D activity in an effector cell, will be a non-depleting antibody (an antibody that does not deplete cells to which it binds). In one aspect the antibody is a chimeric, humanized or human antibody. In one aspect the antibody does not comprise a constant region capable of being bound by an Fcγ3A receptor (CD16), e.g. an antibody of the human IgG4 subtype or an antibody fragment lacking an Fc domain. In one embodiment, the antibody comprises an IgG4 heavy chain comprising a serine to proline mutation in residue 228 according to the EU-index. Preferably the antibody comprises a heavy chain constant region of human IgG4 isotype. Such antibodies are particularly useful in the treatment of inflammation and autoimmune disorders.

The present disclosure further provides antibodies, antibody fragments, and derivatives that specifically bind human MICA. The invention provides such antibody compositions, as well their use in any of the methods of the invention of treating, preventing and diagnosing cancer, inflammatory disorders and autoimmune disorders.

In one embodiment, the antibodies have binding affinity ($K_D$) for a human MICA polypeptide (e.g., a polypeptide of one, two, three or all of the MICA*001, *004, *007, *008, and *019 alleles of SEQ ID NOS 1-5, preferably to each of MICA*001, *004 and *008) of less than $10^{-8}$ M, preferably less than $10^{-9}$ M, or preferably less than $10^{-10}$ M.

In one aspect of any of the embodiments of the invention, the antibody may have a heavy and/or light chain having one, two or three CDRs of the respective heavy and/or light chain of an antibody selected from the group consisting of antibody 6E4, 20C6, 16A8, 9C10, 19E9, 12A10, 10A7, 18E8, 10F3, 15F9 and 14B4.

In one aspect of any of the embodiments of the invention, the antibody competes for binding to a MICA polypeptide with any one or any combination of monoclonal antibodies 6E4, 20C6, 16A8, 9C10, 19E9, 12A10, 10A7, 18E8, 10F3, 15F9 and 14B4. In one embodiment, an antibody of the invention competes for binding to a MICA polypeptide, with an antibody selected from the group consisting of:
  (a) an antibody having respectively a VH and VL region of SEQ ID NOS: 7 and 8 (6E4);
  (b) (a) an antibody having respectively a VH and VL region of SEQ ID NOS: 20 and 21 (20C6);
  (c) an antibody having respectively a VH and VL region of SEQ ID NOS:33 and 34 (16A8);
  (d) an antibody having respectively a VH and VL region of SEQ ID NOS: 46 and 47 (19E9);
  (e) an antibody having respectively a VH and VL region of SEQ ID NOS: 57 and 58 (9C10);
  (f) an antibody having respectively a VH and VL region of SEQ ID NOS: 68 and 69 (12A10);
  (g) an antibody having respectively a VH and VL region of SEQ ID NOS: 79 and 80 (10A7);
  (h) an antibody having respectively a VH and VL region of SEQ ID NOS: 90 and 91 (18E8);
  (i) an antibody having respectively a VH and VL region of SEQ ID NOS: 101 and 102 (10F3);
  (j) an antibody having respectively a VH and VL region of SEQ ID NOS: 112 and 113 (15F9); and
  (k) an antibody having respectively a VH and VL region of SEQ ID NOS: 123 and 124 (14B4).

In one embodiment, the antibody is human-suitable. In one embodiment the antibody is chimeric, e.g. contains a non-murine, optionally a human, constant region. In one embodiment, the antibody is human or humanized. In one aspect of any of the embodiments of the invention, the isotype of the antibody is a human IgG, optionally human IgG1, IgG2, IgG3 or IgG4. In one embodiment the antibody comprises a human Fc domain or is of an isotype that is bound by FcγR (e.g. FcγRIIIA), e.g. an antibody of IgG1 or IgG3 isotype.

In one aspect of any of the embodiments of the invention, the antibody is an antibody fragment selected from Fab, Fab', Fab'-SH, F(ab')2, Fv, diabodies, single-chain antibody fragment, or a multispecific antibody comprising multiple different antibody fragments. Optionally antibodies of the invention are furthermore tetrameric (two heavy and two light chains) and are thus bivalent (e.g. IgG antibodies).

In certain embodiments, the antibodies of the invention further comprise a toxic agent. In one embodiment, the antibodies comprising a toxic agent are able to directly cause the death of cells expressing MICA. In one embodiment, the antibodies are capable of directly inducing (e.g. in the absence of immune effector cells) at least 20%, 30%, 40% or 50% cell death, e.g. in an in vitro assay, of MICA-expressing cells.

In one aspect, the invention provides methods of treatment using the anti-MICA antibodies of the invention. The antibodies can be used as prophylactic or therapeutic treatment; in any of the embodiments herein, a therapeutically effective amount of the antibody can be interchanged with a prophylactically effective amount of an antibody. In one aspect, the invention provides a method of treating a patient with a cancer, an autoimmune disorder or an inflammatory disorder, the method comprising administering to the patient a pharmaceutically effective amount of an antigen-binding compound according to the invention that specifically binds to a MICA polypeptide.

The methods of treatment of the invention and the anti-MICA antibody according to the invention can be used to a treat an individual in combination with a second therapeutic agent, including an anti-cancer agent when used to treat cancer (e.g. chemotherapeutic drugs, tumor vaccines, antibodies that bind to tumor-specific antigens on tumor cells, antibodies that induce ADCC toward tumors cells, antibodies that potentiate immune responses, etc.), or an agent useful for the treatment of autoimmunity or inflammation. In one embodiment, the second therapeutic agent is an agent (e.g. an antibody) that binds to and activates an activating receptor or that binds to and blocks an inhibitory receptor on an effector cell (e.g. an NK cell, a T cell). In one embodiment, the second therapeutic agent is an agent (e.g. a chemotherapeutic agent) that upregulates the expression of an NKG2D ligand on tumor cells. For example, histone deacetylase inhibitors can be used. For example, valproate and hydralazine augment MICA/B expression and decrease shedding. (Chavez-Blanco 2011 Int J Oncol 39(6): 1491-1499).

The presence of increased levels of sMIC in circulation has been associated with poor prognosis and/or MIC expressing tumors. The present invention further concerns a method for selecting subjects having a cancer that responds to a treatment using an anti-MICA agent of the invention (e.g. an antibody that binds to a MICA polypeptide), the method comprising determining whether tumor cells in said subject shed a MICA polypeptide (e.g. as assessed by levels of sMIC in circulation), the presence of shedding of MICA polypeptide from tumor cells being indicative of a responder subject.

The present invention further concerns a method for selecting subjects having a disorder (e.g., a cancer, an autoimmune disorder, an inflammatory disorder) that responds to a treatment using an anti-MICA agent of the invention (e.g. an antibody that binds to a MICA polypeptide), the method comprising determining whether cells (e.g. tumor cells, pro-inflammatory cells, etc.) in said subject express a MICA polypeptide, the expression of a MICA polypeptide being indicative of a responder subject. In one embodiment, the method comprises determining whether cells (e.g. tumor cells, pro-inflammatory cells, etc.) in said subject express a MICA polypeptide selected from the group consisting of SEQ ID NOS 1-5. In one embodiment, the method comprises determining whether cells in said subject express a MICA polypeptide selected from the group consisting of MICA*001, *004, *007, *008, and *019 polypeptides, respectively comprising a sequence of SEQ ID NOS: 1-5, wherein the expression of a MICA polypeptide is indicative of a responder subject. In one embodiment, the step of determining whether cells in said subject express a MICA polypeptide comprising bringing a biological sample from the subject (e.g. by performing a biopsy and/or obtaining a sample of cancer cells, a blood or any tissue sample, etc.) into contact with an anti-MICA antibody of the invention (e.g. an antibody that bind a one, two, three, four or all of the MICA*001, *004, *007, *008, and *019 polypeptides). In one embodiment, the method comprises determining whether said subject comprises shed MICA (e.g. detecting sMICA in circulation or detecting the presence of MICA on the surface of exosomes (*008 allele, for example).

Optionally, in any of the methods, the method further comprises administering to a responder subject an antibody (e.g. an anti-MICA antibody of the invention) that binds to a MICA polypeptide.

In a preferred embodiment, the expression of a MICA polypeptide in a disease-related cell is determined using a MICA-specific ligand. Preferably, the ligand is an antibody, or a fragment or derivative thereof.

In another aspect, the invention comprises a method (e.g., a method of conducting a diagnostic assay, a responder assay, etc.), comprising assessing whether a patient has disease-related cells (e.g., tumor cells) expressing a MICA polypeptide, e.g. a MICA polypeptide (one or more MICA alleles) bound by an antibody of the invention. Said method may comprise, for example, obtaining a biological sample from a patient comprising disease-related cells, bringing said disease-related cells into contact with such antibody and assessing whether the antibody binds to disease-related cells. A finding that MICA is expressed by disease-related cells indicates that the patient has a condition characterized by MICA-expressing cells and/or is suitable for treatment with an anti-MICA antibody of the invention. The patient can further be treated with a treatment suitable for the particular disease characterized by MICA-expressing cells. Optionally the patient is treated with the anti-MICA antibody. In one embodiment, the method is used for selecting subjects having a cancer, and the disease-related cells are cancer cells.

The present invention also provides a method of treating a patient, the method comprising:
a) determining whether the patient has pathogenic MICA-expressing cells, and
b) if the patient is determined to patient have pathogenic MICA-expressing cells, administering an antigen-binding compound (e.g., antibody) of the invention.

The present invention also provides a method of treating a patient, the method comprising:
a) determining the level of shed MICA in the patient, and
b) if the patient is determined to patient have elevated levels of shed MICA, administering an antigen-binding compound (e.g., antibody) of the invention that inhibits the ability of sMICA to cause downmodulation of NKG2D on an immune effector cell.

These and additional advantageous aspects and features of the invention may be further described elsewhere herein.

DETAILED DESCRIPTION OF THE INVENTION

Introduction

Figure 1A:
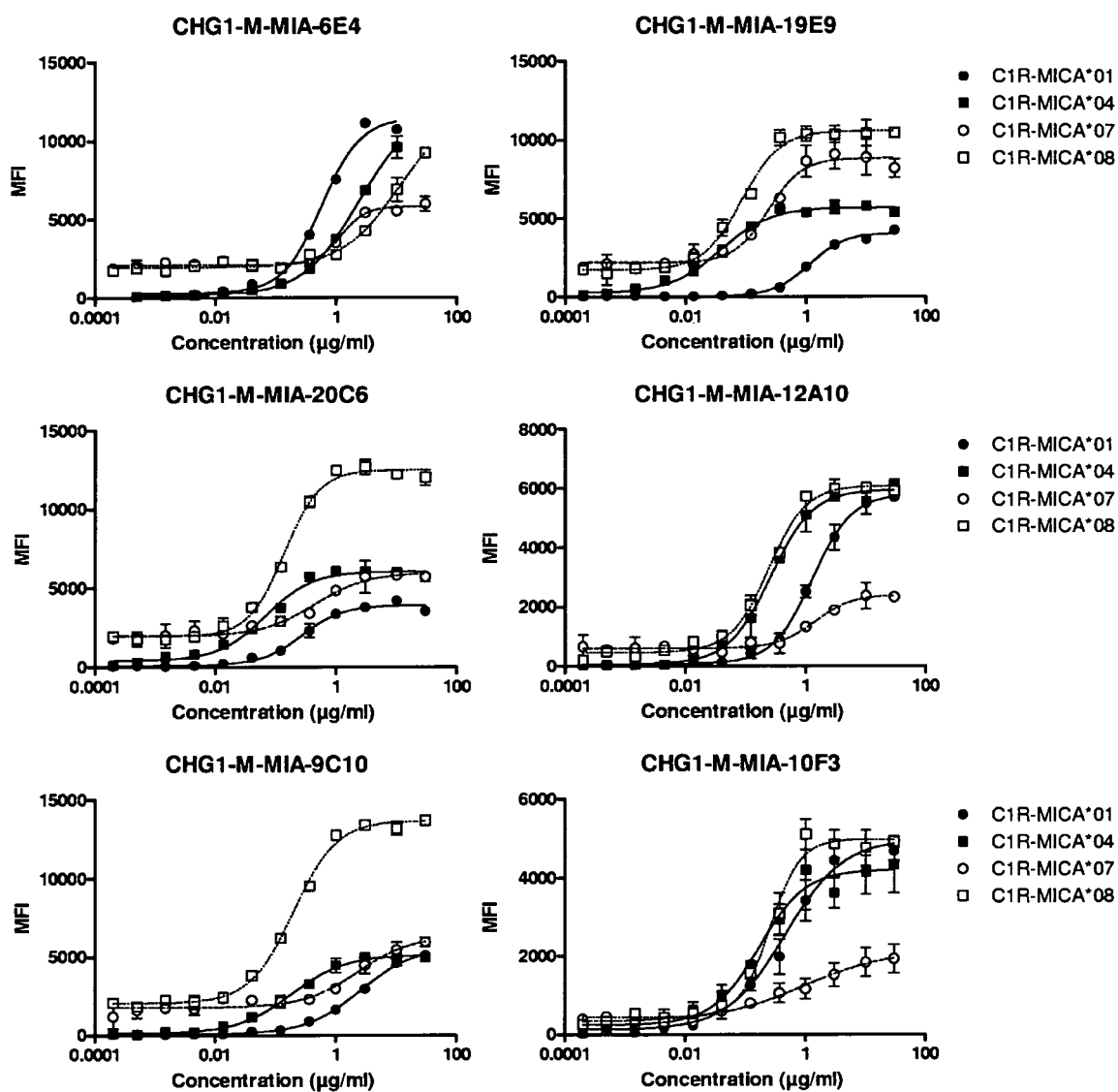
FIGS. 1A and 1B show binding of antibodies obtained from the first, second and third immunization series to MICA-expressing CR1 transfectant cells C1R-MICA*001, C1R-MICA*004, C1R-MICA*007 and C1R-MICA*008, as analysed by flow cytometry.

The antibodies of the invention are able to directly and specifically target MICA-expressing cells, notably tumor cells and cells involved in inflammatory or autoimmune processes. The invention provides a number of antibodies having such properties which bind both Group 1 and Group 2 alleles and moreover across the principal human MICA alleles within these groups. Further provided are different antibodies useful for particular approaches. Some antibodies block the MICA-NKG2D interaction and prevent soluble MICA (sMICA)-induced downmodulation of NKG2D surface expression; there are thereby useful to restore NKG2D expression in a patient. Such antibodies can also be used for their ability to block the NKG2D activation caused by the binding of MICA by NKG2D on a lymphocyte and will be particularly advantageous in the treatment of inflammation and autoimmune disorders. Other antibodies do not compete with NKG2D for binding to MICA and will be advantageous in the treatment of cancer in cases where NKG2D function on effector cells is desired to be maintained. Optionally, the antibodies will not block oshedding of MICA from MICA-expressing tumor cell. Optionally, the antibodies bind the α1α2 domain of MICA (the portion of the MICA protein formed from the α1 domain and α2 domain). Further provided are eptiopes on the α1α2 domain and α3 domain that are present across MICA alleles and can be targeted by antibodies for high binding affinity.

MICA (PERB11.1) refer to MHC class I polypeptide-related sequence A (See, e.g., UniProtKB/Swiss-Prot Q29983), its gene and cDNA and its gene product, or naturally occurring variants thereof. Nomenclature of MICA genes and proteins, together with reference to accession number of sequence for different alleles are described in Frigoul A. and Lefranc, M-P. Recent Res. Devel. Human Genet., 3(2005): 95-145 ISBN: 81-7736-244-5, the disclosure of which is incorporated herein by reference. MICA genes and protein sequence, including polymorphisms at the protein and DNA level, are also available from http://mhc-x.u-strasbg.fr/human.htm maintained by the laboratory of Dr. Bahram.

The amino acid sequences of MICA were first described in Bahram et al (1994) Proc. Nat. Acad. Sci. 91: 6259-6263 and Bahram et al. (1996) Immunogenetics 44:80-81, the disclosures of which are incorporated herein by reference. The MICA gene is polymorphic, displaying an unusual distribution of a number of variant amino acids in their extracellular α1, α2, and α3 domains. To further define the polymorphism of MICA, Petersdorf et al. (1999) examined its alleles among 275 individuals with common and rare HLA genotypes. The amino acid sequence of the extracellular α1, α2, and α3 domains of human MICA are shown in SEQ ID NOS 1-5. The full MICA sequence further comprises a leader sequence of 23 amino acids, as well as a transmembrane domain and a cytoplasmic domain. The amino acid sequence of extracellular α1, α2, and α3 domains of selected human MICA alleles are shown in SEQ ID NOS 1-5. The amino acid sequence of MICA*001 is shown in SEQ ID NO 1, corresponding to Genbank accession no. AAB41060. The amino acid sequence of human MICA allele MICA*004 is shown in SEQ ID NO 2, corresponding to Genbank accession no. AAB41063. The amino acid sequence of human MICA allele MICA*007 is shown in SEQ ID NO 3, corresponding to Genbank accession no. AAB41066. The amino acid sequence of human MICA allele MICA*008 is shown in SEQ ID NO 4, corresponding to Genbank accession no. AAB41067. The amino acid sequence of human MICA allele MICA*019 is shown in SEQ ID NO 5, corresponding to Genbank accession no. AAD27008. The amino acid sequence of human MICB is shown in SEQ ID NO 6, corresponding to Genbank accession no. CA118747.

The MICA gene encodes a protein that belongs to the MhcSF and to the IgSF. This protein is a transmembrane MHC-1-alpha-like (I-alpha-like) chain, which comprises three extracellular domains, two distal G-like domains, G-alpha1-like (also referred to as "D1" or "α1") and G-alpha2-like (also referred to as "D2" or "α2"), and a C-like-domain (also referred to as "D3" or "α3") proximal to the cell membrane, and three regions, a connecting-region, a transmembrane-region and a cytoplasmic-region (labels according to the IMGT Scientific Chart of the IMGT (international ImMunoGeneTics information System®), http://imgt.org and LeFranc et al. In Silico Biology, 2005; 5:45-60). The MICA mature protein including leader, ECD, TM and CY domains, is made up of 360 to 366 amino acids, the difference arising from a microsatellite polymorphism in the transmembrane region. The α1, α2 and α3 can be defined according to any suitable numbering system (e.g., the IMGT numbering system). In one embodiment, the α1 domain comprises residue positions 1 to 88 of the MICA polypeptide of SEQ ID NO 1; the α2 domain comprises residue positions 89 to 181 of the MICA polypeptide of SEQ ID NO 1; and the α3 domain comprises residue positions 182 to 274 of the MICA polypeptide of SEQ ID NO 1. The α1 and α2 domains each comprise A, B, C and D strands, AB, BC and CD turns, and a helix. The α3 domain comprises A, B, C, D, E, F and G strands, a BC loop, a CD strand, a DE-turn and an FG loop. The MICA protein is highly glycosylated with eight potential glycosylation sites, two in α1, one in α2 and five in the α3 domain, including O-glycans (N-acetyllactosamine linked to serine or threonine) and/or N-glycans. While MICA is expressed constitutively in certain cells, low levels of MICA expression do not usually give rise to host immune cell attach. However, on MICA is upregulated on rapidly proliferating cells such as tumor cells. MICA is the most highly expressed of all NKG2D ligands, and it has been found across a wide range of tumor types (e.g. carcinomas in general, bladder cancer, melanoma, lung cancer, hepatocellular cancer, glioblastoma, prostate cancer, hematological malignancies in general, acute myeloid leukemia, acute lymphatic leukemia, chronic myeloid leukemia and chronic lymphatic leukemia. Recently, Tsuboi et al. (2011) (EMBO J: 1-13) reported that the O-glycan branching enzyme, core2 β-1,6-N-acetylglucosaminyltransferase (C2GnT) is active in MICA-expressing tumor cells and that MICA from tumor cells contains core2 O-glycan (an O-glycan comprising an N-acetylglucosamine branch connected to N-acetylgalactosamine).

Bauer et al Science 285: 727-729, 1999 provided a role for MICA as a stress-inducible ligand for NKG2D. As used herein, "MICA" refers to any MICA polypeptide, including any variant, derivative, or isoform of the MICA gene or encoded protein(s) to which they refer. The MICA gene is polymorphic, displaying an unusual distribution of a number of variant amino acids in their extracellular alpha-1, alpha-2, and alpha-3 domains. Various allelic variants have been reported for MICA polypeptides (e.g. MICA), each of these are encompassed by the respective terms, including, e.g., human MICA polypeptides MICA*001, MICA*002, MICA*004, MICA*005, MICA*006, MICA*007, MICA*008, MICA*009, MICA*010, MICA*011, MICA*012, MICA*013, MICA*014, MICA*015, MICA*016, MICA*017, MICA*018, MICA*019, MICA*020, MICA*022, MICA*023, MICA*024, MICA*025, MICA*026, MICA*027, MICA*028, MICA*029, MICA*030, MICA*031, MICA*032, MICA*033, MICA*034, MICA*035, MICA*036, MICA*037, MICA*038, MICA*039, MICA*040, MICA*041, MICA*042, MICA*043, MICA*044, MICA*045, MICA*046, MICA*047, MICA*048, MICA*049, MICA*050, MICA*051, MICA*052, MICA*053, MICA*054, MICA*055 and MICA*056. Also encompassed are any nucleic acid or protein sequences sharing one or more biological properties or functions with wild type, full length MICA, respectively, and sharing at least 70%, 80%, 90%, 95%, 96%, 97%, 98%, 99%, or higher nucleotide or amino acid identity.

As used herein, "hNKG2D" and, unless otherwise stated or contradicted by context, the terms "NKG2D," "NKG2-D," "CD314," "D12S2489E," "KLRK1," "killer cell lectin-like receptor subfamily K, member 1," or "KLRK1," refer to a human killer cell activating receptor gene, its cDNA (e.g., GenBank Accession No. NM_007360), and its gene product (GenBank Accession No. NP_031386), or naturally occurring variants thereof. In NK and T cells, hNKG2D can form heterodimers or higher order complexes with proteins such as DAP10 (GenBank Accession No. AAG29425, AAD50293). Any activity attributed herein to hNKG2D, e.g., cell activation, antibody recognition, etc., can also be attributed to hNKG2D in the form of a heterodimer such as hNKG2D-DAP10, or higher order complexes with these two (and/or other) components.

The 3D structure of MICA in complex with NKG2D has been determined (see, e.g., Li et al., Nat. Immunol. 2001; 2:443-451; code 1hyr, and in IMGT/3Dstructure-DB (Kaas et al. Nucl. Acids Res. 2004; 32:D208-D210)). When MICA is in complex with a NKG2D homodimer, the residues 63 to 73 (IGMT numbering) of MICA α2 are ordered, adding almost two turns of helix. The two monomers of NKG2D equally contribute to interactions with MICA, and seven positions in each NKG2D monomer interact with one of the MICA α1 or α2 helix domains.

The invention provides methods of using the antigen-binding compounds of the invention; for example, the invention provides a method for inhibiting cell proliferation or activity, for delivering a molecule to a cell (e.g. a toxic molecule, a detectable marker, etc.), for targeting, identifying or purifying a cell, for depleting, killing or eliminating a cell, for reducing cell proliferation, the method comprising exposing a cell, such as a tumor cell which expresses a MICA polypeptide, to an antigen-binding compound of the invention that binds a MICA polypeptide. It will be appreciated that for the purposes of the present invention, "cell proliferation" can refer to any aspect of the growth or proliferation of cells, e.g., cell growth, cell division, or any aspect of the cell cycle. The cell may be in cell culture (in vitro) or in a mammal (in vivo), e.g. a mammal suffering from a MICA-expressing pathology. The invention also provides a method for inducing the death of a cell or inhibiting the proliferation or activity of a cell which expresses a MICA polypeptide, comprising exposing the cell to an antigen-binding compound that binds a MICA polypeptide linked to a toxic agent, in an amount effective to induce death and/or inhibit the proliferation of the cell. Thus, the invention provides a method for treating a mammal suffering from a proliferative disease, and any condition characterized by a pathogenic expansion of cells expressing of a MICA polypeptide, the method comprising administering a pharmaceutically effective amount of an antigen-binding compound disclosed herein to the mammal, e.g. for the treatment of a cancer.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can preferably be replaced by "consisting essentially of", more preferably by "consisting of".

Whenever within this whole specification "treatment of a proliferative disease" or "treatment of a tumor", or "treatment of cancer" or the like is mentioned with reference to anti-MICA binding agent (e.g. antibody), there is meant: (a) method of treatment of a proliferative disease, said method comprising the step of administering (for at least one treatment) an anti-MICA binding agent, (preferably in a pharmaceutically acceptable carrier material) to a warm-blooded animal, especially a human, in need of such treatment, in a dose that allows for the treatment of said disease (a therapeutically effective amount), preferably in a dose (amount) as specified to be preferred hereinabove and herein below; (b) the use of an anti-MICA binding agent for the treatment of a proliferative disease, or an anti-MICA binding agent, for use in said treatment (especially in a human); (c) the use of an anti-MICA binding agent, for the manufacture of a pharmaceutical preparation for the treatment of a proliferative disease, a method of using an anti-MICA binding agent for the manufacture of a pharmaceutical preparation for the treatment of a proliferative disease, comprising admixing an anti-MICA binding agent with a pharmaceutically acceptable carrier, or a pharmaceutical preparation comprising an effective dose of an anti-MICA binding agent that is appropriate for the treatment of a proliferative disease; or (d) any combination of a), b), and c), in accordance with the subject matter allowable for patenting in a country where this application is filed.

The terms "cancer" and "tumor" as used herein are defined as a new growth of cells or tissue comprising uncontrolled and progressive multiplication. In a specific embodiment, upon a natural course the cancer is fatal. In specific embodiments, a cancer is invasive, metastatic, and/or anaplastic (loss of differentiation and of orientation to one another and to their axial framework).

The term "biopsy" as used herein is defined as removal of a tissue from an organ for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. MICA, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. 6E4, 20C6 or 16A8), it means that the antibody competes with the monoclonal antibody in a binding assay using either recombinant MICA molecules or surface expressed MICA molecules. For example, if a test antibody reduces the binding of 6E4, 20C6 or 16A8 to a MICA polypeptide or MICA-expressing cell in a binding assay, the antibody is said to "compete" respectively with 6E4, 20C6 or 16A8.

The term "affinity", as used herein, means the strength of the binding of an antibody to an epitope. The affinity of an antibody is given by the dissociation constant KD, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIACORE™ SPR analytical device).

Within the context of this invention a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "depleting", with respect to MICA-expressing cells means a process, method, or compound that can kill, eliminate, lyse or induce such killing, elimination or lysis, so as to negatively affect the number of MICA-expressing cells present in a sample or in a subject.

An "agent" or "compound" according to the present invention comprises small molecules, polypeptides, proteins, antibodies or antibody fragments. Small molecules, in the context of the present invention, mean in one embodiment chemicals with molecular weight smaller than 1000 Daltons, particularly smaller than 800 Daltons, more particularly smaller than 500 Daltons. The term "therapeutic agent" refers to an agent that has biological activity. The term "anti-cancer agent" refers to an agent that has biological activity against cancer cells.

The term "human-suitable", with respect to an antibody, refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes of the present invention, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md., also referred to as "Kabat EU").

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The term "complement-dependent cytotoxicity" or "CDC" is a term well understood in the art, and refers to the ability of a molecule to lyse a target in the presence of complement. The complement activation pathway is initiated by the binding of the first component of the complement system (C1q) to a molecule (e.g. an antibody) complexed with a cognate antigen.

The term "shedding", when referring to MICA, refers to release of a soluble extracellular domain (ECD) fragment of MICA from the cell surface of a cell which expresses MICA. Such shedding may be caused by proteolytic cleavage (e.g. through the action of matrix metalloproteinases (MMPs), e.g. ADAM10 and/or ADAM17) of cell surface MICA resulting in release of an ECD fragment from the cell surface, or the soluble ECD or fragment thereof may be encoded by an alternate transcript.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

As used herein, "NK cells" refers to a sub-population of lymphocytes that is involved in non-conventional immunity. NK cells can be identified by virtue of certain characteristics and biological properties, such as the expression of specific surface antigens including CD56 and/or CD16 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any subpopulation of NK cells will also be encompassed by the term NK cells. Within the context of this invention "active" NK cells designate biologically active NK cells, including NK cells having the capacity of lysing target cells or enhancing the immune function of other cells. For instance, an "active" NK cell can be able to kill cells that express a ligand for an activating NK receptor and/or fail to express MHC/HLA antigens recognized by a KIR on the NK cell. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

As used herein, "T cells" refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art. Within the context of this invention, "active" or "activated" T or NK cells designate biologically active T or NK cells, more particularly T or NK cells having the capacity of cytolysis or of stimulating an immune response by, e.g., secreting cytokines. Active cells can be detected in any of a number of well known methods, including functional assays and expression-based assays such as the expression of cytokines.

Within the context of this invention, the term antibody that "binds" a polypeptide or epitope designates an antibody that binds said determinant with specificity and/or affinity.

Antibodies

The antibodies of the present invention are antibodies that bind human MICA across different alleles. In one embodiment, the antibodies bind to a MICA polypeptide (an anti-MICA antibody) without substantially blocking the interaction of MICA with NKG2D (e.g., the interaction of surface MICA on tumor cells with surface NKG2D on effector cells). In another embodiment, the antibodies bind to a MICA polypeptide (an anti-MICA antibody) and inhibit the interaction of MICA with NKG2D; preferably the antibodies inhibit downmodulation of NKG2D on the surface of immune cells caused by sMICA. In one embodiment, the antibodies bind to a MICA polypeptide on the surface of a cell without substantially blocking shedding of MICA from the cell surface (e.g. of tumor cells). In one embodiment, the antibodies bind a 1 and/or α2 domains of MICA. In one embodiment, the antibodies bind the α3 domain of MICA. In one embodiment, the antibodies have an affinity for human MICA alleles *001, *004 and *008, optionally further *007 and/or *019, optionally characterized by a Kd of less than $10^{-9}$ M, preferably less than $10^{-10}$M.

In one embodiment, the antibody competes for binding to the MICA polypeptide with any one or more of antibodies 6E4, 20C6, 16A8, 9C10, 19E9, 12A10, 10A7, 18E8, 10F3, 15F9 and 14B4. Preferably the antibody recognizes, binds to, or has immunospecificity for substantially or essentially the same, or the same, epitope or "epitopic site" on a MICA polypeptide.

Antibody Epitopes

In another embodiment, the antibodies bind substantially the same epitope as antibody 6E4, 20C6, 16A8, 9C10, 19E9, 12A10, 10A7, 18E8, 10F3, 15F9 and 14B4. In another embodiment, the antibodies at least partially overlaps, or includes at least one residue in the segment corresponding to residues 1-88, residues 89-181, or residues 182-274 of a MICA polypeptide comprising an amino acid sequence of SEQ ID NOS: 1 to 5. In one embodiment, all key residues of the epitope is in a segment corresponding to residues 1-88, residues 89-181, or residues 182-274 of a MICA polypeptide comprising an amino acid sequence of SEQ ID NOS: 1 to 5. In one embodiment, an antibody binds an epitope spanning the junction of (a) the α1 and/or α2 domain and (b) the α3 domain, wherein all key residues of the epitope is in a segment corresponding to residues 1-181 (e.g., residues 1-88 (optionally 1-85) or 89-181 (optionally 86-181)) of a MICA polypeptide comprising an amino acid sequence of SEQ ID NOS: 1 to 5. In one embodiment, the antibodies bind an epitope comprising 1, 2, 3, 4, 5, 6, 7 or more residues in the segment corresponding to residues 1-88 (optionally 1-85) or residues 89-181 (optionally 86-181) of a MICA polypeptide comprising an amino acid sequence of SEQ ID NOS: 1 to 5. Preferably the residues bound by the antibody are present on the surface of the of the MICA polypeptide, e.g. in a MICA polypeptide expressed on the surface of a cell.

In one embodiment, an antibody binds an epitope comprising 1, 2, 3, 4, 5, 6, 7 or more residues selected from the group consisting of R6, N8, Q48, W49, E51, D52, V53, L54, N56, K57, T58, R61, R64, K81, D82, Q83, K84, E97, H99, E100, D101, N102, S103, T104, R105, H109, Y111, D113, E115, L116, N121, E123, T124, E126, Q131, S132, S133, R134, Q136, T137, M140, N141, R143, N144, L178, R179, R180, S224, H225, D226, T227, Q228, Q229, W230 and D232 (with reference to a MICA of any of SEQ ID NOS 1-5).

In one embodiment, an antibody binds an epitope comprising:
(a) one or more residues selected from the group consisting of R6 and N8;
(b) one or more residues selected from the group consisting of N56, K57, T58;
(c) one or more residues selected from the group consisting of R61 and R64;
(d) one or more residues selected from the group consisting of K81, D82;
(e) one or more residues selected from the group consisting of Q83, K84;
(f) one or more residues selected from the group consisting of E97, H99;
(g) one or more residues selected from the group consisting of E100, D101, N102;
(h) one or more residues selected from the group consisting of S103, T104, R105;
(i) one or more residues selected from the group consisting of D113, E115;
(j) one or more residues selected from the group consisting of N121, E123;
(k) one or more residues selected from the group consisting of T124 and E126;
(l) one or more residues selected from the group consisting of H109, Y111, L116;
(m) one or more residues selected from the group consisting of Q131, S132, Q136;
(n) one or more residues selected from the group consisting of S133, R134, T137; or
(o) one or more residues selected from the group consisting of M140, N141, R143 and N144;
(p) one or more residues selected from the group consisting of S224, H225 and D226;
(q) one or more residues selected from the group consisting of T227, Q228 and Q229; and/or
(r) one or more residues selected from the group consisting of W230 and D232.

In one embodiment, an antibody binds an epitope comprising or any combination of 2, 3 or 4 of (a) to (r).

In one embodiment, an antibody binds an epitope comprising 1, 2, 3, 4, 5, or 6 or more residues selected from the group consisting of Q48, W49, E51, D52, V53 and L54.

In one embodiment, an antibody binds an epitope comprising 1, 2, 3, 4, 5, or 6 or more residues selected from the group consisting of N56, K57, T58, R61 and R64.

In one embodiment, an antibody binds an epitope comprising 1, 2, 3, 4, 5, or 6 or more residues selected from the group consisting of K81, D82, Q83, K84, H109, Y111, D113, L116, S133, R134, T137, M140, N141, R143 and N144.

In one embodiment, an antibody binds an epitope comprising 1, 2, 3, 4, 5, or 6 or more residues selected from the group consisting of K81, D82, Q83, K84, H109, Y111, D113, L116, Q131, S132, Q136, M140, N141, R143 and N144.

In one embodiment, an antibody binds an epitope comprising 1, 2, 3, 4, 5, or 6 or more residues selected from the group consisting of E100, D101, N102, S103, T104, R105, N121, E123, T124 and E126.

In one embodiment, the antibodies bind an epitope comprising 1, 2, 3, 4, 5, or 6 or more residues selected from the group consisting of R6, N8, E97, H99, E100, D101, N102, S103, T104, R105, E115, L178, R179 and R180.

In one embodiment, an antibody binds an epitope comprising 1, 2, 3, 4, 5, or 6 or more residues selected from the group consisting of S224, H225, D226, T227, Q228, Q229, W230 and D232. In one embodiment, an antibody binds an epitope comprising 1, 2, 3, 4, 5, or 6 or more residues selected from the group consisting of T227, Q228 and Q229.

In one embodiment, an antibody binds an epitope comprising:
(a) 1 or more residues selected from the group consisting of K81, D82, and 1 or more residues selected from the group consisting of Q83, K84;
(b) 1, 2, 3, 4 or more residues selected from the group consisting of K81, D82, Q83, K84, and 1, 2, or 3 residues selected from the group consisting of H109, Y111, L116;
(c) residue D113, and 1, 2, 3 or 4 residues selected from the group consisting of K81, D82, Q83, K84;
(d) 1, 2, 3, 4 or more residues selected from the group consisting of K81, D82, Q83, K84, and 1, 2, or 3 residues selected from the group consisting of Q131, S132, Q136;
(e) 1, 2, 3, 4 or more residues selected from the group consisting of K81, D82, Q83, K84, and 1, 2, or 3 residues selected from the group consisting of S133, R134, T137;
(f) 1, 2, 3, 4 or more residues selected from the group consisting of K81, D82, Q83, K84, and 1, 2, or 3 residues selected from the group consisting of M140, N141, R143 and N144;
(g) 1, 2, 3, 4 or more residues selected from the group consisting of K81, D82, Q83, K84; 1, 2 or 3 residues selected from the group consisting of H109, Y111, L116; optionally D113; and 1, 2 or 3 residues selected from the group consisting of Q131, S132, Q136;
(h) 1, 2, 3, 4 or more residues selected from the group consisting of K81, D82, Q83, K84; 1, 2 or 3 residues selected from the group consisting of H109, Y111, L116; optionally D113; and 1, 2 or 3 residues selected from the group consisting of S133, R134, T137;

(i) 1, 2, 3, 4 or more residues selected from the group consisting of K81, D82, Q83, K84; 1, 2 or 3 residues selected from the group consisting of H109, Y111, L116; optionally D113; and 1, 2, 3, 4 or more residues selected from the group consisting of M140, N141, R143 and N144;

(j) 1, 2, 3, 4 or more residues selected from the group consisting of K81, D82, Q83, K84; 1, 2 or 3 residues selected from the group consisting of H109, Y111, L116; optionally D113; 1, 2 or 3 residues selected from the group consisting of S133, R134, T137; and 1, 2, 3 or 4 residues selected from the group consisting of M140, N141, R143 and N144;

(k) 1 or more residues selected from the group consisting of R6, N8, and 1, 2, 3, 4 or more residues selected from the group consisting of E100, D101, N102, S103, T104, R105;

(l) 1, 2, 3 or 4 residues selected from the group consisting of N121, E123, T124 and E126, and 1, 2, 3, 4 or more residues selected from the group consisting of E100, D101, N102, S103, T104, R105; or (m) 1, 2, or 3 residues selected from the group consisting of S224, H225 and D226, 1, 2, or 3 residues selected from the group consisting of T227, Q228 and Q229, and one or two residues selected from the group consisting of W230 and D232.

Optionally, the epitope of an antibody of the invention may be entirely within the α1 and/or α2 domains of MICA. Optionally, further, the antibodies can be characterized as not substantially binding to the α3 domain region required for MICA shedding.

In one embodiment, the antibodies of the invention bind one or more amino acids present on the surface of the MICA polypeptide alleles *001, *004 and *008 (and optionally further *007 and *019).

Binding of anti-MICA antibody to cells transfected with the MICA mutants can be measured and compared to the ability of anti-MICA antibody to bind wild-type MICA polypeptide (e.g., any one or more of SEQ ID NOS: 1 to 5). A reduction in binding between an anti-MICA antibody and a mutant MICA polypeptide means that there is a reduction in binding affinity (e.g., as measured by known methods such FACS testing of cells expressing a particular mutant, or by testing of binding to mutant polypeptides using a BIA-CORE™ SPR analytical system) and/or a reduction in the total binding capacity of the anti-MICA antibody (e.g., as evidenced by a decrease in Bmax in a plot of anti-MICA antibody concentration versus polypeptide concentration). A significant reduction in binding indicates that the mutated residue is directly involved in binding to the anti-MICA antibody or is in close proximity to the binding protein when the anti-MICA antibody is bound to MICA.

In some embodiments, a significant reduction in binding means that the binding affinity and/or capacity between an anti-MICA antibody and a mutant MICA polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type MICA polypeptide. In certain embodiments, binding is reduced below detectable limits. In some embodiments, a significant reduction in binding is evidenced when binding of an anti-MICA antibody to a mutant MICA polypeptide is less than 50% (e.g., less than 45%, 40%, 35%, 30%, 25%, 20%, 15% or 10%) of the binding observed between the anti-MICA antibody and a wild-type MICA polypeptide.

In some embodiments, anti-MICA antibodies are provided that exhibit significantly lower binding for a mutant MICA polypeptide in which a residue in a segment corresponding to residues 1-88 (optionally 1-85), residues 89-181 (optionally 86-181), or residues 182-274 (or a subsequence thereof) in a wild-type MICA polypeptide (e.g., comprising a sequence of SEQ ID NOS: 1 to 5) is substituted with a different amino acid. In some embodiments, anti-MICA antibodies are provided that exhibit significantly lower binding for a mutant MICA polypeptide in which a residue in a segment corresponding to residues 1-88 (optionally 1-85), residues 89-181 (optionally 86-181), or residues 182-274 (or a subsequence thereof) in a wild-type MICA polypeptide (e.g., comprising a sequence of SEQ ID NOS: 1 to 5) is substituted with a different amino acid.

In some embodiments, anti-MICA antibodies are provided that exhibit significantly lower binding for a mutant MICA polypeptide in which a residue selected from the group consisting of R6, N8, Q48, W49, E51, D52, V53, L54, N56, K57, T58, R61, R64, K81, D82, Q83, K84, E97, H99, E100, D101, N102, S103, T104, R105, H109, Y111, D113, E115, L116, N121, E123, T124, E126, Q131, S132, S133, R134, Q136, T137, M140, N141, R143, N144, L178, R179, R180, S224, H225, D226, T227, Q228, Q229, W230 and D232 is substituted with a different amino acid, compared to a wild-type MICA polypeptide.

In some embodiments, anti-MICA antibodies are provided that exhibit significantly lower binding for a mutant MICA polypeptide in which:

(a) 1, 2, 3, 4 or more residues selected from the group consisting of Q48, W49, E51, D52, V53 and L54;

(b) 1, 2, 3, 4 or more residues selected from the group consisting of N56, K57, T58, R61 and R64;

(c) 1, 2, 3, 4 or more residues selected from the group consisting of K81, D82, Q83, K84, H109, Y111, D113, L116, S133, R134, T137, M140, N141, R143 and N144;

(d) 1, 2, 3, 4 or more residues selected from the group consisting of K81, D82, Q83, K84, H109, Y111, D113, L116, Q131, S132, Q136, M140, N141, R143 and N144;

(e) 1, 2, 3, 4 or more residues selected from the group consisting of E100, D101, N102, S103, T104, R105, N121, E123, T124 and E126;

(f) 1, 2, 3, 4 or more residues selected from the group consisting of R6, N8, E97, H99, E100, D101, N102, S103, T104, R105, E115, L178, R179 and R180; or (g) 1, 2, 3, 4 or more residues selected from the group consisting of S224, H225, D226, T227, Q228, Q229, W230 and D232, is substituted with a different amino acid, compared to a wild-type MICA polypeptide.

In some embodiments, anti-MICA antibodies are provided that exhibit significantly lower binding for a mutant MICA polypeptide in which:

(a) a residue selected from the group consisting of R6 and N8;

(b) a residue selected from the group consisting of N56, K57, T58;

(c) a residue selected from the group consisting of R61 and R64;

(d) a residue selected from the group consisting of K81, D82;

(e) a residue selected from the group consisting of Q83, K84;

(f) a residue selected from the group consisting of E97, H99;

(g) a residue selected from the group consisting of E100, D101, N102;

(h) a residue selected from the group consisting of S103, T104, R105;

(i) a residue selected from the group consisting of D113, E115;

(j) a residue selected from the group consisting of N121, E123;

(k) a residue selected from the group consisting of T124 and E126;

(l) a residue selected from the group consisting of H109, Y111, L116;

(m) a residue selected from the group consisting of Q131, S132, Q136;

(n) a residue selected from the group consisting of S133, R134, T137;

(o) a residue selected from the group consisting of M140, N141, R143 and N144;

(p) a residue selected from the group consisting of S224, H225 and D226;

(q) a residue selected from the group consisting of T227, Q228 and Q229; and/or (r) a residue selected from the group consisting of W230 and D232, is substituted with a different amino acid, compared to a wild-type MICA polypeptide.

In any embodiments a R6, N8, Q48, W49, E51, D52, V53, L54, N56, K57, T58, R61, R64, K81, D82, Q83, K84, E97, H99, E100, D101, N102, S103, T104, R105, H109, Y111, D113, E115, L116, N121, E123, T124, E126, Q131, S132, S133, R134, Q136, T137, M140, N141, R143, N144, L178, R179, R180, S194, E195, N197, S224, H225, D226, T227, Q228, Q229, W230 or D232 substitution may be specified as being a R6A, N8A, W14A, Q48A, W49S, E51S, D52A, V53S, L54A, N56A, K57A, T58A, R61A, R64A, K81A, D82A, Q83A, K84A, E85A, E97A, H99A, E100A, D101S, N102A, S103A, T104S, R105A, H109A, Y111A, D113A, E115A, L116A, N121A, E123S, T124A, E126A, Q131A, S132A, S133A, R134S, Q136S, T137A, M140S, N141A, R143S, N144A, L178A, R179S, R180A, S224A, H225S, D226A, T227A, Q228S, Q229A, W230A or D232A substitution, respectively.

In some embodiments, anti-MICA antibodies are characterized by not exhibiting significantly lower binding for a mutant MICA polypeptide (e.g. a mutant of any one of mutants 1-61 of Table D) or to a polypeptide having a mutated residue of any one of mutants 1-61 of Table D, compared to a wild-type MICA polypeptide (other than the mutant(s) or residue(s) to which a particular anti-MICA antibody has significantly lower binding as shown in Example 4).

Producing Anti-MICA Antibodies

The antibodies of this invention may be produced by a variety of techniques known in the art. Typically, they are produced by immunization of a non-human animal, preferably a mouse, with an immunogen comprising a MICA polypeptide, preferably a human MICA polypeptide. The MICA polypeptide may comprise the full length sequence of a human MICA polypeptide, or a fragment or derivative thereof, typically an immunogenic fragment, i.e., a portion of the polypeptide comprising an epitope exposed on the surface of cells expressing a MICA polypeptide, preferably the epitope recognized by the 6E4, 20C6, 16A8, 9C10, 19E9, 12A10, 10A7, 18E8, 10F3, 15F9 or 14B4 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In a preferred embodiment, the immunogen comprises a wild-type human MICA polypeptide in a lipid membrane, typically at the surface of a cell. In a specific embodiment, the immunogen comprises intact cells, particularly intact human cells, optionally treated or lysed. In another preferred embodiment, the polypeptide is a recombinant MICA polypeptide. In a specific embodiment, the immunogen comprises intact tumor cells.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with MICA polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For preferred monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A., X63 Ag8653 and SP-2 cells available from the American Type Culture Collection, Rockville, Md. U.S.A The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to MICA polypeptide gene products, optionally the epitope specifically recognized by antibody 6E4, 20C6, 16A8, 9C10, 19E9, 12A10, 10A7, 18E8, 10F3, 15F9 or 14B4. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single colony has given rise to the colony producing the desired antibody.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to MICA, particularly substantially or essentially the same epitope as monoclonal antibody 6E4, 20C6, 16A8, 9C10, 19E9, 12A10, 10A7, 18E8, 10F3, 15F9 or 14B4, can be readily determined using any one of a variety of immunological screening assays in which antibody competition can be assessed. Many such assays are routinely practiced and are well known in the art (see, e. g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (6E4, 20C6, 16A8, 9C10, 19E9, 12A10, 10A7, 18E8, 10F3, 15F9 or 14B4, for example) and test antibodies are admixed (or pre-adsorbed) and applied to a sample containing MICA polypeptides. Protocols based upon western blotting and the use of BIA-CORE™ SPR analytical system and analysis are suitable for use in such competition studies.

In certain embodiments, one pre-mixes the control antibodies (6E4, 20C6 or 16A8, for example) with varying amounts of the test antibodies (e.g., about 1:10 or about 1:100) for a period of time prior to applying to the MICA antigen sample. In other embodiments, the control and varying amounts of test antibodies can simply be admixed during exposure to the MICA antigen sample. As long as one can distinguish bound from free antibodies (e. g., by using separation or washing techniques to eliminate unbound antibodies) and 6E4, 20C6 or 16A8 from the test antibodies (e. g., by using species-specific or isotype-specific secondary antibodies or by specifically labeling 6E4, 20C6 or 16A8 with a detectable label) one can determine if the test antibodies reduce the binding of 6E4, 20C6 or 16A8 to the antigens, indicating that the test antibody recognizes substantially the same epitope as 6E4, 20C6 or 16A8. The binding of the (labeled) control antibodies in the absence of a completely irrelevant antibody can serve as the control high value. The control low value can be obtained by incubating the labeled (6E4, 20C6 or 16A8) antibodies with unlabelled antibodies of exactly the same type (6E4, 20C6 or 16A8), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (6E4, 20C6 or 16A8) antibody. Any test antibody that reduces the binding of 6E4, 20C6 or 16A8 to MICA antigens by at least about 50%, such as at least about 60%, or more preferably at least about 80% or 90% (e. g., about 65-100%), at any ratio of 6E4, 20C6 or 16A8:test antibody between about 1:10 and about 1:100 is considered to be an antibody that binds to substantially the same epitope or determinant as 6E4, 20C6 or 16A8. Preferably, such test antibody will reduce the binding of 6E4, 20C6 or 16A8 to the MICA antigen by at least about 90% (e.g., about 95%).

Competition can also be assessed by, for example, a flow cytometry test. In such a test, cells bearing a given MICA polypeptide can be incubated first with 6E4, 20C6 or 16A8, for example, and then with the test antibody labeled with a fluorochrome or biotin. The antibody is said to compete with 6E4, 20C6 or 16A8 if the binding obtained upon preincubation with a saturating amount of 6E4, 20C6 or 16A8 is about 80%, preferably about 50%, about 40% or less (e.g., about 30%, 20% or 10%) of the binding (as measured by mean of fluorescence) obtained by the antibody without preincubation with 6E4, 20C6 or 16A8. Alternatively, an antibody is said to compete with 6E4, 20C6 or 16A8 if the binding obtained with a labeled 6E4, 20C6 or 16A8 antibody (by a fluorochrome or biotin) on cells preincubated with a saturating amount of test antibody is about 80%, preferably about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a MICA antigen is immobilized may also be employed. The surface in the simple competition assay is preferably a BIACORE™ chip (or other media suitable for surface plasmon resonance analysis). The control antibody (e.g., 6E4, 20C6 or 16A8) is then brought into contact with the surface at a MICA-saturating concentration and the MICA and surface binding of the control antibody is measured. This binding of the control antibody is compared with the binding of the control antibody to the MICA-containing surface in the absence of test antibody. In a test assay, a significant reduction in binding of the MICA-containing surface by the control antibody in the presence of a test antibody indicates that the test antibody recognizes substantially the same epitope as the control antibody such that the test antibody "cross-reacts" with the control antibody. Any test antibody that reduces the binding of control (such as 6E4, 20C6 or 16A8) antibody to a MICA antigen by at least about 30% or more, preferably about 40%, can be considered to be an antibody that binds to substantially the same epitope or determinant as a control (e.g., 6E4, 20C6 or 16A8). Preferably, such a test antibody will reduce the binding of the control antibody (e.g., 6E4, 20C6 or 16A8) to the MICA antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the MICA antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Preferably, monoclonal antibodies that recognize a MICA epitope will react with an epitope that is present on a substantial percentage of or even all relevant MICA alleles. In one aspect, the anti-MICA antibodies of the invention bind MICA*004 and *008, optionally further MICA*001, *007 and/or *0019.

In preferred embodiments, the antibodies will bind to MICA-expressing cells from an individual or individuals with a disease characterized by expression of MICA-positive cells, i.e. an individual that is a candidate for treatment with one of the herein-described methods using an anti-MICA antibody of the invention. Accordingly, once an antibody that specifically recognizes MICA on cells is obtained, it can be tested for its ability to bind to MICA-positive cells (e.g. cancer cells). In particular, prior to treating a patient with one of the present antibodies, it will be beneficial to test the ability of the antibody to bind malignant cells taken from the patient, e.g. in a blood sample or tumor biopsy, to maximize the likelihood that the therapy will be beneficial in the patient.

In one embodiment, the antibodies of the invention are validated in an immunoassay to test their ability to bind to MICA-expressing cells, e.g. malignant cells. For example, a tumor biopsy is performed and tumor cells are collected. The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express MICA, e.g. tumor cells, from a significant percentage of individuals or patients (e.g., 5%, 10%, 20%, 30%, 40%, 50% or more) are suitable for use in the present invention, both for diagnostic purposes to determine the presence or level of malignant cells in a patient or for use in the herein-described therapeutic methods, e.g., for use to increase or decrease malignant cell number or activity. To assess the binding of the antibodies to the cells, the antibodies can either be directly or indirectly labeled. When indirectly labeled, a secondary, labeled antibody is typically added.

Determination of whether an antibody binds within an epitope region can be carried out in ways known to the person skilled in the art. As one example of such mapping/characterization methods, an epitope region for an anti-MICA antibody may be determined by epitope "foot-printing" using chemical modification of the exposed amines/carboxyls in the MICA protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g. by using trypsin in a ratio of about 1:50 to MICA or o/n digestion at and pH 7-8, followed by mass spectrometry (MS) analysis for peptide identification. The peptides protected from trypsin cleavage by the anti-MICA binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the MICA polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE™) and reflectometric interference spectroscopy (RifS). See, e.g., Fagerstam et al., Journal Of Molecular Recognition 1990; 3:208-14; Nice et al., J. Chroma-togr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody of the invention can be identified in one or more of the exemplary competition assays described herein.

Upon immunization and production of antibodies in a vertebrate or cell, particular selection steps may be performed to isolate antibodies as claimed. In this regard, in a specific embodiment, the invention also relates to methods of producing such antibodies, comprising: (a) immunizing a non-human mammal with an immunogen comprising a MICA polypeptide; and (b) preparing antibodies from said immunized animal; and (c) selecting antibodies from step (b) that are capable of binding MICA.

Typically, an anti-MICA antibody provided by the invention has an affinity for a MICA polypeptide in the range of about $10^4$ to about $10^{11}$ M$^{-1}$ (e.g., about $10^8$ to about $10^{10}$ M$^{-1}$). For example, in a particular aspect the invention provides Anti-MICA antibody that have an average disassociation constant ($K_D$) of less than $1 \times 10^{-8}$ M with respect to MICA, as determined by, e.g., surface plasmon resonance (SPR) screening (such as by analysis with a BIACORE™ SPR analytical device). In a more particular exemplary aspect, the invention provides Anti-MICA antibodies that have a KD of about $1 \times 10^{-8}$ M to about $1 \times 10^{-10}$ M, or about $1 \times 10^{-9}$ M to about $1 \times 10^{-11}$ M, for MICA.

Antibodies can be characterized for example by a mean KD of no more than about (i.e. better affinity than) 100, 60, 10, 5, or 1 nanomolar, preferably sub-nanomolar or optionally no more than about 500, 200, 100 or 10 picomolar. KD can be determined for example for example by immobilizing recombinantly produced human MICA proteins on a chip surface, followed by application of the antibody to be tested in solution. In one embodiment, the method further comprises a step (d), selecting antibodies from (b) that are capable of competing for binding to MICA with antibody 6E4, 20C6, 16A8, 9C10, 19E9, 12A10, 10A7, 18E8, 10F3, 15F9 or 14B4.

In one aspect of any of the embodiments, the antibodies prepared according to the present methods are monoclonal antibodies. In another aspect, the non-human animal used to produce antibodies according to the methods of the invention is a mammal, such as a rodent, bovine, porcine, fowl, horse, rabbit, goat, or sheep. The antibodies of the present invention encompass 6E4, 20C6, 16A8, 9C10, 19E9, 12A10, 10A7, 18E8, 10F3, 15F9 or 14B4. Additionally, antibodies of the invention can optionally be specified to be antibodies other than any of antibodies BAMO1 or BAMO3 described in Salih et al. (2003) (Blood 102(4): 1389-1396), antibody 2C10, 3H5, 6D4 or 6G6 described in Groh et al. (1996) Proc. Natl. Acad. Sci USA 93:12445-12450, Groh et al. (1998) Science 279:1737-1740 or WO2008/131406, the disclosures of each of which are incorporated herein by reference, or derivatives of the foregoing, e.g. that comprise the CDRs or the antigen binding region in whole or in part.

According to an alternate embodiment, the DNA encoding an antibody that binds an epitope present on MICA polypeptides is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the invention, e.g., antibody 6E4, 20C6, 16A8, 9C10, 19E9, 12A10, 10A7, 18E8, 10F3, 15F9 or 14B4, can be readily isolated and sequenced using conventional procedures (e. g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. In one embodiment, the invention comprises an isolated nucleic acid sequence encoding a light chain and/or a heavy chain of an antibody (e.g. 6E4, 20C6, 16A8, 9C10, 19E9, 12A10, 10A7, 18E8, 10F3, 15F9 or 14B4), as well as a recombinant host cell comprising (e.g. in its genome) such nucleic acid.

Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Assessing Activity

Once an antigen-binding compound is obtained it will generally be assessed for its ability to block an interaction between NKG2D and MICA (e.g. sMICA or membrane bound MICA), to block shedding of MICA from a cell, to inhibit sMICA-induced downmodulation of NKG2D, to cause the death of a MICA-expressing cell, to induce ADCC or CDC towards, and/or to inhibit the proliferation of and/or cause the elimination of MICA-expressing target cells.

Assessing the antigen-binding compound's ability to reduce binding or block an interaction between MICA and NKG2D can be carried out at any suitable stage of the method, e.g. as in the examples are provided herein. For example, tumor cells expressing MICA on their surface can be brought into contact with cells (e.g. effector cells) expressing NKG2D on their surface, with or without the addition of a candidate anti-MICA antibody. Binding between the MICA- and NKG2D-expressing cells can be assessed, and an antibody that does not reduce binding is selected. Another possibility involves contacting an isolated MICA polypeptide with an isolated NKG2D polypeptide, or a cell expressing an NKG2D polypeptide at its surface, and assessing binding between MICA and NKG2D polypeptide or cells expressing NKG2D. Another possibility involves contacting an isolated NKG2D polypeptide with a cell expressing a MICA polypeptide at its surface, and assessing binding between MICA polypeptide or a cell expressing MICA.

For example, to determine whether an agent blocks MICA interactions with NKG2D, the following test is performed: The cell line C1R or RMA transfected with MICA is incubated with a soluble NKG2D-Fc fusion protein, in the presence or absence of increasing concentrations of a test anti-MICA mAb. The cells are washed, and then incubated with a secondary antibody that recognizes the Fc part of the NKG2D-Fc fusion protein, washed again, and analyzed on a flow cytometer (FACScalibur, Beckton Dickinson), by standard methods. In the absence of anti-MICA mAbs, the NKG2D-Fc protein binds well to C1R or RMA cells. In the presence of an anti-MICA mAb that blocks MICA binding to NKG2D, there is a reduction of binding of NKG2D-Fc to the cells.

Preferably, assessing the antigen-binding compound's ability to reduce binding or block an interaction between MICA and NKG2D can also be carried out by assessing the effect of the anti-MICA antibody on the function of NKG2D-expressing cells (e.g. NK or T cells). Preferably NK or T cells are used that express NKG2D but not CD16 so as to avoid any contribution of a CD16-mediated ADCC effect. If an anti-MICA antibody reduces or blocks MICA-NKG2D interactions it will be expected to dampen NKG2D-mediated activation of NK or T cells. An antibody that does not reduce binding or block an interaction between MICA and NKG2D will therefore not substantially reduce or block NKG2D-mediated activation of NK or T cells. This can be evaluated by a typical cytotoxicity assay, examples of which are described herein. Any of a number of cell-based assays can be used to assess NKG2D activity, including gene expression-based activities, cytotoxicity-based assays, and proliferation assays. In one aspect, in vitro assays will use NK cells or T cells from human patients, or, e.g., T cell lines transfected with an NKG2D-encoding transgene, so long that the expression of the receptor alters the activity of the cells in a detectable way, e.g., renders them activatable by NKG2D ligand. Any suitable physiological change that reflects NKG2D activity can be used to assess the utility of a test compound or antibody. For example, one can measure a variety of effects, such as changes in gene expression, cytokine production, cell growth, cell proliferation, pH, intracellular second messengers, e.g., Ca2+, IP3, cGMP, or cAMP, or activity such as cytotoxic activity or ability to activate other T cells. In one embodiment, the activity of the receptor is assessed by detecting the expression of NKG2D-responsive genes, e.g., CD25, IFN-gamma, or TNF-alpha (see, e.g., Groh et al. (2003) PNAS 100: 9452-9457; André et al. (2004) Eur. J. Immunol 34: 1-11). In one embodiment, NKG2D activity is assessed by incubating NKG2D+ T or NK cells in the presence of MICA-expressing cells and an anti-MICA antibody, and assessing the ability of the compound or test antibody to inhibit the release of TNF-alpha or IFN-gamma by the T or NK cells.

Exemplary cytotoxicity assays are also described in the examples herein where NKG2D-mediated killing of target cells is assessed. Here, the ability of anti-MICA antibodies to reduce or inhibit the NKG2D+ CD16− NK92 cell are used to assess NK cell-mediated killing of MICA*019-transfected BaF/3 by measuring target cell release of 51Cr. The in vitro cytotoxicity assay is carried out by standard methods that are well known in the art, as described for example in Coligan et al., eds., Current Protocols in Immunology, Greene Publishing Assoc. and Wiley Interscience, N.Y., (1992, 1993). The MICA-expressing target cells are labeled with $^{51}$Cr prior to addition of NK cells, and then the killing is estimated as proportional to the release of $^{51}$Cr from the cells to the medium, as a result of killing. Addition of an agent that reduces binding or blocks an interaction between MICA and NKG2D results in prevention of the initiation and propagation of activatory signaling via NKG2D. Therefore addition of such agents results in decreases in NK-mediated killing of the target cells.

An antigen-binding compound that does not reduce or block (e.g. no reduction, or a reduction of less than 5%, 10%, 20% or 30%) the activation of cells by NKG2D (e.g. cytokine production, cell growth, cell proliferation, pH, intracellular second messengers, NK-mediated killing of MICA-expressing cells) is designated a "non-blocking" mAb. An antigen-binding compound that reduces or blocks the activation of cells by NKG2D is designated a "blocking" mAb.

Assessing the antigen-binding compound's ability to block shedding of MICA from a MICA-expressing cell can be carried out at any suitable stage of the method, e.g. as in the examples are provided herein. In one example, a sample of cells is provided and soluble extracellular MICA is detected using ELISA methods. In one example, an antigen-binding compound of the invention is administered to a mammal and the presence or absence, or levels of, circulating sMICA is measured. Examples of in vitro detection assays are described in Nolting et al. (2010) Virology 406(1):12-20. Briefly, a commercially available MICA Elisa kit (Bamomab, Munich, Germany) can be used. Plates are coated overnight with the capture anti-MICA mAb BAMO-1 at 2 µg/ml in PBS, then blocked by addition of 100 µl of 15% BSA for 2 h at 37° C. and washed. Standards and samples are added and the plates and incubated for 2 h at 37° C. Plates are washed and the detection mAb BAMO-3 at 5 µg/ml in 7.5% BSA-PBS was added for 2 h at 37° C. Plates were then washed and anti-mouse IgG2a-HRP (1:8000 in 7.5% BSA-PBS) is added for 1 h at 37° C. Plates are then washed and developed using the Tetramethylbenzidine Peroxidase Substrate System (KPL, Gaithersburg, Md.). The absorbance is measured at 450 nm Assessing the antigen-binding compound's ability to induce ADCC, CDC or otherwise (e.g. by delivery of a toxic agent) lead to the elimination or inhibition of activity of MICA-expressing target cells, can be carried out at any suitable stage of the method, e.g. as in the examples are provided herein. This assessment can be useful at one or more of the various steps involved in the identification, production and/or development of an antibody (or other compound) destined for therapeutic use. For example, activity may be assessed in the context of a screening method to identify candidate antigen-binding compounds, or in methods where an antigen-binding compound is selected and made human suitable (e.g. made chimeric or humanized in the case of an antibody), where a cell expressing the antigen-binding compound (e.g. a host cell expressing a recombinant antigen-binding compound) has been obtained and is assessed for its ability to produce functional antibodies (or other compounds), and/or where a quantity of antigen-binding compound has been produced and is to be assessed for activity (e.g. to test batches or lots of product). Generally the antigen-binding compound will be known to specifically bind to a MICA polypeptide. The step may involve testing a plurality (e.g., a very large number using high throughput screening methods or a smaller number) of antigen-binding compounds.

Testing CDC and ADCC can be carried out can be determined by various assays including those described in the experimental examples herein. Testing ADCC typically involves assessing cell-mediated cytotoxicity in which a MICA-expressing target cell (e.g. a cancer or other MICA-expressing cell) with bound anti-MICA antibody is recognized by an effector cell (e.g. a leukocyte bearing Fc receptors), without the involvement of complement. A cell which does not express a MICA antigen can optionally be used as a control. Activation of NK cell cytotoxicity is assessed by measuring an increase in cytokine production (e.g. IFN-γ production) or cytotoxicity markers (e.g. CD107 mobilization). Preferably the antibody of the invention will induce an increase in cytokine production, expression of cytoxicity markers, or target cell lysis of at least 20%, 50%, 80%, 100%, 200% or 500% in the presence of target (MICA-expressing) cells, compared to a control antibody (e.g. an antibody not binding to MICA, a MICA antibody having murine constant regions). In another example, lysis of target cells is detected, e.g. in a chromium release assay, preferably the antibody of the invention will induce lysis of at least 10%, 20%, 30%, 40% or 50% of target cells.

Antibody CDR Sequences
Antibody 6E4

The amino acid sequence of the heavy chain variable region of antibody 6E4 is listed as SEQ ID NO: 7, the amino acid sequence of the light chain variable region is listed as SEQ ID NO: 8. The amino acid sequences of heavy and light chain variable region of antibody 6E4 fused to a human chain constant region (heavy and light, respectively) are listed as SEQ ID NOS: 9 and 10, respectively. In a specific embodiment, the invention provides an antibody that binds essentially the same epitope or determinant as monoclonal antibodies 6E4; optionally the antibody comprises an antigen binding region of antibody 6E4. In any of the embodiments herein, antibody 6E4 can be characterized by its amino acid sequence and/or nucleic acid sequence encoding it. In one preferred embodiment, the monoclonal antibody comprises the Fab or F(ab')$_2$ portion of 6E4. Also provided is a monoclonal antibody that comprises the heavy chain variable region of 6E4. According to one embodiment, the monoclonal antibody comprises the three CDRs of the heavy chain variable region of 6E4 Also provided is a monoclonal antibody that further comprises the variable light chain variable region of 6E4 or one, two or three of the CDRs of the light chain variable region of 6E4. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 6E4 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence SYYAMS, GFTFSY or GFTFSYYAMS as set forth in SEQ ID NOS: 11-13, or a sequence of at least 4, 5, 6, 7, 8, 9 or 10 contiguous amino acids thereof, wherein one or more of these amino acids may be substituted by a different amino acid; a HCDR2 region comprising an amino acid sequence TISRGGNYIYYTDSVKG or TISRGGNYIY as set forth in SEQ ID NOS: 14-15, or a sequence of at least 4, 5, 6, 7, 8, 9 or 10 contiguous amino acids thereof, wherein one or more of these amino acids may be substituted by a different amino acid; a HCDR3 region comprising an amino acid sequence ISDYDGAWLAY as set forth in SEQ ID NO: 16, or a sequence of at least 4, 5, 6, 7, 8, 9 or 10 contiguous amino acids thereof, wherein one or more of these amino acids may be substituted by a different amino acid; a LCDR1 region comprising an amino acid sequence RSSQSIIHTNGNTYLE as set forth in SEQ ID NO: 17, or a sequence of at least 4, 5, 6, 7, 8, 9 or 10 contiguous amino acids thereof, wherein one or more of these amino acids may be substituted by a different amino acid; a LCDR2 region comprising an amino acid sequence KISNRFS as set forth in SEQ ID NO: 18, or a sequence of at least 4, 5, 6, 7, 8, 9 or 10 contiguous amino acids thereof, wherein one or more of these amino acids may be substituted by a different amino acid; a LCDR3 region comprising an amino acid sequence FQGSHVPWT as set forth in SEQ ID NO: 19, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 7, wherein one, two, three or more amino acids may be substituted by a different amino acid; and/or (b) the light chain variable region of SEQ ID NO: 8, wherein one, two, three or more amino acids may be substituted by a different amino acid; and/or (c) the heavy chain variable region of SEQ ID NO: 7, wherein one or more of these amino acids may be substituted by a different amino acid; and the light chain variable region of SEQ ID NO: 8, wherein one, two, three or more amino acids may be substituted by a different amino acid; and/or (d) the heavy chain CDR 1, 2 and 3 (HCDR1, HCDR2) amino acid sequences as shown in SEQ ID NO: 11 to 16, wherein one, two, three or more amino acids in a CDR may be substituted by a different amino acid; and/or (e) the light chain CDR 1, 2 and 3 (LCDR1, LCDR2, LCDR3) amino acid sequences as shown in SEQ ID NOS: 17, 18 and 19, wherein one, two, three or more amino acids in a CDR may be substituted by a different amino acid; and/or (f) the heavy chain CDR 1, 2 and 3 (HCDR1, HCDR2, HCDR3) amino acid sequences as shown in SEQ ID NOS: 11 to 16, wherein one, two, three or more amino acids in a CDR may be substituted by a different amino acid; and the light chain CDRs 1, 2 and 3 (LCDR1, LCDR2, LCDR3) amino acid sequences as shown in SEQ ID NOS: 17, 18 and 19, wherein one, two, three or more amino acids in a CDR may be substituted by a different amino acid; and/or (g) the heavy chain variable region which is at least 60%, 70%, 80%, 85%, 90% or 95% identical to the variable region having an amino acid sequence of SEQ ID NO: 7, wherein one, two, three or more amino acids in a CDR may be substituted by a different amino acid; and/or (h) the light chain variable region which is at least 60%, 70%, 80%, 85%, 90% or 95% identical to the variable region having an amino acid sequence of SEQ ID NO: 8, wherein one, two, three or more amino acids in a CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (h), above.

Antibody 20C6

The amino acid sequence of the heavy chain variable region of antibody 20C6 is listed in SEQ ID NO: 20, the amino acid sequence of the light chain variable region is listed as SEQ ID NO: 21. The amino acid sequences of the heavy and light chain variable regions of antibody 20C6 fused to a heavy chain constant region (heavy and light, respectively, are listed as SEQ ID NOS: 22 and 23, respectively. In one embodiment, the invention provides an antibody that binds essentially the same epitope or determinant as monoclonal antibody 20C6; optionally the antibody comprises an antigen binding region of antibody 20C6. In any of the embodiments herein, antibody 20C6 can be characterized by its amino acid sequence and/or nucleic acid sequence encoding it. In one preferred embodiment, the monoclonal antibody comprises the Fab or F(ab')₂ portion of 20C6. Also provided is a monoclonal antibody that comprises the heavy chain variable region of 20C6. According to one embodiment, the monoclonal antibody comprises the three CDRs of the heavy chain variable region of 20C6. Also provided is a monoclonal antibody that further comprises the variable light chain variable region of 20C6 or one, two or three of the CDRs of the light chain variable region of 20C6. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 16A8 are fused to an immunoglobulin constant region of the IgG type, optionally a human constant region, optionally an IgG1 or IgG3 isotype.

In another aspect, the invention provides a purified polypeptide which encodes an antibody, wherein the antibody comprises: a HCDR1 region comprising an amino acid sequence TSGMGVG, GFSLSTSG or GFSLSTSGMGVG as set forth in SEQ ID NOS: 24-26, or a sequence of at least 4, 5, 6, 7, 8, 9 or 10 contiguous amino acids thereof, wherein one or more of these amino acids may be substituted by a different amino acid; a HCDR2 region comprising an amino acid sequence HIWWDDDKYYNPSLK or HIWWDDDK as set forth in SEQ ID NOS: 27-28, or a sequence of at least 4, 5, 6, 7, 8, 9 or 10 contiguous amino acids thereof, wherein one or more of these amino acids may be substituted by a different amino acid; a HCDR3 region comprising an amino acid sequence RTQGYFDY as set forth in SEQ ID NO: 29, or a sequence of at least 4, 5, 6, 7, 8, 9 or 10 contiguous amino acids thereof, wherein one or more of these amino acids may be substituted by a different amino acid; a LCDR1 region comprising an amino acid sequence RASQSISDYLH as set forth in SEQ ID NO: 30, or a sequence of at least 4, 5, 6, 7, 8, 9 or 10 contiguous amino acids thereof, wherein one or more of these amino acids may be substituted by a different amino acid; a LCDR2 region comprising an amino acid sequence YASQSIS as set forth in SEQ ID NO: 31, or a sequence of at least 4, 5, 6, 7, 8, 9 or 10 contiguous amino acids thereof, wherein one or more of these amino acids may be substituted by a different amino acid; and/or a LCDR3 region comprising an amino acid sequence QNGHSFPWT as set forth in SEQ ID NO: 32, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, the invention provides an antibody that binds human MICA, comprising:

(a) the heavy chain variable region of SEQ ID NO: 20, wherein one, two, three or more amino acids in a CDR may be substituted by a different amino acid; and/or (b) the light chain variable region of SEQ ID NO: 21, wherein one, two, three or more amino acids in a CDR may be substituted by a different amino acid; and/or (c) the heavy chain variable region of SEQ ID NO: 20, wherein one, two, three or more amino acids may be substituted by a different amino acid; and the light chain variable region of SEQ ID NO: 21, wherein one or amino acids may be substituted by a different amino acid; and/or (d) the heavy chain CDR 1, 2 and 3 (HCDR1, HCDR2, HCDR3) amino acid sequences as shown in SEQ ID NO: 24-29, wherein one, two, three or more amino acids in a CDR may be substituted by a different amino acid; and/or (e) the light chain CDR 1, 2 and 3 (LCDR1, LCDR2, LCDR3) amino acid sequences as shown in SEQ ID NO: 30, 31 and 32, respectively, wherein one, two, three or more amino acids in a CDR may be substituted by a different amino acid; and/or (f) the heavy chain CDR 1, 2 and 3 (HCDR1, HCDR2, HCDR3) amino acid sequences as shown in SEQ ID NO: 24 to 29, wherein one, two, three or more amino acids in a CDR may be substituted by a different amino acid; and the light chain CDR 1, 2 and 3 (LCDR1, LCDR2, LCDR3) amino acid sequences as shown in SEQ ID NO: 30, 31 and 32, wherein one, two, three or more amino acids in a CDR may be substituted by a different amino acid; and/or (g) the heavy chain variable region which is at least 60%, 70%, 80%, 85%, 90% or 95% identical to the variable region having an amino acid sequence of SEQ ID NO: 20, wherein one, two, three or more amino acids may be substituted by a different amino acid; and/or (h) the light chain variable region which is at least 60%, 70%, 80%, 85%, 90% or 95% identical to the variable region having an amino acid sequence of SEQ ID NO: 21, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (h), above.

Antibody 16A8

The amino acid sequence of the heavy chain variable region of antibody 16A8 is listed in SEQ ID NO: 33, the amino acid sequence of the light chain variable region is listed as SEQ ID NO: 34. The amino acid sequences of the heavy and light chain variable regions of antibody 16A8 fused to a heavy chain constant region (heavy and light, respectively, are listed as SEQ ID NOS: 35 and 36, respectively. In one embodiment, the invention provides an antibody that binds essentially the same epitope or determinant as monoclonal antibodies 16A8; optionally the antibody comprises an antigen binding region of antibody 16A8. In any of the embodiments herein, antibody 16A8 can be characterized by its amino acid sequence and/or nucleic acid sequence encoding it. In one preferred embodiment, the monoclonal antibody comprises the Fab or F(ab')$_2$ portion of 16A8. Also provided is a monoclonal antibody that comprises the heavy chain variable region of 16A8. According to one embodiment, the monoclonal antibody comprises the three CDRs of the heavy chain variable region of 16A8. Also provided is a monoclonal antibody that further comprises the variable light chain variable region of 16A8 or one, two or three of the CDRs of the light chain variable region of 16A8. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 16A8 are fused to an immunoglobulin constant region of the IgG type, optionally a human constant region, optionally an IgG1 or IgG3 isotype.

In another aspect, the invention provides a purified polypeptide which encodes an antibody, wherein the antibody comprises: a HCDR1 region comprising an amino acid sequence RYAMS, GFTFSR or GFTFSRYAMS as set forth in SEQ ID NOS: 37-39, or a sequence of at least 4, 5, 6, 7, 8, 9 or 10 contiguous amino acids thereof, wherein one or more of these amino acids may be substituted by a different amino acid; a HCDR2 region comprising an amino acid sequence TIFSGGSYTYYPDSV or TIFSGGSY as set forth in SEQ ID NOS: 40-41, or a sequence of at least 4, 5, 6, 7, 8, 9 or 10 contiguous amino acids thereof, wherein one or more of these amino acids may be substituted by a different amino acid; a HCDR3 region comprising an amino acid sequence PNWERTFDY as set forth in SEQ ID NO: 42, or a sequence of at least 4, 5, 6, 7, 8, 9 or 10 contiguous amino acids thereof, wherein one or more of these amino acids may be substituted by a different amino acid; a LCDR1 region comprising an amino acid sequence KSSQSLLNSSNQK-NYL as set forth in SEQ ID NO: 43, or a sequence of at least 4, 5, 6, 7, 8, 9 or 10 contiguous amino acids thereof, wherein one or more of these amino acids may be substituted by a different amino acid; a LCDR2 region comprising an amino acid sequence FASTRES as set forth in SEQ ID NO: 44, or a sequence of at least 4, 5, 6, 7, 8, 9 or 10 contiguous amino acids thereof, wherein one or more of these amino acids may be substituted by a different amino acid; and/or a LCDR3 region comprising an amino acid sequence QQHYSTPPT as set forth in SEQ ID NO: 45, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, the invention provides an antibody that binds human MICA, comprising:

(a) the heavy chain variable region of SEQ ID NO: 33, wherein one, two, three or more amino acids may be substituted by a different amino acid; and/or (b) the light chain variable region of SEQ ID NO: 34, wherein one, two, three or more amino acids may be substituted by a different amino acid; and/or (c) the heavy chain variable region of SEQ ID NO: 33, wherein one, two, three or more amino acids may be substituted by a different amino acid; and the light chain variable region of SEQ ID NO: 34, wherein one or more amino acids may be substituted by a different amino acid; and/or (d) the heavy chain CDR 1, 2 and 3 (HCDR1, HCDR2, HCDR3) amino acid sequences as shown in SEQ ID NOS: 37-42, wherein one, two, three or more amino acids in a CDR may be substituted by a different amino acid; and/or (e) the light chain CDR 1, 2 and 3 (LCDR1, LCDR2, LCDR3) amino acid sequences as shown in SEQ ID NOS: 43, 44 and 45, respectively, wherein one, two, three or more amino acids in a CDR may be substituted by a different amino acid; and/or (f) the heavy chain CDR 1, 2 and 3 (HCDR1, HCDR2, HCDR3) amino acid sequences as shown in SEQ ID NOS: 37-42, wherein one, two, three or more amino acids in a CDR may be substituted by a different amino acid; and the light chain CDR 1, 2 and 3 (LCDR1, LCDR2, LCDR3) amino acid sequences as shown in SEQ ID NOS: 43, 44 and 45, wherein one, two, three or more amino acids in a CDR may be substituted by a different amino acid; and/or (g) the heavy chain variable region which is at least 60%, 70%, 80%, 85%, 90% or 95% identical to the variable region having an amino acid sequence of SEQ ID NO: 33, wherein one, two, three or more acids may be substituted by a different amino acid; and/or (h) the light chain variable region which is at least 60%, 70%, 80%, 85%, 90% or 95% identical to the variable region having an amino acid sequence of SEQ ID NO: 34, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (h), above.

Antibody 19E9

The amino acid sequence of the heavy chain variable region of antibody 19E9 is listed as SEQ ID NO: 46, the amino acid sequence of the light chain variable region is listed as SEQ ID NO: 47.

In a specific embodiment, the invention provides an antibody that binds essentially the same epitope or determinant as monoclonal antibodies 19E9; optionally the antibody comprises an antigen binding region of antibody 19E9. In any of the embodiments herein, antibody 19E9 can be characterized by its amino acid sequence and/or nucleic acid sequence encoding it. In one preferred embodiment, the monoclonal antibody comprises the Fab or F(ab')$_2$ portion of 19E9. Also provided is a monoclonal antibody that comprises the heavy chain variable region of 19E9. According to one embodiment, the monoclonal antibody comprises the three CDRs of the heavy chain variable region of 19E9. Also provided is a monoclonal antibody that further comprises the variable light chain variable region of 19E9 or one, two or three of the CDRs of the light chain variable region of 19E9. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 19E9 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence SDYAWN, GYSITSD or GYSITSDYAWN as set forth in SEQ ID NOS: 48-50, or a sequence of at least 4, 5, 6, 7, 8, 9 or 10 contiguous amino acids thereof, wherein one or more of these amino acids may be substituted by a different amino acid; a HCDR2 region comprising an amino acid sequence FVSYSGTTKYNPSLKS or FVSYSGTTK as set forth in SEQ ID NOS: 51-52, or a sequence of at least 4, 5, 6, 7, 8, 9 or 10 contiguous amino acids thereof, wherein one or more of these amino acids may be substituted by a different amino acid; a HCDR3 region comprising an amino acid sequence GYGFDY as set forth in SEQ ID NO: 53, or a sequence of at least 4, 5, 6, 7, 8, 9 or 10 contiguous amino acids thereof, wherein one or more of these amino acids may be substituted by a different amino acid; a LCDR1 region comprising an amino acid sequence SATSSISSIYFH as set forth in SEQ ID NO: 54, or a sequence of at least 4, 5, 6, 7, 8, 9 or 10 contiguous amino acids thereof, wherein one or more of these amino acids may be substituted by a different amino acid; a LCDR2 region comprising an amino acid sequence RTSNLAS as set forth in SEQ ID NO: 55, or a sequence of at least 4, 5, 6, 7, 8, 9 or 10 contiguous amino acids thereof, wherein one or more of these amino acids may be substituted by a different amino acid; a LCDR3 region comprising an amino acid sequence QQGTTIPFT as set forth in SEQ ID NO: 56, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 46, wherein one, two, three or more amino acids may be substituted by a different amino acid; and/or (b) the light chain variable region of SEQ ID NO: 47, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 48-53, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 54, 55 and 56, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 48-53, wherein one or more amino acids in a CDR may be substituted by a different amino acid; and the light chain CDRs 1, 2 and 3 (LCDR1, LCDR2, LCDR3) amino acid sequences as shown in SEQ ID NOS: 54, 55 and 56, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 46, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 47, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 9C10

The amino acid sequence of the heavy chain variable region of antibody 9C10 is listed as SEQ ID NO: 57, the amino acid sequence of the light chain variable region is listed as SEQ ID NO: 58. In a specific embodiment, the invention provides an antibody that binds essentially the same epitope or determinant as monoclonal antibodies 9C10; optionally the antibody comprises an antigen binding region of antibody 9C10. In any of the embodiments herein, antibody 9C10 can be characterized by its amino acid sequence and/or nucleic acid sequence encoding it. In one preferred embodiment, the monoclonal antibody comprises the Fab or F(ab')$_2$ portion of 9C10. Also provided is a monoclonal antibody that comprises the heavy chain variable region of 9C10. According to one embodiment, the monoclonal antibody comprises the three CDRs of the heavy chain variable region of 9C10. Also provided is a monoclonal antibody that further comprises the variable light chain variable region of 9C10 or one, two or three of the CDRs of the light chain variable region of 9C10. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 9C10 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence RYWMN, GYSFTR or GYSFTRYWMN as set forth in SEQ ID NOS: 59-61, or a sequence of at least 4, 5, 6, 7, 8, 9 or 10 contiguous amino acids thereof, wherein one or more of these amino acids may be substituted by a different amino acid; a HCDR2 region comprising an amino acid sequence MIHPSDSETRLNQKFKD or MIHPSDSETR as set forth in SEQ ID NOS: 62-63, or a sequence of at least 4, 5, 6, 7, 8, 9 or 10 contiguous amino acids thereof, wherein one or more of these amino acids may be substituted by a different amino acid; a HCDR3 region comprising an amino acid sequence GNFFYVMDY as set forth in SEQ ID NO: 64, or a sequence of at least 4, 5, 6, 7, 8, 9 or 10 contiguous amino acids thereof, wherein one or more of these amino acids may be substituted by a different amino acid; a LCDR1 region comprising an amino acid sequence RASQSIGTSIH as set forth in SEQ ID NO: 65, or a sequence of at least 4, 5, 6, 7, 8, 9 or 10 contiguous amino acids thereof, wherein one or more of these amino acids may be substituted by a different amino acid; a LCDR2 region comprising an amino acid sequence ASESISG as set forth in SEQ ID NO: 66, or a sequence of at least 4, 5, 6, 7, 8, 9 or 10 contiguous amino acids thereof, wherein one or more of these amino acids may be substituted by a different amino acid; a LCDR3 region comprising an amino acid sequence QQSNFWPFT as set forth in SEQ ID NO: 67, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 67, wherein one, two, three or more amino acids may be substituted by a different amino acid; and/or (b) the light chain variable region of SEQ ID NO: 68, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 59-64, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 65, 66 and 67, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 59-64, wherein one or more amino acids in a CDR may be substituted by a different amino acid; and the light chain CDRs 1, 2 and 3 (LCDR1, LCDR2, LCDR3) amino acid sequences as shown in SEQ ID NOS: 65, 66 and 67, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 57, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 58, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 12A10

The amino acid sequence of the heavy chain variable region of antibody 12A10 is listed as SEQ ID NO: 68, the amino acid sequence of the light chain variable region is listed as SEQ ID NO: 69. In a specific embodiment, the invention provides an antibody that binds essentially the same epitope or determinant as monoclonal antibodies 12A10; optionally the antibody comprises an antigen binding region of antibody 12A10. In any of the embodiments herein, antibody 12A10 can be characterized by its amino acid sequence and/or nucleic acid sequence encoding it. In one preferred embodiment, the monoclonal antibody comprises the Fab or F(ab')$_2$ portion of 12A10. Also provided is a monoclonal antibody that comprises the heavy chain variable region of 12A10. According to one embodiment, the monoclonal antibody comprises the three CDRs of the heavy chain variable region of 12A10. Also provided is a monoclonal antibody that further comprises the variable light chain variable region of 12A10 or one, two or three of the CDRs of the light chain variable region of 12A10. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 12A10 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence NYWMN, GYSFTN or GYSFTNYWMN as set forth in SEQ ID NOS: 70-72, or a sequence of at least 4, 5, 6, 7, 8, 9 or 10 contiguous amino acids thereof, wherein one or more of these amino acids may be substituted by a different amino acid; a HCDR2 region comprising an amino acid sequence MIHPSDSETRLNQKFKD or MIHPSDSETR as set forth in SEQ ID NOS: 73-74, or a sequence of at least 4, 5, 6, 7, 8, 9 or 10 contiguous amino acids thereof, wherein one or more of these amino acids may be substituted by a different amino acid; a HCDR3 region comprising an amino acid sequence DDFFTMDY as set forth in SEQ ID NO: 75, or a sequence of at least 4, 5, 6, 7, 8, 9 or 10 contiguous amino acids thereof, wherein one or more of these amino acids may be substituted by a different amino acid; a LCDR1 region comprising an amino acid sequence RASQNIVTSIH as set forth in SEQ ID NO: 76, or a sequence of at least 4, 5, 6, 7, 8, 9 or 10 contiguous amino acids thereof, wherein one or more of these amino acids may be substituted by a different amino acid; a LCDR2 region comprising an amino acid sequence YASESIS as set forth in SEQ ID NO: 77, or a sequence of at least 4, 5, 6, 7, 8, 9 or 10 contiguous amino acids thereof, wherein one or more of these amino acids may be substituted by a different amino acid; a LCDR3 region comprising an amino acid sequence QQSNIWPLT as set forth in SEQ ID NO: 78, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 68, wherein one, two, three or more amino acids may be substituted by a different amino acid; and/or (b) the light chain variable region of SEQ ID NO: 69, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 70-75, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 76, 77 and 78, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 70-75, wherein one or more amino acids in a CDR may be substituted by a different amino acid; and the light chain CDRs 1, 2 and 3 (LCDR1, LCDR2, LCDR3) amino acid sequences as shown in SEQ ID NOS: 76, 77 and 78, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 68, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 69, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 10A7

The amino acid sequence of the heavy chain variable region of antibody 10A7 is listed as SEQ ID NO: 79, the amino acid sequence of the light chain variable region is listed as SEQ ID NO: 80. In a specific embodiment, the invention provides an antibody that binds essentially the same epitope or determinant as monoclonal antibodies 10A7; optionally the antibody comprises an antigen binding region of antibody 10A7. In any of the embodiments herein, antibody 10A7 can be characterized by its amino acid sequence and/or nucleic acid sequence encoding it. In one preferred embodiment, the monoclonal antibody comprises the Fab or F(ab')$_2$ portion of 10A7. Also provided is a monoclonal antibody that comprises the heavy chain variable region of 10A7. According to one embodiment, the monoclonal antibody comprises the three CDRs of the heavy chain variable region of 10A7. Also provided is a monoclonal antibody that further comprises the variable light chain variable region of 10A7 or one, two or three of the CDRs of the light chain variable region of 10A7. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 10A7 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence TSGMGVG, GFSLSTSG or GFSLSTSGMGVG as set forth in SEQ ID NOS: 81-83, or a sequence of at least 4, 5, 6, 7, 8, 9 or 10 contiguous amino acids thereof, wherein one or more of these amino acids may be substituted by a different amino acid; a HCDR2 region comprising an amino acid sequence HIWWDDDRYYNPSLKS or HIW-WDDDRY as set forth in SEQ ID NOS: 84-85, or a sequence of at least 4, 5, 6, 7, 8, 9 or 10 contiguous amino acids thereof, wherein one or more of these amino acids may be substituted by a different amino acid; a HCDR3 region comprising an amino acid sequence RLNGYFDY as set forth in SEQ ID NO: 86, or a sequence of at least 4, 5, 6, 7, 8, 9 or 10 contiguous amino acids thereof, wherein one or more of these amino acids may be substituted by a different amino acid; a LCDR1 region comprising an amino acid sequence RASQSISDYLH as set forth in SEQ ID NO: 87, or a sequence of at least 4, 5, 6, 7, 8, 9 or 10 contiguous amino acids thereof, wherein one or more of these amino acids may be substituted by a different amino acid; a LCDR2 region comprising an amino acid sequence YASQSIS as set forth in SEQ ID NO: 88, or a sequence of at least 4, 5, 6, 7, 8, 9 or 10 contiguous amino acids thereof, wherein one or more of these amino acids may be substituted by a different amino acid; a LCDR3 region comprising an amino acid sequence QNGHSFPFT as set forth in SEQ ID NO: 89, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 79, wherein one, two, three or more amino acids may be substituted by a different amino acid; and/or (b) the light chain variable region of SEQ ID NO: 80, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 81-86, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 87, 88 and 89, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 81 to 86, wherein one or more amino acids in a CDR may be substituted by a different amino acid; and the light chain CDRs 1, 2 and 3 (LCDR1, LCDR2, LCDR3) amino acid sequences as shown in SEQ ID NOS: 87, 88 and 89, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 79, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 80, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 18E8

The amino acid sequence of the heavy chain variable region of antibody 18E8 is listed as SEQ ID NO: 90, the amino acid sequence of the light chain variable region is listed as SEQ ID NO: 91. In a specific embodiment, the invention provides an antibody that binds essentially the same epitope or determinant as monoclonal antibodies 18E8; optionally the antibody comprises an antigen binding region of antibody 18E8. In any of the embodiments herein, antibody 18E8 can be characterized by its amino acid sequence and/or nucleic acid sequence encoding it. In one preferred embodiment, the monoclonal antibody comprises the Fab or F(ab')₂ portion of 18E8. Also provided is a monoclonal antibody that comprises the heavy chain variable region of 18E8. According to one embodiment, the monoclonal antibody comprises the three CDRs of the heavy chain variable region of 18E8. Also provided is a monoclonal antibody that further comprises the variable light chain variable region of 18E8 or one, two or three of the CDRs of the light chain variable region of 18E8. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 18E8 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence SDYSWH, GYSITSD or GYSITSDYSWH as set forth in SEQ ID NOS: 92-94, or a sequence of at least 4, 5, 6, 7, 8, 9 or 10 contiguous amino acids thereof, wherein one or more of these amino acids may be substituted by a different amino acid; a HCDR2 region comprising an amino acid sequence NIHYSGRINYNPSLRS or NIHYSGRIN as set forth in SEQ ID NOS: 95-96, or a sequence of at least 4, 5, 6, 7, 8, 9 or 10 contiguous amino acids thereof, wherein one or more of these amino acids may be substituted by a different amino acid; a HCDR3 region comprising an amino acid sequence RRTFGNFEDY as set forth in SEQ ID NO: 97, or a sequence of at least 4, 5, 6, 7, 8, 9 or 10 contiguous amino acids thereof, wherein one or more of these amino acids may be substituted by a different amino acid; a LCDR1 region comprising an amino acid sequence RSSSSVNYMH as set forth in SEQ ID NO: 98, or a sequence of at least 4, 5, 6, 7, 8, 9 or 10 contiguous amino acids thereof, wherein one or more of these amino acids may be substituted by a different amino acid; a LCDR2 region comprising an amino acid sequence ATSTLAS as set forth in SEQ ID NO: 99, or a sequence of at least 4, 5, 6, 7, 8, 9 or 10 contiguous amino acids thereof, wherein one or more of these amino acids may be substituted by a different amino acid; a LCDR3 region comprising an amino acid sequence QQWSSNPLT as set forth in SEQ ID NO: 100, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 90, wherein one, two, three or more amino acids may be substituted by a different amino acid; and/or (b) the light chain variable region of SEQ ID NO: 91, wherein one, two, three or (c) the heavy chain CDR 1, 2 and 3 (HCDR1, HCDR2, HCDR3) amino acid sequences as shown in SEQ ID NO: 92-97, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 98, 99 and 100, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 92-97, wherein one or more amino acids in a CDR may be substituted by a different amino acid; and the light chain CDRs 1, 2 and 3 (LCDR1, LCDR2, LCDR3) amino acid sequences as shown in SEQ ID NOS: 98, 99 and 100, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 90, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 91, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 10F3

The amino acid sequence of the heavy chain variable region of antibody 10F3 is listed as SEQ ID NO: 101, the amino acid sequence of the light chain variable region is listed as SEQ ID NO: 102. In a specific embodiment, the invention provides an antibody that binds essentially the same epitope or determinant as monoclonal antibodies 10F3; optionally the antibody comprises an antigen binding region of antibody 10F3. In any of the embodiments herein, antibody 10F3 can be characterized by its amino acid sequence and/or nucleic acid sequence encoding it. In one preferred embodiment, the monoclonal antibody comprises the Fab or F(ab')$_2$ portion of 10F3. Also provided is a monoclonal antibody that comprises the heavy chain variable region of 10F3. According to one embodiment, the monoclonal antibody comprises the three CDRs of the heavy chain variable region of 10F3. Also provided is a monoclonal antibody that further comprises the variable light chain variable region of 10F3 or one, two or three of the CDRs of the light chain variable region of 10F3. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 10F3 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence SYTMH, GYTFTS or GYTFTSYTMH as set forth in SEQ ID NOS: 103-105, or a sequence of at least 4, 5, 6, 7, 8, 9 or 10 contiguous amino acids thereof, wherein one or more of these amino acids may be substituted by a different amino acid; a HCDR2 region comprising an amino acid sequence YINPSSGYTEYNQKFKD or YINPSSGYTE as set forth in SEQ ID NOS: 106-107, or a sequence of at least 4, 5, 6, 7, 8, 9 or 10 contiguous amino acids thereof, wherein one or more of these amino acids may be substituted by a different amino acid; a HCDR3 region comprising an amino acid sequence GGDWDVDWFVY as set forth in SEQ ID NO: 108, or a sequence of at least 4, 5, 6, 7, 8, 9 or 10 contiguous amino acids thereof, wherein one or more of these amino acids may be substituted by a different amino acid; a LCDR1 region comprising an amino acid sequence SASSSISYMH as set forth in SEQ ID NO: 109, or a sequence of at least 4, 5, 6, 7, 8, 9 or 10 contiguous amino acids thereof, wherein one or more of these amino acids may be substituted by a different amino acid; a LCDR2 region comprising an amino acid sequence STSKLAS as set forth in SEQ ID NO: 110, or a sequence of at least 4, 5, 6, 7, 8, 9 or 10 contiguous amino acids thereof, wherein one or more of these amino acids may be substituted by a different amino acid; a LCDR3 region comprising an amino acid sequence QHRSTYPFT as set forth in SEQ ID NO: 111, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 101, wherein one, two, three or more amino acids may be substituted by a different amino acid; and/or (b) the light chain variable region of SEQ ID NO: 102, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 103-108, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 109, 110 and 111, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 103-108, wherein one or more amino acids in a CDR may be substituted by a different amino acid; and the light chain CDRs 1, 2 and 3 (LCDR1, LCDR2, LCDR3) amino acid sequences as shown in SEQ ID NOS: 109, 110 and 111, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 101, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 102, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 15F9

The amino acid sequence of the heavy chain variable region of antibody 15F9 is listed as SEQ ID NO: 112, the amino acid sequence of the light chain variable region is listed as SEQ ID NO: 113. In a specific embodiment, the invention provides an antibody that binds essentially the same epitope or determinant as monoclonal antibodies 15F9; optionally the antibody comprises an antigen binding region of antibody 15F9. In any of the embodiments herein, antibody 15F9 can be characterized by its amino acid sequence and/or nucleic acid sequence encoding it. In one preferred embodiment, the monoclonal antibody comprises the Fab or F(ab')$_2$ portion of 15F9. Also provided is a monoclonal antibody that comprises the heavy chain variable region of 15F9. According to one embodiment, the monoclonal antibody comprises the three CDRs of the heavy chain variable region of 15F9. Also provided is a monoclonal antibody that further comprises the variable light chain variable region of 15F9 or one, two or three of the CDRs of the light chain variable region of 15F9. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 15F9 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence SGYSWH, GYSITSG or GYSITSGYSWH as set forth in SEQ ID NOS: 114-116, or a sequence of at least 4, 5, 6, 7, 8, 9 or 10 contiguous amino acids thereof, wherein one or more of these amino acids may be substituted by a different amino acid; a HCDR2 region comprising an amino acid sequence FIHYSGSTDYNPSLKS or FIHYSGSTD as set forth in SEQ ID NOS: 117-118, or a sequence of at least 4, 5, 6, 7, 8, 9 or 10 contiguous amino acids thereof, wherein one or more of these amino acids may be substituted by a different amino acid; a HCDR3 region comprising an amino acid sequence DYGHWYFDV as set forth in SEQ ID NO: 119, or a sequence of at least 4, 5, 6, 7, 8, 9 or 10 contiguous amino acids thereof, wherein one or more of these amino acids may be substituted by a different amino acid; a LCDR1 region comprising an amino acid sequence KASQSVSY-DVA as set forth in SEQ ID NO: 120, or a sequence of at least 4, 5, 6, 7, 8, 9 or 10 contiguous amino acids thereof, wherein one or more of these amino acids may be substituted by a different amino acid; a LCDR2 region comprising an amino acid sequence YASNRYT as set forth in SEQ ID NO: 121, or a sequence of at least 4, 5, 6, 7, 8, 9 or 10 contiguous amino acids thereof, wherein one or more of these amino acids may be substituted by a different amino acid; a LCDR3 region comprising an amino acid sequence QQDYSSLT as set forth in SEQ ID NO: 122, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO:112, wherein one, two, three or more amino acids may be substituted by a different amino acid; and/or (b) the light chain variable region of SEQ ID NO: 113, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 114-119, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 120, 121 and 122, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 114-119, wherein one or more amino acids in a CDR may be substituted by a different amino acid; and the light chain CDRs 1, 2 and 3 (LCDR1, LCDR2, LCDR3) amino acid sequences as shown in SEQ ID NOS: 120, 121 and 122, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 112, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 113, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

Antibody 14B4

The amino acid sequence of the heavy chain variable region of antibody 14B4 is listed as SEQ ID NO: 123, the amino acid sequence of the light chain variable region is listed as SEQ ID NO: 124. In a specific embodiment, the invention provides an antibody that binds essentially the same epitope or determinant as monoclonal antibodies 14B4; optionally the antibody comprises an antigen binding region of antibody 14B4. In any of the embodiments herein, antibody 14B4 can be characterized by its amino acid sequence and/or nucleic acid sequence encoding it. In one preferred embodiment, the monoclonal antibody comprises the Fab or F(ab')$_2$ portion of 14B4. Also provided is a monoclonal antibody that comprises the heavy chain variable region of 14B4. According to one embodiment, the monoclonal antibody comprises the three CDRs of the heavy chain variable region of 14B4. Also provided is a monoclonal antibody that further comprises the variable light chain variable region of 14B4 or one, two or three of the CDRs of the light chain variable region of 14B4. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 14B4 are fused to an immunoglobulin constant region of the human IgG type, optionally a human constant region, optionally a human IgG1 or IgG3 isotype.

In another aspect, the invention provides a purified polypeptide which encodes an antibody, wherein the antibody comprises: a HCDR1 region comprising an amino acid sequence SYWMN, GYSFTS or GYSFTSYWMN, or G as set forth in SEQ ID NOS: 125-127, or a sequence of at least 4, 5, 6, 7, 8, 9 or 10 contiguous amino acids thereof, wherein one or more of these amino acids may be substituted by a different amino acid; a HCDR2 region comprising an amino acid sequence MIHPSDSETRLNQKFKD or MIHPSD-SETR as set forth in SEQ ID NOS: 128-129, or a sequence of at least 4, 5, 6, 7, 8, 9 or 10 contiguous amino acids thereof, wherein one or more of these amino acids may be substituted by a different amino acid; a HCDR3 region comprising an amino acid sequence EMGPYTLDY as set forth in SEQ ID NO: 130, or a sequence of at least 4, 5, 6, 7, 8, 9 or 10 contiguous amino acids thereof, wherein one or more of these amino acids may be substituted by a different amino acid; a LCDR1 region comprising an amino acid sequence RASQNIDTSIH as set forth in SEQ ID NO: 131, or a sequence of at least 4, 5, 6, 7, 8, 9 or 10 contiguous amino acids thereof, wherein one or more of these amino acids may be substituted by a different amino acid; a LCDR2 region comprising an amino acid sequence YASESIS as set forth in SEQ ID NO: 132, or a sequence of at least 4, 5, 6, 7, 8, 9 or 10 contiguous amino acids thereof, wherein one or more of these amino acids may be substituted by a different amino acid; a LCDR3 region comprising an amino acid sequence QQSNYWPLT as set forth in SEQ ID NO: 133, or a sequence of at least 4, 5, 6, 7, 8, 9 or 10 contiguous amino acids thereof, wherein one or more of these amino acids may be deleted or substituted by a different amino acid.

In another aspect, the invention provides an antibody that binds human MICA, comprising:

(a) the heavy chain variable region of SEQ ID NO: 123, wherein one, two, three or more amino acids may be substituted by a different amino acid; and/or (b) the light chain variable region of SEQ ID NO: 124, wherein one, two, three or more amino acids may be substituted by a different amino acid; and/or (c) the heavy chain CDR 1, 2 and 3 (HCDR1, HCDR2, HCDR3) amino acid sequences as shown in SEQ ID NO: 125-130, wherein one, two, three or more amino acids in a CDR may be substituted by a different amino acid; and/or (d) the light chain CDR 1, 2 and 3 (LCDR1, LCDR2, LCDR3) amino acid sequences as shown in SEQ ID NOS: 131, 132 and 133, wherein one, two, three or more amino acids in a CDR may be substituted by a different amino acid; and/or (e) the heavy chain CDR 1, 2 and 3 (HCDR1, HCDR2, HCDR3) amino acid sequences as shown in SEQ ID NOS: 125-130, wherein one or more amino acids in a CDR may be substituted by a different amino acid; and the light chain CDRs 1, 2 and 3 (LCDR1, LCDR2, LCDR3) amino acid sequences as shown in SEQ ID NOS: 131, 132 and 133, wherein one, two, three or more amino acids in a CDR may be substituted by a different amino acid; and/or (f) the heavy chain variable region which is at least 60%, 70%, 80%, 85%, 90% or 95% identical to the variable region having an amino acid sequence of SEQ ID NO: 123, wherein one, two, three or more amino acids may be substituted by a different amino acid; and/or (g) the light chain variable region which is at least 60%, 70%, 80%, 85%, 90% or 95% identical to the variable region having an amino acid sequence of SEQ ID NO: 124, wherein one, two, three or more amino acids may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, the invention provides an antibody that competes for MICA binding with a monoclonal antibody of (a) to (g), above.

In any of the antibodies of the invention, e.g., 6E4, 20C6, 16A8, 9C10, 19E9, 12A10, 10A7, 18E8, 10F3, 15F9 or 14B4, the specified variable region and CDR sequences may comprise conservative sequence modifications (1, 2, 3, 4, 5, 6, 7, 8 or more sequence modifications). A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

The sequences of the CDRs, according to AbM (Oxford Molecular's AbM antibody modelling software definition), Kabat and Chothia definitions systems, have been summarized in Table A below. While any suitable numbering system may be used to designated CDR regions, in the absence of any other indication, the numbering used herein is Abm. Such numbering has been established using the following indications: CDR-L1: Start: approx residue 24, residue before: always a Cys, residue after: always a Trp (typically Trp-Tyr-Gln, but also, Trp-Leu-Gln, Trp-Phe-Gln, Trp-Tyr-Leu), length: 10 to 17 residues; CDR-L2: Start: always 16 residues after the end of L1, Residues before: generally Ile-Tyr (but also, Val-Tyr, Ile-Lys, Ile-Phe), Length: always 7 residues; CDR-L3, Start: always 33 residues after end of L2, Residue before: always Cys, Residues after: always Phe-Gly-Xaa-Gly, Length: 7 to 11 residues; CDR-H1, Start: approx residue 26 (always 4 after a Cys)

(Chothia/AbM definition, the Kabat definition starts 5 residues later), Residues before: always Cys-Xaa-Xaa-Xaa, Residues after: always a Trp (typically Trp-Val, but also, Trp-Ile, Trp-Ala), Length: 10 to 12 residues (AbM definition, Chothia definition excludes the last 4 residues); CDR-H2, Start: always 15 residues after the end of Kabat/AbM definition of CDR-H1, Residues before: typically Leu-Glu-Trp-Ile-Gly (but a number of variations, Residues after Lys/Arg-Leu/Ile/Val/Phe/Thr/Ala-Thr/Ser/Ile/Ala), Length: Kabat definition 16 to 19 residues; AbM (and Chothia) definition ends 7 residues earlier; CDR-H3, Start: always 33 residues after end of CDR-H2 (always 2 after a Cys), Residues before: always Cys-Xaa-Xaa (typically Cys-Ala-Arg), Residues after: always Trp-Gly-Xaa-Gly, Length: 3 to 25 residues.

The sequences of the variable chains of the antibodies according to the invention are listed in Table B below, with the leader sequence underlined at the beginning of each sequence (any antibody chain can be specified to start at the amino acid position immediately following the end of the leader sequence), and each CDRs underlined. In any embodiment herein, a VL or VH sequence can be specified or numbered so as to contain or lack a signal peptide or any part thereof.

In one embodiment, the antibodies of the invention are of the human IgG1 or IgG3 isotype. In one embodiment, the antibodies of the invention are antibody fragments that retain their binding and/or functional properties.

TABLE A

| mAb | CDR definition | HCDR1 SEQ ID | Sequence | HCDR2 SEQ ID | Sequence | HCDR3 SEQ ID | Sequence |
|---|---|---|---|---|---|---|---|
| 6E4 | Kabat | 11 | SYYAMS | 14 | TISRGGNYIYYTDSVKG | 16 | ISDYDGAWLAY |
|  | Chotia | 12 | GFTFSY | 15 | TISRGGNYIY | 16 | ISDYDGAWLAY |
|  | Abm | 13 | GFTFSYYAMS | 15 | TISRGGNYIY | 16 | ISDYDGAWLAY |
| 20C6 | Kabat | 24 | TSGMGVG | 27 | HIWWDDDKYYNPSLK | 29 | RTQGYFDY |
|  | Chotia | 25 | GFSLSTSG | 28 | HIWWDDDK | 29 | RTQGYFDY |
|  | Abm | 26 | GFSLSTSGMGVG | 28 | HIWWDDDK | 29 | RTQGYFDY |
| 16A8 | Kabat | 37 | RYAMS | 40 | TIFSGGSYTYYPDSV | 42 | PNWERTFDY |
|  | Chotia | 38 | GFTFSR | 41 | TIFSGGSY | 42 | PNWERTFDY |
|  | Abm | 39 | GFTFSRYAMS | 41 | TIFSGGSY | 42 | PNWERTFDY |
| 19E9 | Kabat | 48 | SDYAWN | 51 | FVSYSGTTKYNPSLKS | 53 | GYGFDY |
|  | Chotia | 49 | GYSITSD | 52 | FVSYSGTTK | 53 | GYGFDY |
|  | Abm | 50 | GYSITSDYAWN | 52 | FVSYSGTTK | 53 | GYGFDY |
| 9C10 | Kabat | 59 | RYWMN | 62 | MIHPSDSETRLNQKFKD | 64 | GNFFYVMDY |
|  | Chotia | 60 | GYSFTR | 63 | MIHPSDSETR | 64 | GNFFYVMDY |
|  | Abm | 61 | GYSFTRYWMN | 63 | MIHPSDSETR | 64 | GNFFYVMDY |
| 12A10 | Kabat | 70 | NYWMN | 73 | MIHPSDSETRLNQKFKD | 75 | DDFFTMDY |
|  | Chotia | 71 | GYSFTN | 74 | MIHPSDSETR | 75 | DDFFTMDY |
|  | Abm | 72 | GYSFTNYWMN | 74 | MIHPSDSETR | 75 | DDFFTMDY |
| 10A7 | Kabat | 81 | TSGMGVG | 84 | HIWWDDDRYYNPSLKS | 86 | RLNGYFDY |
|  | Chotia | 82 | GFSLSTSG | 85 | HIWWDDDRY | 86 | RLNGYFDY |
|  | Abm | 83 | GFSLSTSGMGVG | 85 | HIWWDDDRY | 86 | RLNGYFDY |
| 18E8 | Kabat | 92 | SDYSWH | 95 | NIHYSGRINYNPSLRS | 97 | RRTFGNFEDY |
|  | Chotia | 93 | GYSITSD | 96 | NIHYSGRIN | 97 | RRTFGNFEDY |
|  | Abm | 94 | GYSITSDYSWH | 96 | NIHYSGRIN | 97 | RRTFGNFEDY |
| 10F3 | Kabat | 103 | SYTMH | 106 | YINPSSGYTEYNQKFKD | 108 | GGDWDVDWFVY |
|  | Chotia | 104 | GYTFTS | 107 | YINPSSGYTE | 108 | GGDWDVDWFVY |
|  | Abm | 105 | GYTFTSYTMH | 107 | YINPSSGYTE | 108 | GGDWDVDWFVY |
| 15F9 | Kabat | 114 | SGYSWH | 117 | FIHYSGSTDYNPSLKS | 119 | DYGHWYFDV? |
|  | Chotia | 115 | GYSITSG | 118 | FIHYSGSTD | 119 | DYGHWYFDV |
|  | Abm | 116 | GYSITSGYSWH | 118 | FIHYSGSTD | 119 | DYGHWYFDV |

TABLE A-continued

| mAb | CDR definition | HCDR1 | HCDR2 | HCDR3 |
|---|---|---|---|---|
| 14B4 | Kabat | 125 SYWMN | 128 MIHPSDSETRLNQKFKD | 130 EMGPYTLDY |
|  | Chotia | 126 GYSFTS | 129 MIHPSDSETR | 130 EMGPYTLDY |
|  | Abm | 127 GYSFTSYWMN | 129 MIHPSDSETR | 130 EMGPYTLDY |

| mAb | CDR definition | LCDR1 SEQ ID Sequence | LCDR2 SEQ ID Sequence | LCDR3 SEQ ID Sequence |
|---|---|---|---|---|
| 6E4 | Kabat | 17 RSSQSIIHTNGNTYLE | 18 KISNRFS | 19 FQGSHVPWT |
| 20C6 | Kabat | 30 RASQSISDYLH | 31 YASQSIS | 32 QNGHSFPWT |
| 16A8 | Kabat | 43 KSSQSLLNSSNQKNYL | 44 FASTRES | 45 QQHYSTPPT |
| 19E9 |  | 54 SATSSISSIYFH | 55 RTSNLAS | 56 QQGTTIPFT |
| 9C10 |  | 65 RASQSIGTSIH | 66 ASESISG | 67 QQSNFWPFT |
| 12A10 | Kabat, Chotia, Abm | 76 RASQNIVTSIH | 77 YASESIS | 78 QQSNIWPLT |
| 10A7 | Kabat, Chotia, Abm | 87 RASQSISDYLH | 88 YASQSIS | 89 QNGHSFPFT |
| 18E8 | Kabat, Chotia, Abm | 98 RSSSSVNYMH | 99 ATSTLAS | 100 QQWSSNPLT |
| 10F3 | Kabat, Chotia, Abm | 109 SASSSISYMH | 110 STSKLAS | 111 QHRSTYPFT |
| 15F9 | Kabat, Chotia, Abm | 120 KASQSVSYDVA | 121 YASNRYT | 122 QQDYSSLT |
| 14B4 | Kabat, Chotia, Abm | 131 RASQNIDTSIH | 132 YASESIS | 133 QQSNYWPLT |

TABLE B

| Antibody portion | SEQ ID NO | Sequence |
|---|---|---|
| 6E4 VH | 7 | MNFVLSLIFLALILKGVQCEVQLVESGGALVKPGGSLKLSCAAS<u>GFTFSYYA</u><u>MS</u>WVRQTPEKRLEWVA<u>TISRGGNYIY</u><u>YTDSVKG</u>RFTISRDNAKNTLYLQMTSLRSEDTAMFYCAS<u>ISDYDGAWLAY</u>WGQGTLVTV |
| 6E4 VL | 8 | MKLPVRLLVLMFWIPVSSDVLMTQTPLSLPVSLGDQASISC<u>RSSQSIIHTNGNTYLE</u>WYLQKPGQSPKLLIY<u>KISNRFS</u>GVPDRFSGSGSGTDFTLKISRVEAEDLGVYYC<u>FQGSHVPWT</u>FGGGTKLEIK |
| 20C6 VH | 20 | MDRLTSSFLLLIVPAYVLSQITLKESGPGILKPSQTLSLTCSFS<u>GFSLSTSGMGVG</u>WIRQPSGKGLEWLA<u>HIWWDDDKYYNPSLKS</u>QLTISKDTSRNQVFLRITSVDTADTATYYCARR<u>RTQGYFDY</u>WGQGTTLTVSS |
| 20C6 VL | 21 | MVSTSQLLGLLLFWTSASRCDIVMTQSPATLSVTPGDRVSLSC<u>RASQSISDYLH</u>WYQQKSHESPRLLIK<u>YASQSISG</u>I |

TABLE B-continued

| Antibody portion | SEQ ID NO | Sequence |
|---|---|---|
| | | PSRFSGSGSGSDFTLSINSVEPEDVG VYYC<u>QNGHSFPWT</u>FGGGTKLEIK |
| 16A8 VH | 33 | <u>MNFVLSLIFLALILKGVRC</u>EVQLVES GGGLVKPGGSLKLSCAAS<u>GFTFSRYA MS</u>WVRQTPEKRLEWVA<u>TIFSGGSYTY YPDSV</u>KGRFTISRDNANNTLYLQMSS LKAEDTAMYFCAR<u>PNWERTFDY</u>WGQG TTLTVSS |
| 16A8 VL | 34 | <u>MESQTQVLMFLLLWVSGACT</u>DIVMTQ SPSSLAMSVGQKVTMSC<u>KSSQSLLNS SNQKNYLA</u>WYQQKPGQSPKLLVY<u>FAS TRES</u>GVPDRFMGSGSGTDFTLTISSV QAEDLADYFC<u>QQHYSTPPT</u>FGGGTKL EIK |
| 19E9 VH | 46 | MRVLILLWLFTAFPGLLSDVQLQESG PGLVKPSQSLSLTCTVT<u>GYSITSDYA WN</u>WIRQFPGNKLEWMG<u>FVSYSGTTKY NPSLKS</u>RISITRDTSENQFFLQLNSV TSEDTATYYCAR<u>GYGFDY</u>WGQGTTLT VSS |
| 19E9 VL | 47 | MQIISLLLISVTVIVSNGEIVLTQSP TTMAASPGEKITITC<u>SATSSISSIYF H</u>WYQQRPGFSPKLLIY<u>RTSNLAS</u>GVP ARFSGSGSGTSYSLTIGTMEAEDVAT YYC<u>QQGTTIPFT</u> FGSGTKLEIK |
| 9C10 VH | 57 | <u>MGWSSIILFLVATSTGVHS</u>QVQLQQP GAELVRPGTSVNLSCKAS<u>GYSFTRYW MN</u>WVKQRPGQGLEWIG<u>MIHPSDSETR LNQKFKD</u>KATLTVDKSSSTAYMQLSS PTSEDSAVYYCGY<u>GNFFYVMDY</u>WGQG TSVTVSS |
| 9C10 VL | 58 | <u>MVSTPQFLVFLLFWIPASRG</u>DILLTQ SPAILSVSPGERVSFSC<u>RASQSIGTS IH</u>WYQQRTNGSPRLLIK<u>FASESISG</u>I PSRFSGSGSGTDFTLNINSVESEDIA DYYC<u>QQSNFWPFT</u>FGSGTKLEVK |
| 12A10 VH | 68 | <u>MEWSWVFLFFLSVTTGVHS</u>QVQLQQS GADLVRPGASVRLSCRAS<u>GYSFTNYW MN</u>WVKQRPGQGLEWIG<u>MIHPSDSETR LNQKFKD</u>KATLTVDKSSNTAYMQLSS PTSEDSAIYYCAR<u>DDFFTMDY</u>WGQGT SVTVSSASTK |
| 12A10 VL | 69 | <u>MSVPTQVLGLLLLWTDARC</u>DILLTQ SPAILSVSPGERVSFSC<u>RASQNIVTS IH</u>WYQQSTNGSPRLLIK<u>YASESISG</u>I PSRFSGSGSGTDFTLTINSVESEDVA DYYC<u>QQSNIWPLT</u>FGAGTKLELK |
| 10A7 VH | 79 | <u>MEWSWVFLFFLSVTTGVHS</u>QVTLKES GPGILKPSQTLSLTCSFS<u>GFSLSTSG MGVG</u>WIRQPSGKGLEWLA<u>HIWWDDR YYNPSLKS</u>QLTISKDTSRNQVFLKIT SVDTADTATYYCAR<u>RLNGYFDY</u>WGQG TTLTVSSASTK |
| 10A7 VL | 80 | <u>MSVPTQVLGLLLLWTDARC</u>DIVMTQ SPATLSVTLGDRVSLSC<u>RASQSISDY LH</u>WYQQKSHESPRLLIK<u>YASQSISG</u>I PSRFSGSGSGSDFTLSINSVEPEDVG VYYC<u>QNGHSFPFT</u>FGSGTKLEIK |
| 18E8 VH | 90 | <u>MEWSWVFLFFLSVTTGVHS</u>DVQLQES GPDLVNPQSLSLICTVT<u>GYSITSDY SW</u>HWIRQFPGNKLEWMG<u>NIHYSGRIN YNPSLRS</u>RISITRDTSKNQFFLQLIS VTTEDTATYYCAT<u>RRTFGNFEDY</u>WGQ GTTLTVSSASTK |

TABLE B-continued

| Antibody portion | SEQ ID NO | Sequence |
|---|---|---|
| 18E8 VL | 91 | M S V P T Q V L G L L L L W L T D A R C Q I V L S Q S P A T L S V S P G E K V T M T C R S S S V N Y M H W Y Q Q K P G S S P K P W I Y A T S T L A S G V P A R F S G S G S G T S Y S L T I S R V E A E D A A T Y Y C Q Q W S S N P L T F G A G T K L E L K |
| 10F3 VH | 101 | M E W S W V F L F F L S V T T G V H S Q V Q L Q Q S A A E L A R P G A S V K M S C K A S G Y T F T S Y T M H W V K Q R P G Q G L E W I G Y I N P S S G Y T E Y N Q K F K D K T T L T V D K S S T T S Y M Q L S S L T S D N S A V Y Y C A R G G D W D V D W F V Y W G Q G T L V T V S A A S T K |
| 10F3 VL | 102 | M S V P T Q V L G L L L L W L T D A R C Q I V L T Q S P A I M S A S P G E K V T I T C S A S S S I S Y M H W F Q Q K P G T S P K L W I Y S T S K L A S G V P A R F S G S G S G T S H S L T I S R M E A E D A A T Y Y C Q H R S T Y P F T F G S G T K L E I K |
| 15F9 VH | 112 | M E W S W V F L F F L S V T T G V H S D V Q L Q E S G P D L V K P S Q S L S L T C T V T G Y S I T S G Y S W H W I R Q F P G N K L E W M G F I H Y S G S T D Y N P S L K S R I S L T R D T S K N Q F F L Q L N S V S T E D T A T Y Y C A K D Y G H W Y F D V W G A G T T V T V S S A S T K |
| 15F9 VL | 113 | M S V P T Q V L G L L L L W L T D A R C S I V M T Q T P K F L L V S A G D R V T I T C K A S Q S V S Y D V A W Y Q Q K P G Q S P K L L I F Y A S N R Y T G V P A R F T G S G Y G T D F T F T I S T V Q A E D L A V Y F C Q Q D Y S S L T F G A G T K L E L K |
| 14B4 VH | 123 | M E W S W V F L F F L S V T T G V H S Q V Q L Q Q P G A E L V R P G A S V K L S C K A S G Y S F T S Y W M N W M K Q R P G Q G L E W I G M I H P S D S E T R L N Q K F K D K A T L T V D K S S T A Y M Q L N S P T S E D S A V Y Y C A R E M G P Y T L D Y W G Q G T S V T V S S A S T K |
| 14B4 VL | 124 | M S V P T Q V L G L L L L W L T D A R C D I L L T Q S P A I L S V S P G A R V S F S C R A S Q N I D T S I H W Y Q Q R T N G S P R L L I K Y A S E S I S G I P S R F S G S G S G T D F T L S I N S V E S E D I A D Y Y C Q Q S N Y W P L T F G A G T K L E L K |

In one aspect of any of the embodiments of the invention, any antibody of the invention may comprise a heavy and/or light chain having CDR1, 2 and/or 3 sequences according to the respective formula selected from Formulas (I) to (VIII). In any embodiment herein, a particular HCDR1-3 or LCDR-1-3 may be specified as having a sequence of Formulas (I) to (VIII). In one preferred embodiment, the antibody comprises a light chain comprising the three LCDRs and a heavy chain comprising the three HCDRs.

In one embodiment, HCDR1 comprises an amino acid sequence of Formula (I):

G-$Xaa_1$-$Xaa_2$-$Xaa_3$-$Xaa_4$-$Xaa_5$ (SEQ ID NO: 261), wherein $Xaa_1$ may be Phe or Tyr, $Xaa_2$ may be Thr or Ser, $Xaa_3$ may be Ile, Leu or Phe, $Xaa_4$ may be Ser or Thr and $Xaa_5$ may be Asn, Tyr, Ser, Thr or Arg. Optionally any 1, 2 or 3 of said $Xaa_{1-5}$ may be a conservative or non-conservative substitution of any of the amino acids indicated or a deletion or insertion.

In one embodiment, HCDR1 comprises an amino acid sequence of Formula (II):

$Xaa_1$-$Xaa_2$-$Xaa_3$-$Xaa_4$-$Xaa_5$ (SEQ ID NO: 262), wherein $Xaa_1$ may be Asn, Ser, Thr or Arg, $Xaa_2$ may be Gly, Asp, Ser or Tyr, $Xaa_3$ may be Thr, Tyr, Ala, Gly, Trp, $Xaa_4$ may be Ser, Ala or Met, and $Xaa_5$ may be His, Trp, Gln, Ser or Asn. Optionally any 1, 2 or 3 of said $Xaa_{1-5}$ may be a conservative or non-conservative substitution of any of the amino acids indicated or a deletion or insertion.

In one embodiment, HCDR1 comprises an amino acid sequence of Formula (III):

$Xaa_1$-Y-$Xaa_2$-M-$Xaa_3$ (SEQ ID NO: 263), wherein $Xaa_{1-3}$ may each be a conservative or non-conservative substitution of any of the amino acids indicated or a deletion or insertion, wherein $Xaa_1$ may be Asn, Ser, Thr or Arg, $Xaa_2$ may be Thr, Tyr, Ala, Gly, Trp, and $Xaa_3$ may be His, Trp, Gln, Ser or Asn.

In one embodiment, HCDR2 comprises an amino acid sequence of Formula (IV):

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$ (SEQ ID NO: 264), wherein $Xaa_1$ may be Phe, Thr, His, Asn, Tyr or Met, $Xaa_2$ may be Val or Ile, $Xaa_3$ may be Ser, Phe, His, Asn or Trp, $Xaa_4$ may be Arg, Tyr, Ser, Trp or Pro, $Xaa_5$ may be Gly, Asp or Ser, $Xaa_6$ may be Thr, Gly, Asp or Ser, $Xaa_7$ may be Asn, Thr, Ser, Asp, Arg or Gly, Xaa$_8$ may be Tyr, Lys, Glu, Arg, Ile or Thr, Xaa$_9$ may be Ile, Thr, Tyr, Asn or Asp, and Xaa$_{10}$ may be Tyr, Arg or Glu. Optionally any 1, 2, 3 or 4 of said Xaa$_{1-10}$ may be a conservative or non-conservative substitution of any of the amino acids indicated or a deletion or insertion.

In one embodiment, HCDR3 comprises an amino acid sequence of Formula (V):

Xaa$_1$-Xaa$_2$-Xaa$_3$-Xaa$_4$-Xaa$_5$-Xaa$_6$-Xaa$_7$-Xaa$_8$-Xaa$_9$(SEQ ID NO: 265), wherein Xaa$_1$ may be Ile, Pro, Arg, Gly, Asp or Glu, Xaa$_2$ may be Ser, Tyr, Thr, Asn, Asp, Leu, Arg, Glu or Met, Xaa$_3$ may be Asp, Glu, Trp, Gln, Phe, Asn or Thr, Xaa$_4$ may be Tyr, Glu, Gly, Phe, Trp, His or Pro, Xaa$_5$ may be Asp, Arg, Tyr, Thr, Gly or Trp, Xaa$_6$ may be Gly, Tyr, Thr, Phe, Val, Met or Asn, Xaa$_7$ may be Ala, Phe, Asp, Met or Leu, Xaa$_8$ may be Trp, Tyr, Asp or Glu, and Xaa$_9$ may be Leu, Tyr, Asp, Phe or Val. Optionally any 1, 2, 3 or 4 of said Xaa$_{1-9}$ may be a conservative or non-conservative substitution of any of the amino acids indicated or a deletion or insertion.

In one embodiment, LCDR1 comprises an amino acid sequence of Formula (VI):

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$ (SEQ ID NO: 266), wherein Xaa, may be Ser, Lys or Arg, Xaa$_2$ may be Ser or Ala, Xaa$_3$ may be Thr or Ser, Xaa$_4$ may be Ser or Gln, Xaa$_5$ may be Asn or Ser, Xaa$_6$ may be Val, Leu or Ile, Xaa$_7$ may be Asp, Asn, Val, Leu, Gly or Ser, Xaa$_8$ may be Tyr, Ser, Asn, Thr or Asp, Xaa$_9$ may be Asp, Met, Ile, Ser or Tyr, Xaa$_{10}$ may be Val, His, Tyr, Ser, Ile, or Leu, and Xaa$_{11}$ may be Ala, Phe, Asn or His. Optionally any 1, 2, 3 or 4 of said Xaa$_{1-11}$ may be a conservative or non-conservative substitution of any of the amino acids indicated, or a deletion or insertion.

In one embodiment, LCDR2 comprises an amino acid sequence of Formula (VII):

Xaa$_1$-Xaa$_2$-Xaa$_3$-Xaa$_4$-Xaa$_5$-Xaa$_6$-Xaa$_7$ (SEQ ID NO: 267), wherein Xaa, may be Ser, Lys, Arg, Phe, Tyr or Ala, Xaa$_2$ may be Ile, Thr, Ala or Ser, Xaa$_3$ may be Ser or Glu, Xaa$_4$ may be Lys, Glu, Asn, Thr, Gln or Ser, Xaa$_5$ may be Leu, Arg, Ser or Ile, Xaa$_6$ may be Tyr, Phe, Ala, Glu, Ile or Ser, and Xaa$_7$ may be Thr, Ser or Gly. Optionally any 1, 2, 3 or 4 of said Xaa$_{1-7}$ may be a conservative or non-conservative substitution of any of the amino acids indicated or a deletion or insertion.

In one embodiment, LCDR3 comprises an amino acid sequence of Formula (VIII):

Xaa$_1$-Xaa$_2$-Xaa$_3$-Xaa$_4$-Xaa$_5$-Xaa$_6$-Xaa$_7$-Xaa$_8$-Xaa$_9$(SEQ ID NO: 268), wherein Xaa$_1$ may be Phe or Gln, Xaa$_2$ may be His, Asn or Gln, Xaa$_3$ may be Ser, Gly, His, Trp or Arg, Xaa$_4$ may be Asn, His, Tyr, Thr or Ser, Xaa$_5$ may be Phe, Ser, Thr, His, Ile or Tyr, Xaa$_6$ may be Trp, Phe, Thr, Ile, Val, Asn or Try, Xaa$_7$ is Pro, Xaa$_8$ may be Phe, Trp, Pro or Leu, and Xaa$_9$ is Thr. Optionally any 1, 2, 3 or 4 of said Xaa$_{1-9}$ may be a conservative or non-conservative substitution of any of the amino acids indicated or a deletion or insertion.

In one embodiment, an antibody of the invention may comprise a light chain comprising:
  a a light chain CDR1 (LCDR1) comprising an amino acid sequence of SEQ ID NO: 266; and/or
  b a light chain CDR2 (LCDR2) comprising an amino acid sequence of SEQ ID NO: 267; and/or
  c a light chain CDR3 (LCDR3) comprising an amino acid sequence of SEQ ID NO: 268.

In one embodiment, an antibody of the invention may comprise a heavy chain comprising:
  d a heavy chain CDR1 (HCDR1) comprising an amino acid sequence selected from SEQ ID NOS: 261, 262 and 263; and/or
  e a heavy chain CDR2 (HCDR2) comprising an amino acid sequence of SEQ ID NO: 264; and/or
  f a heavy chain CDR3 (HCDR3) comprising an amino acid sequence of SEQ ID NO: 265.

Fragments and Derivatives

Fragments and derivatives of antibodies of this invention (which are encompassed by the term "antibody" or "antibodies" as used in this application, unless otherwise stated or clearly contradicted by context), preferably a 6E4, 20C6, 16A8, 9C10, 19E9, 12A10, 10A7, 18E8, 10F3, 15F9 or 14B4-like antibody, can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG).

Alternatively, the DNA of a hybridoma producing an antibody of the invention may be modified so as to encode a fragment of the invention. The modified DNA is then inserted into an expression vector and used to transform or transfect an appropriate cell, which then expresses the desired fragment.

In certain embodiments, the DNA of a hybridoma producing an antibody of this invention can be modified prior to insertion into an expression vector, for example, by substituting the coding sequence for human heavy- and light-chain constant domains in place of the homologous non-human sequences, or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention is humanized. "Humanized" forms of antibodies according to this invention are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.)

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for MICA receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XENOMOUSE transgenic mouse (Abgenix, Fremont, Calif.) as the mouse used for immunization. A XENOMOUSE is a murine host according to this invention that has had its immunoglobulin genes replaced by functional human immunoglobulin genes. Thus, antibodies produced by this mouse or in hybridomas made from the B cells of this mouse, are already humanized. The XENOMOUSE is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

The antibodies of the present invention may also be derivatized to "chimeric" antibodies (immunoglobulins) in which a portion of the heavy/light chain(s) is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A, pp. 6851 (1984)).

The invention provides anti-MICA antibody molecules which are directed to and, in embodiments, are internalized into cells. They are capable of delivering therapeutic agents or detectable agents to or into cells expressing MICA, but not to or into cells where MICA polypeptides are not expressed. Thus, the invention also provides anti-MICA immunoconjugates comprising an anti-MICA antibody as described herein, which is conjugated to a therapeutic agent or a detectable agent (or any other moiety that serves as a payload of interest to be delivered to a MICA-expressing cell. In embodiments, the affinity for MICA of an anti-MICA immunoconjugate is at least 10, 25, 50, 75, 80, 90, or 95% of that for the unconjugated antibody. This can be determined using cell surface MICA or isolated MICA.

Useful detectable agents with which an antibody or an antibody portion of the invention may be derivatized (or labeled) include fluorescent compounds, various enzymes, prosthetic groups, luminescent materials, bioluminescent materials, fluorescent emitting metal atoms, e.g., europium (Eu), and other anthanides, and radioactive materials (described above). Exemplary fluorescent detectable agents include fluorescein, fluorescein isothiocyanate, rhodamine, 5-dimethylamine-I-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin;

an example of a luminescent material includes luminol; and examples of bioluminescent materials include luciferase, luciferin, and aequorin. Alternatively, the anti-MICA antibody may be associated with a second antibody that binds to the anti-MICA antibody, wherein the second antibody is derivatized with a detectable label; binding said second antibody into contact with the anti-MICA antibody, in vitro or in vivo, will allow the anti-MICA to serve as a labeled antibody.

Conjugation to a detectable moiety is useful, inter alia, when an antibody of the invention is used for diagnostic purposes. Such purposes include, but are not limited to, assaying biological samples, e.g., a blood sample or tissue biopsy, for the presence of MICA-expressing cells, and detecting the presence, level, or activity of MICA-expressing cells in an individual. Such assay and detection methods can be used in the diagnostic/therapeutic methods of the invention, e.g., involving detecting MICA expression in cells of a patient and if the patient's cells are determined to express MICA, subsequently administering a MICA modulating antibody of the invention.

In certain embodiments, the present antibodies are used to purify MICA-expressing cells from a biological sample. Biological samples can be obtained from a patient, e.g. for diagnostic or ex vivo therapeutic purposes, or from individuals or non-human primates to obtain a source of such cells for research purposes.

In one such embodiment, labeled antibodies of the invention can be used in FACS sorting to purify or isolate MICA-expressing cells from a biological sample. Alternatively, in some embodiments conjugation of an antibody of this invention to a solid support can be useful as a tool for affinity purification of cells bearing a MICA receptor on their cell surface from a biological sample, such as a blood sample or cells from a tissue biopsy from an individual. This method of purification is another alternate embodiment of the present invention, as is the resulting purified population of cells.

Regardless of the method used to isolate or purify the MICA-expressing cells, the ability to do so is useful for numerous purposes, e.g. to diagnose a MICA-associated disorder by assessing the number or activity of MICA-expressing cells, e.g., prior to administration of anti-MICA antibodies as described herein. Further, purified MICA-expressing cells are useful in a research context, e.g., to better characterize the cells and their various properties and behaviors, as well as to identify compounds or methods that can be used to modulate their behavior, activity, survival, or proliferation.

Modified Constant Regions

In view of the ability of the anti-MICA antibodies of the invention to induce ADCC and CDC, the antibodies of the invention can also be made with modifications that increase their ability to bind Fc receptors which can affect effector functions such as antibody-dependent cytotoxicity, mast cell degranulation, and phagocytosis, as well as immunomodulatory signals such as regulation of lymphocyte proliferation and antibody secretion. Typical modifications include modified human IgG1 constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD 16). FcγRI (CD64), FcγRIIA (CD32A) and FcγRIII (CD 16) are activating (i.e., immune system enhancing) receptors while FcγRIIB (CD32B) is an inhibiting (i.e., immune system dampening) receptor. A modification may, for example, increase binding of the Fc domain to FcγRIIIa on effector (e.g. NK) cells.

Anti-MICA antibodies preferably comprise an Fc domain (or portion thereof) of human IgG1 or IgG3 isotype, optionally modified. The amino acid sequence of positions 230 to 447 sequence of a human IgG1 Fc region (GenBank accession #: J00228) is shown as follows:

```
                                          (SEQ ID NO: 134)
PAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALH

NHYTQKSLSLSPGK;
```

Residues 230-341 (Kabat EU) are the Fc CH2 region. Residues 342-447 (Kabat EU) are the Fc CH3 region. Anti-MICA antibodies may comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (i.e., an antibody having the same amino acid sequence as the antibody of the invention except for the one or more amino acid modifications in the Fc region). For example, the one or both of the histidine residues at amino acid positions 310 and 435 may be substituted, for example by lysine, alanine, glycine, valine, leucine, isoleucine, proline, methionine, tryptophan, phenylalanine, serine or threonine (see, e.g. PCT publication no. WO 2007/080277); such substituted constant regions provide decreased binding to the inhibitory FcγRIIB without decreasing binding to the activatory FcγRIIIA. In some embodiments, such modifications increase the affinity of the variant Fc region for FcγRIIIA and/or FcγRIIA and also enhance the affinity of the variant Fc region for FcγyRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells.

In one embodiment, said one or more modifications to the amino acids of the Fc region reduce the affinity and avidity of the antibody for one or more FcγR receptors. In a specific embodiment, the invention encompasses antibodies comprising a variant Fc region, wherein said variant Fc region comprises at least one amino acid modification relative to a wild type Fc region, which variant Fc region only binds one FcγR, wherein said FcγR is FcγRIIIA or FcγRIIA.

The affinities and binding properties of the molecules, e.g., antibodies, of the invention for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, immunoprecipitation assays.

In some embodiments, the molecules of the invention comprising a variant Fc region comprise at least one amino acid modification (for example, possessing 1, 2, 3, 4, 5, 6, 7, 8, 9, or more amino acid modifications) in the CH3 domain of the Fc region. In other embodiments, the molecules of the invention comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, the molecules of the invention comprise at least two amino acid modifications (for example, possessing 2, 3, 4, 5, 6, 7, 8, 9, or more amino acid modifications), wherein at least one such modification is in the CH3 region and at least one such modification is in the CH2 region. The invention further encompasses amino acid modification in the hinge region. In a particular embodiment, the invention encompasses amino acid modification in the CH1 domain of the Fc region, which is defined as extending from amino acids 216-230.

Any combination of Fc modifications can be made, for example any combination of different modifications disclosed in United States Patents Nos. U.S. Pat. Nos. 7,632,497; 7,521,542; 7,425,619; 7,416,727; 7,371,826; 7,355,008; 7,335,742; 7,332,581; 7,183,387; 7, 122,637; 6,821,505 and 6,737,056; in PCT Publications Nos. WO2011/109400; WO 2008/105886; WO 2008/002933; WO 2007/021841; WO 2007/106707; WO 06/088494; WO 05/1 15452; WO 05/110474; WO 04/1032269; WO 00/42072; WO 06/088494; WO 07/024249; WO 05/047327; WO 04/099249 and WO 04/063351; and in Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

The invention encompasses anti-MICA antibodies a which comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 333, 334, 335, 337, 338, 339, 340, 359, 360, 370, 373, 376, 378, 392, 396, 399, 402, 404, 416, 419, 421, 430, 434, 435, 437, 438 and/or 439.

The invention encompasses anti-MICA antibodies a which comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 329, 298, 330, 332, 333 and/or 334 (e.g. S239D, S298A, A330L, I332E, E333A and/or K334A substitutions).

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 06/133148; WO 03/035835; WO 99/54342, each of which is incorporated herein by reference in its entirety.

Generally, such antibodies with altered glycosylation are "glyco-optimized" such that the antibody has a particular N-glycan structure that produces certain desireable properties, including but not limited to, enhanced ADCC and effector cell receptor binding activity when compared to non-modified antibodies or antibodies having a naturally occurring constant region and produced by murine myeloma NSO and Chinese Hamster Ovary (CHO) cells (Chu and Robinson, Current Opinion Biotechnol. 2001, 12: 180-7), HEK293T-expressed antibodies as produced herein in the Examples section, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biatennary structures with very low or no bisecting N-acetylglucosamine (bisecting GlcNAc) and high levels of core fucosylation. Glycan temini contain very low or no terminal sialic acid and variable amounts of galactose. For a review of effects of glycosylation on antibody function, see, e.g., Wright & Morrison, Trend Biotechnol. 15:26-31(1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002).

FcγR binding requires the presence of oligosaccharides covalently attached at the conserved Asn297 in the Fc region of human IgGI, IgG2 or IgG3 type. Non-fucosylated oligosaccharides structures have recently been associated with dramatically increased in vitro ADCC activity. "Asn 297" according to the invention means amino acid asparagine located at about position 297 in the Fc region; based on minor sequence variations of antibodies, Asn297 can also be located some amino acids (usually not more than +3 amino acids) upstream or downstream.

Historically, antibodies produced in CHO cells contain about 2 to 6% in the population that are nonfucosylated. YB2/0 (rat myeloma) and LecI3 cell line (a lectin mutant of CHO line which has a deficient GDP-mannose 4,6-dehydratase leading to the deficiency of GDP-fucose or GDP sugar intermediates that are the substrate of alpha6-fucosyltransferase have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

The invention comprises an antibody binding to MICA being glycosylated with a sugar chain at Asn297, said antibody showing increased binding affinity via its Fc portion to FcγRIII. In one embodiment of the invention, an antibody will comprise a constant region comprising at least one amino acid alteration in the Fc region that improves antibody binding to FcγRIIIa and/or ADCC.

In one aspect, the antibodies of the invention are hypofucosylated in their constant region. Such antibodies may comprise an amino acid alteration or may not comprise an amino acid alteration but be produced or treated under conditions so as to yield such hypofucosylation. In one aspect, an antibody composition of the invention comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is an antibody composition which is free of antibodies comprising a core carbohydrate structure having fucose. The core carbohydrate will preferably be a sugar chain at Asn297.

In one embodiment, the invention comprises an antibody composition of the invention, e.g. a composition comprising antibodies which bind to MICA, are glycosylated with a sugar chain at Asn297, wherein the antibodies are partially fucosylated. Partially fucosylated antibodies are characterized in that the proportion of anti-MICA antibodies in the composition that lack fucose within the sugar chain at Asn297 is between 20% and 90%, preferably between 20% and 80%, preferably between 20% and 50%, 55%, 60%, 70% or 75%, between 35% and 50%, 55%, 60%, 70% or 75%, or between 45% and 50%, 55%, 60%, 70% or 75%. Preferably the antibody is of human IgGI or IgG3 type.

The sugar chain show can further show any characteristics (e.g. presence and proportion of complex, hybrid and high mannose structures), including the characteristics of N-linked glycans attached to Asn297 of an antibody from a human cell, or of an antibody recombinantly expressed in a rodent cell, murine cell (e.g. CHO cell) or in an avian cell.

In one embodiment, the antibody is expressed in a cell that is lacking in a fucosyltransferase enzyme such that the cell line produces proteins lacking fucose in their core carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their core carbohydrates. These cell lines were created by the targeted disruption of the FUT8 gene in CHO/DG44 cells using two replacement vectors (see U.S. Patent Publication No. 20040110704 by Yamane et al.; and Yamane-Ohnuki et al. (2004) Biotechnol Bioeng 87:614-22, the disclosures of which are incorporated herein by reference). Other examples have included use of antisense suppression, double-stranded RNA (dsRNA) interference, hairpin RNA (hpRNA) interference or intron-containing hairpin RNA (ihpRNA) interference to functionally disrupt the FUT8 gene. In one embodiment, the antibody is expressed in a cell line with a functionally disrupted FUT8 gene, which encodes a fucosyl transferase, such that antibodies expressed in such a cell line exhibit hypofucosylation by reducing or eliminating the alpha 1,6 bond-related enzyme.

In one embodiment, the antibody is expressed in cell lines engineered to express glycoprotem-modifying glycosyl transferases (e.g., beta(I,4)-N-acetylglucosaminyl-transferase III (GnTHI)) such that antibodies expressed in the engineered cell lines exhibit increased bisecting GlcNac structures which results in increased ADCC activity of the antibodies (PCT Publication WO 99/54342 by Umana et al.; and Umana et al. (1999) Nat. Biotech. 17:176-180, the disclosures of which are incorporated herein by reference).

In another embodiment, the antibody is expressed and the fucosyl residue(s) is cleaved using a fucosidase enzyme. For example, the fucosidase alpha-L-fucosidase removes fucosyl residues from antibodies (Tarentino, et al. (1975) Biochem. 14:5516-5523). In other examples, a cell line producing an antibody can be treated with a glycosylation inhibitor; Zhou et al. Biotech. and Bioengin. 99: 652-665 (2008) described treatment of CHO cells with the alpha-mannosidase I inhibitor, kifunensine, resulting in the production of antibodies with non-fucosylated oligomannose-type N-glucans.

In one embodiment, the antibody is expressed in a cell line which naturally has a low enzyme activity for adding fucosyl to the N-acetylglucosamine that binds to the Fc region of the antibody or does not have the enzyme activity, for example the rat myeloma cell line YB2/0 (ATCC CRL 1662). Other example of cell lines include a variant CHO cell line, Led 3 cells, with reduced ability to attach fucosyl to Asn(297)-linked carbohydrates, also resulting in hypofucosylation of antibodies expressed in that host cell (WO 03/035835 (Presta et al); and Shields, R X. et al. (2002) J. Biol. Chem. 277:26733-26740, the disclosures of which are incorporated herein by reference). In another embodiment, the antibody is expressed in an avian cell, preferably a EBx® cell (Vivalis, France) which naturally yields antibodies with low fucose content e.g WO2008/142124. Hypofucosylated glycans can also be produced in cell lines of plant origin, e.g. WO 07/084926A2 (Biolex Inc.), WO 08/006554 (Greenovation Biotech GMBH), the disclosures of which are incorporated herein by reference.

Uses in Diagnostics and Therapy

In certain embodiments, the present antibodies are used to purify or identify MICA positive cells from a biological sample. Biological samples can be obtained from a patient, e.g. for diagnostic or ex vivo therapeutic purposes, or from individuals or non-human primates to obtain a source of such cells for research purposes.

MICA positive cells can be purified or identified using the present antibodies with any of a number of standard methods. For example, peripheral blood cells can be sorted using a FACS scanner using labeled antibodies specific for MICA, and optionally to other cell surface molecules typically present on cells.

In addition, the antibodies of the invention can be conjugated or covalently linked to a solid support and used to purify or identify MICA positive cells or any cells expressing MICA from a biological sample, e.g., from a blood sample or tissue biopsy from a patient or other individual. Specifically, the biological sample is placed into contact with the antibodies under conditions that allow cells within the sample to bind to the antibody, and then the cells are eluted from the solid-support-bound antibody.

Regardless of the method used to isolate, purify or identify the MICA positive cells, the ability to do so is useful for numerous purposes, e.g. to diagnose a disorder characterized by a pathogenic expansion of MICA-expressing cells, by assessing the number or activity or other characteristics of MICA positive cells obtained from a patient, or to evaluate the ability of the antibodies of the invention, or fragments or derivatives thereof, to modulate the activity or behavior of the cells of a patient prior, e.g., to one of the herein-described treatments using the antibodies. Further, purified MICA positive cells are useful in a research context, e.g., to better characterize the cells and their various properties and behaviors, as well as to identify compounds or methods that can be used to modulate their behavior, activity, or proliferation. The antibodies of the invention can also be useful in diagnostic methods, for example in methods of detecting MICA polypeptides on cells, e.g. disease cells from a patient.

The present invention also provides pharmaceutical compositions that comprise an antigen-binding agent (e.g. an antibody) according to the invention which specifically binds to MICA polypeptides on the surface of cells. The antibody preferably inhibits the growth or activity of the cells and/or leads to the elimination of the MICA positive cells, preferably via induction of CDC and/or ADCC. The composition further comprises a pharmaceutically acceptable carrier.

The invention further provides a method of inhibiting the growth or activity of, and/or depleting, MICA-positive cells, in a patient in need thereof, comprising the step of administering to said patient a composition according to the invention. Such treatment methods can be used for a number of disorders, including, but not limited to the treatment of cancers.

As demonstrated herein, non-blocking anti-MICA antibodies are particularly effective at inducing lysis of MICA-expressing cells by effector cells. The antibodies have a dual mode of action, by binding MICA and engaging activating Fcγ receptors on effector cells they induce lysis by effector cells, and by not blocking NKG2D signaling they prevent a neutralization of NKG2D-mediated activation of NK cell reactivity, or by blocking NKG2D signaling and reducing sMICA-induced NKG2D downmodulation. The antibodies preferably comprise human heavy chain constant regions sequences that lead to the depletion of MICA-expression cells (e.g. tumor cells) to which they are bound and preferably comprise an Fc portion that induces CDC and/or ADCC. The composition further comprises a pharmaceutically acceptable carrier. Such compositions are also referred to as "antibody compositions" of the invention. In one embodiment, antibody compositions of this invention comprise an antibody disclosed in the antibody embodiments above.

In one aspect, the methods of treatment of the invention comprise administering to an individual a composition comprising an antigen-binding compound that binds MICA in a therapeutically effective amount. A therapeutically effective amount may be for example an sufficient to cause an increase in the depletion of MICA cells in vivo, or an increase in the frequency of activated, reactive, cytotoxic and/or IFNγ-production of NKG2D+ effector cells (e.g. NK cells) towards MICA-expressing tumor cells.

The methods of the present invention are utilized advantageously for the treatment of cancers and other proliferative diseases including, but not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma. Other exemplary disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In some embodiments, prior to the administration of the anti-MICA antibody or composition, the presence of MICA on cells (e.g. tumor cells) of the patient will be assessed, e.g., to determine the relative level and activity of MICA-positive cells in the patient as well as to confirm the binding efficacy of the antibodies to the cells of the patient. A patient whose tumor cells express MICA can then be treated with an anti-MICA antibody or composition. This can be accomplished by obtaining a sample of PBLs or tumor cells from the site of the disorder, and testing e.g., using immunoassays, to determine the relative prominence of MICA and optionally further other markers on the cells. Other methods can also be used to detect expression of MICA and other genes, such as RNA-based methods, e.g., RT-PCR or Northern blotting.

In one embodiment, where it is sought to inhibit the activity or growth of, or deplete, a patient's MICA-positive cells, the ability of the anti-MICA antibody to inhibit proliferation of or deplete a patient's MICA-positive cells is assessed. If the MICA-positive cells are depleted by the anti-MICA antibody or composition, the patient is determined to be responsive to therapy with an anti-MICA antibody or composition, and optionally the patient is treated with an anti-MICA antibody or composition.

The treatment may involve multiple rounds of antibody or compound administration. For example, following an initial round of administration, the level and/or activity of MICA-expressing cells (e.g., on malignant tumor cells), in the patient will generally be re-measured, and, if still elevated, an additional round of administration can be performed. In this way, multiple rounds of MICA detection and antibody or compound administration can be performed, e.g., until the disorder is brought under control.

In some embodiments, the method may comprise the additional step of administering to said patient an appropriate additional (second) therapeutic agent selected from an immunomodulatory agent, a hormonal agent, a chemotherapeutic agent, or a second antibody (e.g. a depleting antibody) that binds to a polypeptide present on a MICA-expressing cell. Such additional agents can be administered to said patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

For tumor (e.g. solid tumor) treatment, for example, the administration of a composition of the present invention may be used in combination with classical approaches, such as surgery, radiotherapy, chemotherapy, and the like. The invention therefore provides combined therapies in which the present antibodies are used simultaneously with, before, or after surgery or radiation treatment; or are administered to patients with, before, or after conventional chemotherapeutic, radiotherapeutic or anti-angiogenic agents, or targeted immunotoxins or coaguligands.

Exemplary anti-cancer anti-angiogenic agents inhibit signaling by a receptor tyrosine kinase including but not limited to FGFR (fibroblast growth factor receptor, FGF-1,2), PDGFR (platelet derived growth factor receptor), angiopoietins receptors (Ang-1,2), HGFR (hepatocytary growth factor receptor), ephrines receptor (Eph), VEGFR1, VEGFR-2,3 PDGFR-α, PDGFR-β, CSF-1R, MET, Flt-3, c-Kit, bcr/abl, p38 alpha and FGFR-1. Further anti-angiogenic agents may include agents that inhibit one or more of the various regulators of VEGF expression and production, such as EGFR, fit-1, KDR, HER-2, COX-2, or HIF-1α. Another preferred class of agents includes IMiD (immunomodulatory drugs), analogs derived from thalidomide that have a wide range of effects, including both immune and non-immune related effects. Representatives of the IMiD class include CC-5013 (lenalidomide, Revlimid™), CC-4047 (Actimid™), and ENMD-0995. Another class of anti-angiogenic agent includes cilengitide (EMD 121974, integrin inhibitor), metalloproteinases (MPP) such as marinastat (BB-251). Another class of anti-angiogenic agents includes farnesylation inhibitors such as lonafarnib (Sarasar™), tipifarnib (Zarnestra™). Other anti-angiogenic agents can also be suitable such as Bevacuzimab (mAb, inhibiting VEGF-A, Genentech); IMC-1121B (mAb, inhibiting VEGFR-2, ImClone Systems); CDP-791 (Pegylated DiFab, VEGFR-2, Celltech); 2C3 (mAb, VEGF-A, Peregrine Pharmaceuticals); VEGF-trap (Soluble hybrid receptor VEGF-A, PlGF (placenta growth factor) Aventis/Regeneron). Another preferred class of agents includes the tyrosine kinase inhibitor (TKI) class, including, e.g., PTK-787 (TKI, VEGFR-1,-2, Vatalanib, Novartis); AEE788 (TKI, VEGFR-2 and EGFR, Novartis); ZD6474 (TKI, VEGFR-1,-2,-3, EGFR, Zactima, AstraZeneca); AZD2171 (TKI, VEGFR-1,-2, AstraZeneca); SU11248 (TKI, VEGFR-1,-2, PDGFR, Sunitinib, Pfizer); AG13925 (TKI, VEGFR-1,-2, Pfizer); AG013736 (TKI, VEGFR-1,-2, Pfizer); CEP-7055 (TKI, VEGFR-1,-2,-3, Cephalon); CP-547,632 (TKI, VEGFR-1,-2, Pfizer); GW786024 (TKI, VEGFR-1,-2,-3, GlaxoSmithKline); GW786034 (TKI, VEGFR-1,-2,-3, GlaxoSmithKline); sorafenib (TKI, Bay 43-9006, VEGFR-1,-2, PDGFR Bayer/Onyx); SU4312 (TKI, VEGFR, PDGFR, Pfizer), AMG706 (TKI, VEGFR-1,-2,-3, Amgen), XL647 (TKI, EGFR, HER2, VEGFR, ErbB4, Exelixis), XL999 (TKI, FGFR, VEGFR, PDGFR, Flt-3, Exelixis), PKC412 (TKI, KIT, PDGFR, PKC, FLT3, VEGFR-2, Novartis), AEE788 (TKI, EGFR, HER2, VEGFR, Novartis), OSI-930 (TKI, c-kit, VEGFR, OSI Pharmaceuticals), OSI-817 (TKI, c-kit, VEGFR, OSI Pharmaceuticals), DMPQ (TKI, ERGF, PDGFR, erbB2, p56, pkA, pkC), MLN518 (TKI, FLT3, PDGFR, c-KIT, CT53518, Millennium Pharmaceuticals), lestaurinib (TKI, FLT3, CEP-701, Cephalon), ZD1839 (TKI, EGFR, gefitinib, Iressa, AstraZeneca), OSI-774 (TKI, EGFR, Erlotininb, Tarceva, OSI Pharmaceuticals), lapatinib (TKI, ErbB-2, EGFR, GD-2016, Tykerb, GlaxoSmithKline). Most preferred are tyrosine kinase inhibitors that inhibit one or more receptor tyrosine kinases selected from the group consisting of VEGFR-1, VEGFR-2, VEGFR-3, PDGFR-α, β, Flt-3, c-Kit, p38 alpha, MET, c-RAF, b-RAF, bcr/abl and FGFR-1.

In one embodiment, the second agent is a natural ligand of an effector cell (e.g. NK cell) activating receptor or an antibody that binds and activates an NK cell activating receptor other than NKG2D. In one embodiment the agent is an agent that increases the presence of a natural ligand of an NK cell activating receptor other than NKG2D on the surface of a target cell (e.g., infected cells, tumor cells, pro-inflammatory cells). NK cell activating receptors include, for example, natural cytotoxicity receptors such as NKp30, NKp46, NKp44 or activating KIR receptors (KIR2DS receptors, KIR2DS2, KIR2DS4). As used herein, the term "activating NK receptor" refers to any molecule on the surface of NK cells that, when stimulated, causes a measurable increase in any property or activity known in the art as associated with NK activity, such as cytokine (for example IFN-γ and TNF-α production, increases in intracellular free calcium levels, the ability to target cells in a redirected killing assay as described, e.g. elsewhere in the present specification, or the ability to stimulate NK cell proliferation. The term "activating NK receptor" includes but is not limited to activating forms or KIR proteins (for example KIR2DS proteins), NKp30, NKp46, NKp44, NKG2D, IL-2R, IL-12R, IL-15R, IL-18R and IL-21R.

In one embodiment, the anti-cancer agent is a chemotherapeutic agent or radiation that upregulates expression of NKG2D ligands on the surface of tumor cells. This includes well known chemotherapies including ionizing and UV radiation, inhibitors of DNA replication, inhibitors of DNA polymerase, chromatin modifying treatments, as well as apoptosis inducing agents such as HDAC inhibitors trichostatin A and valproic acid. Preferred therapies are those that activate the DNA damage response pathway, more preferably those that activate the ATM (ataxia telangiectasia, mutated) or ATR (ATM- and Rad3-related) protein kinases, or CHK1, or yet further CHK2 or p53. Examples of the latter include ionizing radiation, inhibitors of DNA replication, DNA polymerase inhibitors and chromatic modifying agents or treatment including HDAC inhibitors. Compositions that upregulate NKG2D ligands are further described in Gasser et al (2005) *Nature* 436(7054):1186-90. NKG2D is an activating receptor that interacts with the MHC class I-related MICA and MICB glycoproteins, among other ligands. MICA and MICB (Bauer et al. (1999) *Science* 285:727-729, the disclosure of which is incorporated herein by reference) have no role in antigen presentation, are generally only found in intestinal epithelium, and can be stress-induced in permissive types of cells by viral and bacterial infections, malignant transformation, and proliferation. NKG2D is a C-type lectin-like activating receptor that signals through the associated DAP10 adaptor protein, which is similar to CD28. It is expressed on most natural killer (NK) cells, NKT cells, γδ T cells CD8 T cells, and T cells, but not, in general, on CD4 T cells. Other NKG2D ligands include ULBP proteins, e.g., ULBP-1, -2, and -3, originally identified as ligands for the human cytomegalovirus glycoprotein UL16 (Cosman et al, (2001) *Immunity* 14: 123-133, the disclosure of which is incorporated herein by reference). Further NKG2D ligands include RAE1TG, a member of the ULBP-like family of proteins (Bacon et al (2004) *J. Immunol.* 173:1078-1084).

Further anti-cancer agents include alkylating agents, cytotoxic antibiotics such as topoisomerase I inhibitors, topoisomerase II inhibitors, plant derivatives, RNA/DNA antimetabolites, and antimitotic agents. Preferred examples may include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, taxol, gemcitabine, navelbine, transplatinum, 5-fluorouracil, vincristin, vinblastin and methotrexate, or any analog or derivative variant of the foregoing.

Alkylating agents are substances that form compounds that are highly chemically reactive and rapidly form covalent bonds with suitable substances. One such target is DNA, not in its normal state but when the double helix has been unpaired by helicases. This exposes the 'inside' of the DNA, which is susceptible to alkylation. Most alkylating agents are bipolar, i.e., they contain two groups capable of reacting with DNA. They can thus form 'bridges' between two parts of a single strand of DNA or two separate strands; either way, this interferes with the actions of the enzymes involved with the replication process, which are unable to complete their effects. The cell then either dies because it is physically unable to divide or because the abnormal DNA stimulates apoptosis. Examples include nitrogen mustards (e.g. chlorambucil, cyclophosphamide), nitrosureas (e.g. carmustine, lomustine), metal salts (e.g. cisplatin, carboplatin, oxaliplatin), ethylenamine derivatives (e.g. thiotepa), alkyl sulphonates (e.g. busulphan) and triazenes (e.g. dacarbazine).

Antimetabolites are a group of chemicals that are similar in structure or function to naturally occurring metabolites required for the synthesis of nucleic acids. Antimetabolite molecules mimic these normal metabolites and either block the enzymes responsible for nucleic acid synthesis or become incorporated into DNA, which produces an incorrect genetic code and leads to apoptosis. There are three main classes of antimetabolites. Folate is a substance that is necessary for the synthesis of purine molecules. Folate analogues (e.g. methotrexate, raltritrexed) are similar to the folate molecule—substances such as methotrexate can be used to inhibit the enzyme dihydrofolate reductase, resulting in insufficient production of the purine thymine. Pyrimidine analogues (e.g. cytarabine, fluoroacil (5-FU), gemcitabine) resemble pyrimidine molecules and work by either inhibiting the synthesis of nucleic acids (e.g. fluorouracil) or by becoming incorporated into DNA (e.g. cytarabine). Purine analogues (e.g. mercaptopurine, thioguanine, cladribine, fludarabine) work in similar ways to pyrimidine analogues, but may have additional (and ill-characterized) mechanisms of action.

Cytotoxic antibiotics are so called because they are all derived from a natural source, the *Streptomyces* group of bacteria. They affect the function and synthesis of nucleic acids in different ways. The anthracycline group includes doxorubicin, daunorubicin and idarubicin. They intercalate with DNA and affect the topoisomerase II enzyme. This DNA gyrase splits the DNA double helix and reconnects it once torsional forces have been relieved; the anthracyclines stabilize the DNA-topoisomerase II complex and thus prevent reconnection of the strands. Dactinomycin and mitoxantrone have a similar mechanism of action. Bleomycin causes fragmentation of DNA chains. Mitomycin functions similar to the alkylating agents, causing DNA cross-linkage.

Plant derivatives include the vinca alkaloids such as vincristine and vinblastine bind to precursors of microtubules, preventing their formation. This inhibits the process of mitosis. The taxanes (paclitaxel and docetaxel) also act on microtubules. They stabilize them in their polymerized state, which also causes the arrest of mitosis. Podophyllyum derivatives such as etoposide and teniposide are thought to inhibit topoisomerase II, while irinotecan and topotecan inhibit topoisomerase I.

When infectious diseases are treated, the treatment may employ a composition according to the invention, either alone or in combination with other treatments and/or therapeutic agents known for treating such diseases, including anti-viral agents, anti-fungal agents, antibacterial agents, antibiotics, anti-parasitic agents and anti-protozoal agents. When these methods involve additional treatments with additional therapeutic agents, those agents may be administered together with the antibodies of this invention as either a single dosage form or as separate, multiple dosage forms. When administered as a separate dosage form, the additional agent may be administered prior to, simultaneously with, of following administration of the antibody of this invention.

The methods and antibodies of the present invention, particularly non-depleting antibodies that block the interaction between MICA and NKG2D and/or inhibit MICA-induced NKG2D activity, can also be utilized advantageously for the treatment of inflammatory and autoimmune disorders. Exemplary autoimmune or inflammatory conditions or disorders to be treated with the polypeptides, antibodies and other compounds of the invention, include, but are not limited to systemic lupus erythematosis, rheumatoid arthritis, juvenile chronic arthritis, psoriatic arthritis, osteoarthritis, spondyloarthropathies (ankylosing spondylitis), systemic sclerosis (scleroderma), idiopathic inflammatory myopathies (dermatomyositis, polymyositis), Sjogren's syndrome, vasculitis, systemic vasculitis, temporal arteritis, atherosclerosis, sarcoidosis, myasthenia gravis, autoimmune hemolytic anemia (immune pancytopenia, paroxysmal nocturnal hemoglobinuria), pernicious anemia, autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis, autoimmune oophiritis), autoimmune orchitis, autoimmune uveitis, anti-phospholipid syndrome, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B. C, D, E and other non-hepatotropic viruses), autoimmune chronic active hepatitis, viral hepatitis, primary biliary cirrhosis, granulomatous hepatitis, Wegener's granulomatosis, Behcet's disease, and sclerosing cholangitis, inflammatory bowel diseases such as ulcerative colitis or Crohn's disease, celiac disease, gluten-sensitive enteropathy, and Whipple's disease, autoimmune or immune-mediated skin diseases including bullous skin diseases, erythema multiforme and contact dermatitis, dermitis herpetiformis, psoriasis, pemphigus vulgaris, vitiligo (leukoderma), allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, chronic obstructive pulmonary disease, and transplantation associated diseases including graft rejection and graft-versus-host-disease.

When inflammatory or autoimmune diseases are treated with anti-MICA antibody, the treatment methods this invention may further comprise treating an individual with a second therapeutic agent, including agents normally utilized for the particular therapeutic purpose for which the antibody is being administered. The second therapeutic agent will normally be administered in amounts typically used for that agent in a monotherapy for the particular disease or condition being treated. In one embodiment, the second therapeutic agent is administered in a dose less than the generally accepted efficacious dose; for example, in various embodiments, the composition comprises a dosage that is less than about 10% to 75% of the generally accepted efficacious dose is administered. Preferably, the second therapeutic agent is an agent that reduces proteolytic enzymes, an inflammatory mediator, or a proinflammatory cytokine such as TNF-α and/or interleukin-1 (IL-1). Preferably, the second therapeutic agent is DMARD or a DMD, optionally further wherein the second therapeutic agent is methotrexate (Rheumatrex™, Trexall™), hydroxychloroquine (Plaquenil™), sulfasalazine (Azulfidine®), leflunomide (Arava™), a tumor necrosis factor inhibitor (e.g. a soluble TNFα receptor such as etanercept (Enbrel®), a neutralizing (preferably non-depleting) anti-TNFα antibody such as adalimumab (Humira™) or Certolizumab pegol (Cimzia™)), a T-cell costimulatory blocking agent (e.g. abatacept (Orencia™)), an interleukin-1 (IL-1) receptor antagonist therapy (anakinra (Kineret™)), an anti-BlyS antibody (Benlysta™), a proteosome inhibitor (e.g. bortezomib), a tyrosine kinase inhibitor, intramuscular gold, or another immunomodulatory or cytotoxic agent (e.g. azathioprine (Imuran™), cyclophosphamide, cyclosporine A (Neoral™, Sandimmune™)) or a kinase inhibitor (e.g. a SYK kinase inhibitor such as fostimatinib (R788) or a JAK1, JAK2 inhibitors such as INCB28050, tanezumab or tasocitinib (CP-690,550)).

In the treatment methods of the invention, the antigen-binding compound of the invention and the second therapeutic agent can be administered separately, together or sequentially, or in a cocktail. In some embodiments, the antigen-binding compound of the invention is administered prior to the administration of the second therapeutic agent. For example, the antigen-binding compound of the invention can be administered approximately 0 to 30 days prior to the administration of the second therapeutic agent. In some embodiments, an antigen-binding compound of the invention is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, an antigen-binding compound of the invention is administered concurrently with the administration of the therapeutic agents. In some embodiments, an antigen-binding compound of the invention is administered after the administration of the second therapeutic agent. For example, an antigen-binding compound of the invention can be administered approximately 0 to 30 days after the administration of the second therapeutic agent. In some embodiments, an antigen-binding compound of the invention is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

The antigen-binding compounds of the invention can be included in kits. The kits may optionally further contain any number of antibodies and/or other compounds, e.g., 1, 2, 3, 4, or any other number of anti-MICA antibodies and/or other compounds. It will be appreciated that this description of the contents of the kits is not limiting in any way. For example, the kit may contain other types of therapeutic or diagnostic agents. Preferably, the kits also include instructions for using the antibodies and/or agents, e.g., detailing the herein-described methods.

Pharmaceutical Formulations

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies of this invention may be employed in a method of modulating, e.g. inhibiting, the activity of MICA-expressing cells in a patient. This method comprises the step of contacting said composition with said patient. Such method will be useful for both prophylaxis and therapeutic purposes.

For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. The antibody can be present in a single dose in an amount, for example, of between about 25 mg and 500 mg.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The present antibodies can be included in kits. The kits may optionally further contain any number of antibodies and/or other compounds, e.g., 1, 2, 3, 4, or any other number of therapeutic antibodies and/or compounds. It will be appreciated that this description of the contents of the kits is not limiting in any way. For example, the kit may contain other types of therapeutic compounds. Preferably, the kits also include instructions for using the antibodies, e.g., detailing the herein-described methods.

Dosage forms Therapeutic formulations of the antagonists used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.), The Pharmacological Bases of Therapeutics, 8$^{th}$ Ed. (Pergamon Press, 1990); Gennaro (ed.), Remington's Pharmaceutical Sciences, 18$^{th}$ Edition (Mack Publishing Co., Easton, Pa., 1990); Avis et al. (eds.), Pharmaceutical Dosage Forms: Parenteral Medications (Dekker, New York, 1993); Lieberman et al. (eds.), Pharmaceutical Dosage Forms: Tablets (Dekker, New York, 1990); Lieberman et al. (eds.) Pharmaceutical Dosage Forms: Disperse Systems (Dekker, New York, 1990); and Walters (ed.), Dermatological and Transdermal Formulations (Drugs and the Pharmaceutical Sciences), Vol 119 (Dekker, New York, 2002).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as ethylenediaminetetraacetic acid (EDTA); sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or PEG.

Exemplary antibody formulations are described for instance in WO 1998/56418, which describes a liquid multidose formulation for an anti-CD20 antibody, comprising 40 mg/mL rituximab, 25 mM acetate, 150 mM trehalose, 0.9% benzyl alcohol, and 0.02% polysorbate20™ at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate80™, and Sterile Water for Injection, pH 6.5.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

The formulation herein may also contain more than one active compound (a second medicament as noted above), preferably those with complementary activities that do not adversely affect each other. The type and effective amounts of such medicaments depend, for example, on the amount and type of B-cell antagonist present in the formulation, and clinical parameters of the subjects. The preferred such second medicaments are noted above.

The active ingredients may also be entrapped in microcapsules prepared, e.g., by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra, for example.

Sustained-release formulations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Further aspects and advantages of this invention will be disclosed in the following experimental section, which should be regarded as illustrative and not limiting the scope of this application.

EXAMPLES

Example 1: Generation of Anti-MICA Antibodies

Immunization #1

To obtain anti-human MICA antibodies, Balb/c mice were immunized with a recombinant human MICA extracellular domain recombinant-Fc protein (MICA*019 allele, available from R&D Systems). Mice received one primo-immunization with an emulsion of 50 µg MICA protein and Complete Freund Adjuvant, intraperitoneally, a $2^{nd}$ immunization with an emulsion of 50 µg MICA protein and Incomplete Freund Adjuvant, intraperitoneally, and finally a boost with 10 µg MICA protein, intravenously. Immune spleen cells were fused 3 days after the boost with X63.Ag8.653 immortalized B cells, and cultured in the presence of irradiated spleen cells.

Primary screen: Supernatant (SN) of growing clones were tested in a primary screen by flow cytometry using Baf/3 cell line transfected with a MICA*019 construct. Positive supernatants were selected and tested for lack of binding by flow cytometry to untransfected Baf/3 cell line. Briefly, for FACS screening, the presence of reacting antibodies in supernanants was revealed by Goat anti-mouse polyclonal antibody (pAb) labeled with PE.

Secondary screen: Supernatants of the clones were also tested using an ELISA assay to assess the capacity to block the interaction between MICA extracellular domain recombinant-Fc protein (R&D Systems) and NKG2D extracellular domain recombinant-Fc protein. Potentially interesting hybridomas selected from the initial screening were cloned by limiting dilution techniques in 96-wells plates. The resulting antibodies supernatant 9C10 of IgG2b isotype and 6E4, 20C6 and 19E9 of IgG1 isotype were obtained.

Immunization #2

To obtain anti-human MICA antibodies, Balb/c mice were immunized with a recombinant human MICA extracellular domain recombinant-His protein (MICA*001 allele). Mice received one primo-immunization with an emulsion of 50 µg MICA protein and Complete Freund Adjuvant, intraperitoneally, a $2^{nd}$ immunization with an emulsion of 50 µg MICA protein and Incomplete Freund Adjuvant, intraperitoneally, and one boost with 10 µg MICA protein, intravenously. Immune spleen cells were fused with X63.Ag8.653 immortalized B cells, and cultured in the presence of irradiated spleen cells.

Primary screen: Supernatant (SN) of growing clones were tested in a primary screen by flow cytometry using a mixture of cells of different C1R-based cell lines, wherein each cell line was transfected with a different construct (either MICA*001, MICA*004, MICA*007 or MICA*008). Briefly, for FACS screening, the presence of reacting antibodies in supernanants was revealed by Goat anti-mouse polyclonal antibody (pAb) labeled with PE.

Secondary screen: Supernatants of the clones were also tested using an ELISA assay to assess the capacity to bind MICA extracellular domain α3 recombinant protein without binding to recombinant human MICA full extracellular domain recombinant-His protein (MICA*001 allele). Potentially interesting hybridomas selected from the initial screening were cloned by limiting dilution techniques in 96-wells plates.

MICA extracellular domain α3 antibodies were obtained, including clone 16A8 of IgG2a isotype.

Immunization #3

To obtain anti-human MICA antibodies, Balb/c mice were immunized with a mix of 10 millions C1R cells transfected with MICA*01, MICA*04, MICA*07 or MICA*08 at a 1:1:1:1 ratio (2.5 millions of each transfectant cells). Mice received one primo-immunization with a total of 10 millions transfectant cells and Complete Freund Adjuvant, intraperitoneally, a $2^{nd}$ immunization with 10 millions transfectants cells (2.5 millions of each transfectant cells) and Incomplete Freund Adjuvant, intraperitoneally, and one boost with 1 million transfectant cells (0.25 million of each transfectant cells), intravenously. Immune spleen cells were fused with X63.Ag8.653 immortalized B cells, and cultured in the presence of irradiated spleen cells.

Primary screen: Supernatant (SN) of growing clones were tested in a primary screen by flow cytometry using a mixture of cells of different C1R-based cell lines and Baf/3 cell line, wherein each cell line was transfected with a different construct (either MICA*001, MICA*004, MICA*007 or MICA*008 for C1R and MICA*019 for Baf/3). Briefly, for FACS screening, the presence of reacting antibodies in supernanants was revealed by Goat anti-mouse polyclonal antibody (pAb) labeled with PE.

Secondary screen: Supernatants of the clones were also tested using an ELISA assay to assess the capacity to bind MICA extracellular domain α3 recombinant protein without binding to recombinant human MICA full extracellular domain recombinant-Fc protein (MICA*019 allele). Potentially interesting hybridomas selected from the initial screening were cloned by limiting dilution techniques in 96-wells plates.

The resulting antibodies supernatant 12A10, 10A7, 18E8, 10F3 and 15F9 of IgG1 isotype and 14B4 of IgM isotype were obtained.

Antibodies 9C10, 19E9, 6E4, 20C6, 16A8, 12A10, 10A7, 18E8, 10F3, 15F9 and 14B4 were subsequently chimerized to human IgG1 isotype (also referred to as CHG1-M-MIA-9C10, CHG1-M-MIA-19E9, CHG1-M-MIA-6E4, CHG1-M-MIA-20C6, CHG1-M-MIA-16A8, CHG1-M-MIA-12A10, CHG1-M-MIA-10A7, CHG1-M-MIA-18E8, CHG1-M-MIA-10F3, CHG1-M-MIA-15F9 and CHG1-M-MIA-14B4 respectively).

Example 2—Binding to Immobilized MICA Proteins

The binding of 6E4, 20C6 and 16A8 to either recombinant human MICA extracellular domain recombinant protein monomers or dimers (MICA*019 allele-Fc protein or MICA*001-His protein) as well as other NKG2D ligands MICB and ULBP1-2 was analyzed by Surface Plasmon Resonance (SPR) using a T100 BIACORE™ SPR analytical apparatus to obtain monovalent and bivalent affinity, respectively.

For protein immobilization, recombinant proteins: MICA-Fc MICB-Fc (R&D Systems 1599-MB, Accession no. CAI18747, SEQ ID NO: 6), ULBP1-Fc, ULBP2-Fc were immobilized covalently to carboxyl groups in the dextran layer on a Sensor Chip CM5 (chip). The chip surface was activated with EDC/NHS (N-ethyl-N'-(3-dimethylaminopropyl) carbodiimidehydrochloride and N-hydroxysuccinimide (Biacore GE Healthcare)). Proteins were diluted to 10 µg/ml in coupling buffer (10 mM acetate, pH 5.6) and injected until the appropriate immobilization level was reached (i.e. 1000 to 1600 RU for binding study). Deactivation of the remaining activated groups was performed using 100 mM ethanolamine pH 8 (BIACORE™, GE Healthcare).

Antibody binding analysis was run using HBS-EP+ (neutral pH). The anti-MICA antibodies (diluted at a concentration of 10 µg/ml in the running buffer), were injected for 2 min at a constant flow rate of 10 µl/min on dextran layers containing immobilized recombinant target proteins and allowed to dissociate for 2 min before regeneration by a ten second injection of 10 mM NaOH, 500 mM NaCl regeneration buffer at a flow rate of 40 µl/min.

For bivalent affinity measurement, MICA-His protein was immobilized via $Ni^{2+}$/NTA chelation on a Sensor Chip NTA (carboxymethylated dextran pre-immobilized with nitrilotriacetic acid (NTA)). Anti-MICA antibodies were diluted to a concentration series (0.01 to 100 nM) in the running buffer HBS-P and injected over the immobilized antigen.

Each cycle consisted of three steps. Firstly, the NTA chip was activated with $NiSO_4$ (500 mM). Secondly, the MICA-His protein (diluted to 10 µg/ml in running buffer HBS-P) was immobilized onto the surface via a 2 min injection at a constant flowrate of 10 µL/min. Then the antibody was injected over the immobilized antigen for 2 min at the flow rate of 40 µl/min. Subsequently, the running buffer was injected for 5 min at 40 µl/min for antibody dissociation analysis. After each cycle, the surface was regenerated by a 60s injection of 0.5M EDTA, pH 8.3 to completely strip the surface of the remaining antigen and antibody. The resulting sensorgrams were analyzed by global fitting using the appropriate model.

For monovalent affinity measurement, chimeric anti-MICA antibodies were captured onto a Protein-G chip.

Affinities were determined using single cycle kinetics (SCK). SCK cycles were as follows: Successive 120s injections at 30 l/min of 5 serial dilutions (0.01 to 100 nM) of MICA-His or MICA-BirA in ascending order (or of buffer for the blank injections to be subtracted during the analysis). After the last concentration is injected, complex is left to dissociate for 600s before regeneration by a 10s injection of appropriate regeneration buffer at 40 µl/min. After the regeneration, chip is left to stabilise for 60s in running buffer. Curves are fitted using BIACORE™ T100 Evaluation software.

The bivalent mean $K_D$ (M) at pH 7.4 for MICA binding for biotin-conjugated mouse antibody 6E4 (on MICA*001-His) was $3.099^{-11}$ M), while the monovalent affinity was $2.0*10^{-9}$ M. The bivalent mean $K_D$ (M) at pH 7.4 for biotin-conjugated mouse antibody 20C6 (on MICA*001-His) was $3.3*10^{-10}$ M, while the monovalent affinity was $6.5*10^{-9}$ M.

The bivalent mean $K_D$ (M) at pH 7.4 for MICA binding for biotin-conjugated mouse antibody 9C10 (on MICA*001-His) was $6.2*10^{-13}$ M. The bivalent mean $K_D$ (M) at pH 7.4 for MICA binding for biotin-conjugated mouse antibody 19E9 (on MICA*001-His) was $3.2*10^{-13}$ M, while the monovalent affinity was $7.8*10^{-10}$ M.

The monovalent affinity (mean KD) at pH7.4 on MICA-BirA for CHG1-M-MIA-19E9 antibody was $6.5*10^{-9}$ M (n=3)

The monovalent affinity (mean KD) at pH7.4 on MICA-BirA for CHG1-M-MIA-20C6 antibody was $4*10^{-8}$ M (n=3)

The monovalent affinity (mean KD) at pH7.4 on MICA-BirA for CHG1-M-MIA-6E4 antibody was $8.9*10^{-9}$ M (n=4)

The monovalent affinity (mean KD) at pH7.4 on MICA-BirA for CHG1-M-MIA2-16A8 antibody was $1.15*10^{-8}$ M (n=4)

The monovalent affinity (mean KD) at pH7.4 on MICA-BirA for CHG1-M-MIA-15F9 antibody was $6.1*10^{-8}$ M (n=1)

The monovalent affinity (mean KD) at pH7.4 on MICA-BirA for CHG1-M-MIA-12A10 antibody was $5.3*10^{-8}$ M (n=1)

The monovalent affinity (mean KD) at pH7.4 on MICA-BirA for CHG1-M-MIA-18E8 antibody was $5.4*10^{-8}$ M (n=1)

The monovalent affinity (mean KD) at pH7.4 on MICA-BirA for CHG1-M-MIA-10F3 antibody was $8.3*10^{-9}$ M (n=1)

Example 3—Binding to MICA Alleles

The binding of antibodies obtained from the first, second and third immunization series (including CHG1-M-MIA-19E9, CHG1-M-MIA-9C10, CHG1-M-MIA-6E4, CHG1-M-MIA-20C6, CHG1-M-MIA-16A8, CHG1-M-MIA-12A10, CHG1-M-MIA-10A7, CHG1-M-MIA-18E8, CHG1-M-MIA-10F3, CHG1-M-MIA-15F9 and CHG1-M-MIA-14B4) were tested for binding to MICA-expressing CR1 transfectant cells C1R-MICA*001, C1R-MICA*004, C1R-MICA*007 and C1R-MICA*008 (Pr. A. Steinle, Eberhard-Karls University Tuebingen, Germany) described in Salih et al. (2003) Blood 102(4): 1389-91396. Binding was analyzed by flow cytometry.

Flow Cytometry.

Cells were harvested and stained in PBS 1×/BSA 0.2%/EDTA 2 mM buffer during 30 minutes at 4° C. using a dose-range of the anti-MICA mAbs. After two washes in staining buffer, cells were stained for 30 min at 4° C. with mouse anti-human IgG1-PE monoclonal antibodies (1/11). After two washes, stainings were acquired on a BD FACS Canto II and analyzed using the FlowJo software.

Results.

Figure 1B:
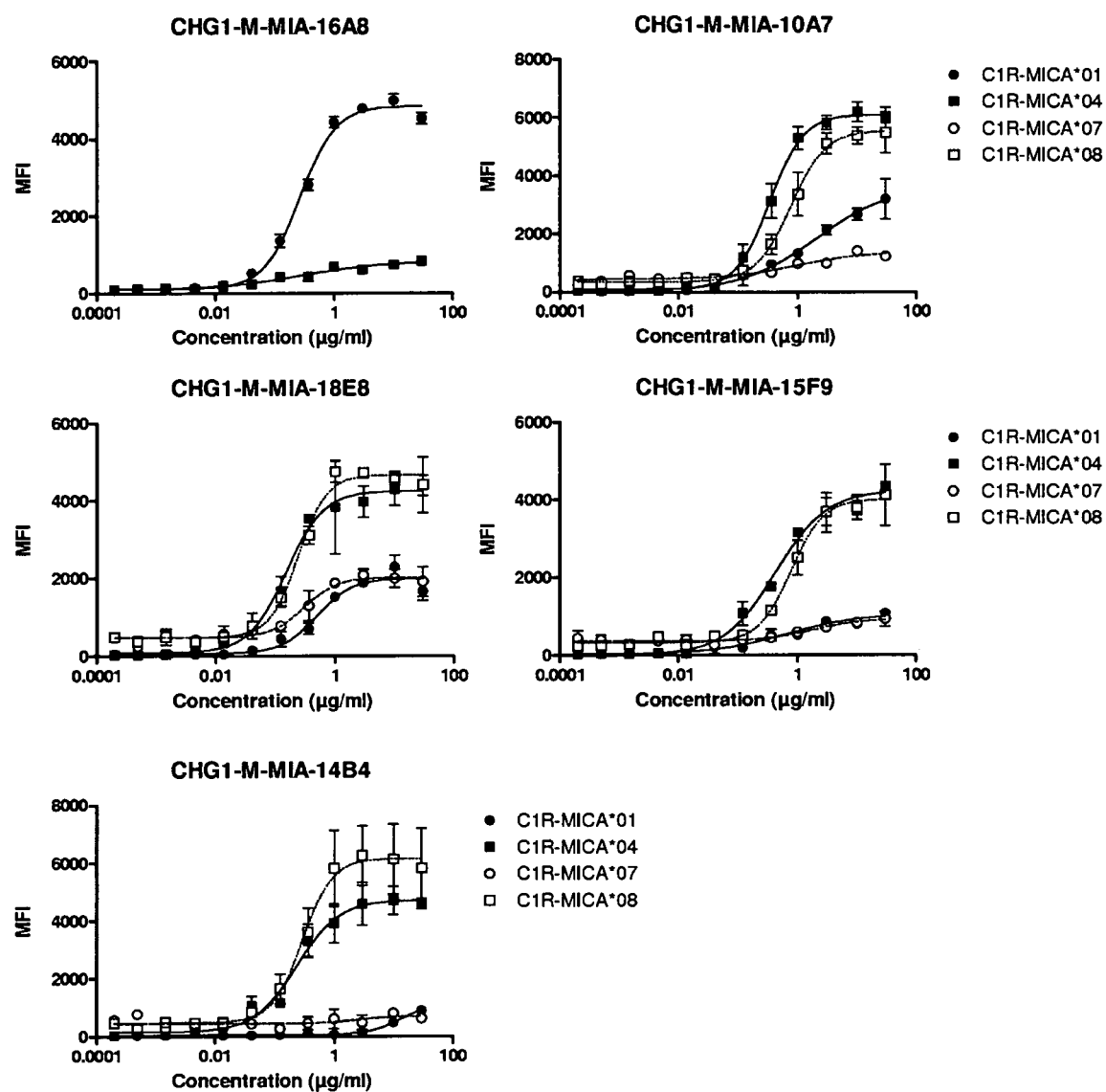

Antibodies CHG1-M-MIA-19E9, CHG1-M-MIA-9C10, CHG1-M-MIA-6E4, CHG1-M-MIA-20C6, CHG1-M-MIA-12A10, CHG1-M-MIA-10A7, CHG1-M-MIA-18E8, CHG1-M-MIA-10F3, and CHG1-M-MIA-15F9 bound to each of the C1R-MICA*001, C1R-MICA*004, C1R-MICA*007 and C1R-MICA*008 cells (see FIG. 1A for antibodies CHG1-M-MIA-19E9, CHG1-M-MIA-9C10, CHG1-M-MIA-6E4, CHG1-M-MIA-20C6, CHG1-M-MIA-12A10, CHG1-M-MIA-10F3, and FIG. 1B for antibodies, CHG1-M-MIA-18E8, CHG1-M-MIA-15F9, CHG1-M-MIA-10A7). However other antibodies tested were allele specific and did not recognize all of MICA*001,*004, *007 and *008. As an example of antibodies that do not recognize all of tested MICA alleles, two anti-alpha3 domain antibodies, CHG1-M-MIA-16A8 and CHG1-M-MIA-14B4 are shown in FIG. 1B. EC50 values are shown in Table C in µg/ml (calculated using a 4-parameter logistic fit).

TABLE C

EC50 values in µg/ml of indicated chimeric anti-MICA antibodies on C1R transfectant cells

| | C1R-MICA*01 | C1R-MICA*04 | C1R-MICA*07 | C1R-MICA*08 |
|---|---|---|---|---|
| CHG1-M-MIA-9C10 | 2.09 | 0.13 | 2.83 | 0.13 |
| CHG1-M-MIA-12A10 | 1.30 | 0.26 | 1.43 | 0.25 |
| CHG1-M-MIA-19E9 | 1.40 | 0.04 | 0.23 | 0.07 |
| CHG1-M-MIA-18E8 | 0.50 | 0.15 | 0.30 | 0.24 |
| CHG1-M-MIA-10F3 | 0.47 | 0.17 | 0.94 | 0.26 |
| CHG1-M-MIA-15F9 | 0.68 | 0.43 | 1.81 | 0.79 |
| CHG1-M-MIA-6E4 | 1.96 | 2.67 | 1.23 | |
| CHG1-M-MIA-20C6 | 0.26 | 0.05 | 0.40 | 0.13 |
| CHG1-M-MIA-10A7 | 2.03 | 0.34 | 0.97 | 0.77 |
| CHG1-M-MIA-16A8 | 1.07 | 0.44 | | |
| CHG1-M-MIA-14B4 | 12.7 | 0.24 | | 0.30 |

Example 4—Epitope Mapping

Antibodies were further tested for binding to various MICA*001 mutants. MICA mutants were generated by PCR (see Table D below). All the Mx-R primers were used with the following 5' primer TACGACTCACAAGCTTACCGC-CACCATGGGGCT GGGACCGGTCTTC (SEQ ID NO: 135). All the Mx-F primers were used with the following 3' primer CCGCCCCGACTCTAGATTACTAGGCGC-CCTCAGTGGAGC (SEQ ID NO: 136). The sequences amplified were run on agarose gel then purified using the Macherey Nagel PCR Clean-Up Gel Extraction kit (reference 740609). To create mutant 3, it was necessary to do a third PCR. Primers used for these PCR were M3a-F primer (5'-ACGGTGCTGTCCGCGGATGGATCTGTGCA-GTCAG-3') (SEQ ID NO: 137) with the M3b-R primer (5'-CCTGCTTTCTGGTCCTTGATATGAGCCAGGGTC-3') (SEQ ID NO: 138). The two or three PCR products generated for each mutant were then ligated into a SELEXIS pSUREtech 192 (HYGRO) vector, digested with the restriction enzyme HindIII and XBaI, with the ClonTech InFusion system (reference 639644) according to the manufacturer's instructions.

After sequencing, the vectors containing the mutated sequences were prepared as Miniprep using the Promega PureYield™ Plasmid Miniprep System (reference A1222). Vectors were then used for CHOK1SV cell transfection using OZ BIOSCIENCES's HYPE-5TM Transfection Kit (reference HYR10003) according to the manufacturer instructions. Transfection were performed using 300 ng of DNA at 1:8 ratio HYPE-5:DNA.

TABLE D

MICA*001 mutant list with targeted amino acid and primers sequences used to generate mutant

| Mutants | Reverse primers | Forward primers |
|---|---|---|
| Number 1 R6A + N8A | M1-R 5' - AGGGCATAAGCAAGACTGTGGGGCTCAGC AGCAG- 3' (SEQ ID NO: 139) | M1-F 5' - TCTTGCTTATGCCCTCACGGTGCTGTCCTG GGATG- 3' (SEQ ID NO: 140) |
| Number 2 L12A + Q19A | M2-R 5' - ACGCCACAGATCCATCCCAGGACGCCACC GTGAG- 3' (SEQ ID NO: 141) | M2-F 5' - ATGGATCTGTGGCGTCAGGGTTTCTCACTG AGG- 3' (SEQ ID NO: 142) |
| Number 3 W14A + E85A | M3a-R 5' - CGCGGACAGCACCGTGAGGTTATAACGAA GACTGTG- 3' (SEQ ID NO: 143) | M3b-F 5' - GGACCAGAAAGCAGGCTTGCATTCCCTACA GGAG- 3' (SEQ ID NO: 144) |
| Number 4 D15A +30 S17A | M4-R 5' - CTCCAGCCCAGGACAGCACCGTGAGGTTA TAACGA- 3' (SEQ ID NO: 145) | M4-F 5' - TGTCCTGGGCTGGAGCTGTGCAGTCAGGGT TTCTC- 3' (SEQ ID NO: 146) |
| Number 5 S20A | M5-R 5' - AGTGAGAAACCCTGCCTGCACAGATCCAT CCCAGGACA- 3' (SEQ ID NO: 147) | M5-F 5' - GCAGGGTTTCTCACTGAGGTACATCTGGAT GGTCA- 3' (SEQ ID NO: 148) |
| Number 6 E25A + H27A + P32A | M6-R 5' - CCAGAGCTACCGCAGTGAGAAACCCTGAC TGCAC- 3' (SEQ ID NO: 149) | M6-F 5' - CTGCGGTAGCTCTGGATGGTCAGGCCTTCC TGCG- 3' (SEQ ID NO: 150) |
| Number 7 R35A + K44A | M7-R 5' - TGCCTGTCACAGGCCAGGAAGGGCTGACC ATCCAGA- 3' (SEQ ID NO: 151) | M7-F 5' - GGCCTGTGACAGGCAGAAATGCAGGGCAGC GCCCCAGGGA- 3' (SEQ ID NO: 152) |

TABLE D-continued

MICA*001 mutant list with targeted amino acid and primers sequences used to generate mutant

| Mutants | Reverse primers | Forward primers |
| --- | --- | --- |
| Number 8<br>D37A +<br>R38S +<br>Q39A | M8-R<br>5'-<br>CATTTCGCACTGGCACAGCGCAGGAAGGG<br>CTGACCATC- 3' (SEQ ID NO: 153) | M8-F<br>5'-<br>TGCCAGTGCGAAATGCAGGGCAAAGCCCCA<br>GGGACAG- 3' (SEQ ID NO: 154) |
| Number 9<br>K40A +<br>R42A | M9-R<br>5'-<br>CCGCGCATGCCTGCCTGTCACAGCGCAGG<br>AAGG- 3' (SEQ ID NO: 155) | M9-F<br>5'-<br>GGCAGGCATGCGCGGCAAAGCCCCAGGGAC<br>AGTG- 3' (SEQ ID NO: 156) |
| Number 10<br>Q48A +<br>W49S | M10-R<br>5'-<br>TTCTGCCGACGCTCCCTGGGGCTTTGCTC<br>TGCATTTC- 3' (SEQ ID NO: 157) | M10-F<br>5'-<br>GGAGCGTCGGCAGAAGATGTCCTGGGAAAT<br>AAGAC- 3' (SEQ ID NO: 158) |
| Number 11<br>E51S +<br>D52A +<br>V53S +L54 | M11-R<br>5'-<br>CGCGGAAGCTGATGCCCACTGTCCCTGAG<br>AGCTTTG- 3' (SEQ ID NO: 159) | M11-F<br>5'-<br>GCATCAGCTTCCGCGGGAAATAAGACATGG<br>GACAG- 3' (SEQ ID NO: 160) |
| Number 12<br>N56A +<br>K57S +<br>T58A | M12-R<br>5'-<br>TCCCATGCACTAGCTCCCAGGACATCTTC<br>TGCCCAC- 3' (SEQ ID NO: 161) | M12-F<br>5'-<br>AGCTAGTGCATGGGACAGAGAGACCAGAGA<br>CTTGAC- 3' (SEQ ID NO: 162) |
| Number 13<br>R61A +<br>R64A | M13-R<br>5'-<br>CTGCGGTCTCTGCGTcccatgtcttattt<br>cccaggacatc- 3' (SEQ ID NO: 163) | M13-F<br>5'-<br>ACGCAGAGACCGCAGACTTGACAGGGAACG<br>GAAAGGAC- 3' (SEQ ID NO: 164) |
| Number 14<br>K71A | M14-R<br>5'-<br>CTGAGGTCCGCTCCGTTCCCTGTCAAGTC<br>TCTG- 3' (SEQ ID NO: 165) | M14-F<br>5'-<br>CGGAGCGGACCTCAGGATGACCCTGGCTCA<br>TATC- 3' (SEQ ID NO: 166) |
| Number 15<br>R74A +<br>M75S +<br>A78S +H79 | M15-R<br>5'-<br>AGCAGACAGGGTACTCGCGAGGTCCTTTC<br>ACGTTCCCTG- 3' (SEQ ID NO: 167) | M15-F<br>5'-<br>AGTACCCTGTCTGCTATCAAGGACCAGAAA<br>GAAGG- 3' (SEQ ID NO: 168) |
| Number 16<br>K81A +<br>D82A | M16-R<br>5'-<br>TTCTTTCTGGGCCGCGATATGAGCCAGGG<br>TCATC- 3' (SEQ ID NO: 169) | M16-F<br>5'-<br>GCGGCCCAGAAAGAAGGCTTGCATTCCCTC<br>CAG- 3' (SEQ ID NO: 170) |
| Number 17<br>Q83A +<br>K84A | M17-R<br>5'-<br>TGCCGCGTCCTTGATATGAGCCAGGGTCA<br>TCCTGAG- 3' (SEQ ID NO: 171) | M17-F<br>5'-<br>ATCAAGGACGCGGCAGAAGGCTTGCATTCC<br>CTCCAG- 3' (SEQ ID NO: 172) |
| Number 18<br>E97A +<br>H99A | M18-R<br>5'-<br>TCTTCAGCGATCGCACAGACCCTAATCTC<br>CTGGAGG- 3' (SEQ ID NO: 173) | M18-F<br>5'-<br>TGCGATCGCTGAAGACAACAGCACCAGGAG<br>TTCCCAGC- 3'(SEQ ID NO: 174) |
| Number 19<br>E100A +<br>D101S +<br>N102A | M19-R<br>5'-<br>TGGCGGATGCATGGATCTCACAGACCCTA<br>ATCTCC- 3' (SEQ ID NO: 175) | M19-F<br>5'-<br>TCCATGCATCCGCCAGCACCAGGAGCTCCC<br>AGCATTTC- 3' (SEQ ID NO: 176) |
| Number 20<br>S103A +<br>T104S +<br>R105A | M20-R<br>5'-<br>CTCGCGGAGGCGTTGTCTTCATGGATCTC<br>ACAGACC- 3' (SEQ ID NO: 177) | M20-F<br>5'-<br>CAACGCCTCCGCGAGCTCCCAGCATTTCTA<br>CTACG- 3' (SEQ ID NO: 178) |
| Number 21<br>H109A +<br>Y111A +<br>L116A | M21-R<br>5'-<br>GGCGAAAGCCTGGGAGCTCCTGGTGCTGT<br>TGTCTTCATGGATCTCAC- 3' (SEQ ID NO: 179) | M21-F<br>5'-<br>TCCCAGGCTTTCGCCTACGATGGCGAGGCC<br>TTCCTCTCCCAAAACC- 3' (SEQ ID NO: 180) |

TABLE D-continued

MICA*001 mutant list with targeted amino acid and primers sequences used to generate mutant

| Mutants | Reverse primers | Forward primers |
|---|---|---|
| Number 22<br>D113A +<br>E115A | M22-R<br>5' - GCCCCAGCGTAGTAGAAATGCTGGGAGCT CCTGGTGC- 3' (SEQ ID NO: 181) | M22-F<br>5' - CTACTACGCTGGGGCGCTCTTCCTCTCCCA AAACCTG- 3' (SEQ ID NO: 182) |
| Number 23<br>N121A +<br>E123S | M23-R<br>5' - TCGACAGGGCTTGGGAGAGGAAGAGCTCC CCATCG- 3' (SEQ ID NO: 183) | M23-F<br>5' - CCCAAGCCCTGTCGACTAAGGAATGGACAA TGCC- 3' (SEQ ID NO: 184) |
| Number 24<br>T124A +<br>E126A | M24-R<br>5' - TCCATGCCTTAGCCTCCAGGTTTTGGGAG AGGAAG- 3' (SEQ ID NO: 185) | M24-F<br>5' - AGGCTAAGGCATGGACAATGCCCCAGTCCT CCAG- 3' (SEQ ID NO: 186) |
| Number 25<br>T128A +<br>M129S +<br>P130A | M25-R<br>5' - GACTGGGCCGATGCCCATTCCTTAGTCTC CAGGTTTTG- 3' (SEQ ID NO: 187) | M25-F<br>5' - GGCATCGGCCCAGTCCTCCAGAGCTCAGAC CTTG- 3' (SEQ ID NO: 188) |
| Number 26<br>Q131A +<br>S132A +<br>Q136S | M26-R<br>5' - GGAGGCCGCGGGCATTGTCCATTCCTTAG TCTCCAG- 3' (SEQ ID NO: 189) | M26-F<br>5' - ATGCCCGCGGCCTCCAGAGCTTCGACCTTG GCCATGAAC- 3' (SEQ ID NO: 190) |
| Number 27<br>S133A +<br>R134S +<br>T137A | M27-R<br>5' - GCCTGAGCGCTGGCGGATTGTGGCATTGT CCATTCCTTAGTCTCCAG- 3' (SEQ ID NO: 191) | M27-F<br>5' - CGCCAGCGCTCAGGCCTTGGCCATGAACGT CAGG- 3' (SEQ ID NO: 192) |
| Number 28<br>M140S +<br>N141A +<br>R143S<br>+N144A | M28-R<br>5' - GCGGAGGCCGAGGCCAAGGTCTGAGCTCT GGAGG- 3' (SEQ ID NO: 193) | M28-F<br>5' - GGCCTCGGCCTCCGCGAATTTCTTGAAGGA AGATGCC- 3' (SEQ ID NO: 194) |
| Number 29<br>K147S +<br>E148A +<br>D149S | M29-R<br>5' - CAGATGCCGACAAGAAATTCCTGACGTTC ATGG- 3' (SEQ ID NO: 195) | M29-F<br>5' - TCTTGTCGGCATCTGCCATGAAGACCAAGA CACAC- 3' (SEQ ID NO: 196) |
| Number 30<br>A150S +<br>M151A +<br>H156A | M30-R<br>5' - TGTCTTGGTCTTCGCGGAATCTTCCTTCA AGAAATTCCTG- 3' (SEQ ID NO: 197) | M30-F<br>5' - GCGAAGACCAAGACAGCCTATCACGCTATG CATGCAG- 3' (SEQ ID NO: 198) |
| Number 31<br>T153A +<br>K154S +<br>T155A | M31-R<br>5' - ATAGTGTGCCGAGGCCTTCATGGCATCTT CCTTC- 3' (SEQ ID NO: 199) | M31-F<br>5' - GCCTCGGCACACTATCACGCTATGCATGCA GAC- 3' (SEQ ID NO: 200) |
| Number 32<br>H158A +<br>H161S | M32-R<br>5' - CAGACATAGCGGCATAGTGTGTCTTGGTC TTCATGG- 3' (SEQ ID NO: 201) | M32-F<br>5' - ATGCCGCTATGTCTGCAGACTGCCTGCAGG AACTAC- 3' (SEQ ID NO: 202) |
| Number 33<br>A162S +<br>D163A +<br>Q166A | M33-R<br>5' - CGCCAGGCAGGCTGAATGCATAGCGTGAT AGTGTGTC- 3' (SEQ ID NO: 203) | M33-F<br>5' - TCAGCCTGCCTGGCGGAACTACGGCGATAT CTAAAATCC- 3' (SEQ ID NO: 204) |
| Number 34<br>E167A +<br>R169S +<br>R170A | M34-R<br>5' - TATGCCGATAGTGCCTGCAGGCAGTCTGC ATGCATAG- 3' (SEQ ID NO: 205) | M34-F<br>5' - GGCACTATCGGCATATCTAAAATCCGGCGT AGTCCTG- 3' (SEQ ID NO: 206) |
| Number 35<br>L172A +<br>K173S +<br>S174A | M35-R<br>5' - TACGCCGGCTGATGCATATCGCCGTAGTT CCTGC- 3' (SEQ ID NO: 207) | M35-F<br>5' - GCATCAGCCGGCGTAGTCCTGAGGAGAACA GTGC- 3' (SEQ ID NO: 208) |

TABLE D-continued

MICA*001 mutant list with targeted amino acid and primers sequences used to generate mutant

| Mutants | Reverse primers | Forward primers |
|---|---|---|
| Number 36<br>L178A +<br>R179S +<br>R180A | M36-R<br>5' - GCGCTCGCGACTACGCCGGATTTTAGATA TCGCCGTAG- 3' (SEQ ID NO: 209) | M36-F<br>5' - CGTAGTCGCGAGCGCAACAGTGCCTCCCAT GGTGAATGTC- 3' (SEQ ID NO: 210) |
| Number 37<br>P183A +<br>P184A | M37-R<br>5' - TTCACCATGGCGGCCACTGTTCTCCTCAG GACTACGC- 3' (SEQ ID NO: 211) | M37-F<br>5' - GGCCGCCATGGTGAATGTCACCCGCAGCGA GGCCTCAG- 3' (SEQ ID NO: 212) |
| Number 38<br>M185A +<br>V186S +<br>N187A | M38-R<br>5' - CAGCCGACGCGGGGGGCACTGTTCTCCTC AGGACTAC- 3' (SEQ ID NO: 213) | M38-F<br>5' - CCCCCGCGTCGGCTGTCACCCGCAGCGAGG CCTCAGAG- 3' (SEQ ID NO: 214) |
| Number 39<br>R190S +<br>S191A +<br>E192S +<br>A193A | M39-R<br>5' - CCGAGGCGCTGGTGACATTCACCATGGGG GGCACTGTTC- 3' (SEQ ID NO: 215) | M39-F<br>5' - TCACCAGCGCCTCGGCCTCAGAGGGCAACA TTACC 3' (SEQ ID NO: 216) |
| Number 40<br>N197A | M40-R<br>5' - ATGGCGCCCGATGCGGCCTCGCTGCGGGT GACATTC- 3' (SEQ ID NO: 217) | M40-F<br>5' - CGCATCGGGCGCCATTACCGTGACATGCAG GGCTTC- 3' (SEQ ID NO: 218) |
| Number 41<br>R203S +<br>S205A +<br>Q242A | M41-R<br>5' - GCTCAAAGATACCCCATCCTGACGCCAGC TCAGTGTGATATTCCAGGGATAGAAGCCA GCAGCACTGCATGTCACGGTAATG- 3' (SEQ ID NO: 219) | M41-F<br>5' - GGGGTATCTTTGAGCCACGACACCCAGCAG TGGGGGGATGTCCTGCCTGATGGGAATGGA ACCTACGCGACCTGGGTGGCCACCAG- 3' (SEQ ID NO: 220) |
| Number 42<br>W210A +<br>N211S +<br>I212A | M42-R<br>5' - CAGTGTGGCACTCGCGGGATAGAAGCCAG AAGC- 3' (SEQ ID NO: 221) | M42-F<br>5' - GCGAGTGCCACACTGAGCTGGCGTCAGGAT GG- 3' (SEQ ID NO: 222) |
| Number 43<br>R217A +<br>V221A | M43-R<br>5' - AGATGCCCCATCCTGAGCCCAGCTCAGTG TGATATTCCAG- 3' (SEQ ID NO: 223) | M43-F<br>5' - CAGGATGGGGCATCTTTGAGCCACGACACC CAGCAG- 3' (SEQ ID NO: 224) |
| Number 44<br>Q218A +<br>D219A +<br>R256A | M44-R<br>5' - TCCCATCAGGCAGGACATCCCCCCACTGC TGGGTGTCGTGGCTCAAAGATACCCCAGC CGCACGCCAGCTCAGTGTG- 3' (SEQ ID NO: 225) | M44-F<br>5' - TCCTGCCTGATGGGAATGGAACCTACCAGA CCTGGGTGGCCACCAGGATTTGCCAAGGAG AGGAGCAGGCGTTCACCTGCTACATG- 3' (SEQ ID NO: 226) |
| Number 45<br>S224A +<br>H2255 +<br>D226A | M45-R<br>5' - TGGGTGGCGCTGGCCAAAGATACCCCATC CTGAC- 3' (SEQ ID NO: 227) | M45-F<br>5' - GGCCAGCGCCACCCAGCAGTGGGGGGATGT CCTG- 3' (SEQ ID NO: 228) |
| Number 46<br>T227A +<br>Q228S +<br>Q229A | M46-R<br>5' - CCCCCACGCCGAGGCGTCGTGGCTCAAAG ATACC- 3' (SEQ ID NO: 229) | M46-F<br>5' - GCCTCGGCGTGGGGGGATGTCCTGCCTGAT GGGAATG- 3' (SEQ ID NO: 230) |
| Number 47<br>W230A +<br>D232A | M47-R<br>5' - GCCCCCGCCTGCTGGGTGTCGTGGCTCAA AGATACC- 3' (SEQ ID NO: 231) | M47-F<br>5' - CCAGCAGGCGGGGGCTGTCCTGCCTGATGG GAATGG- 3' (SEQ ID NO: 232) |
| Number 48<br>L234A +<br>P235S +<br>D236A | M48-R<br>5' - TCCCAGCAGACGCGACATCCCCCCACTGC TGGGTGTC- 3' (SEQ ID NO: 233) | M48-F<br>5' - TCGCGTCTGCTGGGAATGGAACCTACCAGA CCTGGGTG- 3' (SEQ ID NO: 234) |
| Number 49<br>N238A +<br>Y241A | M49-R<br>5' - CAGGTCTGGGCGGTTCCAGCCCCATCAGG CAGGACA- 3' (SEQ ID NO: 235) | M49-F<br>5' - AACCGCCCAGACCTGGGTTGCCACCAGGAT TTGCCAAG- 3' (SEQ ID NO: 236) |

TABLE D-continued

MICA*001 mutant list with targeted amino acid and primers sequences used to generate mutant

| Mutants | Reverse primers | Forward primers |
|---|---|---|
| Number 50 W244A | M50-R 5'-GTGGCCACCGCGGTCTGGTAGGTTCCATTCCCATC-3' (SEQ ID NO: 237) | M50-F 5'-GACCGCGGTGGCCACCAGGATTTGCCAAGGAGAGGAG-3' (SEQ ID NO: 238) |
| Number 51 R248A | M51-R 5'-GGCAAATCGCGGTGGCCACCCAGGTCTGGTAGGTTC-3' (SEQ ID NO: 239) | M51-F 5'-CCACCGCGATTTGCCAAGGAGAGGAGCAGAGGTTCAC-3' (SEQ ID NO: 240) |
| Number 52 C250A + E253A | M52-R 5'-CCGCTCCTTGGGCAATCCTGGTGGCCACCCAGGTC-3' (SEQ ID NO: 241) | M52-F 5'-TTGCCCAAGGAGCGGAGCAGAGGTTCACCTGCTAC-3' (SEQ ID NO: 242) |
| Number 53 Q251A + E254A | M53-R 5'-GCCTCTCCTGCGCAAATCCTGGTGGCCACCCAGGTC-3' (SEQ ID NO: 243) | M53-F 5'-TTGCGCAGGAGAGGCGCAGAGGTTCACCTGCTAC-3' (SEQ ID NO: 244) |
| Number 54 Q255A | M54-R 5'-GCCTCCTCTCCTTGGCAAATCCTGGTGGCCACCCAG-3' (SEQ ID NO: 245) | M54-F 5'-CCAAGGAGAGGAGGCGAGGTTCACCTGCTACATGG-3' (SEQ ID NO: 246) |
| Number 55 T258A + T269A + P271A | M55-R 5'-TTCCCGCTGTGTTCCATGTAGCAGGCAACCTCTGCTCCTC-3' (SEQ ID NO: 247) | M55-F 5'-GGAACACAGCGGGAATCACAGCGCTCACGCTGTGCCCTCTGGGAAAG-3' (SEQ ID NO: 248) |
| Number 56 Y260A + E262S + H267A | M56-R 5'-GCTGTGTGACATGGCGCAGGTGAACCTCTGCTCCTC-3' (SEQ ID NO: 249) | M56-F 5'-GCCATGTCACACAGCGGGAATGCCAGCACTCACCCTGTGC-3' (SEQ ID NO: 250) |
| Number 57 N266A | M57-R 5'-TGTGAGCCCCGCTGTGTTCCATGTAGCAGGTGAACCTC-3' (SEQ ID NO: 251) | M57-F 5'-ACAGCGGGGCTCACAGCACTCACCCTGTGCCCTCTG-3' (SEQ ID NO: 252) |
| Number 58 W14A | M3a-R 5'-CGCGGACAGCACCGTGAGGTTATAACGAAGACTGTG-3' (SEQ ID NO: 253) | M3a-F 5'-ACGGTGCTGTCCGCGGATGGATCTGTGCAGTCAG-3' (SEQ ID NO: 254) |
| Number 59 E85A | M3b-R 5'-CCTGCTTTCTGGTCCTTGATATGAGCCAGGGTC-3' (SEQ ID NO: 255) | M3b-F 5'-GGACCAGAAAGCAGGCTTGCATTCCCTACAGGAG-3' (SEQ ID NO: 256) |
| Number 60 D113A | M22D113-R 5'-TCCCCAGCGTAGTAGAAATGCTGGGAGCTCCTGGTGC-3' (SEQ ID NO: 257) | M22D113-F 5'-CTACTACGCTGGGGAGCTCTTCCTCTCCCAAAACCTG-3' (SEQ ID NO: 258) |
| Number 61 E115A | M22E115-R 5'-GCCCCATCGTAGTAGAAATGCTGGGAGCTCCTGGTGC-3' (SEQ ID NO: 259) | M22E115-F 5'-CTACTACGATGGGCGCTCTTCCTCTCCCAAAACCTG-3' (SEQ ID NO: 260) |

Antibodies did not show any loss of binding to unmutated wild type MICA but lost binding to one or more mutants, thereby identifying several epitopes.

Antibody 6E4 had loss of binding to mutants 10 and 11 having Q48A, W49S, E51 S, D52A, V53S and L54A substitutions, but did not lose binding to any other mutants. The principal epitope of 6E4 therefore includes one or more of residues Q48 and W49, and/or one or more of residues E51, D52, V53 and L54. These residues are within the α1 domain of MICA (the epitope may further include residues within the α2 or α3 domains).

FIG. 2A shows a view of the MICA polypeptide, including in dark shading the amino acid residues mutated which resulted (in different combinations) in loss of binding by antibodies. The NKG2D binding site is shown at the top of the MICA polypeptide in medium shading (and also in ribbon diagram bound to MICA). It can be seen that 6E4 binds to the α1 domain at the lateral side of MICA away from the NKG2D binding surface, consistent with the finding that 6E4 does not block MICA-NKG2D interactions.

Antibodies 9C10 and 12A10 had loss of binding to mutants 12 and 13 having N56A, K57S, T58A, R61A and R64A substitutions, but did not lose binding to any other mutants. The principal epitope of 9C10 and 12A10 therefore includes one or more of residues N56 and K57, and/or one or more of residues T58, R61, and R64. These residues are within the α1 domain of MICA (the epitope may further include residues within the α2 or α3 domains).

Figure 2A:
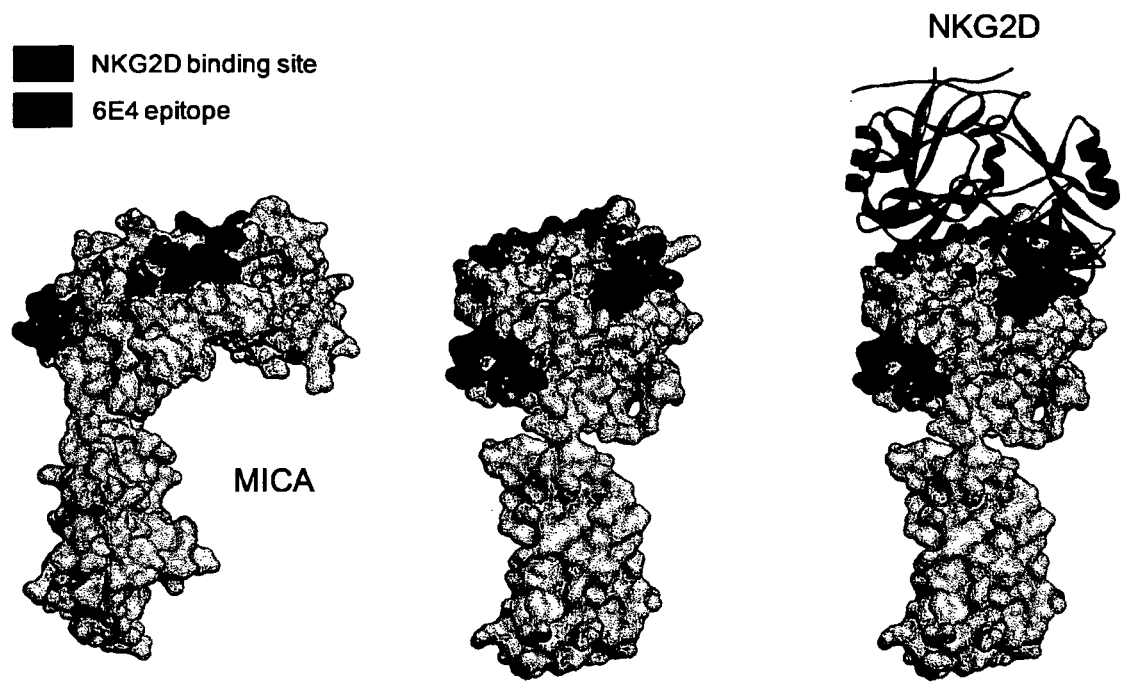
FIGS. 2A-2G show views of the MICA polypeptide, including in dark shading the amino acid residues mutated which resulted (in different combinations) in loss of binding by antibodies. The NKG2D binding site is shown at the top of the MICA polypeptides in medium shading (and also in ribbon diagrams bound to MICA)
Figure 2B:
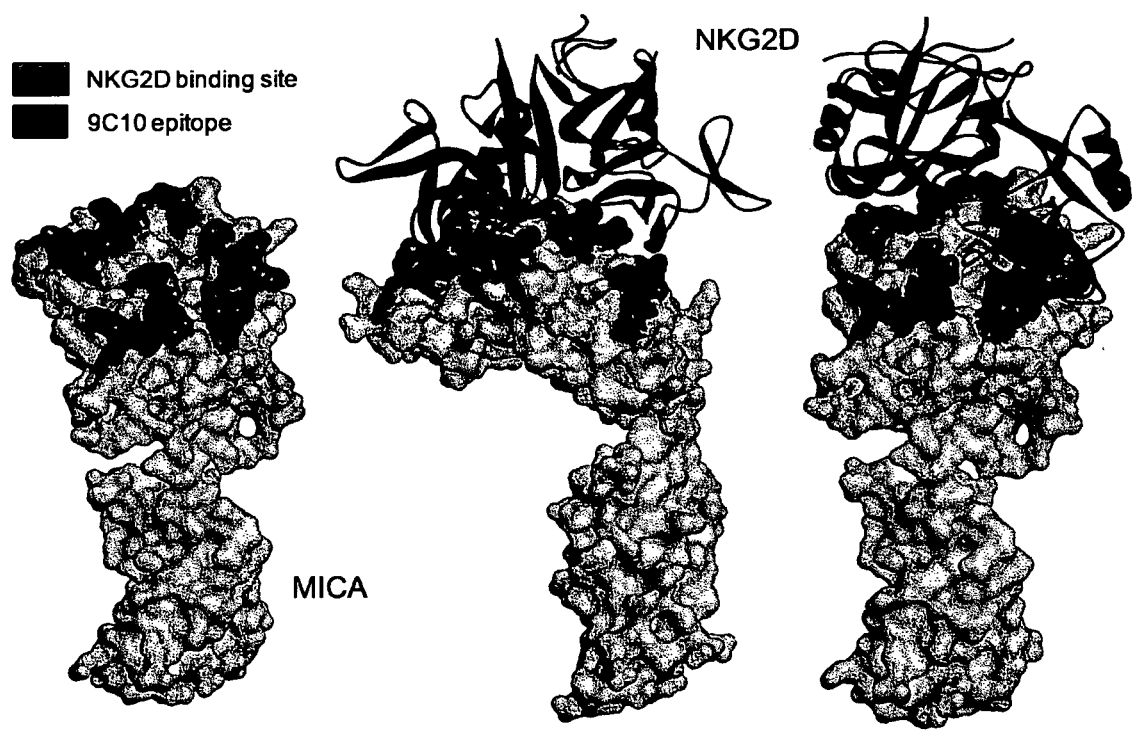

FIG. 2B shows a view of the MICA polypeptide, including in dark shading the amino acid residues mutated which resulted (in different combinations) in loss of binding by 9C10 and 12A10. It can be seen that 9C10 and 12A10 bind to the α1 domain at the lateral side of MICA near the NKG2D binding surface with possible partial overlap, consistent with the finding that 9C10 and 12A10 block MICA-NKG2D interactions.

Antibody 20C6 had loss of binding to each of mutants 16, 17, 21, 60, 27 and 28 having K81A D82A Q83A K84A H109A Y111A D113A L116A S133A R134S T137A M140S N141A R143S N144A substitutions, but did not lose binding to any other mutants. The principal epitope of 20C6 therefore includes one or more of residues K81 and D82, one or more of residues Q83 and K84, one or more of residues H109, Y111 and L116, residue D113, one or more of residues S133, R134 and T137, and/or one or more of residues M140, N141, R143 and N144. These residues are within the α1 and α2 domains of MICA (the epitope may further include residues within the α3 domains).

Antibody 10A7 had partial overlap of epitope with 20C6. 10A7 had loss of binding to each of mutants 16, 17, 21, 60, 26 and 28 having K81A, D82A, Q83A, K84A, H109A, Y111A, D113A, L116A, Q131A, S132A, Q136S, M140S, N141A, R143S and N144A substitutions, but did not lose binding to any other mutants. The principal epitope of 10A7 therefore includes one or more of residues K81 and D82, one or more of residues Q83 and K84, one or more of residues H109, Y111 and L116, residue D113, one or more of residues Q131, S132 and Q136, and/or one or more of residues M140, N141, R143 and N144. These residues are within the α1 and α2 domains of MICA (the epitope may further include residues within the α3 domains).

Figure 2C:
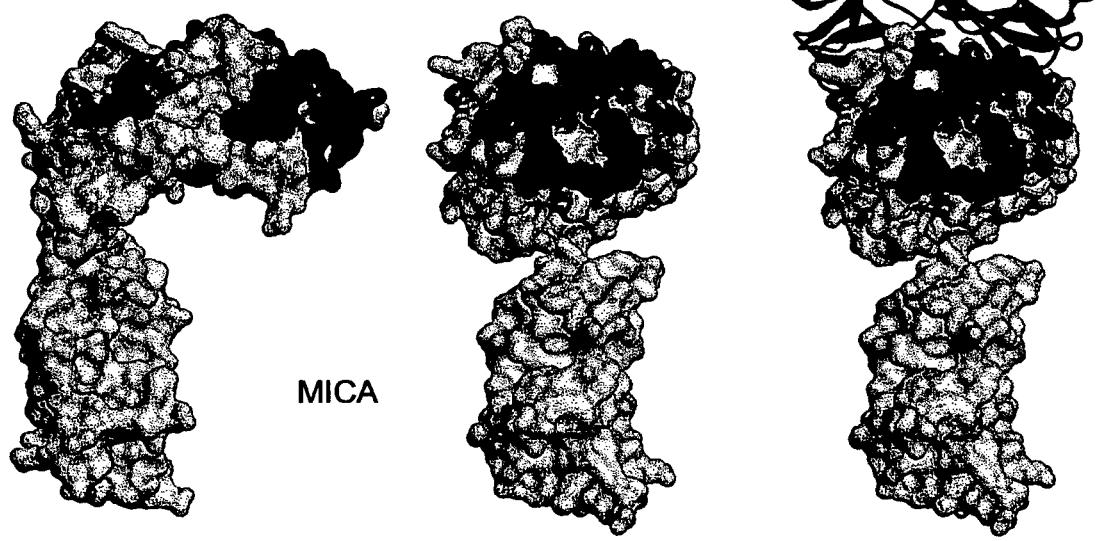
Figure 2D:
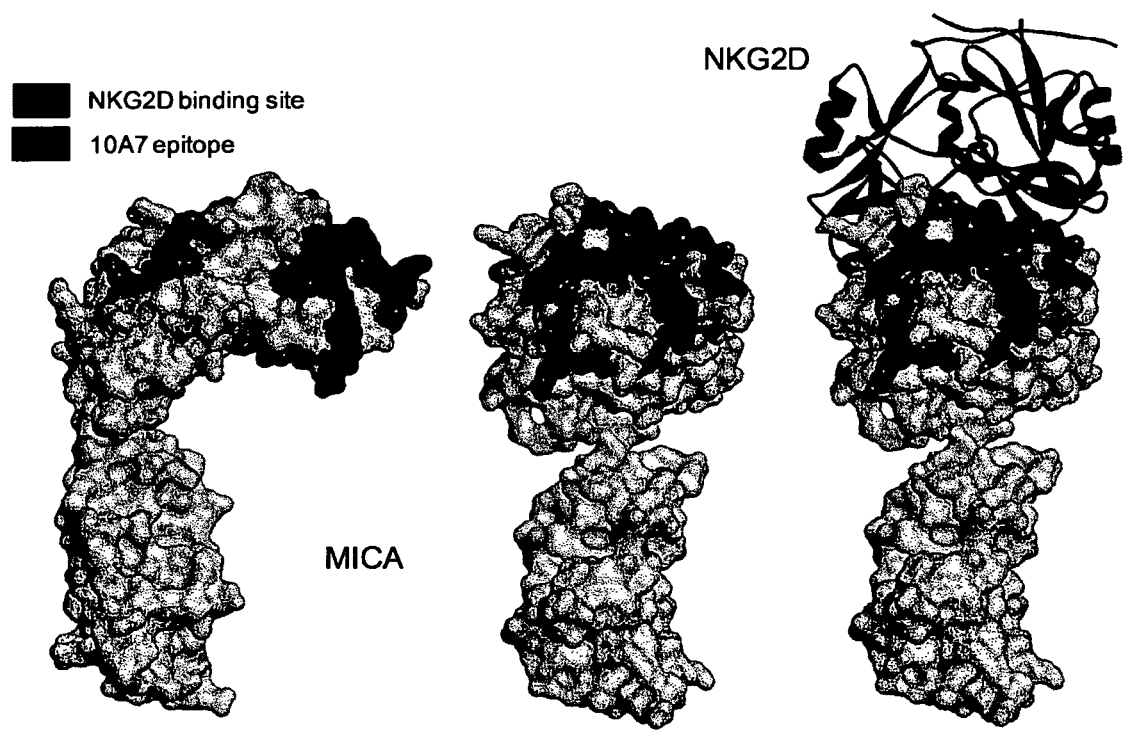

FIG. 2C shows a view of the MICA polypeptide, including in dark shading the amino acid residues mutated which resulted (in different combinations) in loss of binding by 20C6. FIG. 2D shows a view of the MICA polypeptide, including in dark shading the amino acid residues mutated which resulted (in different combinations) in loss of binding by 10A7. It can be seen that 20C6 and 10A7 bind to the α1 and α2 domains at the lateral side of MICA near the NKG2D binding surface with possible partial overlap. This is consistent with the finding that 20C6 blocks MICA NKG2D interactions.

Antibodies 19E9, 18E8 and 10F3 had loss of binding to mutants 19, 20, 23 and 24 having E100A, D101S, N102A, S103A, T104S, R105A, N121A, E123S, T124A and E126A substitutions, but did not lose binding to any other mutants. The principal epitope of 19E9, 18E8 and 10F3 therefore includes one or more of residues E100, D101 and N102, one or more of residues S103, T104, and R105, one or more of residues N121, and E123, and/or one or more of residues T124 and E126. These residues are within the α2 domain of MICA (the epitope may further include residues within the α1 or α3 domains).

Figure 2E:
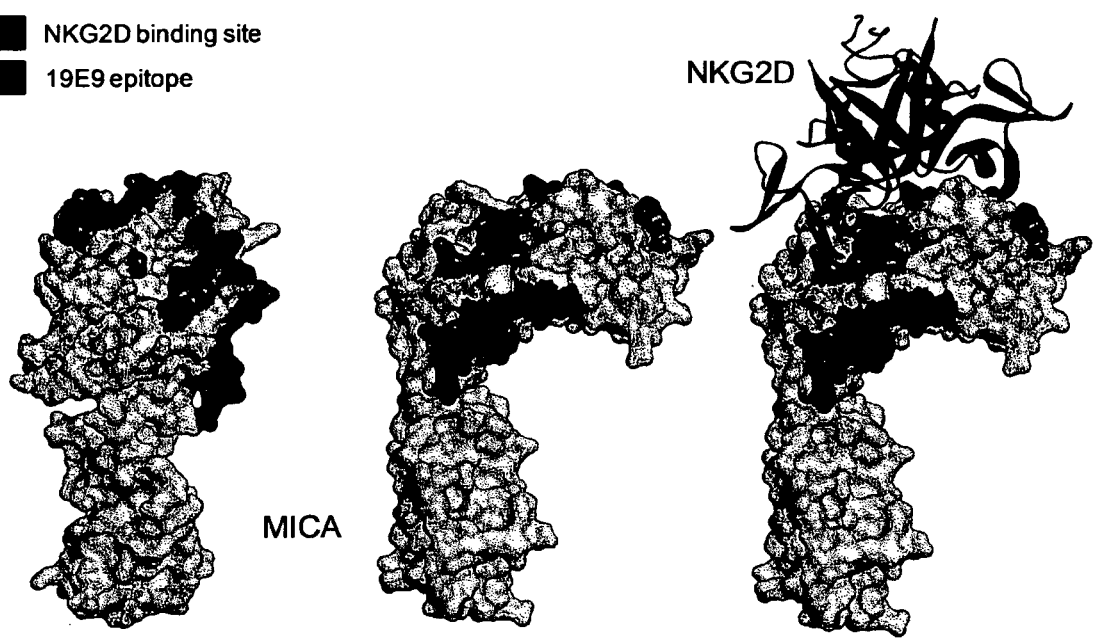

FIG. 2E shows a view of the MICA polypeptide, including in dark shading the amino acid residues mutated which resulted (in different combinations) in loss of binding by 19E9, 18E8 and 10F3. It can be seen that 19E9, 18E8 and 10F3 bind to the α2 domain at the lateral side of MICA near the NKG2D binding surface, consistent with the finding that 19E9, 18E8 and 10F3 block MICA-NKG2D interactions.

Antibody 15F9 had loss of binding to mutants 1, 18, 19, 20, 61 and 36, having R6A, N8A, E97A, H99A, E100A, D101S, N102A, S103A, T104S, R105A, E115A, L178A, R179S and R180A substitutions, but did not lose binding to any other mutants. The principal epitope of 15F9 therefore includes one or more of residues R6 and N8, one or more of residues E97 and H99, one or more of residues E100, D101 and N102, one or more of residues S103, T104 and R105, residue E115, and/or one or more of residues L178, R179 and R180. These residues are within the α2 domain of MICA (the epitope may further include residues within the α1 or α3 domains).

Figure 2F:
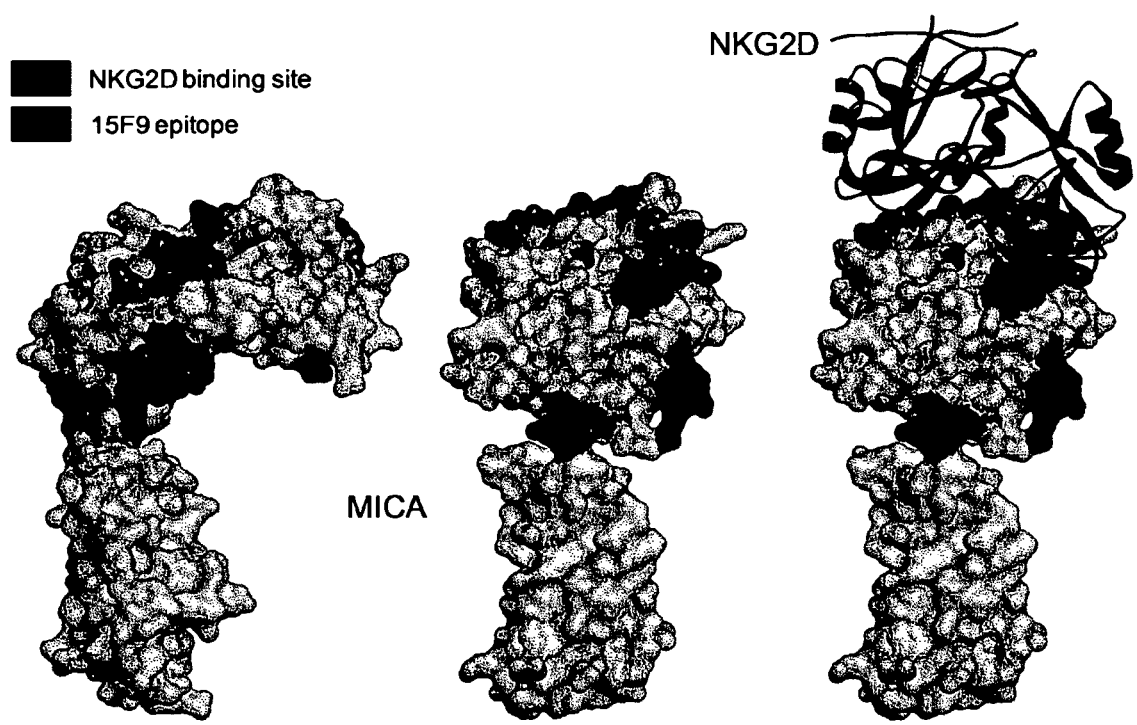

FIG. 2F shows a view of the MICA polypeptide, including in dark shading the amino acid residues mutated which resulted (in different combinations) in loss of binding by 15F9. It can be seen that 15F9 binds to the α2 domain at the lateral side of MICA below the NKG2D binding surface. 15F9 blocks sMICA-NKG2D interactions.

Antibody 16A8 had loss of binding to mutants, 45, 46, and 47, having, S224A, H225S, D226A, T227A, Q228S, Q229A, W230A and D232A substitutions, but did not lose binding to any other mutants. The principal epitope of 16A8 therefore includes one or more of residues W230 and/or D232, one or more of residues T227, Q228 and Q229, one or more of residues S224, H225 and D226. The epitope of 16A8 is primarily within the α3 domain of MICA.

Figure 2G:
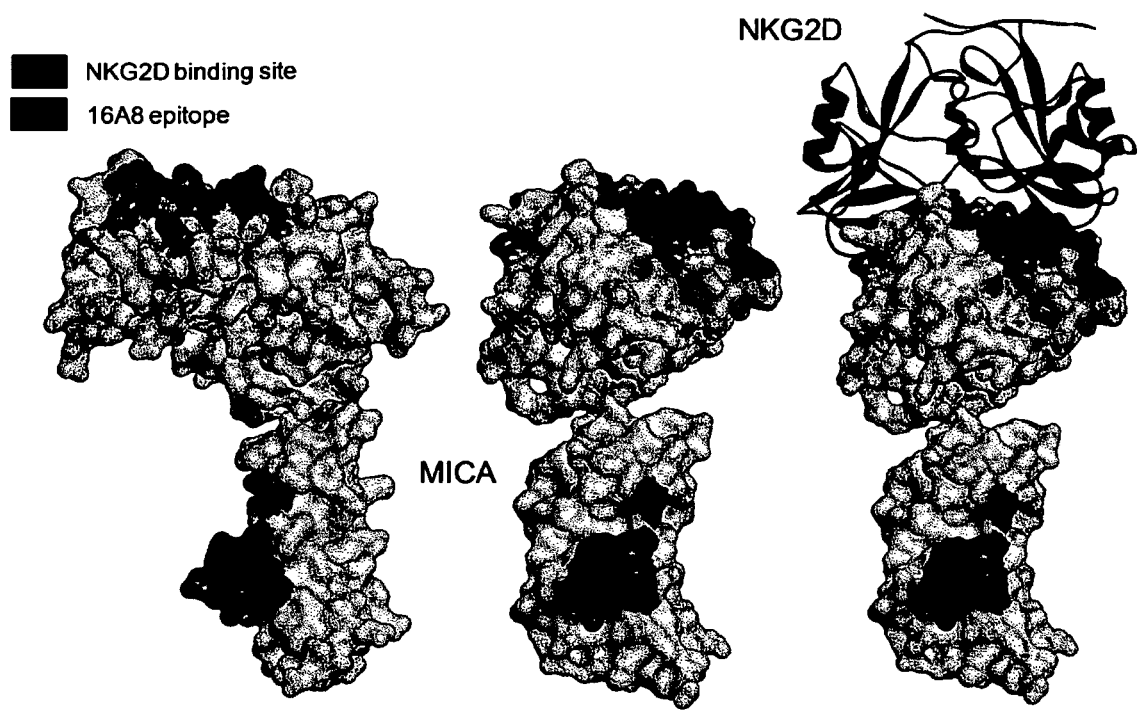

FIG. 2G shows a view of the MICA polypeptide, including in dark shading the amino acid residues mutated which resulted (in different combinations) in loss of binding by 16A8. It can be seen that 16A8 binds to the α3 domain away from the NKG2D binding surface.

Antibody 14B4 had loss of binding to mutant 46, having T227A, Q228S, and Q229A substitutions, but did not lose binding to any other mutants. The principal epitope of 14B4 therefore includes one or more of residues T227, Q228 and Q229, and had a partial overlap with antibody 16A8. The epitope of 14B4 is primarily within the α3 domain of MICA. It can be seen that 14B4 binds to the α3 domain away from the NKG2D binding surface (however 14B4 is a functionally blocking antibody).

Example 5—Ability of Anti-MICA Antibodies to Block NKG2D-MICA Interactions

A. Binding of MICA*001-his to NKG2D-Fc in Presence of Anti-MICA Antibodies Assessed by Surface Plasmon Resonance SPR measurements were performed on a BIACORE™ T100 apparatus (Biacore GE Healthcare) at 25° C. In all BIACORE™ experiments HBS-EP+ buffer (BIACORE™, GE Healthcare) served as running buffer, 10 mM NaOH, 500 mM NaCl served as regeneration buffer and sensorgrams were analyzed with Biaevaluation 4.1 and BIACORE™ T100 Evaluation software.

Figure 3:
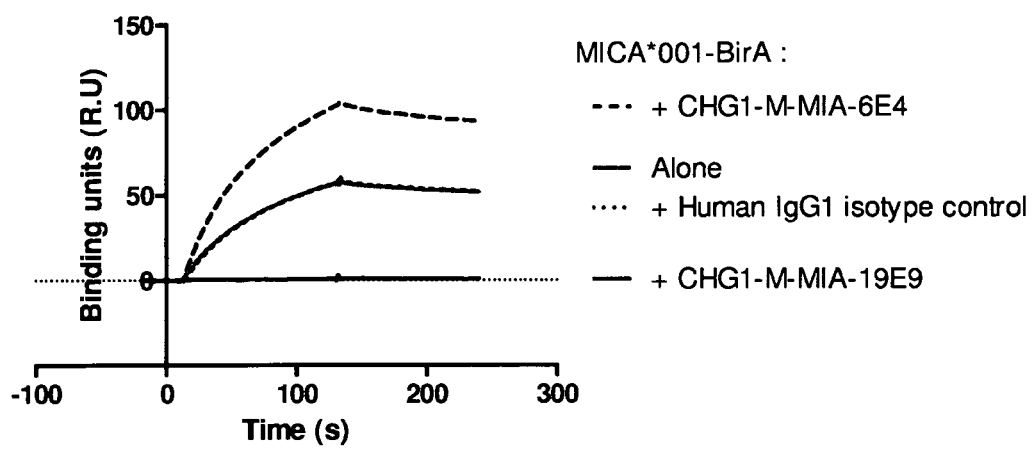
FIG. 3 shows superimposed sensorgrams showing the injections onto NKG2D-Fc chip of MICA*01-BirA alone or pre-incubated with isotype control or chimeric anti-MICA antibodies. Sensorgrams were normalized in the Y axis and aligned in the X axis at the end of injection. Sensorgrams are representative of two independent experiments.

For solution competition experiments, the human NKG2D-Fc (R&D systems) recombinant proteins were covalently immobilized onto a CM5 sensorchip. Soluble human MICA*01-BirA or human MICA*019-Fc (R&D systems) recombinant proteins at a constant concentration of 10 μg/ml were pre-incubated with a 5 to 10 molar equivalent excess of antibodies and injected for 2 minutes at a flow rate of 10 μl/min onto the NKG2D-Fc chip. After each cycle, Sensorchips were regenerated by a five second injection of appropriate regeneration buffer. FIG. 3 shows a representative example of results and results are summarized in Table E B. Ability of Anti-MICA Antibodies to Block NKG2D-Dependent Lysis of Raji-MICA*08 Transfectant Cells by the NK92 NK Cell Line.

Figure 4:
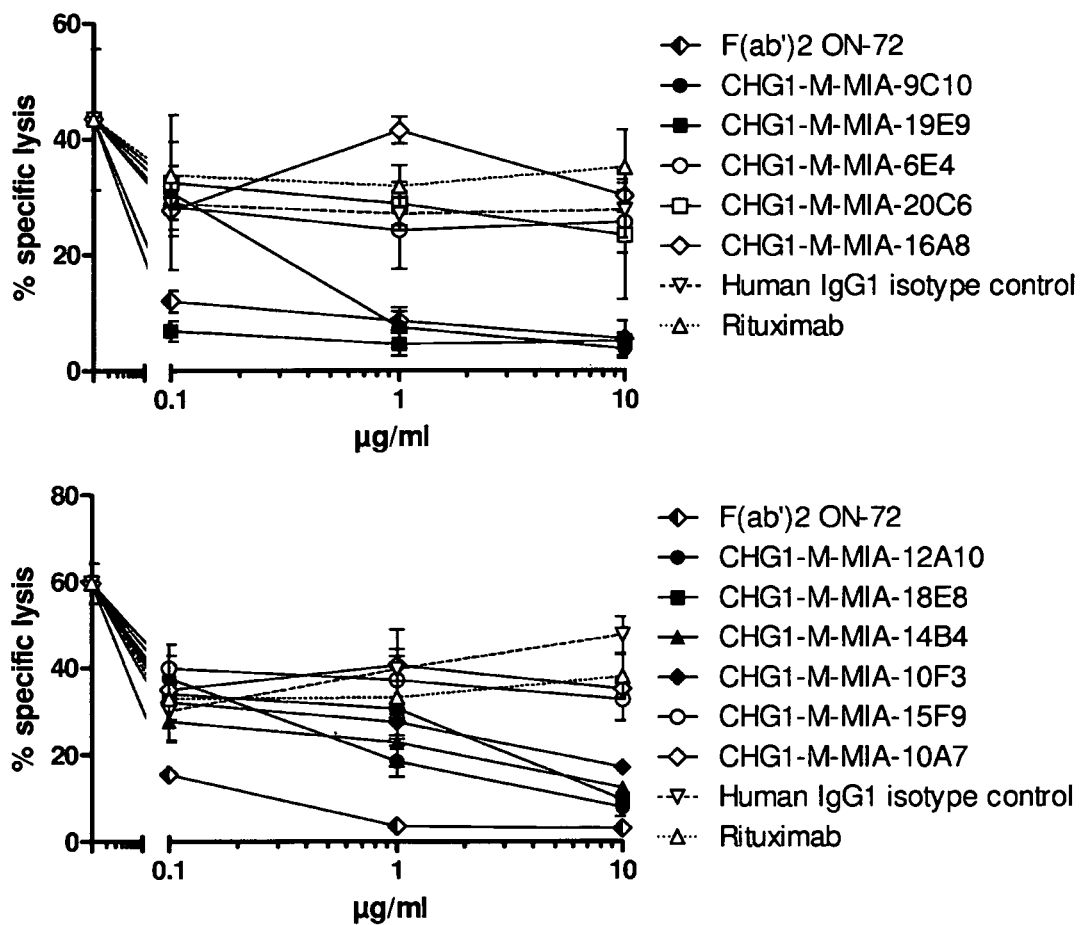
FIG. 4 shows the results of a functional assay for MICA-NKG2A blockade, showing the ability of anti-MICA antibodies to reduce or inhibit the NKG2D+ CD16− NK92 cell-mediated killing of MICA*019-transfected BaF/3 as determined by measuring target cell release of $^{51}$Cr.

The ability of anti-MICA antibodies to block the NKG2D-MICA interaction was assessed. Antibodies were tested for the ability to reduce or inhibit the NKG2D+ CD16− NK92 cell-mediated killing of MICA*008-transfected Raji by measuring target cell release of $^{51}$Cr. The in vitro cytotoxicity assay was carried out by standard methods that are well known in the art, as described for example in Coligan et al., eds., Current Protocols in Immunology, Greene Publishing Assoc. and Wiley Interscience, N.Y., (1992, 1993). The MICA-expressing target cells were labeled with $^{51}$Cr prior to addition of NK cell line, and then the killing was estimated as proportional to the release of $^{51}$Cr from the cells to the medium, as a result of killing. Addition of an agent that reduces binding or blocks an interaction between MICA and NKG2D resulted in prevention of the initiation and propagation of activatory signalling via NKG2D. Therefore addition of such agents results in decreases in NK-mediated killing of the target cells. F(ab')2 fragment of the commercially available blocking anti-NKG2D antibody is used as a positive control of NKG2D-MICA blocking, Rituximab (chimeric human IgG1 anti-CD20) is used as a negative control to ensure that lysis is not mediated through ADCC and an additional negative control in the form of an irrelevant chimeric human IgG1 produced in the same conditions as the anti-MICA is used. Examples of results are shown in FIG. 4 and summarized in Table E.

The CHG1-M-MIA-20C6, CHG1-M-MIA-10A7 do block the interaction of recombinant non-glycosylated MICA*001-BirA with bivalent NKG2D-Fc recombinant protein whereas they do not block the NKG2D-mediated killing of Raji-MICA*08 by NK92. The first hypothesis is that these two anti-MICA have the lowest monovalent affinities for recombinant MICA*001, thus resulting in a higher amount of antibody than tested required to block the NKG2D-MICA interaction in a cell-to-cell cytotoxic assay. Interestingly, this would imply that when used in vivo in the treatment of a tumor, the antibodies might have some blocking ability at high dose (i.e. at a time when ADCC/CDC is the predominant active mechanism because the mAb concentration is sufficient to cause significant depletion of MICA+ cells by ADCC/CDC), but that as the antibody concentration in vivo decreases in the days/weeks after administration of a (high) dose, the antibodies will become non-blocking, permitting patients' endogenous NKG2D receptors to function optimally. Alternatively, the blocking capacity assessed using recombinant proteins in BIACORE™ may not be predictive of the complexity of the molecular NKG2D-MICA interaction between native fully glycosylated proteins presented at the cell membrane. Both NKG2D-Fc and MICA recombinant proteins may not be in their native conformation during the test. Finally, there may exist some discrete alleles specificities in term of quaternary structure that could be responsible for the differences in blocking capacity observed between the two experimental procedures used.

Finally, there may exist some discrete alleles specificities in term of quaternary structure that could be responsible for the differences in blocking capacity observed between the two experimental procedures used.

In addition, epitopes are not predictive of the NKG2D-MICA blocking capacity as CHG1-M-MIA-19E9 for example is a blocking anti-MICA antibody in both assay with an epitope not directly on the NKG2D binding site (FIG. 2E). CHG1-M-MIA-14B4, when binding to tested allele, is blocking NKG2D-MICA interaction although its epitope is on the α3 domain suggesting that MICA conformation is altered upon CHG1-M-MIA-14B4 binding. The epitope for CHG1-M-MIA-20C6 is near the NKG2D binding site but not overlapping (FIGS. 2C, 2D and 2F) and appears to be not functionally blocking on MICA*008.

TABLE E

Summary of NKG2D-MICA blocking capacity of chimeric anti-MICA antibodies assessed by surface plasmon resonance or by a functional cytotoxicity assay

|  | NKG2D-Fc/MICA*001-BirA interaction (Surface Plasmon Resonance) | NKG2D-Fc/MICA*019-Fc interaction (Surface Plasmon Resonance) | NK92/Raji-MICA*08 lysis (Cytotoxicity Assay) |
|---|---|---|---|
| CHG1-M-MIA-9C10 | Blocking | Blocking | Blocking |
| CHG1-M-MIA-12A10 | Blocking |  | Blocking |
| CHG1-M-MIA-19E9 | Blocking | Blocking | Blocking |
| CHG1-M-MIA-18E8 | Blocking |  | Blocking |
| CHG1-M-MIA-10F3 | Blocking |  | Blocking |
| CHG1-M-MIA-15F9 | Non Blocking |  | Non Blocking |
| CHG1-M-MIA-6E4 | Non Blocking | Non Blocking | Non Blocking |
| CHG1-M-MIA-20C6 | Blocking | Blocking | Non Blocking |
| CHG1-M-MIA-10A7 | Blocking |  | Non Blocking |
| CHG1-M-MIA-16A8 | Non Blocking | Not Binding to MICA*019-Fc | Non Blocking |

TABLE E-continued

Summary of NKG2D-MICA blocking capacity of chimeric anti-MICA antibodies assessed by surface plasmon resonance or by a functional cytotoxicity assay

| | NKG2D-Fc/MICA*001-BirA interaction (Surface Plasmon Resonance) | NKG2D-Fc/MICA*019-Fc interaction (Surface Plasmon Resonance) | NK92/Raji-MICA*08 lysis (Cytotoxicity Assay) |
|---|---|---|---|
| CHG1-M-MIA-14B4 | Not binding to MICA*001-BirA | Blocking | Blocking |

Example 6—Crossreaction of Anti-MICA Antibodies with Human MICB, ULBP1, ULBP2 and ULBP3

For cross-binding study, the human ULBP-1-Fc (R&D systems*), MICB-Fc (*), ULBP-2-Fc (*) and ULBP-3-Fc (*) recombinant proteins were covalently immobilized respectively on the flow cell one to four of a CM5 sensorchip. Anti-MICA antibodies (at a constant concentration of 10 µg/ml) were injected for 2 minutes at a flow rate of 10 µl/min onto the four flow cells in parallel. After each cycle, Sensorchip was regenerated by a five second injection of appropriate regeneration buffer.

Figure 5:
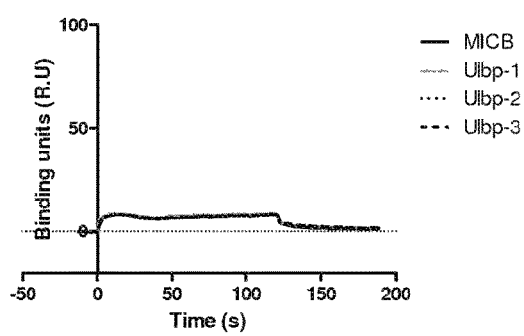
FIGS. 5A, 5B and 5C show superimposed sensorgrams showing the injections onto ULBP-1-Fc (Fc1), MICB-Fc (Fc2), ULBP-2-Fc (Fc3) and ULBP-3-Fc (Fc4) of Anti-MICA antibodies. Sensorgrams were aligned in the X axis at the start of injection.
Figure 5:
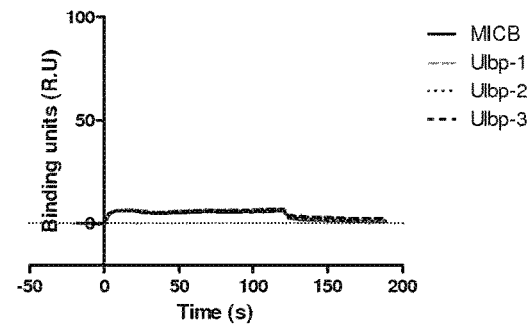
Figure 5:
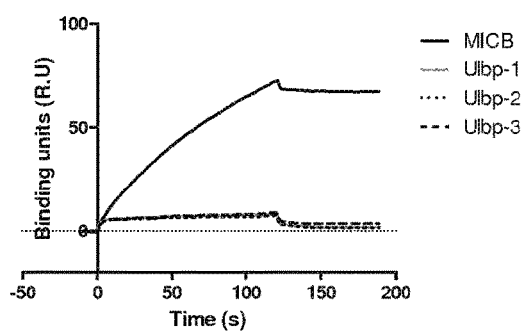
Figure 5:
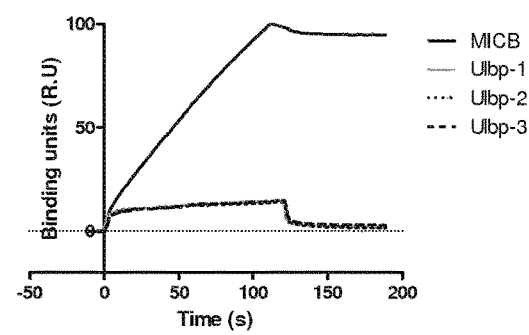
Figure 5:
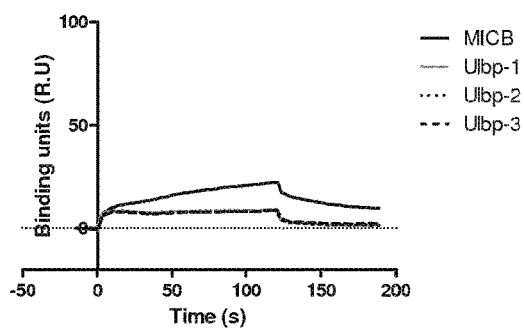

FIG. 5A shows absence of crossreaction to MICB and ULPB-1, -2 and -3 of CHG1-M-MIA-20C6 and CHG1-M-MIA-9C10. FIG. 5B shows that CHG1-M-MIA-6E4 and CHG1-M-MIA-19E9 bind to MICB but not to ULBP-1, -2 and -3. FIG. 5C shows that CHG1-M-MIA-16A8 binds weakly but significantly to MICB but not to ULBP-1, -2 and -3. Antibodies that were not tested are expected to have similar profiles as other antibodies that share same epitope regions.

Table F summarizes results with all tested anti-MICA antibodies.

Example 7—Crossreaction of Anti-MICA Antibodies with *Macaca fascicularis* MIC Proteins The binding of antibodies obtained from the first, second and third immunization series (including CHG1-M-MIA-19E9, CHG1-M-MIA-9C10, CHG1-M-MIA-6E4, CHG1-M-MIA-20C6, CHG1-M-MIA-16A8, CHG1-M-MIA-12A10, CHG1-M-MIA-18E8, CHG1-M-MIA-10F3, CHG1-M-MIA-15F9 and CHG1-M-MIA-14B4) were tested for binding to *Macaca fascicularis* (Cynomolgus) MIC homologs proteins. 3 sequences were successfully cloned from *Macaca fascicularis* cDNA including MIC#9-1, MIC#9-2 and MIC#2-7 and transfected in the mouse cell line Baf/3. Binding was analyzed by flow cytometry, NKG2D-Fc recombinant protein is used as a control to detect surface expression of *Macaca fascicularis* MIC proteins.

Flow Cytometry.

Cells were harvested and stained in PBS 1×/BSA 0.2%/EDTA 2 mM buffer during 30 minutes at 4° C. using a dose-range of the anti-MICA mAbs or with NKG2D-Fc recombinant protein (R&D systems). After two washes in staining buffer, cells incubated with anti-MICA antibodies were stained for 30 min at 4° C. with mouse anti-human

TABLE F

Crossreaction of chimeric anti-MICA antibodies to MICB, ULBP-1, ILBP-2 and ULBP-3 assessed by surface plasmon resonance.

| | Crossreaction on human MICB-Fc | Crossreaction on human ULBP1-Fc | Crossreaction on human ULBP2-Fc | Crossreaction on human ULBP3-Fc |
|---|---|---|---|---|
| CHG1-M-MIA-9C10 | No | No | No | No |
| CHG1-M-MIA-12A10 | No | Not Tested | Not Tested | Not Tested |
| CHG1-M-MIA-19E9 | Yes | No | No | No |
| CHG1-M-MIA-18E8 | Yes | Not Tested | Not Tested | Not Tested |
| CHG1-M-MIA-10F3 | Yes | Not Tested | Not Tested | Not Tested |
| CHG1-M-MIA-15F9 | Yes | Not Tested | Not Tested | Not Tested |
| CHG1-M-MIA-6E4 | Yes | No | No | No |
| CHG1-M-MIA-20C6 | No | No | No | No |
| CHG1-M-MIA-10A7 | No | Not Tested | Not Tested | Not Tested |
| CHG1-M-MIA-16A8 | Yes (low) | No | No | No |
| CHG1-M-MIA-14B4 | No | Not Tested | Not Tested | Not Tested |

IgG1-PE monoclonal antibodies (1/11). Cells incubated with NKG2D-Fc were stained for 30 min at 4° C. with goat anti-human IgG polyclonal antibodies (1/200). After two washes, stainings were acquired on a BD FACS Canto II and analyzed using the BD FACSDiva software.

Figure 6:
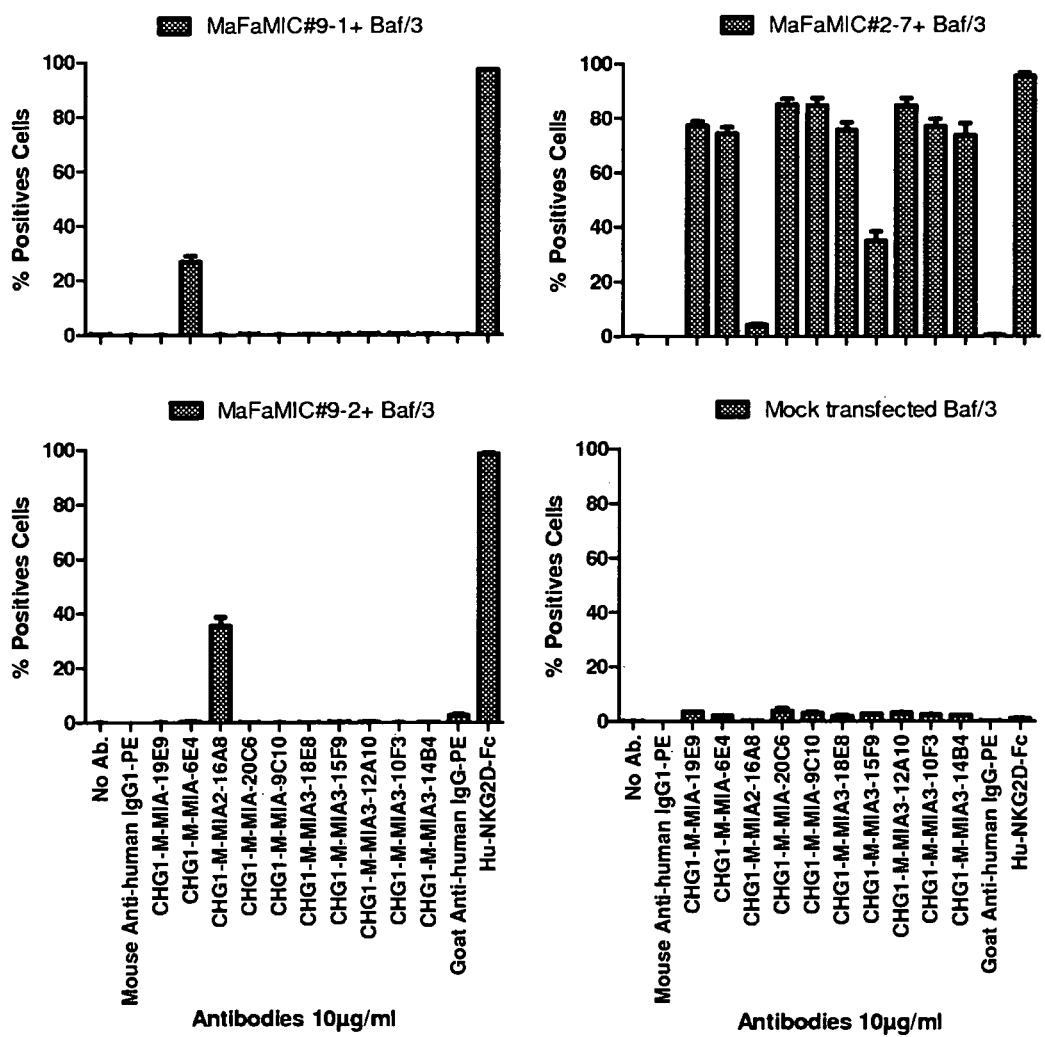
FIG. 6 shows binding of anti-MICA antibodies to *Macaca fascicularis* MICA.

CHG1-M-MIA-19E9, CHG1-M-MIA-9C10, CHG1-M-MIA-6E4, CHG1-M-MIA-20C6, CHG1-M-MIA-16A8, CHG1-M-MIA-12A10, CHG1-M-MIA-10F3, CHG1-M-MIA-15F9 and CHG1-M-MIA-14B4 antibodies bind to MIC#2-7 *Macaca fascicularis* protein. MIC#2-7 presents 99.6%, 97.8%, 95.6% and 86.9% protein homology with MICA*019, MICA*044, MICA*001 and MICB*002 respectively. In addition to MIC#2-7, CHG1-M-MIA-6E4 also binds to MIC#9-1. CHG1-M-MIA-16A8 binds to MIC#9-2 protein in the experimental conditions tested. Results are shown in FIG. 6.

Example 8—Inhibition of MICA Shedding

Figure 7:
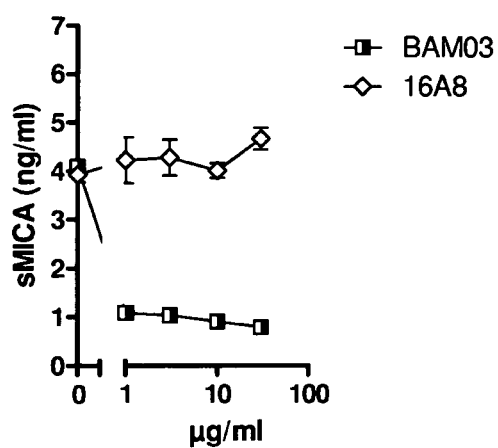
FIG. 7 shows inhibition of the MICA shedding mediated by the anti-α3 domain BAM03 but not by 16A8, in an assay for capacity to block MICA shedding as assessed by measuring soluble MICA concentration in the supernatant after overnight incubation of MICA-expressing cells with anti-MICA antibodies.

Anti-α3 domain 16A8 antibody was compared to commercially available BAM03 (see Salih et al (2003), supra) for its capacity to block MICA shedding. A mix of C1R-MICA*01 and C1R-MICA*04 cells were washed in PBS 1× to remove soluble MICA present in the culture and then cultured overnight in complete medium in the presence or absence of a dose range (0/1/3/10/30 µg/ml) of 16A8 or BAM03. Then cell culture supernatants were harvested and tested in ELISA for the presence of soluble MICA. Neither 16A8 nor BAM03 are interfering with the anti-MICA antibodies used in the ELISA (data not shown). Overnight incubation of the cells with BAM03 results in a decrease of the soluble MICA concentration in the supernatant whereas 16A8 does not induce a decrease of the soluble MICA. Results are shown in FIG. 7, showing an inhibition of the MICA shedding mediated by BAM03 but not by 16A8.

Example 9—Effect of Anti-MICA Antibodies on NKG2D Downmodulation

Reports have emerged that NKG2D on NK cells is downregulated by sMICA (Groh et al. (2002) Nature; Arreygue-Garcia (2008) BMC; Jinushi et al. (2005) J. Hepatol.), leading to less reactive NK cells. To mimic downregulation induced by soluble MICA the following experiments were performed.

Thawed PBMC from four healthy donors were enriched in lymphocytes following non-specific removal of monocytes by cold-aggregation (Rubinstien (1989) J. Clin. Lab. Immunol.). Cells (1.10e5 cells per wells) were incubated in a 96-well plate in the presence of increasing concentrations of soluble MICA*019-Fc (R&D systems) in the presence or absence of anti-MICA antibodies (CHG1-M-MIA-9C10, CHG1-M-MIA-19E9, CHG1-M-MIA-20C6 at 10 µg/mL) for 24h at 4° C. or 37° C. NKG2D downmodulation induced by soluble MICA and its blockade by anti-MICA antibodies was assessed by flow cytometry. Cells were stained with the following human-specific mouse antibodies: anti-CD14 FITC, anti-CD3 Pacific blue (Becton Dickinson), anti-CD56 PE-Cy7 (BioLegend), anti-NKG2D PE (Beckman Coulter) and analyzed for NKG2D expression on gated CD3-CD56+ NK cells.

Figure 8:
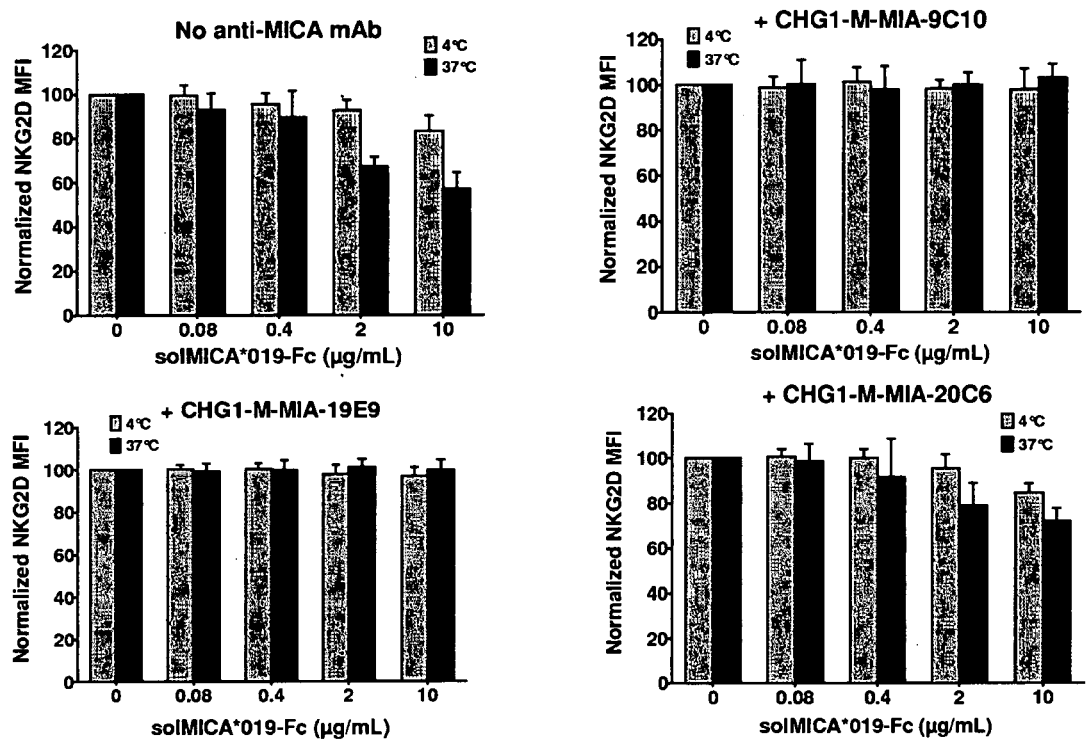
FIG. 8 shows that NKG2D is downmodulated by 30 to 40% of its initial level in presence of increasing doses of recombinant bivalent MICA*019*Fc protein (R&D systems), and that anti-MICA antibodies, blocking NKG2D-MICA interaction in the cytotoxic assay of Example 5B (Table E), are blocking the interaction of NKG2D expressed on NK cells with MICA*019-Fc, hence reversing the NKG2D downmodulation induced by the MICA*019-Fc protein.

In this experimental setting, NKG2D is downmodulated by 30 to 40% of its initial level in presence of increasing doses of recombinant bivalent MICA*019*Fc protein (R&D systems) (FIG. 8). This effect is seen between 2 to 10 µg/ml in the culture medium, much above described levels of soluble MICA observed in sera from cancer patients (ranging 30 to 1557 µg/ml in malignant disorders, n=296, Holdenrieder (2006) Int. J. Cancer). The NKG2D downmodulation is not observed in these experimental conditions using monovalent MICA*01-His recombinant protein (data not shown). CHG1-M-MIA-9C10 and CHG1-M-MIA-19E9 anti-MICA antibodies, blocking NKG2D-MICA interaction in the cytotoxic assay of Example 5B (Table E), are blocking the interaction of NKG2D expressed on NK cells with MICA*019-Fc, hence reversing the NKG2D downmodulation induced by the MICA*019-Fc protein (FIG. 8). CHG1-M-MIA-20C6 anti-MICA does not reverse MICA*019-Fc-mediated NKG2D downmodulation (FIG. 8). Although this antibody is blocking NKG2D-Fc/MICA*019-Fc binding by surface plasmon resonance (Table E), it is not blocking NKG2D/MICA*08 in the cellular cytotoxic assay of Example 5B (Table E) and is not reversing the NKG2D downmodulation on primary cells emphasizing the fact that NKG2D/MICA blocking experiments using recombinant proteins may not be predictive of the biological function, at least in the experimental conditions tested.

Example 10—Anti-MICA Antibodies are Able to Mediate Killing of MICA Expressing Targets Via CDC CHG1-M-MIA-9C10, CHG1-M-MIA-19E9, CHG1-M-MIA-6E4, CHG1-M-MIA-20C6 and CHG1-M-MIA-16A8, were tested for their ability to mediate CDC towards human Raji tumor cells transduced with a lentivirus encoding forMICA*001 full protein. These Raji-MICA*01 cells express MICA*01 at their cell surface.

Briefly, 100 000 Raji-MICA*01 cells were incubated 1h with the indicated doses of anti-MICA antibodies at 4° C. Then, culture medium containing 20% (final concentration) of Human Serum Complement (Quidel) was added to the cells and incubated at 37° C. for 3 hours. Cells were washed and incubated with 7-AAD to stain dead cells. Cells were acquired by flow cytometry on a BD FACS Canto II and analyzed using the BD FACSDiva software. Results are expressed as a percentage of 7-AAD positive cells in the indicated condition.

Figure 9:
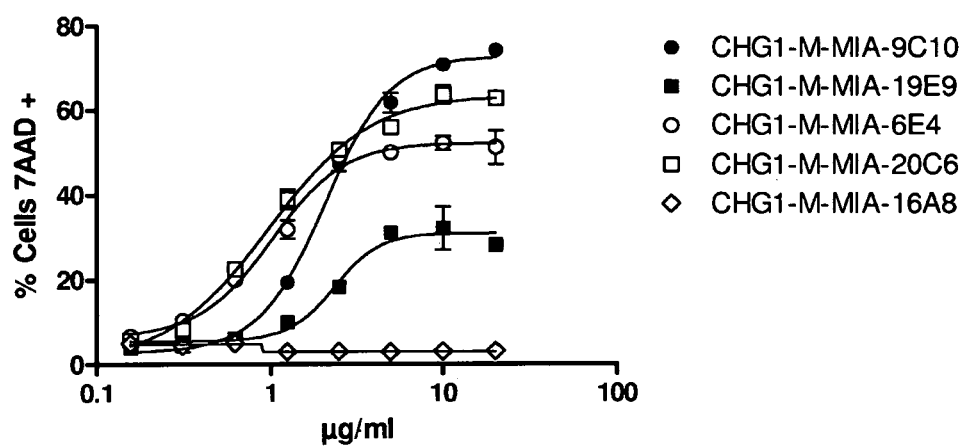
FIG. 9 shows viability of indicated Raji-MICA*01 cells, in the presence of human complement. The results show that anti-MICA (isotype matched) cause an increase the number of dead cells and are capable of inducing CDC in an epitope dependent fashion.

Results are shown in FIG. 9. The results show viability of indicated Raji-MICA*01 cells, in the presence of human complement. The results show that CHG1-M-MIA-20C6, CHG1-M-MIA-9C10, CHG1-M-MIA-6E4, and CHG1-M-MIA-19E9 cause an increase the number of dead cells (with EC50 values of 0.97, 2, 1.01 and 2.35 µg/ml respectively) (FIG. 9). The maximum percentage of dead cells varies with the different anti-MICA tested (FIG. 9). Notably, CHG1-M-MIA-16A8 is not mediating complement cytotoxicity. As these 5 anti-MICA have EC50 values for staining C1R-MICA*01 of the same order (Table C), complement-mediated cytotoxicity appears to be epitope-dependent (9C10>20C6=6E4>19E9>>16A8).

Example 11—Antibodies are Able to Kill MICA Expressing Targets Via ADCC

CHG1-M-MIA-19E9, CHG1-M-MIA-9C10, CHG1-M-MIA-6E4, CHG1-M-MIA-20C6, CHG1-M-MIA-16A8, CHG1-M-MIA-12A10, CHG1-M-MIA-18E8, CHG1-M-MIA-10F3, CHG1-M-MIA-15F9 and CHG1-M-MIA-14B4 were tested for their ability to mediate ADCC towards C1R tumor cells transfected with MICA*008 (C1R-MICA*008).

Briefly, the cytolytic activity of human NK cell line KHYG-1 transfected with human CD16 (V isoform) was assessed in a classical 4-h 31Cr-release assay in 96 well plates V from (Greiner). Briefly, C1R-MICA*008 cells were labelled with 51Cr (100 μCi (3.7 MBq)/1×106 cells), then mixed with KHYG-transfected with hCD16V (to bind human IgG1) at an effector/target ratio equal to 20, in the presence of antibody at indicated concentrations and of 10 g/ml F(ab')2 ON-72 to block any NKG2D-mediated cytotoxicity). After brief centrifugation and 4 hours of incubation at 37° C., 50 μL supernatant were removed, and the 51Cr release was measured with a TOPCOUNT NXT benchtop microplate scintillation and luminescence beta detector (PerkinElmer Life Sciences, Boston, Mass.). All experimental groups were analyzed in triplicate, and the percentage of specific lysis was determined as follows: 100×(mean cpm experimental release−mean cpm spontaneous release)/(mean cpm total release−mean cpm spontaneous release). Percentage of total release obtained by lysis of target cells with 2% Triton X100 (Sigma).

Figure 10:
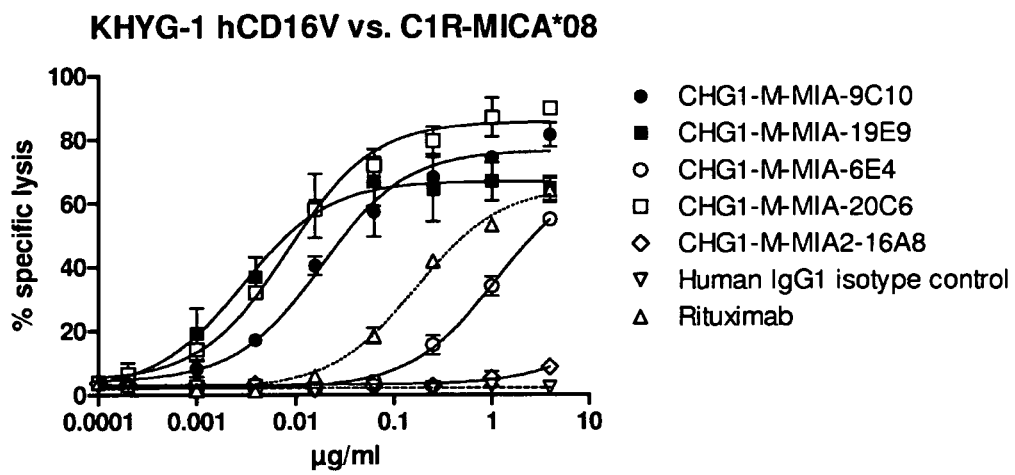
FIG. 10A shows that anti-MICA each induced specific lysis of C1R-MICA*008 cells by human KHYG-1 hCD16V NK cells line compared to negative controls (Human IgG1 isotype control antibody), thereby showing that these antibodies induce ADCC toward MICA*008-expressing target cells.
FIG. 10B shows level of antibody binding to the cell.
Figure 10:
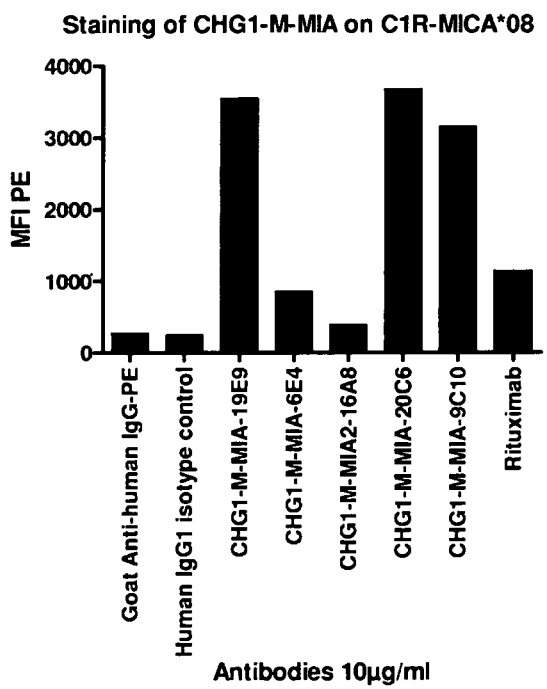

Results are shown in FIG. 10A. CHG1-M-MIA-9C10, CHG1-M-MIA-19E9, CHG1-M-MIA-6E4, CHG1-M-MIA-20C6 and CHG1-M-MIA-16A8 each induced specific lysis of C1R-MICA*008 cells by human KHYG-1 hCD16V NK cells line compared to negative controls (Human IgG1 isotype control antibody), thereby showing that these antibodies induce ADCC toward MICA*008-expressing target cells. The extent of target cell lysis is correlated to antibody binding to the cell (FIG. 10B).

Example 12—Chimeric Anti-MICA 9C10, 19E9, 6E4, 20C6 and 16A8 Show Anti-Tumoral Efficacy in a Mouse Model of RAJI-MICA*01 High Xenograft Antibodies were tested in a mouse long-term RAJI-MICA*01 tumor model in which RAJI cells expressed high level of antigen MICA*01. Nod SCID mice were intravenously (IV) engrafted with 15.10⁶ RAJI-MICA*01High and treated with either control isotype control antibody (IC) or chimeric antibodies CHG1-M-MIA-9C10, CHG1-M-MIA-19E9, CHG1-M-MIA-6E4, CHG1-M-MIA-20C6, or CHG1-M-MIA-16A8 at the dosage of 300 μg/mouse, IP twice/week for 3 weeks from the day of tumor cell graft.

RAJI-MICA*01High were cultured in complete RPMI 1640 culture medium containing supplemented with 10% of Fetal Bovine Serum Heat Inactivated, 1% L-glutamine, 1% Sodium/Pyruvate and without antibodies prior to injection into mice.

Mice were weighed twice per week. Kaplan-Meier survival curves were established to assess survival of treated mice.

Figure 11:
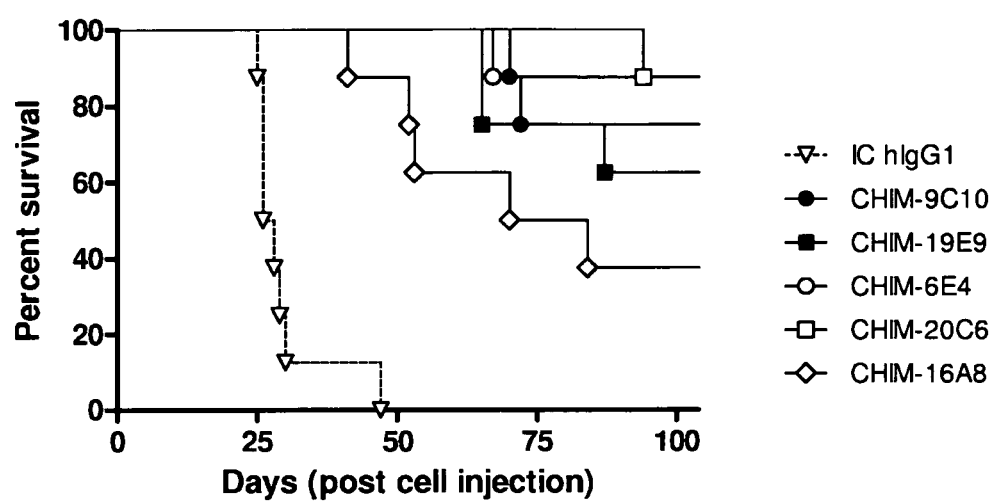
FIG. 11 shows results of testing of in a mouse long-term RAJI-MICA*01 tumor model. Survival of Nod SCID mice engrafted Raji-MICA01 High 15M IV treated with chimeric anti-MICA or IC (300 μg IP 2×/week for 3 weeks) or PBS. Anti-MICA antibodies of the invention increased survival.

Results are shown in FIG. 11. All chimeric antibodies showed anti-tumoral activity. Animals receiving isotype control had a median survival of 27 days whereas mice treated with the least effective chimeric antibody (16A8) had a median survival of 77 days. For all other antibodies, more than 50% of animals are still alive at day 100, preventing the calculation of the median survival and indicating a very strong anti-tumoral effect.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A monoclonal antibody comprising (i) a heavy chain comprising the CDR 1 (SEQ ID NO: 48), 2 (SEQ ID NO: 51) and 3 (SEQ ID NO: 53) of the heavy chain variable region of SEQ ID NO: 46 and (ii) a light chain comprising the CDR 1 (SEQ ID NO: 54), 2 (SEQ ID NO: 55) and 3 (SEQ ID NO: 56) of the light chain variable region of SEQ ID NO: 47.

2. A pharmaceutical composition comprising an antibody of claim 1, and a pharmaceutically acceptable carrier.

3. The antibody of claim 1, wherein said antibody is coupled to a cytotoxic agent.

* * * * *

SEQUENCE LISTING

<160> NUMBER OF SEQ ID NOS: 268

<210> SEQ ID NO 1
<211> LENGTH: 274
<212> TYPE: PRT
<213> ORGANISM: Homo sapiens

<400> SEQUENCE: 1

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 2
<211> LENGTH: 274
<212> TYPE: PRT
<213> ORGANISM: Homo sapiens

<400> SEQUENCE: 2

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

```
Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Val Glu Thr Glu Trp Thr
            115                 120                 125

Val Pro Gln Ser Ser Arg Ala Gln Thr Leu Ala Met Asn Val Arg Asn
            130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Ser Val
                165                 170                 175

Val Leu Arg Arg Arg Val Pro Pro Met Val Asn Val Thr Arg Ser Glu
            180                 185                 190

Ala Ser Glu Gly Asn Ile Thr Val Thr Cys Arg Ala Ser Ser Phe Tyr
            195                 200                 205

Pro Arg Asn Ile Thr Leu Thr Trp Arg Gln Asp Gly Val Ser Leu Ser
            210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser

<210> SEQ ID NO 3
<211> LENGTH: 274
<212> TYPE: PRT
<213> ORGANISM: Homo sapiens

<400> SEQUENCE: 3

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
        50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Met Pro Gln Ser Ser Arg Ala Gln Thr Leu Ala Met Asn Val Arg Asn
            130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175
```

```
Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser
```

<210> SEQ ID NO 4
<211> LENGTH: 274
<212> TYPE: PRT
<213> ORGANISM: Homo sapiens

<400> SEQUENCE: 4

```
Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Val Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Ile Leu Thr Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Arg Gly Glu Glu Gln Arg
                245                 250                 255

Phe Thr Cys Tyr Met Glu His Ser Gly Asn His Ser Thr His Pro Val
            260                 265                 270
```

Pro Ser

<210> SEQ ID NO 5
<211> LENGTH: 274
<212> TYPE: PRT
<213> ORGANISM: Homo sapiens

<400> SEQUENCE: 5

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
        115                 120                 125

Val Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Ser Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Ile Leu Thr Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Arg Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 6
<211> LENGTH: 383
<212> TYPE: PRT
<213> ORGANISM: Homo sapiens

<400> SEQUENCE: 6

Met Gly Leu Gly Arg Val Leu Leu Phe Leu Ala Val Ala Phe Pro Phe
1               5                   10                  15

Ala Pro Pro Ala Ala Ala Ala Glu Pro His Ser Leu Arg Tyr Asn Leu
            20                  25                  30

Met Val Leu Ser Gln Asp Gly Ser Val Gln Ser Gly Phe Leu Ala Glu
        35                  40                  45

Gly His Leu Asp Gly Gln Pro Phe Leu Arg Tyr Asp Arg Gln Lys Arg
            50                  55                  60

Arg Ala Lys Pro Gln Gly Gln Trp Ala Glu Asp Val Leu Gly Ala Lys
 65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Gly Leu His Ser
                100                 105                 110

Leu Gln Glu Ile Arg Val Cys Glu Ile His Glu Asp Ser Ser Thr Arg
                115                 120                 125

Gly Ser Arg His Phe Tyr Tyr Asp Gly Glu Leu Phe Leu Ser Gln Asn
            130                 135                 140

Leu Glu Thr Gln Glu Ser Thr Val Pro Gln Ser Ser Arg Ala Gln Thr
145                 150                 155                 160

Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln
                180                 185                 190

Arg Tyr Leu Lys Ser Gly Val Ala Ile Arg Arg Thr Val Pro Pro Met
            195                 200                 205

Val Asn Val Thr Cys Ser Glu Val Ser Glu Gly Asn Ile Thr Val Thr
            210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Gln Trp Gly Asp Val
                245                 250                 255

Leu Pro Asp Gly Asn Gly Thr Tyr Gln Thr Trp Val Ala Thr Arg Ile
                260                 265                 270

Arg Gln Gly Glu Glu Gln Arg Phe Thr Cys Tyr Met Glu His Ser Gly
            275                 280                 285

Asn His Gly Thr His Pro Val Pro Ser Gly Lys Ala Leu Val Leu Gln
            290                 295                 300

Ser Gln Arg Thr Asp Phe Pro Tyr Val Ser Ala Ala Met Pro Cys Phe
305                 310                 315                 320

Val Ile Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
                340                 345                 350

Pro Val Gly Thr Gly Asp His Arg Asp Ala Ala Gln Leu Gly Phe Gln
            355                 360                 365

Pro Leu Met Ser Ala Thr Gly Ser Thr Gly Ser Thr Glu Gly Ala
            370                 375                 380

<210> SEQ ID NO 7
<211> LENGTH: 137
<212> TYPE: PRT
<213> ORGANISM: Mus musculus

<400> SEQUENCE: 7

Met Asn Phe Val Leu Ser Leu Ile Phe Leu Ala Leu Ile Leu Lys Gly
 1               5                   10                  15

Val Gln Cys Glu Val Gln Leu Val Glu Ser Gly Gly Ala Leu Val Lys
                20                  25                  30

Pro Gly Gly Ser Leu Lys Leu Ser Cys Ala Ala Ser Gly Phe Thr Phe

```
                35                  40                  45
Ser Tyr Tyr Ala Met Ser Trp Val Arg Gln Thr Pro Glu Lys Arg Leu
 50                  55                  60

Glu Trp Val Ala Thr Ile Ser Arg Gly Gly Asn Tyr Ile Tyr Tyr Thr
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Thr Ser Leu Arg Ser Glu Asp Thr Ala Met
            100                 105                 110

Phe Tyr Cys Ala Ser Ile Ser Asp Tyr Asp Gly Ala Trp Leu Ala Tyr
        115                 120                 125

Trp Gly Gln Gly Thr Leu Val Thr Val
130                 135

<210> SEQ ID NO 8
<211> LENGTH: 131
<212> TYPE: PRT
<213> ORGANISM: Mus musculus

<400> SEQUENCE: 8

Met Lys Leu Pro Val Arg Leu Leu Val Leu Met Phe Trp Ile Pro Val
 1               5                  10                  15

Ser Ser Ser Asp Val Leu Met Thr Gln Thr Pro Leu Ser Leu Pro Val
                 20                  25                  30

Ser Leu Gly Asp Gln Ala Ser Ile Ser Cys Arg Ser Ser Gln Ser Ile
             35                  40                  45

Ile His Thr Asn Gly Asn Thr Tyr Leu Glu Trp Tyr Leu Gln Lys Pro
 50                  55                  60

Gly Gln Ser Pro Lys Leu Leu Ile Tyr Lys Ile Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
        115                 120                 125

Glu Ile Lys
130

<210> SEQ ID NO 9
<211> LENGTH: 469
<212> TYPE: PRT
<213> ORGANISM: Artificial
<220> FEATURE:
<223> OTHER INFORMATION: Chimeric mouse-human

<400> SEQUENCE: 9

Met Asn Phe Val Leu Ser Leu Ile Phe Leu Ala Leu Ile Leu Lys Gly
 1               5                  10                  15

Val Gln Cys Glu Val Gln Leu Val Glu Ser Gly Gly Ala Leu Val Lys
                 20                  25                  30

Pro Gly Gly Ser Leu Lys Leu Ser Cys Ala Ala Ser Gly Phe Thr Phe
             35                  40                  45

Ser Tyr Tyr Ala Met Ser Trp Val Arg Gln Thr Pro Glu Lys Arg Leu
 50                  55                  60

Glu Trp Val Ala Thr Ile Ser Arg Gly Gly Asn Tyr Ile Tyr Tyr Thr
 65                  70                  75                  80
```

```
Asp Ser Val Lys Gly Arg Phe Thr Ile Ser Arg Asp Asn Ala Lys Asn
                85                  90                  95

Thr Leu Tyr Leu Gln Met Thr Ser Leu Arg Ser Glu Asp Thr Ala Met
            100                 105                 110

Phe Tyr Cys Ala Ser Ile Ser Asp Tyr Asp Gly Ala Trp Leu Ala Tyr
        115                 120                 125

Trp Gly Gln Gly Thr Thr Leu Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 10
<211> LENGTH: 239
```

<212> TYPE: PRT
<213> ORGANISM: Artificial
<220> FEATURE:
<223> OTHER INFORMATION: Chimeric mouse-human

<400> SEQUENCE: 10

```
Met Ser Val Pro Thr Gln Val Leu Gly Leu Leu Leu Leu Trp Leu Thr
1               5                   10                  15

Asp Ala Arg Cys Asp Val Leu Met Thr Gln Thr Pro Leu Ser Leu Pro
            20                  25                  30

Val Ser Leu Gly Asp Gln Ala Ser Ile Ser Cys Arg Ser Ser Gln Ser
        35                  40                  45

Ile Ile His Thr Asn Gly Asn Thr Tyr Leu Glu Trp Tyr Leu Gln Lys
    50                  55                  60

Pro Gly Gln Ser Pro Lys Leu Leu Ile Tyr Lys Ile Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Phe Gln Gly Ser His Val Pro Trp Thr Phe Gly Gly Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 11
<211> LENGTH: 6
<212> TYPE: PRT
<213> ORGANISM: Mus musculus

<400> SEQUENCE: 11

```
Ser Tyr Tyr Ala Met Ser
1               5
```

<210> SEQ ID NO 12
<211> LENGTH: 6
<212> TYPE: PRT
<213> ORGANISM: Mus musculus

<400> SEQUENCE: 12

```
Gly Phe Thr Phe Ser Tyr
1               5
```

<210> SEQ ID NO 13
<211> LENGTH: 10
<212> TYPE: PRT
<213> ORGANISM: Mus musculus

```
<400> SEQUENCE: 13

Gly Phe Thr Phe Ser Tyr Tyr Ala Met Ser
1               5                   10

<210> SEQ ID NO 14
<211> LENGTH: 17
<212> TYPE: PRT
<213> ORGANISM: Mus musculus

<400> SEQUENCE: 14

Thr Ile Ser Arg Gly Gly Asn Tyr Ile Tyr Tyr Thr Asp Ser Val Lys
1               5                   10                  15

Gly

<210> SEQ ID NO 15
<211> LENGTH: 10
<212> TYPE: PRT
<213> ORGANISM: Mus musculus

<400> SEQUENCE: 15

Thr Ile Ser Arg Gly Gly Asn Tyr Ile Tyr
1               5                   10

<210> SEQ ID NO 16
<211> LENGTH: 11
<212> TYPE: PRT
<213> ORGANISM: Mus musculus

<400> SEQUENCE: 16

Ile Ser Asp Tyr Asp Gly Ala Trp Leu Ala Tyr
1               5                   10

<210> SEQ ID NO 17
<211> LENGTH: 16
<212> TYPE: PRT
<213> ORGANISM: Mus musculus

<400> SEQUENCE: 17

Arg Ser Ser Gln Ser Ile Ile His Thr Asn Gly Asn Thr Tyr Leu Glu
1               5                   10                  15

<210> SEQ ID NO 18
<211> LENGTH: 7
<212> TYPE: PRT
<213> ORGANISM: Mus musculus

<400> SEQUENCE: 18

Lys Ile Ser Asn Arg Phe Ser
1               5

<210> SEQ ID NO 19
<211> LENGTH: 9
<212> TYPE: PRT
<213> ORGANISM: Mus musculus

<400> SEQUENCE: 19

Phe Gln Gly Ser His Val Pro Trp Thr
1               5

<210> SEQ ID NO 20
<211> LENGTH: 137
<212> TYPE: PRT
<213> ORGANISM: Mus musculus
```

<400> SEQUENCE: 20

Met Asp Arg Leu Thr Ser Ser Phe Leu Leu Ile Val Pro Ala Tyr
1               5                   10                  15

Val Leu Ser Gln Ile Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
50                  55                  60

Gly Leu Glu Trp Leu Ala His Ile Trp Trp Asp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Arg Ile Thr Ser Val Asp Thr Ala Asp Thr Ala
            100                 105                 110

Thr Tyr Tyr Cys Ala Arg Arg Thr Gln Gly Tyr Phe Asp Tyr Trp Gly
        115                 120                 125

Gln Gly Thr Thr Leu Thr Val Ser Ser
        130                 135

<210> SEQ ID NO 21
<211> LENGTH: 127
<212> TYPE: PRT
<213> ORGANISM: Mus musculus

<400> SEQUENCE: 21

Met Val Ser Thr Ser Gln Leu Leu Gly Leu Leu Leu Phe Trp Thr Ser
1               5                   10                  15

Ala Ser Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
            35                  40                  45

Ile Ser Asp Tyr Leu His Trp Tyr Gln Gln Lys Ser His Glu Ser Pro
50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln Asn Gly His
            100                 105                 110

Ser Phe Pro Trp Thr Phe Gly Gly Gly Thr Lys Leu Glu Ile Lys
        115                 120                 125

<210> SEQ ID NO 22
<211> LENGTH: 467
<212> TYPE: PRT
<213> ORGANISM: Artificial
<220> FEATURE:
<223> OTHER INFORMATION: Chimeric mouse-human

<400> SEQUENCE: 22

Met Glu Trp Ser Trp Val Phe Leu Phe Phe Leu Ser Val Thr Thr Gly
1               5                   10                  15

Val His Ser Gln Ile Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu

-continued

```
                35                  40                  45
Ser Thr Ser Gly Met Gly Val Gly Trp Ile Arg Gln Pro Gly Lys
 50                  55                  60

Gly Leu Glu Trp Leu Ala His Ile Trp Trp Asp Asp Lys Tyr Tyr
 65                  70                  75                  80

Asn Pro Ser Leu Lys Ser Gln Leu Thr Ile Ser Lys Asp Thr Ser Arg
                 85                  90                  95

Asn Gln Val Phe Leu Arg Ile Thr Ser Val Asp Thr Ala Asp Thr Ala
                100                 105                 110

Thr Tyr Tyr Cys Ala Arg Arg Thr Gln Gly Tyr Phe Asp Tyr Trp Gly
                115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
450                 455                 460
```

Pro Gly Lys
465

<210> SEQ ID NO 23
<211> LENGTH: 234
<212> TYPE: PRT
<213> ORGANISM: Artificial
<220> FEATURE:
<223> OTHER INFORMATION: Chimeric mouse-human

<400> SEQUENCE: 23

Met Ser Val Pro Thr Gln Val Leu Gly Leu Leu Leu Trp Leu Thr
1               5                   10                  15

Asp Ala Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Tyr Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Asp Phe Thr Leu Ser Ile Asn
                85                  90                  95

Ser Val Glu Pro Glu Asp Val Gly Val Tyr Tyr Cys Gln Asn Gly His
            100                 105                 110

Ser Phe Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 24
<211> LENGTH: 7
<212> TYPE: PRT
<213> ORGANISM: Mus musculus

<400> SEQUENCE: 24

Thr Ser Gly Met Gly Val Gly
1               5

<210> SEQ ID NO 25
<211> LENGTH: 8
<212> TYPE: PRT
<213> ORGANISM: Mus musculus

<400> SEQUENCE: 25

Gly Phe Ser Leu Ser Thr Ser Gly

<210> SEQ ID NO 26
<211> LENGTH: 12
<212> TYPE: PRT
<213> ORGANISM: Mus musculus

<400> SEQUENCE: 26

Gly Phe Ser Leu Ser Thr Ser Gly Met Gly Val Gly
1               5                   10

<210> SEQ ID NO 27
<211> LENGTH: 15
<212> TYPE: PRT
<213> ORGANISM: Mus musculus

<400> SEQUENCE: 27

His Ile Trp Trp Asp Asp Asp Lys Tyr Tyr Asn Pro Ser Leu Lys
1               5                   10                  15

<210> SEQ ID NO 28
<211> LENGTH: 8
<212> TYPE: PRT
<213> ORGANISM: Mus musculus

<400> SEQUENCE: 28

His Ile Trp Trp Asp Asp Asp Lys
1               5

<210> SEQ ID NO 29
<211> LENGTH: 8
<212> TYPE: PRT
<213> ORGANISM: Mus musculus

<400> SEQUENCE: 29

Arg Thr Gln Gly Tyr Phe Asp Tyr
1               5

<210> SEQ ID NO 30
<211> LENGTH: 11
<212> TYPE: PRT
<213> ORGANISM: Mus musculus

<400> SEQUENCE: 30

Arg Ala Ser Gln Ser Ile Ser Asp Tyr Leu His
1               5                   10

<210> SEQ ID NO 31
<211> LENGTH: 7
<212> TYPE: PRT
<213> ORGANISM: Mus musculus

<400> SEQUENCE: 31

Tyr Ala Ser Gln Ser Ile Ser
1               5

<210> SEQ ID NO 32
<211> LENGTH: 9
<212> TYPE: PRT
<213> ORGANISM: Mus musculus

<400> SEQUENCE: 32

Gln Asn Gly His Ser Phe Pro Trp Thr
1               5

<210> SEQ ID NO 33
<211> LENGTH: 137
<212> TYPE: PRT
<213> ORGANISM: Mus musculus

<400> SEQUENCE: 33

Met Asn Phe Val Leu Ser Leu Ile Phe Leu Ala Leu Ile Leu Lys Gly
1               5                   10                  15

Val Arg Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Arg Tyr Ala Met Ser Trp Val Arg Gln Thr Pro Glu Lys Arg Leu
    50                  55                  60

Glu Trp Val Ala Thr Ile Phe Ser Gly Gly Ser Tyr Thr Tyr Tyr Pro
65                  70                  75                  80

Asp Ser Val Lys Gly Arg Phe Thr Ile Ser Arg Asp Asn Ala Asn Asn
                85                  90                  95

Thr Leu Tyr Leu Gln Met Ser Ser Leu Lys Ala Glu Asp Thr Ala Met
            100                 105                 110

Tyr Phe Cys Ala Arg Pro Asn Trp Glu Arg Thr Phe Asp Tyr Trp Gly
        115                 120                 125

Gln Gly Thr Thr Leu Thr Val Ser Ser
    130                 135

<210> SEQ ID NO 34
<211> LENGTH: 133
<212> TYPE: PRT
<213> ORGANISM: Mus musculus

<400> SEQUENCE: 34

Met Glu Ser Gln Thr Gln Val Leu Met Phe Leu Leu Leu Trp Val Ser
1               5                   10                  15

Gly Ala Cys Thr Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Met Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Pro Thr Phe Gly Gly Gly Thr
        115                 120                 125

Lys Leu Glu Ile Lys
    130

<210> SEQ ID NO 35
<211> LENGTH: 467
<212> TYPE: PRT
<213> ORGANISM: Artificial
<220> FEATURE:
<223> OTHER INFORMATION: Chimeric mouse-human

<400> SEQUENCE: 35

```
Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
            35                  40                  45

Ser Arg Tyr Ala Met Ser Trp Val Arg Gln Thr Pro Glu Lys Arg Leu
50                  55                  60

Glu Trp Val Ala Thr Ile Phe Ser Gly Gly Ser Tyr Thr Tyr Tyr Pro
65                  70                  75                  80

Asp Ser Val Lys Gly Arg Phe Thr Ile Ser Arg Asp Asn Ala Asn Asn
                85                  90                  95

Thr Leu Tyr Leu Gln Met Ser Ser Leu Lys Ala Glu Asp Thr Ala Met
                100                 105                 110

Tyr Phe Cys Ala Arg Pro Asn Trp Glu Arg Thr Phe Asp Tyr Trp Gly
            115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

```
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 36
<211> LENGTH: 240
<212> TYPE: PRT
<213> ORGANISM: Artificial
<220> FEATURE:
<223> OTHER INFORMATION: Chimeric mouse-human

<400> SEQUENCE: 36

Met Ser Val Pro Thr Gln Val Leu Gly Leu Leu Leu Leu Trp Leu Thr
1               5                   10                  15

Asp Ala Arg Cys Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Met Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Pro Thr Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 37
<211> LENGTH: 5
<212> TYPE: PRT
<213> ORGANISM: Mus musculus

<400> SEQUENCE: 37

Arg Tyr Ala Met Ser
1               5
```

```
<210> SEQ ID NO 38
<211> LENGTH: 6
<212> TYPE: PRT
<213> ORGANISM: Mus musculus

<400> SEQUENCE: 38

Gly Phe Thr Phe Ser Arg
1               5

<210> SEQ ID NO 39
<211> LENGTH: 10
<212> TYPE: PRT
<213> ORGANISM: Mus musculus

<400> SEQUENCE: 39

Gly Phe Thr Phe Ser Arg Tyr Ala Met Ser
1               5                   10

<210> SEQ ID NO 40
<211> LENGTH: 15
<212> TYPE: PRT
<213> ORGANISM: Mus musculus

<400> SEQUENCE: 40

Thr Ile Phe Ser Gly Gly Ser Tyr Thr Tyr Tyr Pro Asp Ser Val
1               5                   10                  15

<210> SEQ ID NO 41
<211> LENGTH: 8
<212> TYPE: PRT
<213> ORGANISM: Mus musculus

<400> SEQUENCE: 41

Thr Ile Phe Ser Gly Gly Ser Tyr
1               5

<210> SEQ ID NO 42
<211> LENGTH: 9
<212> TYPE: PRT
<213> ORGANISM: Mus musculus

<400> SEQUENCE: 42

Pro Asn Trp Glu Arg Thr Phe Asp Tyr
1               5

<210> SEQ ID NO 43
<211> LENGTH: 16
<212> TYPE: PRT
<213> ORGANISM: Mus musculus

<400> SEQUENCE: 43

Lys Ser Ser Gln Ser Leu Leu Asn Ser Ser Asn Gln Lys Asn Tyr Leu
1               5                   10                  15

<210> SEQ ID NO 44
<211> LENGTH: 7
<212> TYPE: PRT
<213> ORGANISM: Mus musculus

<400> SEQUENCE: 44

Phe Ala Ser Thr Arg Glu Ser
1               5

<210> SEQ ID NO 45
<211> LENGTH: 9
```

```
<212> TYPE: PRT
<213> ORGANISM: Mus musculus

<400> SEQUENCE: 45

Gln Gln His Tyr Ser Thr Pro Pro Thr
1               5

<210> SEQ ID NO 46
<211> LENGTH: 133
<212> TYPE: PRT
<213> ORGANISM: Mus musculus

<400> SEQUENCE: 46

Met Arg Val Leu Ile Leu Leu Trp Leu Phe Thr Ala Phe Pro Gly Leu
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Phe Val Ser Tyr Ser Gly Thr Thr Lys Tyr Asn Pro
65                  70                  75                  80

Ser Leu Lys Ser Arg Ile Ser Ile Thr Arg Asp Thr Ser Glu Asn Gln
                85                  90                  95

Phe Phe Leu Gln Leu Asn Ser Val Thr Ser Glu Asp Thr Ala Thr Tyr
            100                 105                 110

Tyr Cys Ala Arg Gly Tyr Gly Phe Asp Tyr Trp Gly Gln Gly Thr Thr
        115                 120                 125

Leu Thr Val Ser Ser
    130

<210> SEQ ID NO 47
<211> LENGTH: 126
<212> TYPE: PRT
<213> ORGANISM: Mus musculus

<400> SEQUENCE: 47

Met Gln Ile Ile Ser Leu Leu Leu Ile Ser Val Thr Val Ile Val Ser
1               5                   10                  15

Asn Gly Glu Ile Val Leu Thr Gln Ser Pro Thr Thr Met Ala Ala Ser
            20                  25                  30

Pro Gly Glu Lys Ile Thr Ile Thr Cys Ser Ala Thr Ser Ser Ile Ser
        35                  40                  45

Ser Ile Tyr Phe His Trp Tyr Gln Gln Arg Pro Gly Phe Ser Pro Lys
    50                  55                  60

Leu Leu Ile Tyr Arg Thr Ser Asn Leu Ala Ser Gly Val Pro Ala Arg
65                  70                  75                  80

Phe Ser Gly Ser Gly Ser Gly Thr Ser Tyr Ser Leu Thr Ile Gly Thr
                85                  90                  95

Met Glu Ala Glu Asp Val Ala Thr Tyr Tyr Cys Gln Gln Gly Thr Thr
            100                 105                 110

Ile Pro Phe Thr Phe Gly Ser Gly Thr Lys Leu Glu Ile Lys
        115                 120                 125

<210> SEQ ID NO 48
<211> LENGTH: 6
<212> TYPE: PRT
```

<213> ORGANISM: Mus musculus

<400> SEQUENCE: 48

Ser Asp Tyr Ala Trp Asn
1               5

<210> SEQ ID NO 49
<211> LENGTH: 7
<212> TYPE: PRT
<213> ORGANISM: Mus musculus

<400> SEQUENCE: 49

Gly Tyr Ser Ile Thr Ser Asp
1               5

<210> SEQ ID NO 50
<211> LENGTH: 11
<212> TYPE: PRT
<213> ORGANISM: Mus musculus

<400> SEQUENCE: 50

Gly Tyr Ser Ile Thr Ser Asp Tyr Ala Trp Asn
1               5                   10

<210> SEQ ID NO 51
<211> LENGTH: 16
<212> TYPE: PRT
<213> ORGANISM: Mus musculus

<400> SEQUENCE: 51

Phe Val Ser Tyr Ser Gly Thr Thr Lys Tyr Asn Pro Ser Leu Lys Ser
1               5                   10                  15

<210> SEQ ID NO 52
<211> LENGTH: 9
<212> TYPE: PRT
<213> ORGANISM: Mus musculus

<400> SEQUENCE: 52

Phe Val Ser Tyr Ser Gly Thr Thr Lys
1               5

<210> SEQ ID NO 53
<211> LENGTH: 6
<212> TYPE: PRT
<213> ORGANISM: Mus musculus

<400> SEQUENCE: 53

Gly Tyr Gly Phe Asp Tyr
1               5

<210> SEQ ID NO 54
<211> LENGTH: 12
<212> TYPE: PRT
<213> ORGANISM: Mus musculus

<400> SEQUENCE: 54

Ser Ala Thr Ser Ser Ile Ser Ser Ile Tyr Phe His
1               5                   10

<210> SEQ ID NO 55
<211> LENGTH: 7
<212> TYPE: PRT
<213> ORGANISM: Mus musculus

```
<400> SEQUENCE: 55

Arg Thr Ser Asn Leu Ala Ser
1               5

<210> SEQ ID NO 56
<211> LENGTH: 9
<212> TYPE: PRT
<213> ORGANISM: Mus musculus

<400> SEQUENCE: 56

Gln Gln Gly Thr Thr Ile Pro Phe Thr
1               5

<210> SEQ ID NO 57
<211> LENGTH: 137
<212> TYPE: PRT
<213> ORGANISM: Mus musculus

<400> SEQUENCE: 57

Met Gly Trp Ser Ser Ile Ile Leu Phe Leu Val Ala Thr Ser Thr Gly
1               5                   10                  15

Val His Ser Gln Val Gln Leu Gln Gln Pro Gly Ala Glu Leu Val Arg
            20                  25                  30

Pro Gly Thr Ser Val Asn Leu Ser Cys Lys Ala Ser Gly Tyr Ser Phe
        35                  40                  45

Thr Arg Tyr Trp Met Asn Trp Val Lys Gln Arg Pro Gly Gln Gly Leu
    50                  55                  60

Glu Trp Ile Gly Met Ile His Pro Ser Asp Ser Glu Thr Arg Leu Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Gly Tyr Gly Asn Phe Phe Tyr Val Met Asp Tyr Trp Gly
        115                 120                 125

Gln Gly Thr Ser Val Thr Val Ser Ser
    130                 135

<210> SEQ ID NO 58
<211> LENGTH: 127
<212> TYPE: PRT
<213> ORGANISM: Mus musculus

<400> SEQUENCE: 58

Met Val Ser Thr Pro Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Ser Phe Ser Cys Arg Ala Ser Gln Ser
        35                  40                  45

Ile Gly Thr Ser Ile His Trp Tyr Gln Gln Arg Thr Asn Gly Ser Pro
    50                  55                  60

Arg Leu Leu Ile Lys Phe Ala Ser Glu Ser Ile Ser Gly Ile Pro Ser
65                  70                  75                  80

Arg Phe Ser Gly Ser Gly Ser Gly Thr Asp Phe Thr Leu Asn Ile Asn
                85                  90                  95

Ser Val Glu Ser Glu Asp Ile Ala Asp Tyr Tyr Cys Gln Gln Ser Asn
            100                 105                 110
```

```
Phe Trp Pro Phe Thr Phe Gly Ser Gly Thr Lys Leu Glu Val Lys
        115                 120                 125
```

<210> SEQ ID NO 59
<211> LENGTH: 5
<212> TYPE: PRT
<213> ORGANISM: Mus musculus

<400> SEQUENCE: 59

```
Arg Tyr Trp Met Asn
1               5
```

<210> SEQ ID NO 60
<211> LENGTH: 6
<212> TYPE: PRT
<213> ORGANISM: Mus musculus

<400> SEQUENCE: 60

```
Gly Tyr Ser Phe Thr Arg
1               5
```

<210> SEQ ID NO 61
<211> LENGTH: 10
<212> TYPE: PRT
<213> ORGANISM: Mus musculus

<400> SEQUENCE: 61

```
Gly Tyr Ser Phe Thr Arg Tyr Trp Met Asn
1               5                   10
```

<210> SEQ ID NO 62
<211> LENGTH: 17
<212> TYPE: PRT
<213> ORGANISM: Mus musculus

<400> SEQUENCE: 62

```
Met Ile His Pro Ser Asp Ser Glu Thr Arg Leu Asn Gln Lys Phe Lys
1               5                   10                  15

Asp
```

<210> SEQ ID NO 63
<211> LENGTH: 10
<212> TYPE: PRT
<213> ORGANISM: Mus musculus

<400> SEQUENCE: 63

```
Met Ile His Pro Ser Asp Ser Glu Thr Arg
1               5                   10
```

<210> SEQ ID NO 64
<211> LENGTH: 9
<212> TYPE: PRT
<213> ORGANISM: Mus musculus

<400> SEQUENCE: 64

```
Gly Asn Phe Phe Tyr Val Met Asp Tyr
1               5
```

<210> SEQ ID NO 65
<211> LENGTH: 11
<212> TYPE: PRT
<213> ORGANISM: Mus musculus

<400> SEQUENCE: 65

```
Arg Ala Ser Gln Ser Ile Gly Thr Ser Ile His
1               5                   10
```

<210> SEQ ID NO 66
<211> LENGTH: 7
<212> TYPE: PRT
<213> ORGANISM: Mus musculus

<400> SEQUENCE: 66

```
Ala Ser Glu Ser Ile Ser Gly
1               5
```

<210> SEQ ID NO 67
<211> LENGTH: 9
<212> TYPE: PRT
<213> ORGANISM: Mus musculus

<400> SEQUENCE: 67

```
Gln Gln Ser Asn Phe Trp Pro Phe Thr
1               5
```

<210> SEQ ID NO 68
<211> LENGTH: 140
<212> TYPE: PRT
<213> ORGANISM: Mus musculus

<400> SEQUENCE: 68

```
Met Glu Trp Ser Trp Val Phe Leu Phe Phe Leu Ser Val Thr Thr Gly
1               5                   10                  15

Val His Ser Gln Val Gln Leu Gln Gln Ser Gly Ala Asp Leu Val Arg
            20                  25                  30

Pro Gly Ala Ser Val Arg Leu Ser Cys Arg Ala Ser Gly Tyr Ser Phe
        35                  40                  45

Thr Asn Tyr Trp Met Asn Trp Val Lys Gln Arg Pro Gly Gln Gly Leu
    50                  55                  60

Glu Trp Ile Gly Met Ile His Pro Ser Asp Ser Glu Thr Arg Leu Asn
65                  70                  75                  80

Gln Lys Phe Lys Asp Lys Ala Thr Leu Thr Val Asp Lys Ser Ser Asn
                85                  90                  95

Thr Ala Tyr Met Gln Leu Ser Ser Pro Thr Ser Glu Asp Ser Ala Ile
            100                 105                 110

Tyr Tyr Cys Ala Arg Asp Asp Phe Phe Thr Met Asp Tyr Trp Gly Gln
        115                 120                 125

Gly Thr Ser Val Thr Val Ser Ser Ala Ser Thr Lys
    130                 135                 140
```

<210> SEQ ID NO 69
<211> LENGTH: 127
<212> TYPE: PRT
<213> ORGANISM: Mus musculus

<400> SEQUENCE: 69

```
Met Ser Val Pro Thr Gln Val Leu Gly Leu Leu Leu Leu Trp Leu Thr
1               5                   10                  15

Asp Ala Arg Cys Asp Ile Leu Leu Thr Gln Ser Pro Ala Ile Leu Ser
            20                  25                  30

Val Ser Pro Gly Glu Arg Val Ser Phe Ser Cys Arg Ala Ser Gln Asn
        35                  40                  45

Ile Val Thr Ser Ile His Trp Tyr Gln Gln Ser Thr Asn Gly Ser Pro
```

```
                50                  55                  60
Arg Leu Leu Ile Lys Tyr Ala Ser Glu Ser Ile Ser Gly Ile Pro Ser
 65                  70                  75                  80

Arg Phe Ser Gly Ser Gly Ser Gly Thr Asp Phe Thr Leu Thr Ile Asn
                 85                  90                  95

Ser Val Glu Ser Glu Asp Val Ala Asp Tyr Tyr Cys Gln Gln Ser Asn
            100                 105                 110

Ile Trp Pro Leu Thr Phe Gly Ala Gly Thr Lys Leu Glu Leu Lys
        115                 120                 125
```

<210> SEQ ID NO 70
<211> LENGTH: 5
<212> TYPE: PRT
<213> ORGANISM: Mus musculus

<400> SEQUENCE: 70

```
Asn Tyr Trp Met Asn
 1               5
```

<210> SEQ ID NO 71
<211> LENGTH: 6
<212> TYPE: PRT
<213> ORGANISM: Mus musculus

<400> SEQUENCE: 71

```
Gly Tyr Ser Phe Thr Asn
 1               5
```

<210> SEQ ID NO 72
<211> LENGTH: 10
<212> TYPE: PRT
<213> ORGANISM: Mus musculus

<400> SEQUENCE: 72

```
Gly Tyr Ser Phe Thr Asn Tyr Trp Met Asn
 1               5                  10
```

<210> SEQ ID NO 73
<211> LENGTH: 17
<212> TYPE: PRT
<213> ORGANISM: Mus musculus

<400> SEQUENCE: 73

```
Met Ile His Pro Ser Asp Ser Glu Thr Arg Leu Asn Gln Lys Phe Lys
 1               5                  10                  15

Asp
```

<210> SEQ ID NO 74
<211> LENGTH: 10
<212> TYPE: PRT
<213> ORGANISM: Mus musculus

<400> SEQUENCE: 74

```
Met Ile His Pro Ser Asp Ser Glu Thr Arg
 1               5                  10
```

<210> SEQ ID NO 75
<211> LENGTH: 8
<212> TYPE: PRT
<213> ORGANISM: Mus musculus

<400> SEQUENCE: 75

```
<210> SEQ ID NO 76
<211> LENGTH: 11
<212> TYPE: PRT
<213> ORGANISM: Mus musculus

<400> SEQUENCE: 76

Arg Ala Ser Gln Asn Ile Val Thr Ser Ile His
1               5                   10

<210> SEQ ID NO 77
<211> LENGTH: 7
<212> TYPE: PRT
<213> ORGANISM: Mus musculus

<400> SEQUENCE: 77

Tyr Ala Ser Glu Ser Ile Ser
1               5

<210> SEQ ID NO 78
<211> LENGTH: 9
<212> TYPE: PRT
<213> ORGANISM: Mus musculus

<400> SEQUENCE: 78

Gln Gln Ser Asn Ile Trp Pro Leu Thr
1               5

<210> SEQ ID NO 79
<211> LENGTH: 141
<212> TYPE: PRT
<213> ORGANISM: Mus musculus

<400> SEQUENCE: 79

Met Glu Trp Ser Trp Val Phe Leu Phe Phe Leu Ser Val Thr Thr Gly
1               5                   10                  15

Val His Ser Gln Val Thr Leu Lys Glu Ser Gly Pro Gly Ile Leu Lys
                20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Arg Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
                100                 105                 110

Thr Tyr Tyr Cys Ala Arg Arg Leu Asn Gly Tyr Phe Asp Tyr Trp Gly
            115                 120                 125

Gln Gly Thr Thr Leu Thr Val Ser Ser Ala Ser Thr Lys
    130                 135                 140

<210> SEQ ID NO 80
<211> LENGTH: 127
<212> TYPE: PRT
<213> ORGANISM: Mus musculus

<400> SEQUENCE: 80
```

(Asp Asp Phe Phe Thr Met Asp Tyr at top of page, continuation from previous)

```
Asp Asp Phe Phe Thr Met Asp Tyr
1               5
```

```
Met Ser Val Pro Thr Gln Val Leu Gly Leu Leu Leu Trp Leu Thr
1               5                   10                  15

Asp Ala Arg Cys Asp Ile Val Met Thr Gln Ser Pro Ala Thr Leu Ser
            20                  25                  30

Val Thr Leu Gly Asp Arg Val Ser Leu Ser Cys Arg Ala Ser Gln Ser
            35                  40                  45

Ile Ser Asp Tyr Leu His Trp Tyr Gln Gln Lys Ser His Glu Ser Pro
50              55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln Asn Gly His
                100                 105                 110

Ser Phe Pro Phe Thr Phe Gly Ser Gly Thr Lys Leu Glu Ile Lys
                115                 120                 125
```

```
<210> SEQ ID NO 81
<211> LENGTH: 7
<212> TYPE: PRT
<213> ORGANISM: Mus musculus

<400> SEQUENCE: 81

Thr Ser Gly Met Gly Val Gly
1               5

<210> SEQ ID NO 82
<211> LENGTH: 8
<212> TYPE: PRT
<213> ORGANISM: Mus musculus

<400> SEQUENCE: 82

Gly Phe Ser Leu Ser Thr Ser Gly
1               5

<210> SEQ ID NO 83
<211> LENGTH: 12
<212> TYPE: PRT
<213> ORGANISM: Mus musculus

<400> SEQUENCE: 83

Gly Phe Ser Leu Ser Thr Ser Gly Met Gly Val Gly
1               5                   10

<210> SEQ ID NO 84
<211> LENGTH: 16
<212> TYPE: PRT
<213> ORGANISM: Mus musculus

<400> SEQUENCE: 84

His Ile Trp Trp Asp Asp Asp Arg Tyr Tyr Asn Pro Ser Leu Lys Ser
1               5                   10                  15

<210> SEQ ID NO 85
<211> LENGTH: 9
<212> TYPE: PRT
<213> ORGANISM: Mus musculus

<400> SEQUENCE: 85

His Ile Trp Trp Asp Asp Asp Arg Tyr
1               5
```

```
<210> SEQ ID NO 86
<211> LENGTH: 8
<212> TYPE: PRT
<213> ORGANISM: Mus musculus

<400> SEQUENCE: 86

Arg Leu Asn Gly Tyr Phe Asp Tyr
1               5

<210> SEQ ID NO 87
<211> LENGTH: 11
<212> TYPE: PRT
<213> ORGANISM: Mus musculus

<400> SEQUENCE: 87

Arg Ala Ser Gln Ser Ile Ser Asp Tyr Leu His
1               5                   10

<210> SEQ ID NO 88
<211> LENGTH: 7
<212> TYPE: PRT
<213> ORGANISM: Mus musculus

<400> SEQUENCE: 88

Tyr Ala Ser Gln Ser Ile Ser
1               5

<210> SEQ ID NO 89
<211> LENGTH: 9
<212> TYPE: PRT
<213> ORGANISM: Mus musculus

<400> SEQUENCE: 89

Gln Asn Gly His Ser Phe Pro Phe Thr
1               5

<210> SEQ ID NO 90
<211> LENGTH: 142
<212> TYPE: PRT
<213> ORGANISM: Mus musculus

<400> SEQUENCE: 90

Met Glu Trp Ser Trp Val Phe Leu Phe Phe Leu Ser Val Thr Thr Gly
1               5                   10                  15

Val His Ser Asp Val Gln Leu Gln Glu Ser Gly Pro Asp Leu Val Asn
                20                  25                  30

Pro Ser Gln Ser Leu Ser Leu Ile Cys Thr Val Thr Gly Tyr Ser Ile
            35                  40                  45

Thr Ser Asp Tyr Ser Trp His Trp Ile Arg Gln Phe Pro Gly Asn Lys
        50                  55                  60

Leu Glu Trp Met Gly Asn Ile His Tyr Ser Gly Arg Ile Asn Tyr Asn
65                  70                  75                  80

Pro Ser Leu Arg Ser Arg Ile Ser Ile Thr Arg Asp Thr Ser Lys Asn
                85                  90                  95

Gln Phe Phe Leu Gln Leu Ile Ser Val Thr Thr Glu Asp Thr Ala Thr
            100                 105                 110

Tyr Tyr Cys Ala Thr Arg Arg Thr Phe Gly Asn Phe Glu Asp Tyr Trp
        115                 120                 125

Gly Gln Gly Thr Thr Leu Thr Val Ser Ser Ala Ser Thr Lys
    130                 135                 140
```

<210> SEQ ID NO 91
<211> LENGTH: 126
<212> TYPE: PRT
<213> ORGANISM: Mus musculus

<400> SEQUENCE: 91

Met Ser Val Pro Thr Gln Val Leu Gly Leu Leu Leu Leu Trp Leu Thr
1               5                   10                  15

Asp Ala Arg Cys Gln Ile Val Leu Ser Gln Ser Pro Ala Thr Leu Ser
            20                  25                  30

Val Ser Pro Gly Glu Lys Val Thr Met Thr Cys Arg Ser Ser Ser Ser
        35                  40                  45

Val Asn Tyr Met His Trp Tyr Gln Gln Lys Pro Gly Ser Ser Pro Lys
    50                  55                  60

Pro Trp Ile Tyr Ala Thr Ser Thr Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Ser
            100                 105                 110

Asn Pro Leu Thr Phe Gly Ala Gly Thr Lys Leu Glu Leu Lys
        115                 120                 125

<210> SEQ ID NO 92
<211> LENGTH: 6
<212> TYPE: PRT
<213> ORGANISM: Mus musculus

<400> SEQUENCE: 92

Ser Asp Tyr Ser Trp His
1               5

<210> SEQ ID NO 93
<211> LENGTH: 7
<212> TYPE: PRT
<213> ORGANISM: Mus musculus

<400> SEQUENCE: 93

Gly Tyr Ser Ile Thr Ser Asp
1               5

<210> SEQ ID NO 94
<211> LENGTH: 11
<212> TYPE: PRT
<213> ORGANISM: Mus musculus

<400> SEQUENCE: 94

Gly Tyr Ser Ile Thr Ser Asp Tyr Ser Trp His
1               5                   10

<210> SEQ ID NO 95
<211> LENGTH: 16
<212> TYPE: PRT
<213> ORGANISM: Mus musculus

<400> SEQUENCE: 95

Asn Ile His Tyr Ser Gly Arg Ile Asn Tyr Asn Pro Ser Leu Arg Ser
1               5                   10                  15

<210> SEQ ID NO 96
<211> LENGTH: 9

```
<212> TYPE: PRT
<213> ORGANISM: Mus musculus

<400> SEQUENCE: 96

Asn Ile His Tyr Ser Gly Arg Ile Asn
1               5

<210> SEQ ID NO 97
<211> LENGTH: 10
<212> TYPE: PRT
<213> ORGANISM: Mus musculus

<400> SEQUENCE: 97

Arg Arg Thr Phe Gly Asn Phe Glu Asp Tyr
1               5                   10

<210> SEQ ID NO 98
<211> LENGTH: 10
<212> TYPE: PRT
<213> ORGANISM: Mus musculus

<400> SEQUENCE: 98

Arg Ser Ser Ser Val Asn Tyr Met His
1               5                   10

<210> SEQ ID NO 99
<211> LENGTH: 7
<212> TYPE: PRT
<213> ORGANISM: Mus musculus

<400> SEQUENCE: 99

Ala Thr Ser Thr Leu Ala Ser
1               5

<210> SEQ ID NO 100
<211> LENGTH: 9
<212> TYPE: PRT
<213> ORGANISM: Mus musculus

<400> SEQUENCE: 100

Gln Gln Trp Ser Ser Asn Pro Leu Thr
1               5

<210> SEQ ID NO 101
<211> LENGTH: 143
<212> TYPE: PRT
<213> ORGANISM: Mus musculus

<400> SEQUENCE: 101

Met Glu Trp Ser Trp Val Phe Leu Phe Phe Leu Ser Val Thr Thr Gly
1               5                   10                  15

Val His Ser Gln Val Gln Leu Gln Gln Ser Ala Ala Glu Leu Ala Arg
                20                  25                  30

Pro Gly Ala Ser Val Lys Met Ser Cys Lys Ala Ser Gly Tyr Thr Phe
            35                  40                  45

Thr Ser Tyr Thr Met His Trp Val Lys Gln Arg Pro Gly Gln Gly Leu
        50                  55                  60

Glu Trp Ile Gly Tyr Ile Asn Pro Ser Ser Gly Tyr Thr Glu Tyr Asn
65                  70                  75                  80

Gln Lys Phe Lys Asp Lys Thr Thr Leu Thr Val Asp Lys Ser Ser Thr
                85                  90                  95

Thr Ser Tyr Met Gln Leu Ser Ser Leu Thr Ser Asp Asn Ser Ala Val
```

```
                100              105              110
Tyr Tyr Cys Ala Arg Gly Gly Asp Trp Asp Val Asp Trp Phe Val Tyr
            115              120              125

Trp Gly Gln Gly Thr Leu Val Thr Val Ser Ala Ala Ser Thr Lys
            130              135              140

<210> SEQ ID NO 102
<211> LENGTH: 126
<212> TYPE: PRT
<213> ORGANISM: Mus musculus

<400> SEQUENCE: 102

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Ile Met Ser
            20                  25                  30

Ala Ser Pro Gly Glu Lys Val Thr Ile Thr Cys Ser Ala Ser Ser Ser
        35                  40                  45

Ile Ser Tyr Met His Trp Phe Gln Gln Lys Pro Gly Thr Ser Pro Lys
    50                  55                  60

Leu Trp Ile Tyr Ser Thr Ser Lys Leu Ala Ser Gly Val Pro Ala Arg
65                  70                  75                  80

Phe Ser Gly Ser Gly Ser Gly Thr Ser His Ser Leu Thr Ile Ser Arg
                85                  90                  95

Met Glu Ala Glu Asp Ala Ala Thr Tyr Tyr Cys Gln His Arg Ser Thr
            100                 105                 110

Tyr Pro Phe Thr Phe Gly Ser Gly Thr Lys Leu Glu Ile Lys
        115                 120                 125

<210> SEQ ID NO 103
<211> LENGTH: 5
<212> TYPE: PRT
<213> ORGANISM: Mus musculus

<400> SEQUENCE: 103

Ser Tyr Thr Met His
1               5

<210> SEQ ID NO 104
<211> LENGTH: 6
<212> TYPE: PRT
<213> ORGANISM: Mus musculus

<400> SEQUENCE: 104

Gly Tyr Thr Phe Thr Ser
1               5

<210> SEQ ID NO 105
<211> LENGTH: 10
<212> TYPE: PRT
<213> ORGANISM: Mus musculus

<400> SEQUENCE: 105

Gly Tyr Thr Phe Thr Ser Tyr Thr Met His
1               5                   10

<210> SEQ ID NO 106
<211> LENGTH: 17
<212> TYPE: PRT
<213> ORGANISM: Mus musculus
```

-continued

```
<400> SEQUENCE: 106

Tyr Ile Asn Pro Ser Ser Gly Tyr Thr Glu Tyr Asn Gln Lys Phe Lys
1               5                   10                  15

Asp

<210> SEQ ID NO 107
<211> LENGTH: 10
<212> TYPE: PRT
<213> ORGANISM: Mus musculus

<400> SEQUENCE: 107

Tyr Ile Asn Pro Ser Ser Gly Tyr Thr Glu
1               5                   10

<210> SEQ ID NO 108
<211> LENGTH: 11
<212> TYPE: PRT
<213> ORGANISM: Mus musculus

<400> SEQUENCE: 108

Gly Gly Asp Trp Asp Val Asp Trp Phe Val Tyr
1               5                   10

<210> SEQ ID NO 109
<211> LENGTH: 10
<212> TYPE: PRT
<213> ORGANISM: Mus musculus

<400> SEQUENCE: 109

Ser Ala Ser Ser Ser Ile Ser Tyr Met His
1               5                   10

<210> SEQ ID NO 110
<211> LENGTH: 7
<212> TYPE: PRT
<213> ORGANISM: Mus musculus

<400> SEQUENCE: 110

Ser Thr Ser Lys Leu Ala Ser
1               5

<210> SEQ ID NO 111
<211> LENGTH: 9
<212> TYPE: PRT
<213> ORGANISM: Mus musculus

<400> SEQUENCE: 111

Gln His Arg Ser Thr Tyr Pro Phe Thr
1               5

<210> SEQ ID NO 112
<211> LENGTH: 141
<212> TYPE: PRT
<213> ORGANISM: Mus musculus

<400> SEQUENCE: 112

Met Glu Trp Ser Trp Val Phe Leu Phe Phe Leu Ser Val Thr Thr Gly
1               5                   10                  15

Val His Ser Asp Val Gln Leu Gln Glu Ser Gly Pro Asp Leu Val Lys
                20                  25                  30

Pro Ser Gln Ser Leu Ser Leu Thr Cys Thr Val Thr Gly Tyr Ser Ile
            35                  40                  45
```

Thr Ser Gly Tyr Ser Trp His Trp Ile Arg Gln Phe Pro Gly Asn Lys
    50              55                  60
Leu Glu Trp Met Gly Phe Ile His Tyr Ser Gly Ser Thr Asp Tyr Asn
65                  70                  75                  80
Pro Ser Leu Lys Ser Arg Ile Ser Leu Thr Arg Asp Thr Ser Lys Asn
                85                  90                  95
Gln Phe Phe Leu Gln Leu Asn Ser Val Ser Thr Glu Asp Thr Ala Thr
                100                 105                 110
Tyr Tyr Cys Ala Lys Asp Tyr Gly His Trp Tyr Phe Asp Val Trp Gly
            115                 120                 125
Ala Gly Thr Thr Val Thr Val Ser Ser Ala Ser Thr Lys
    130                 135                 140

<210> SEQ ID NO 113
<211> LENGTH: 126
<212> TYPE: PRT
<213> ORGANISM: Mus musculus

<400> SEQUENCE: 113

Met Ser Val Pro Thr Gln Val Leu Gly Leu Leu Leu Trp Leu Thr
1               5                   10                  15
Asp Ala Arg Cys Ser Ile Val Met Thr Gln Thr Pro Lys Phe Leu Leu
                20                  25                  30
Val Ser Ala Gly Asp Arg Val Thr Ile Thr Cys Lys Ala Ser Gln Ser
            35                  40                  45
Val Ser Tyr Asp Val Ala Trp Tyr Gln Gln Lys Pro Gly Gln Ser Pro
    50                  55                  60
Lys Leu Leu Ile Phe Tyr Ala Ser Asn Arg Tyr Thr Gly Val Pro Ala
65                  70                  75                  80
Arg Phe Thr Gly Ser Gly Tyr Gly Thr Asp Phe Thr Phe Thr Ile Ser
                85                  90                  95
Thr Val Gln Ala Glu Asp Leu Ala Val Tyr Phe Cys Gln Gln Asp Tyr
                100                 105                 110
Ser Ser Leu Thr Phe Gly Ala Gly Thr Lys Leu Glu Leu Lys
            115                 120                 125

<210> SEQ ID NO 114
<211> LENGTH: 6
<212> TYPE: PRT
<213> ORGANISM: Mus musculus

<400> SEQUENCE: 114

Ser Gly Tyr Ser Trp His
1               5

<210> SEQ ID NO 115
<211> LENGTH: 7
<212> TYPE: PRT
<213> ORGANISM: Mus musculus

<400> SEQUENCE: 115

Gly Tyr Ser Ile Thr Ser Gly
1               5

<210> SEQ ID NO 116
<211> LENGTH: 11
<212> TYPE: PRT
<213> ORGANISM: Mus musculus

<400> SEQUENCE: 116

Gly Tyr Ser Ile Thr Ser Gly Tyr Ser Trp His
1               5                   10

<210> SEQ ID NO 117
<211> LENGTH: 16
<212> TYPE: PRT
<213> ORGANISM: Mus musculus

<400> SEQUENCE: 117

Phe Ile His Tyr Ser Gly Ser Thr Asp Tyr Asn Pro Ser Leu Lys Ser
1               5                   10                  15

<210> SEQ ID NO 118
<211> LENGTH: 9
<212> TYPE: PRT
<213> ORGANISM: Mus musculus

<400> SEQUENCE: 118

Phe Ile His Tyr Ser Gly Ser Thr Asp
1               5

<210> SEQ ID NO 119
<211> LENGTH: 9
<212> TYPE: PRT
<213> ORGANISM: Mus musculus

<400> SEQUENCE: 119

Asp Tyr Gly His Trp Tyr Phe Asp Val
1               5

<210> SEQ ID NO 120
<211> LENGTH: 11
<212> TYPE: PRT
<213> ORGANISM: Mus musculus

<400> SEQUENCE: 120

Lys Ala Ser Gln Ser Val Ser Tyr Asp Val Ala
1               5                   10

<210> SEQ ID NO 121
<211> LENGTH: 7
<212> TYPE: PRT
<213> ORGANISM: Mus musculus

<400> SEQUENCE: 121

Tyr Ala Ser Asn Arg Tyr Thr
1               5

<210> SEQ ID NO 122
<211> LENGTH: 8
<212> TYPE: PRT
<213> ORGANISM: Mus musculus

<400> SEQUENCE: 122

Gln Gln Asp Tyr Ser Ser Leu Thr
1               5

<210> SEQ ID NO 123
<211> LENGTH: 141
<212> TYPE: PRT
<213> ORGANISM: Mus musculus

<400> SEQUENCE: 123

Met Glu Trp Ser Trp Val Phe Leu Phe Phe Leu Ser Val Thr Thr Gly

```
              1               5                  10                 15
            Val His Ser Gln Val Gln Leu Gln Gln Pro Gly Ala Glu Leu Val Arg
                            20                  25                 30
            Pro Gly Ala Ser Val Lys Leu Ser Cys Lys Ala Ser Gly Tyr Ser Phe
                            35                  40             45
            Thr Ser Tyr Trp Met Asn Trp Met Lys Gln Arg Pro Gly Gln Gly Leu
                50                      55                 60
            Glu Trp Ile Gly Met Ile His Pro Ser Asp Ser Glu Thr Arg Leu Asn
             65                     70                  75                 80
            Gln Lys Phe Lys Asp Lys Ala Thr Leu Thr Val Asp Lys Ser Ser Ser
                            85                  90                 95
            Thr Ala Tyr Met Gln Leu Asn Ser Pro Thr Ser Glu Asp Ser Ala Val
                            100                 105            110
            Tyr Tyr Cys Ala Arg Glu Met Gly Pro Tyr Thr Leu Asp Tyr Trp Gly
                            115                 120            125
            Gln Gly Thr Ser Val Thr Val Ser Ser Ala Ser Thr Lys
                            130                 135            140
```

<210> SEQ ID NO 124
<211> LENGTH: 127
<212> TYPE: PRT
<213> ORGANISM: Mus musculus

<400> SEQUENCE: 124

```
            Met Ser Val Pro Thr Gln Val Leu Gly Leu Leu Leu Trp Leu Thr
             1               5                  10                 15
            Asp Ala Arg Cys Asp Ile Leu Leu Thr Gln Ser Pro Ala Ile Leu Ser
                            20                  25                 30
            Val Ser Pro Gly Ala Arg Val Ser Phe Ser Cys Arg Ala Ser Gln Asn
                            35                  40             45
            Ile Asp Thr Ser Ile His Trp Tyr Gln Gln Arg Thr Asn Gly Ser Pro
                50                      55                 60
            Arg Leu Leu Ile Lys Tyr Ala Ser Glu Ser Ile Ser Gly Ile Pro Ser
             65                     70                  75                 80
            Arg Phe Ser Gly Ser Gly Ser Gly Thr Asp Phe Thr Leu Ser Ile Asn
                            85                  90                 95
            Ser Val Glu Ser Glu Asp Ile Ala Asp Tyr Tyr Cys Gln Gln Ser Asn
                            100                 105            110
            Tyr Trp Pro Leu Thr Phe Gly Ala Gly Thr Lys Leu Glu Leu Lys
                            115                 120            125
```

<210> SEQ ID NO 125
<211> LENGTH: 5
<212> TYPE: PRT
<213> ORGANISM: Mus musculus

<400> SEQUENCE: 125

```
            Ser Tyr Trp Met Asn
             1               5
```

<210> SEQ ID NO 126
<211> LENGTH: 6
<212> TYPE: PRT
<213> ORGANISM: Mus musculus

<400> SEQUENCE: 126

```
            Gly Tyr Ser Phe Thr Ser
             1               5
```

```
<210> SEQ ID NO 127
<211> LENGTH: 10
<212> TYPE: PRT
<213> ORGANISM: Mus musculus

<400> SEQUENCE: 127

Gly Tyr Ser Phe Thr Ser Tyr Trp Met Asn
1               5                   10

<210> SEQ ID NO 128
<211> LENGTH: 17
<212> TYPE: PRT
<213> ORGANISM: Mus musculus

<400> SEQUENCE: 128

Met Ile His Pro Ser Asp Ser Glu Thr Arg Leu Asn Gln Lys Phe Lys
1               5                   10                  15

Asp

<210> SEQ ID NO 129
<211> LENGTH: 10
<212> TYPE: PRT
<213> ORGANISM: Mus musculus

<400> SEQUENCE: 129

Met Ile His Pro Ser Asp Ser Glu Thr Arg
1               5                   10

<210> SEQ ID NO 130
<211> LENGTH: 9
<212> TYPE: PRT
<213> ORGANISM: Mus musculus

<400> SEQUENCE: 130

Glu Met Gly Pro Tyr Thr Leu Asp Tyr
1               5

<210> SEQ ID NO 131
<211> LENGTH: 11
<212> TYPE: PRT
<213> ORGANISM: Mus musculus

<400> SEQUENCE: 131

Arg Ala Ser Gln Asn Ile Asp Thr Ser Ile His
1               5                   10

<210> SEQ ID NO 132
<211> LENGTH: 7
<212> TYPE: PRT
<213> ORGANISM: Mus musculus

<400> SEQUENCE: 132

Tyr Ala Ser Glu Ser Ile Ser
1               5

<210> SEQ ID NO 133
<211> LENGTH: 9
<212> TYPE: PRT
<213> ORGANISM: Mus musculus

<400> SEQUENCE: 133

Gln Gln Ser Asn Tyr Trp Pro Leu Thr
1               5
```

<210> SEQ ID NO 134
<211> LENGTH: 218
<212> TYPE: PRT
<213> ORGANISM: Homo sapiens

<400> SEQUENCE: 134

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 135
<211> LENGTH: 46
<212> TYPE: DNA
<213> ORGANISM: Artificial
<220> FEATURE:
<223> OTHER INFORMATION: Primer

<400> SEQUENCE: 135
tacgactcac aagcttaccg ccaccatggg gctgggaccg gtcttc                46

<210> SEQ ID NO 136
<211> LENGTH: 39
<212> TYPE: DNA
<213> ORGANISM: Artificial
<220> FEATURE:
<223> OTHER INFORMATION: Primer

<400> SEQUENCE: 136
ccgccccgac tctagattac taggcgccct cagtggagc                        39

<210> SEQ ID NO 137
<211> LENGTH: 34
<212> TYPE: DNA

```
<213> ORGANISM: Artificial
<220> FEATURE:
<223> OTHER INFORMATION: Primer

<400> SEQUENCE: 137
acggtgctgt ccgcggatgg atctgtgcag tcag                              34

<210> SEQ ID NO 138
<211> LENGTH: 33
<212> TYPE: DNA
<213> ORGANISM: Artificial
<220> FEATURE:
<223> OTHER INFORMATION: Primer

<400> SEQUENCE: 138
cctgctttct ggtccttgat atgagccagg gtc                               33

<210> SEQ ID NO 139
<211> LENGTH: 34
<212> TYPE: DNA
<213> ORGANISM: Artificial
<220> FEATURE:
<223> OTHER INFORMATION: Primer

<400> SEQUENCE: 139
agggcataag caagactgtg gggctcagca gcag                              34

<210> SEQ ID NO 140
<211> LENGTH: 35
<212> TYPE: DNA
<213> ORGANISM: Artificial
<220> FEATURE:
<223> OTHER INFORMATION: Primer

<400> SEQUENCE: 140
tcttgcttat gccctcacgg tgctgtcctg ggatg                             35

<210> SEQ ID NO 141
<211> LENGTH: 34
<212> TYPE: DNA
<213> ORGANISM: Artificial
<220> FEATURE:
<223> OTHER INFORMATION: Primer

<400> SEQUENCE: 141
acgccacaga tccatcccag gacgccaccg tgag                              34

<210> SEQ ID NO 142
<211> LENGTH: 33
<212> TYPE: DNA
<213> ORGANISM: Artificial
<220> FEATURE:
<223> OTHER INFORMATION: Primer

<400> SEQUENCE: 142
atggatctgt ggcgtcaggg tttctcactg agg                               33

<210> SEQ ID NO 143
<211> LENGTH: 36
<212> TYPE: DNA
<213> ORGANISM: Artificial
<220> FEATURE:
<223> OTHER INFORMATION: Primer

<400> SEQUENCE: 143
cgcggacagc accgtgaggt tataacgaag actgtg                            36
```

<210> SEQ ID NO 144
<211> LENGTH: 34
<212> TYPE: DNA
<213> ORGANISM: Artificial
<220> FEATURE:
<223> OTHER INFORMATION: Primer

<400> SEQUENCE: 144
ggaccagaaa gcaggcttgc attccctaca ggag                                34

<210> SEQ ID NO 145
<211> LENGTH: 35
<212> TYPE: DNA
<213> ORGANISM: Artificial
<220> FEATURE:
<223> OTHER INFORMATION: Primer

<400> SEQUENCE: 145
ctccagccca ggacagcacc gtgaggttat aacga                               35

<210> SEQ ID NO 146
<211> LENGTH: 35
<212> TYPE: DNA
<213> ORGANISM: Artificial
<220> FEATURE:
<223> OTHER INFORMATION: Primer

<400> SEQUENCE: 146
tgtcctgggc tggagctgtg cagtcagggt ttctc                               35

<210> SEQ ID NO 147
<211> LENGTH: 38
<212> TYPE: DNA
<213> ORGANISM: Artificial
<220> FEATURE:
<223> OTHER INFORMATION: Primer

<400> SEQUENCE: 147
agtgagaaac cctgcctgca cagatccatc ccaggaca                            38

<210> SEQ ID NO 148
<211> LENGTH: 35
<212> TYPE: DNA
<213> ORGANISM: Artificial
<220> FEATURE:
<223> OTHER INFORMATION: Primer

<400> SEQUENCE: 148
gcagggtttc tcactgaggt acatctggat ggtca                               35

<210> SEQ ID NO 149
<211> LENGTH: 34
<212> TYPE: DNA
<213> ORGANISM: Artificial
<220> FEATURE:
<223> OTHER INFORMATION: Primer

<400> SEQUENCE: 149
ccagagctac cgcagtgaga accctgact gcac                                 34

<210> SEQ ID NO 150
<211> LENGTH: 34
<212> TYPE: DNA
<213> ORGANISM: Artificial
<220> FEATURE:

<223> OTHER INFORMATION: Primer

<400> SEQUENCE: 150
ctgcggtagc tctggatggt caggccttcc tgcg                                      34

<210> SEQ ID NO 151
<211> LENGTH: 36
<212> TYPE: DNA
<213> ORGANISM: Artificial
<220> FEATURE:
<223> OTHER INFORMATION: Primer

<400> SEQUENCE: 151
tgcctgtcac aggccaggaa gggctgacca tccaga                                    36

<210> SEQ ID NO 152
<211> LENGTH: 40
<212> TYPE: DNA
<213> ORGANISM: Artificial
<220> FEATURE:
<223> OTHER INFORMATION: Primer

<400> SEQUENCE: 152
ggcctgtgac aggcagaaat gcagggcagc gccccaggga                                40

<210> SEQ ID NO 153
<211> LENGTH: 38
<212> TYPE: DNA
<213> ORGANISM: Artificial
<220> FEATURE:
<223> OTHER INFORMATION: Primer

<400> SEQUENCE: 153
catttcgcac tggcacagcg caggaagggc tgaccatc                                  38

<210> SEQ ID NO 154
<211> LENGTH: 37
<212> TYPE: DNA
<213> ORGANISM: Artificial
<220> FEATURE:
<223> OTHER INFORMATION: Primer

<400> SEQUENCE: 154
tgccagtgcg aaatgcaggg caaagcccca gggacag                                   37

<210> SEQ ID NO 155
<211> LENGTH: 33
<212> TYPE: DNA
<213> ORGANISM: Artificial
<220> FEATURE:
<223> OTHER INFORMATION: Primer

<400> SEQUENCE: 155
ccgcgcatgc ctgcctgtca cagcgcagga agg                                       33

<210> SEQ ID NO 156
<211> LENGTH: 34
<212> TYPE: DNA
<213> ORGANISM: Artificial
<220> FEATURE:
<223> OTHER INFORMATION: Primer

<400> SEQUENCE: 156
ggcaggcatg cgcggcaaag ccccagggac agtg                                      34

```
<210> SEQ ID NO 157
<211> LENGTH: 37
<212> TYPE: DNA
<213> ORGANISM: Artificial
<220> FEATURE:
<223> OTHER INFORMATION: Primer

<400> SEQUENCE: 157
ttctgccgac gctccctggg gctttgctct gcatttc                              37

<210> SEQ ID NO 158
<211> LENGTH: 35
<212> TYPE: DNA
<213> ORGANISM: Artificial
<220> FEATURE:
<223> OTHER INFORMATION: Primer

<400> SEQUENCE: 158
ggagcgtcgg cagaagatgt cctgggaaat aagac                                35

<210> SEQ ID NO 159
<211> LENGTH: 35
<212> TYPE: DNA
<213> ORGANISM: Artificial
<220> FEATURE:
<223> OTHER INFORMATION: Primer

<400> SEQUENCE: 159
cgcggaagct gatgcccact gtccctgagg ctttg                                35

<210> SEQ ID NO 160
<211> LENGTH: 35
<212> TYPE: DNA
<213> ORGANISM: Artificial
<220> FEATURE:
<223> OTHER INFORMATION: Primer

<400> SEQUENCE: 160
gcatcagctt ccgcgggaaa taagacatgg gacag                                35

<210> SEQ ID NO 161
<211> LENGTH: 36
<212> TYPE: DNA
<213> ORGANISM: Artificial
<220> FEATURE:
<223> OTHER INFORMATION: Primer

<400> SEQUENCE: 161
tcccatgcac tagctcccag gacatcttct gcccac                               36

<210> SEQ ID NO 162
<211> LENGTH: 36
<212> TYPE: DNA
<213> ORGANISM: Artificial
<220> FEATURE:
<223> OTHER INFORMATION: Primer

<400> SEQUENCE: 162
agctagtgca tgggacagag agaccagaga cttgac                               36

<210> SEQ ID NO 163
<211> LENGTH: 40
<212> TYPE: DNA
<213> ORGANISM: Artificial
<220> FEATURE:
<223> OTHER INFORMATION: Primer
```

<400> SEQUENCE: 163
ctgcggtctc tgcgtcccat gtcttatttc ccaggacatc                                40

<210> SEQ ID NO 164
<211> LENGTH: 38
<212> TYPE: DNA
<213> ORGANISM: Artificial
<220> FEATURE:
<223> OTHER INFORMATION: Primer

<400> SEQUENCE: 164
acgcagagac cgcagacttg acagggaacg gaaaggac                                  38

<210> SEQ ID NO 165
<211> LENGTH: 33
<212> TYPE: DNA
<213> ORGANISM: Artificial
<220> FEATURE:
<223> OTHER INFORMATION: Primer

<400> SEQUENCE: 165
ctgaggtccg ctccgttccc tgtcaagtct ctg                                       33

<210> SEQ ID NO 166
<211> LENGTH: 34
<212> TYPE: DNA
<213> ORGANISM: Artificial
<220> FEATURE:
<223> OTHER INFORMATION: Primer

<400> SEQUENCE: 166
cggagcggac ctcaggatga ccctggctca tatc                                      34

<210> SEQ ID NO 167
<211> LENGTH: 38
<212> TYPE: DNA
<213> ORGANISM: Artificial
<220> FEATURE:
<223> OTHER INFORMATION: Primer

<400> SEQUENCE: 167
agcagacagg gtactcgcga ggtcctttcc gttccctg                                  38

<210> SEQ ID NO 168
<211> LENGTH: 35
<212> TYPE: DNA
<213> ORGANISM: Artificial
<220> FEATURE:
<223> OTHER INFORMATION: Primer

<400> SEQUENCE: 168
agtaccctgt ctgctatcaa ggaccagaaa gaagg                                     35

<210> SEQ ID NO 169
<211> LENGTH: 34
<212> TYPE: DNA
<213> ORGANISM: Artificial
<220> FEATURE:
<223> OTHER INFORMATION: Primer

<400> SEQUENCE: 169
ttctttctgg gccgcgatat gagccagggt catc                                      34

<210> SEQ ID NO 170
<211> LENGTH: 33

```
<212> TYPE: DNA
<213> ORGANISM: Artificial
<220> FEATURE:
<223> OTHER INFORMATION: Primer

<400> SEQUENCE: 170
gcggcccaga aagaaggctt gcattccctc cag                            33

<210> SEQ ID NO 171
<211> LENGTH: 36
<212> TYPE: DNA
<213> ORGANISM: Artificial
<220> FEATURE:
<223> OTHER INFORMATION: Primer

<400> SEQUENCE: 171
tgccgcgtcc ttgatatgag ccagggtcat cctgag                         36

<210> SEQ ID NO 172
<211> LENGTH: 36
<212> TYPE: DNA
<213> ORGANISM: Artificial
<220> FEATURE:
<223> OTHER INFORMATION: Primer

<400> SEQUENCE: 172
atcaaggacg cggcagaagg cttgcattcc ctccag                         36

<210> SEQ ID NO 173
<211> LENGTH: 36
<212> TYPE: DNA
<213> ORGANISM: Artificial
<220> FEATURE:
<223> OTHER INFORMATION: Primer

<400> SEQUENCE: 173
tcttcagcga tcgcacagac cctaatctcc tggagg                         36

<210> SEQ ID NO 174
<211> LENGTH: 38
<212> TYPE: DNA
<213> ORGANISM: Artificial
<220> FEATURE:
<223> OTHER INFORMATION: Primer

<400> SEQUENCE: 174
tgcgatcgct gaagacaaca gcaccaggag ttcccagc                       38

<210> SEQ ID NO 175
<211> LENGTH: 35
<212> TYPE: DNA
<213> ORGANISM: Artificial
<220> FEATURE:
<223> OTHER INFORMATION: Primer

<400> SEQUENCE: 175
tggcggatgc atggatctca cagaccctaa tctcc                          35

<210> SEQ ID NO 176
<211> LENGTH: 38
<212> TYPE: DNA
<213> ORGANISM: Artificial
<220> FEATURE:
<223> OTHER INFORMATION: Primer

<400> SEQUENCE: 176
```
tccatgcatc cgccagcacc aggagctccc agcatttc                                    38

<210> SEQ ID NO 177
<211> LENGTH: 36
<212> TYPE: DNA
<213> ORGANISM: Artificial
<220> FEATURE:
<223> OTHER INFORMATION: Primer

<400> SEQUENCE: 177
ctcgcggagg cgttgtcttc atggatctca cagacc                                      36

<210> SEQ ID NO 178
<211> LENGTH: 35
<212> TYPE: DNA
<213> ORGANISM: Artificial
<220> FEATURE:
<223> OTHER INFORMATION: Primer

<400> SEQUENCE: 178
caacgcctcc gcgagctccc agcatttcta ctacg                                       35

<210> SEQ ID NO 179
<211> LENGTH: 47
<212> TYPE: DNA
<213> ORGANISM: Artificial
<220> FEATURE:
<223> OTHER INFORMATION: Primer

<400> SEQUENCE: 179
ggcgaaagcc tgggagctcc tggtgctgtt gtcttcatgg atctcac                          47

<210> SEQ ID NO 180
<211> LENGTH: 46
<212> TYPE: DNA
<213> ORGANISM: Artificial
<220> FEATURE:
<223> OTHER INFORMATION: Prmier

<400> SEQUENCE: 180
tcccaggctt tcgcctacga tggcgaggcc ttcctctccc aaaacc                           46

<210> SEQ ID NO 181
<211> LENGTH: 37
<212> TYPE: DNA
<213> ORGANISM: Artificial
<220> FEATURE:
<223> OTHER INFORMATION: Primer

<400> SEQUENCE: 181
gccccagcgt agtagaaatg ctgggagctc ctggtgc                                     37

<210> SEQ ID NO 182
<211> LENGTH: 37
<212> TYPE: DNA
<213> ORGANISM: Artificial
<220> FEATURE:
<223> OTHER INFORMATION: Primer

<400> SEQUENCE: 182
ctactacgct ggggcgctct tcctctccca aaacctg                                     37

<210> SEQ ID NO 183
<211> LENGTH: 35
<212> TYPE: DNA
<213> ORGANISM: Artificial

```
<220> FEATURE:
<223> OTHER INFORMATION: Primer

<400> SEQUENCE: 183
tcgacagggc ttgggagagg aagagctccc catcg                            35

<210> SEQ ID NO 184
<211> LENGTH: 34
<212> TYPE: DNA
<213> ORGANISM: Artificial
<220> FEATURE:
<223> OTHER INFORMATION: Primer

<400> SEQUENCE: 184
cccaagccct gtcgactaag gaatggacaa tgcc                             34

<210> SEQ ID NO 185
<211> LENGTH: 35
<212> TYPE: DNA
<213> ORGANISM: Artificial
<220> FEATURE:
<223> OTHER INFORMATION: Primer

<400> SEQUENCE: 185
tccatgcctt agcctccagg ttttgggaga ggaag                            35

<210> SEQ ID NO 186
<211> LENGTH: 34
<212> TYPE: DNA
<213> ORGANISM: Artificial
<220> FEATURE:
<223> OTHER INFORMATION: Primer

<400> SEQUENCE: 186
aggctaaggc atggacaatg ccccagtcct ccag                             34

<210> SEQ ID NO 187
<211> LENGTH: 38
<212> TYPE: DNA
<213> ORGANISM: Artificial
<220> FEATURE:
<223> OTHER INFORMATION: Primer

<400> SEQUENCE: 187
gactgggccg atgcccattc cttagtctcc aggttttg                         38

<210> SEQ ID NO 188
<211> LENGTH: 34
<212> TYPE: DNA
<213> ORGANISM: Artificial
<220> FEATURE:
<223> OTHER INFORMATION: Primer

<400> SEQUENCE: 188
ggcatcggcc cagtcctcca gagctcagac cttg                             34

<210> SEQ ID NO 189
<211> LENGTH: 36
<212> TYPE: DNA
<213> ORGANISM: Artificial
<220> FEATURE:
<223> OTHER INFORMATION: Primer

<400> SEQUENCE: 189
ggaggccgcg ggcattgtcc attccttagt ctccag                           36
```

<210> SEQ ID NO 190
<211> LENGTH: 39
<212> TYPE: DNA
<213> ORGANISM: Artificial
<220> FEATURE:
<223> OTHER INFORMATION: Primer

<400> SEQUENCE: 190
atgcccgcgg cctccagagc ttcgaccttg gccatgaac                        39

<210> SEQ ID NO 191
<211> LENGTH: 47
<212> TYPE: DNA
<213> ORGANISM: Artificial
<220> FEATURE:
<223> OTHER INFORMATION: Primer

<400> SEQUENCE: 191
gcctgagcgc tggcggattg tggcattgtc cattccttag tctccag               47

<210> SEQ ID NO 192
<211> LENGTH: 34
<212> TYPE: DNA
<213> ORGANISM: Artificial
<220> FEATURE:
<223> OTHER INFORMATION: Primer

<400> SEQUENCE: 192
cgccagcgct caggccttgg ccatgaacgt cagg                             34

<210> SEQ ID NO 193
<211> LENGTH: 34
<212> TYPE: DNA
<213> ORGANISM: Artificial
<220> FEATURE:
<223> OTHER INFORMATION: Primer

<400> SEQUENCE: 193
gcggaggccg aggccaaggt ctgagctctg gagg                             34

<210> SEQ ID NO 194
<211> LENGTH: 37
<212> TYPE: DNA
<213> ORGANISM: Artificial
<220> FEATURE:
<223> OTHER INFORMATION: Primer

<400> SEQUENCE: 194
ggcctcggcc tccgcgaatt tcttgaagga agatgcc                          37

<210> SEQ ID NO 195
<211> LENGTH: 33
<212> TYPE: DNA
<213> ORGANISM: Artificial
<220> FEATURE:
<223> OTHER INFORMATION: Primer

<400> SEQUENCE: 195
cagatgccga caagaaattc ctgacgttca tgg                              33

<210> SEQ ID NO 196
<211> LENGTH: 35
<212> TYPE: DNA
<213> ORGANISM: Artificial
<220> FEATURE:
<223> OTHER INFORMATION: Primer

```
<400> SEQUENCE: 196
tcttgtcggc atctgccatg aagaccaaga cacac                              35

<210> SEQ ID NO 197
<211> LENGTH: 40
<212> TYPE: DNA
<213> ORGANISM: Artificial
<220> FEATURE:
<223> OTHER INFORMATION: Primer

<400> SEQUENCE: 197
tgtcttggtc ttcgcggaat cttccttcaa gaaattcctg                         40

<210> SEQ ID NO 198
<211> LENGTH: 37
<212> TYPE: DNA
<213> ORGANISM: Artificial
<220> FEATURE:
<223> OTHER INFORMATION: Primer

<400> SEQUENCE: 198
gcgaagacca agacagccta tcacgctatg catgcag                            37

<210> SEQ ID NO 199
<211> LENGTH: 34
<212> TYPE: DNA
<213> ORGANISM: Artificial
<220> FEATURE:
<223> OTHER INFORMATION: Primer

<400> SEQUENCE: 199
atagtgtgcc gaggccttca tggcatcttc cttc                               34

<210> SEQ ID NO 200
<211> LENGTH: 33
<212> TYPE: DNA
<213> ORGANISM: Artificial
<220> FEATURE:
<223> OTHER INFORMATION: Primer

<400> SEQUENCE: 200
gcctcggcac actatcacgc tatgcatgca gac                                33

<210> SEQ ID NO 201
<211> LENGTH: 36
<212> TYPE: DNA
<213> ORGANISM: Artificial
<220> FEATURE:
<223> OTHER INFORMATION: Primer

<400> SEQUENCE: 201
cagacatagc ggcatagtgt gtcttggtct tcatgg                             36

<210> SEQ ID NO 202
<211> LENGTH: 36
<212> TYPE: DNA
<213> ORGANISM: Artificial
<220> FEATURE:
<223> OTHER INFORMATION: Primer

<400> SEQUENCE: 202
atgccgctat gtctgcagac tgcctgcagg aactac                             36

<210> SEQ ID NO 203
```

```
<211> LENGTH: 37
<212> TYPE: DNA
<213> ORGANISM: Artificial
<220> FEATURE:
<223> OTHER INFORMATION: Primer

<400> SEQUENCE: 203
cgccaggcag gctgaatgca tagcgtgata gtgtgtc                              37

<210> SEQ ID NO 204
<211> LENGTH: 39
<212> TYPE: DNA
<213> ORGANISM: Artificial
<220> FEATURE:
<223> OTHER INFORMATION: Primer

<400> SEQUENCE: 204
tcagcctgcc tggcggaact acggcgatat ctaaaatcc                            39

<210> SEQ ID NO 205
<211> LENGTH: 37
<212> TYPE: DNA
<213> ORGANISM: Artificial
<220> FEATURE:
<223> OTHER INFORMATION: Primer

<400> SEQUENCE: 205
tatgccgata gtgcctgcag gcagtctgca tgcatag                              37

<210> SEQ ID NO 206
<211> LENGTH: 37
<212> TYPE: DNA
<213> ORGANISM: Artificial
<220> FEATURE:
<223> OTHER INFORMATION: Primer

<400> SEQUENCE: 206
ggcactatcg gcatatctaa aatccggcgt agtcctg                              37

<210> SEQ ID NO 207
<211> LENGTH: 34
<212> TYPE: DNA
<213> ORGANISM: Artificial
<220> FEATURE:
<223> OTHER INFORMATION: Primer

<400> SEQUENCE: 207
tacgccggct gatgcatatc gccgtagttc ctgc                                 34

<210> SEQ ID NO 208
<211> LENGTH: 34
<212> TYPE: DNA
<213> ORGANISM: Artificial
<220> FEATURE:
<223> OTHER INFORMATION: Primer

<400> SEQUENCE: 208
gcatcagccg gcgtagtcct gaggagaaca gtgc                                 34

<210> SEQ ID NO 209
<211> LENGTH: 38
<212> TYPE: DNA
<213> ORGANISM: Artificial
<220> FEATURE:
<223> OTHER INFORMATION: Primer

<400> SEQUENCE: 209
```

```
gcgctcgcga ctacgccgga ttttagatat cgccgtag                              38
```

<210> SEQ ID NO 210
<211> LENGTH: 40
<212> TYPE: DNA
<213> ORGANISM: Artificial
<220> FEATURE:
<223> OTHER INFORMATION: Primer

<400> SEQUENCE: 210

```
cgtagtcgcg agcgcaacag tgcctcccat ggtgaatgtc                            40
```

<210> SEQ ID NO 211
<211> LENGTH: 37
<212> TYPE: DNA
<213> ORGANISM: Artificial
<220> FEATURE:
<223> OTHER INFORMATION: Primer

<400> SEQUENCE: 211

```
ttcaccatgg cggccactgt tctcctcagg actacgc                               37
```

<210> SEQ ID NO 212
<211> LENGTH: 38
<212> TYPE: DNA
<213> ORGANISM: Artificial
<220> FEATURE:
<223> OTHER INFORMATION: Primer

<400> SEQUENCE: 212

```
ggccgccatg gtgaatgtca cccgcagcga ggcctcag                              38
```

<210> SEQ ID NO 213
<211> LENGTH: 37
<212> TYPE: DNA
<213> ORGANISM: Artificial
<220> FEATURE:
<223> OTHER INFORMATION: Primer

<400> SEQUENCE: 213

```
cagccgacgc gggggcact gttctcctca ggactac                                37
```

<210> SEQ ID NO 214
<211> LENGTH: 38
<212> TYPE: DNA
<213> ORGANISM: Artificial
<220> FEATURE:
<223> OTHER INFORMATION: Primer

<400> SEQUENCE: 214

```
cccccgcgtc ggctgtcacc cgcagcgagg cctcagag                              38
```

<210> SEQ ID NO 215
<211> LENGTH: 39
<212> TYPE: DNA
<213> ORGANISM: Artificial
<220> FEATURE:
<223> OTHER INFORMATION: Primer

<400> SEQUENCE: 215

```
ccgaggcgct ggtgacattc accatggggg gcactgttc                             39
```

<210> SEQ ID NO 216
<211> LENGTH: 35
<212> TYPE: DNA

<213> ORGANISM: Artificial
<220> FEATURE:
<223> OTHER INFORMATION: Primer

<400> SEQUENCE: 216
tcaccagcgc ctcggcctca gagggcaaca ttacc                         35

<210> SEQ ID NO 217
<211> LENGTH: 36
<212> TYPE: DNA
<213> ORGANISM: Artificial
<220> FEATURE:
<223> OTHER INFORMATION: Primer

<400> SEQUENCE: 217
atggcgcccg atgcggcctc gctgcgggtg acattc                        36

<210> SEQ ID NO 218
<211> LENGTH: 36
<212> TYPE: DNA
<213> ORGANISM: Artificial
<220> FEATURE:
<223> OTHER INFORMATION: Primer

<400> SEQUENCE: 218
cgcatcgggc gccattaccg tgacatgcag ggcttc                        36

<210> SEQ ID NO 219
<211> LENGTH: 82
<212> TYPE: DNA
<213> ORGANISM: Artificial
<220> FEATURE:
<223> OTHER INFORMATION: Primer

<400> SEQUENCE: 219
gctcaaagat accccatcct gacgccagct cagtgtgata ttccagggat agaagccagc    60
agcactgcat gtcacggtaa tg                                            82

<210> SEQ ID NO 220
<211> LENGTH: 86
<212> TYPE: DNA
<213> ORGANISM: Artificial
<220> FEATURE:
<223> OTHER INFORMATION: Primer

<400> SEQUENCE: 220
ggggtatctt tgagccacga cacccagcag tgggggatg tcctgcctga tgggaatgga     60
acctacgcga cctgggtggc caccag                                        86

<210> SEQ ID NO 221
<211> LENGTH: 33
<212> TYPE: DNA
<213> ORGANISM: Artificial
<220> FEATURE:
<223> OTHER INFORMATION: Primer

<400> SEQUENCE: 221
cagtgtggca ctcgcgggat agaagccaga agc                           33

<210> SEQ ID NO 222
<211> LENGTH: 32
<212> TYPE: DNA
<213> ORGANISM: Artificial
<220> FEATURE:
<223> OTHER INFORMATION: Primer

<400> SEQUENCE: 222
gcgagtgcca cactgagctg gcgtcaggat gg                                    32

<210> SEQ ID NO 223
<211> LENGTH: 40
<212> TYPE: DNA
<213> ORGANISM: Artificial
<220> FEATURE:
<223> OTHER INFORMATION: Primer

<400> SEQUENCE: 223
agatgcccca tcctgagccc agctcagtgt gatattccag                            40

<210> SEQ ID NO 224
<211> LENGTH: 36
<212> TYPE: DNA
<213> ORGANISM: Artificial
<220> FEATURE:
<223> OTHER INFORMATION: Primer

<400> SEQUENCE: 224
caggatgggg catctttgag ccacgacacc cagcag                                36

<210> SEQ ID NO 225
<211> LENGTH: 77
<212> TYPE: DNA
<213> ORGANISM: Artificial
<220> FEATURE:
<223> OTHER INFORMATION: Primer

<400> SEQUENCE: 225
tcccatcagg caggacatcc ccccactgct gggtgtcgtg gctcaaagat accccagccg      60
cacgccagct cagtgtg                                                     77

<210> SEQ ID NO 226
<211> LENGTH: 86
<212> TYPE: DNA
<213> ORGANISM: Artificial
<220> FEATURE:
<223> OTHER INFORMATION: Primer

<400> SEQUENCE: 226
tcctgcctga tgggaatgga acctaccaga cctgggtggc caccaggatt tgccaaggag      60
aggagcaggc gttcacctgc tacatg                                           86

<210> SEQ ID NO 227
<211> LENGTH: 34
<212> TYPE: DNA
<213> ORGANISM: Artificial
<220> FEATURE:
<223> OTHER INFORMATION: Primer

<400> SEQUENCE: 227
tgggtggcgc tggccaaaga taccccatcc tgac                                  34

<210> SEQ ID NO 228
<211> LENGTH: 34
<212> TYPE: DNA
<213> ORGANISM: Artificial
<220> FEATURE:
<223> OTHER INFORMATION: Primer

<400> SEQUENCE: 228

```
ggccagcgcc acccagcagt gggggatgt cctg                                    34
```

<210> SEQ ID NO 229
<211> LENGTH: 34
<212> TYPE: DNA
<213> ORGANISM: Artificial
<220> FEATURE:
<223> OTHER INFORMATION: Primer

<400> SEQUENCE: 229

```
cccccacgcc gaggcgtcgt ggctcaaaga tacc                                   34
```

<210> SEQ ID NO 230
<211> LENGTH: 37
<212> TYPE: DNA
<213> ORGANISM: Artificial
<220> FEATURE:
<223> OTHER INFORMATION: Primer

<400> SEQUENCE: 230

```
gcctcggcgt gggggatgt cctgcctgat gggaatg                                 37
```

<210> SEQ ID NO 231
<211> LENGTH: 36
<212> TYPE: DNA
<213> ORGANISM: Artificial
<220> FEATURE:
<223> OTHER INFORMATION: Primer

<400> SEQUENCE: 231

```
gcccccgcct gctgggtgtc gtggctcaaa gatacc                                 36
```

<210> SEQ ID NO 232
<211> LENGTH: 36
<212> TYPE: DNA
<213> ORGANISM: Artificial
<220> FEATURE:
<223> OTHER INFORMATION: Primer

<400> SEQUENCE: 232

```
ccagcaggcg ggggctgtcc tgcctgatgg gaatgg                                 36
```

<210> SEQ ID NO 233
<211> LENGTH: 37
<212> TYPE: DNA
<213> ORGANISM: Artificial
<220> FEATURE:
<223> OTHER INFORMATION: Primer

<400> SEQUENCE: 233

```
tcccagcaga cgcgacatcc ccccactgct gggtgtc                                37
```

<210> SEQ ID NO 234
<211> LENGTH: 38
<212> TYPE: DNA
<213> ORGANISM: Artificial
<220> FEATURE:
<223> OTHER INFORMATION: Primer

<400> SEQUENCE: 234

```
tcgcgtctgc tgggaatgga acctaccaga cctgggtg                               38
```

<210> SEQ ID NO 235
<211> LENGTH: 36
<212> TYPE: DNA
<213> ORGANISM: Artificial

```
<220> FEATURE:
<223> OTHER INFORMATION: Primer

<400> SEQUENCE: 235
caggtctggg cggttccagc cccatcaggc aggaca                              36

<210> SEQ ID NO 236
<211> LENGTH: 38
<212> TYPE: DNA
<213> ORGANISM: Artificial
<220> FEATURE:
<223> OTHER INFORMATION: Primer

<400> SEQUENCE: 236
aaccgcccag acctgggttg ccaccaggat ttgccaag                            38

<210> SEQ ID NO 237
<211> LENGTH: 35
<212> TYPE: DNA
<213> ORGANISM: Artificial
<220> FEATURE:
<223> OTHER INFORMATION: Primer

<400> SEQUENCE: 237
gtggccaccg cggtctggta ggttccattc ccatc                               35

<210> SEQ ID NO 238
<211> LENGTH: 37
<212> TYPE: DNA
<213> ORGANISM: Artificial
<220> FEATURE:
<223> OTHER INFORMATION: Primer

<400> SEQUENCE: 238
gaccgcggtg gccaccagga tttgccaagg agaggag                             37

<210> SEQ ID NO 239
<211> LENGTH: 36
<212> TYPE: DNA
<213> ORGANISM: Artificial
<220> FEATURE:
<223> OTHER INFORMATION: Primer

<400> SEQUENCE: 239
ggcaaatcgc ggtggccacc caggtctggt aggttc                              36

<210> SEQ ID NO 240
<211> LENGTH: 37
<212> TYPE: DNA
<213> ORGANISM: Artificial
<220> FEATURE:
<223> OTHER INFORMATION: Primer

<400> SEQUENCE: 240
ccaccgcgat tgccaagga gaggagcaga ggttcac                              37

<210> SEQ ID NO 241
<211> LENGTH: 35
<212> TYPE: DNA
<213> ORGANISM: Artificial
<220> FEATURE:
<223> OTHER INFORMATION: Primer

<400> SEQUENCE: 241
ccgctccttg gcaatcctg gtggccaccc aggtc                                35
```

```
<210> SEQ ID NO 242
<211> LENGTH: 35
<212> TYPE: DNA
<213> ORGANISM: Artificial
<220> FEATURE:
<223> OTHER INFORMATION: Primer

<400> SEQUENCE: 242
ttgcccaagg agcggagcag aggttcacct gctac                              35

<210> SEQ ID NO 243
<211> LENGTH: 36
<212> TYPE: DNA
<213> ORGANISM: Artificial
<220> FEATURE:
<223> OTHER INFORMATION: Primer

<400> SEQUENCE: 243
gcctctcctg cgcaaatcct ggtggccacc caggtc                             36

<210> SEQ ID NO 244
<211> LENGTH: 34
<212> TYPE: DNA
<213> ORGANISM: Artificial
<220> FEATURE:
<223> OTHER INFORMATION: Primer

<400> SEQUENCE: 244
ttgcgcagga gaggcgcaga ggttcacctg ctac                               34

<210> SEQ ID NO 245
<211> LENGTH: 36
<212> TYPE: DNA
<213> ORGANISM: Artificial
<220> FEATURE:
<223> OTHER INFORMATION: Primer

<400> SEQUENCE: 245
gcctcctctc cttggcaaat cctggtggcc acccag                             36

<210> SEQ ID NO 246
<211> LENGTH: 35
<212> TYPE: DNA
<213> ORGANISM: Artificial
<220> FEATURE:
<223> OTHER INFORMATION: Primer

<400> SEQUENCE: 246
ccaaggagag gaggcgaggt tcacctgcta catgg                              35

<210> SEQ ID NO 247
<211> LENGTH: 41
<212> TYPE: DNA
<213> ORGANISM: Artificial
<220> FEATURE:
<223> OTHER INFORMATION: Primer

<400> SEQUENCE: 247
ttcccgctgt gttccatgta gcaggcgaac ctctgctcct c                       41

<210> SEQ ID NO 248
<211> LENGTH: 47
<212> TYPE: DNA
<213> ORGANISM: Artificial
<220> FEATURE:
<223> OTHER INFORMATION: Primer
```

```
<400> SEQUENCE: 248
ggaacacagc gggaatcaca gcgctcacgc tgtgccctct gggaaag          47

<210> SEQ ID NO 249
<211> LENGTH: 36
<212> TYPE: DNA
<213> ORGANISM: Artificial
<220> FEATURE:
<223> OTHER INFORMATION: Primer

<400> SEQUENCE: 249
gctgtgtgac atggcgcagg tgaacctctg ctcctc                      36

<210> SEQ ID NO 250
<211> LENGTH: 40
<212> TYPE: DNA
<213> ORGANISM: Artificial
<220> FEATURE:
<223> OTHER INFORMATION: Primer

<400> SEQUENCE: 250
gccatgtcac acagcgggaa tgccagcact caccctgtgc                  40

<210> SEQ ID NO 251
<211> LENGTH: 38
<212> TYPE: DNA
<213> ORGANISM: Artificial
<220> FEATURE:
<223> OTHER INFORMATION: Primer

<400> SEQUENCE: 251
tgtgagcccc gctgtgttcc atgtagcagg tgaacctc                    38

<210> SEQ ID NO 252
<211> LENGTH: 36
<212> TYPE: DNA
<213> ORGANISM: Artificial
<220> FEATURE:
<223> OTHER INFORMATION: Primer

<400> SEQUENCE: 252
acagcggggc tcacagcact caccctgtgc cctctg                      36

<210> SEQ ID NO 253
<211> LENGTH: 36
<212> TYPE: DNA
<213> ORGANISM: Artificial
<220> FEATURE:
<223> OTHER INFORMATION: Primer

<400> SEQUENCE: 253
cgcggacagc accgtgaggt tataacgaag actgtg                      36

<210> SEQ ID NO 254
<211> LENGTH: 34
<212> TYPE: DNA
<213> ORGANISM: Artificial
<220> FEATURE:
<223> OTHER INFORMATION: Primer

<400> SEQUENCE: 254
acggtgctgt ccgcggatgg atctgtgcag tcag                        34

<210> SEQ ID NO 255
```

<211> LENGTH: 33
<212> TYPE: DNA
<213> ORGANISM: Artificial
<220> FEATURE:
<223> OTHER INFORMATION: Primer

<400> SEQUENCE: 255
cctgctttct ggtccttgat atgagccagg gtc                           33

<210> SEQ ID NO 256
<211> LENGTH: 34
<212> TYPE: DNA
<213> ORGANISM: Artificial
<220> FEATURE:
<223> OTHER INFORMATION: Primer

<400> SEQUENCE: 256
ggaccagaaa gcaggcttgc attccctaca ggag                          34

<210> SEQ ID NO 257
<211> LENGTH: 37
<212> TYPE: DNA
<213> ORGANISM: Artificial
<220> FEATURE:
<223> OTHER INFORMATION: Primer

<400> SEQUENCE: 257
tccccagcgt agtagaaatg ctgggagctc ctggtgc                       37

<210> SEQ ID NO 258
<211> LENGTH: 37
<212> TYPE: DNA
<213> ORGANISM: Artificial
<220> FEATURE:
<223> OTHER INFORMATION: Primer

<400> SEQUENCE: 258
ctactacgct ggggagctct tcctctccca aaacctg                       37

<210> SEQ ID NO 259
<211> LENGTH: 37
<212> TYPE: DNA
<213> ORGANISM: Artificial
<220> FEATURE:
<223> OTHER INFORMATION: Primer

<400> SEQUENCE: 259
gccccatcgt agtagaaatg ctgggagctc ctggtgc                       37

<210> SEQ ID NO 260
<211> LENGTH: 37
<212> TYPE: DNA
<213> ORGANISM: Artificial
<220> FEATURE:
<223> OTHER INFORMATION: Primer

<400> SEQUENCE: 260
ctactacgat ggggcgctct tcctctccca aaacctg                       37

<210> SEQ ID NO 261
<211> LENGTH: 6
<212> TYPE: PRT
<213> ORGANISM: mus musculus
<220> FEATURE:
<221> NAME/KEY: Xaa
<222> LOCATION: (2)..(2)
<223> OTHER INFORMATION: Xaa may be Phe or Tyr

```
<220> FEATURE:
<221> NAME/KEY: Xaa
<222> LOCATION: (3)..(3)
<223> OTHER INFORMATION: Xaa may be Thr or Ser
<220> FEATURE:
<221> NAME/KEY: Xaa
<222> LOCATION: (4)..(4)
<223> OTHER INFORMATION: Xaa may be Ile, Leu or Phe
<220> FEATURE:
<221> NAME/KEY: Xaa
<222> LOCATION: (5)..(5)
<223> OTHER INFORMATION: Xaa may be Ser or Thr
<220> FEATURE:
<221> NAME/KEY: Xaa
<222> LOCATION: (6)..(6)
<223> OTHER INFORMATION: Xaa may be Asn, Tyr, Ser, Thr or Arg

<400> SEQUENCE: 261

Gly Xaa Xaa Xaa Xaa Xaa
1               5

<210> SEQ ID NO 262
<211> LENGTH: 5
<212> TYPE: PRT
<213> ORGANISM: Mus musculus
<220> FEATURE:
<221> NAME/KEY: Xaa
<222> LOCATION: (1)..(1)
<223> OTHER INFORMATION: Xaa may be Asn, Ser, Thr or Arg
<220> FEATURE:
<221> NAME/KEY: Xaa
<222> LOCATION: (2)..(2)
<223> OTHER INFORMATION: Xaa may be Gly, Asp, Ser or Tyr
<220> FEATURE:
<221> NAME/KEY: Xaa
<222> LOCATION: (3)..(3)
<223> OTHER INFORMATION: Xaa may be Thr, Tyr, Ala, Gly, Trp
<220> FEATURE:
<221> NAME/KEY: Xaa
<222> LOCATION: (4)..(4)
<223> OTHER INFORMATION: Xaa may be Ser, Ala or Met
<220> FEATURE:
<221> NAME/KEY: Xaa
<222> LOCATION: (5)..(5)
<223> OTHER INFORMATION: Xaa may be His, Trp, Gln, Ser or Asn

<400> SEQUENCE: 262

Xaa Xaa Xaa Xaa Xaa
1               5

<210> SEQ ID NO 263
<211> LENGTH: 5
<212> TYPE: PRT
<213> ORGANISM: Mus musculus
<220> FEATURE:
<221> NAME/KEY: Xaa
<222> LOCATION: (1)..(1)
<223> OTHER INFORMATION: Xaa may be Asn, Ser, Thr or Arg
<220> FEATURE:
<221> NAME/KEY: Xaa
<222> LOCATION: (3)..(3)
<223> OTHER INFORMATION: Xaa may be Thr, Tyr, Ala, Gly, Trp
<220> FEATURE:
<221> NAME/KEY: Xaa
<222> LOCATION: (5)..(5)
<223> OTHER INFORMATION: Xaa may be His, Trp, Gln, Ser or Asn

<400> SEQUENCE: 263

Xaa Tyr Xaa Met Xaa
1               5

<210> SEQ ID NO 264
<211> LENGTH: 10
```

```
<212> TYPE: PRT
<213> ORGANISM: Mus musculus
<220> FEATURE:
<221> NAME/KEY: Xaa
<222> LOCATION: (1)..(1)
<223> OTHER INFORMATION: Xaa may be Phe, Thr, His, Asn, Tyr or Met
<220> FEATURE:
<221> NAME/KEY: Xaa
<222> LOCATION: (2)..(2)
<223> OTHER INFORMATION: Xaa may be Val or Ile
<220> FEATURE:
<221> NAME/KEY: Xaa
<222> LOCATION: (3)..(3)
<223> OTHER INFORMATION: Xaa may be Ser, Phe, His, Asn or Trp
<220> FEATURE:
<221> NAME/KEY: Xaa
<222> LOCATION: (4)..(4)
<223> OTHER INFORMATION: Xaa may be Arg, Tyr, Ser, Trp or Pro
<220> FEATURE:
<221> NAME/KEY: Xaa
<222> LOCATION: (5)..(5)
<223> OTHER INFORMATION: Xaa may be Gly, Asp or Ser
<220> FEATURE:
<221> NAME/KEY: Xaa
<222> LOCATION: (6)..(6)
<223> OTHER INFORMATION: Xaa may be Thr, Gly, Asp or Ser
<220> FEATURE:
<221> NAME/KEY: Xaa
<222> LOCATION: (7)..(7)
<223> OTHER INFORMATION: Xaa may be Asn, Thr, Ser, Asp, Arg or Gly
<220> FEATURE:
<221> NAME/KEY: Xaa
<222> LOCATION: (8)..(8)
<223> OTHER INFORMATION: Xaa may be Tyr, Lys, Glu, Arg, Ile or Thr
<220> FEATURE:
<221> NAME/KEY: Xaa
<222> LOCATION: (9)..(9)
<223> OTHER INFORMATION: Xaa may be Ile, Thr, Tyr, Asn or Asp
<220> FEATURE:
<221> NAME/KEY: Xaa
<222> LOCATION: (10)..(10)
<223> OTHER INFORMATION: Xaa may be Tyr, Arg or Glu

<400> SEQUENCE: 264

Xaa Xaa Xaa Xaa Xaa Xaa Xaa Xaa Xaa Xaa
1               5                   10

<210> SEQ ID NO 265
<211> LENGTH: 9
<212> TYPE: PRT
<213> ORGANISM: Mus musculus
<220> FEATURE:
<221> NAME/KEY: Xaa
<222> LOCATION: (1)..(1)
<223> OTHER INFORMATION: Xaa may be Ile, Pro, Arg, Gly, Asp or Glu
<220> FEATURE:
<221> NAME/KEY: Xaa
<222> LOCATION: (2)..(2)
<223> OTHER INFORMATION: Xaa may be Ser, Tyr, Thr, Asn, Asp, Leu, Arg,
      Glu or Met
<220> FEATURE:
<221> NAME/KEY: Xaa
<222> LOCATION: (3)..(3)
<223> OTHER INFORMATION: Xaa may be Asp, Glu, Trp, Gln, Phe, Asn or Thr
<220> FEATURE:
<221> NAME/KEY: Xaa
<222> LOCATION: (4)..(4)
<223> OTHER INFORMATION: Xaa may be Tyr, Glu, Gly, Phe, Trp, His or Pro
<220> FEATURE:
<221> NAME/KEY: Xaa
<222> LOCATION: (5)..(5)
<223> OTHER INFORMATION: Xaa may be Asp, Arg, Tyr, Thr, Gly or Trp
<220> FEATURE:
<221> NAME/KEY: Xaa
<222> LOCATION: (6)..(6)
<223> OTHER INFORMATION: Xaa may be Gly, Tyr, Thr, Phe, Val, Met or Asn
<220> FEATURE:
```

```
<221> NAME/KEY: Xaa
<222> LOCATION: (7)..(7)
<223> OTHER INFORMATION: Xaa may be Ala, Phe, Asp, Met or Leu
<220> FEATURE:
<221> NAME/KEY: Xaa
<222> LOCATION: (8)..(8)
<223> OTHER INFORMATION: Xaa may be Trp, Tyr, Asp or Glu
<220> FEATURE:
<221> NAME/KEY: Xaa
<222> LOCATION: (9)..(9)
<223> OTHER INFORMATION: Xaa may be Leu, Tyr, Asp, Phe or Val

<400> SEQUENCE: 265

Xaa Xaa Xaa Xaa Xaa Xaa Xaa Xaa Xaa
1               5

<210> SEQ ID NO 266
<211> LENGTH: 11
<212> TYPE: PRT
<213> ORGANISM: Mus musculus
<220> FEATURE:
<221> NAME/KEY: Xaa
<222> LOCATION: (1)..(1)
<223> OTHER INFORMATION: Xaa may be Ser, Lys or Arg
<220> FEATURE:
<221> NAME/KEY: Xaa
<222> LOCATION: (2)..(2)
<223> OTHER INFORMATION: Xaa may be Ser or Ala
<220> FEATURE:
<221> NAME/KEY: Xaa
<222> LOCATION: (3)..(3)
<223> OTHER INFORMATION: Xaa may be Thr or Ser
<220> FEATURE:
<221> NAME/KEY: Xaa
<222> LOCATION: (4)..(4)
<223> OTHER INFORMATION: Xaa may be Ser or Gln
<220> FEATURE:
<221> NAME/KEY: Xaa
<222> LOCATION: (5)..(5)
<223> OTHER INFORMATION: Xaa may be Asn or Ser
<220> FEATURE:
<221> NAME/KEY: Xaa
<222> LOCATION: (6)..(6)
<223> OTHER INFORMATION: Xaa may be Val, Leu or Ile
<220> FEATURE:
<221> NAME/KEY: Xaa
<222> LOCATION: (7)..(7)
<223> OTHER INFORMATION: Xaa may be Asp, Asn, Val, Leu, Gly or Ser
<220> FEATURE:
<221> NAME/KEY: Xaa
<222> LOCATION: (8)..(8)
<223> OTHER INFORMATION: Xaa may be Tyr, Ser, Asn, Thr or Asp
<220> FEATURE:
<221> NAME/KEY: Xaa
<222> LOCATION: (9)..(9)
<223> OTHER INFORMATION: Xaa may be Asp, Met, Ile, Ser or Tyr
<220> FEATURE:
<221> NAME/KEY: Xaa
<222> LOCATION: (10)..(10)
<223> OTHER INFORMATION: Xaa may be Val, His, Tyr, Ser, Ile, or Leu
<220> FEATURE:
<221> NAME/KEY: Xaa
<222> LOCATION: (11)..(11)
<223> OTHER INFORMATION: Xaa may be Ala, Phe, Asn or His

<400> SEQUENCE: 266

Xaa Xaa Xaa Xaa Xaa Xaa Xaa Xaa Xaa Xaa Xaa
1               5                   10

<210> SEQ ID NO 267
<211> LENGTH: 7
<212> TYPE: PRT
<213> ORGANISM: Mus musculus
<220> FEATURE:
<221> NAME/KEY: Xaa
```

```
<222> LOCATION: (1)..(1)
<223> OTHER INFORMATION: Xaa may be Ser, Lys, Arg, Phe, Tyr or Ala
<220> FEATURE:
<221> NAME/KEY: Xaa
<222> LOCATION: (2)..(2)
<223> OTHER INFORMATION: Xaa may be Ile, Thr, Ala or Ser
<220> FEATURE:
<221> NAME/KEY: Xaa
<222> LOCATION: (3)..(3)
<223> OTHER INFORMATION: Xaa may be Ser or Glu
<220> FEATURE:
<221> NAME/KEY: Xaa
<222> LOCATION: (4)..(4)
<223> OTHER INFORMATION: Xaa may be Lys, Glu, Asn, Thr, Gln or Ser
<220> FEATURE:
<221> NAME/KEY: Xaa
<222> LOCATION: (5)..(5)
<223> OTHER INFORMATION: Xaa may be Leu, Arg, Ser or Ile
<220> FEATURE:
<221> NAME/KEY: Xaa
<222> LOCATION: (6)..(6)
<223> OTHER INFORMATION: Xaa may be Tyr, Phe, Ala, Glu, Ile or Ser
<220> FEATURE:
<221> NAME/KEY: Xaa
<222> LOCATION: (7)..(7)
<223> OTHER INFORMATION: Xaa may be Thr, Ser or Gly

<400> SEQUENCE: 267

Xaa Xaa Xaa Xaa Xaa Xaa Xaa
1               5

<210> SEQ ID NO 268
<211> LENGTH: 9
<212> TYPE: PRT
<213> ORGANISM: Mus musculus
<220> FEATURE:
<221> NAME/KEY: Xaa
<222> LOCATION: (1)..(1)
<223> OTHER INFORMATION: Xaa may be Phe or Gln
<220> FEATURE:
<221> NAME/KEY: Xaa
<222> LOCATION: (2)..(2)
<223> OTHER INFORMATION: Xaa may be His, Asn or Gln
<220> FEATURE:
<221> NAME/KEY: Xaa
<222> LOCATION: (3)..(3)
<223> OTHER INFORMATION: Xaa may be Ser, Gly, His, Trp or Arg
<220> FEATURE:
<221> NAME/KEY: Xaa
<222> LOCATION: (4)..(4)
<223> OTHER INFORMATION: Xaa may be Asn, His, Tyr, Thr or Ser
<220> FEATURE:
<221> NAME/KEY: Xaa
<222> LOCATION: (5)..(5)
<223> OTHER INFORMATION: Xaa may be Phe, Ser, Thr, His, Ile or Tyr
<220> FEATURE:
<221> NAME/KEY: Xaa
<222> LOCATION: (6)..(6)
<223> OTHER INFORMATION: Xaa may be Trp, Phe, Thr, Ile, Val, Asn or Try
<220> FEATURE:
<221> NAME/KEY: Xaa
<222> LOCATION: (7)..(7)
<223> OTHER INFORMATION: Xaa may be Pro
<220> FEATURE:
<221> NAME/KEY: Xaa
<222> LOCATION: (7)..(7)
<223> OTHER INFORMATION: Xaa may be Pro
<220> FEATURE:
<221> NAME/KEY: Xaa
<222> LOCATION: (8)..(8)
<223> OTHER INFORMATION: Xaa may be Phe, Trp, Pro or Leu
<220> FEATURE:
<221> NAME/KEY: Xaa
<222> LOCATION: (9)..(9)
<223> OTHER INFORMATION: Xaa may be Thr

<400> SEQUENCE: 268
```

```
Xaa Xaa Xaa Xaa Xaa Xaa Xaa Xaa Xaa
1           5
```